United States Patent
Osbourn et al.

(10) Patent No.: US 12,247,209 B2
(45) Date of Patent: Mar. 11, 2025

(54) TRANSFERASE ENZYMES

(71) Applicant: PLANT BIOSCIENCE LIMITED, Norwich (GB)

(72) Inventors: Anne Osbourn, Norwich (GB); James Reed, Norwich (GB); Anastasia Orme, Norwich (GB); Thomas Louveau, Norwich (GB)

(73) Assignee: PLANT BIOSCIENCE LIMITED, Norwich (GB)

( * ) Notice: Subject to any disclaimer, the term of this patent is extended or adjusted under 35 U.S.C. 154(b) by 186 days.

(21) Appl. No.: 17/618,856

(22) PCT Filed: Jun. 25, 2020

(86) PCT No.: PCT/EP2020/067866
§ 371 (c)(1),
(2) Date: Dec. 13, 2021

(87) PCT Pub. No.: WO2020/260475
PCT Pub. Date: Dec. 30, 2020

(65) Prior Publication Data
US 2023/0106588 A1    Apr. 6, 2023

(30) Foreign Application Priority Data

Jun. 25, 2019 (GB) .................................. 1909104

(51) Int. Cl.
*C12N 15/82* (2006.01)
*C12P 5/00* (2006.01)

(52) U.S. Cl.
CPC .......... *C12N 15/8243* (2013.01); *C12P 5/007* (2013.01); *C12Y 204/01017* (2013.01)

(58) Field of Classification Search
CPC .............................. C12N 15/8243; C12P 5/007
See application file for complete search history.

(56) References Cited

U.S. PATENT DOCUMENTS

| | | | |
|---|---|---|---|
| 11,130,945 B2* | 9/2021 | Muranaka | C12P 19/18 |
| 2019/0059314 A1 | 2/2019 | Aharoni et al. | |
| 2023/0279444 A1* | 9/2023 | Osbourn | C12N 15/8243 800/278 |

FOREIGN PATENT DOCUMENTS

| | | | | |
|---|---|---|---|---|
| GB | 1721600.3 | * 12/2017 | ......... | C12N 15/8243 |
| WO | WO 92/01047 A1 | 1/1992 | | |
| WO | WO 2009/087391 A1 | 7/2009 | | |
| WO | WO 2019/122259 A1 | 6/2019 | | |
| WO | WO 2020/263524 | * 6/2019 | ................ | C12P 1/00 |
| WO | WO 2020/049572 A1 | 3/2020 | | |

(Continued)

OTHER PUBLICATIONS

EMBL protein sequence SPD01343.1; filed Feb. 14, 2018. (Year: 2018).*

(Continued)

*Primary Examiner* — Russell Kallis
(74) *Attorney, Agent, or Firm* — James S. Keddie; Bozicevic, Field & Francis LLP

(57) ABSTRACT

The present invention relates generally to genes and polypeptides which have utility in glycosylating quillaic acid in host cells, including enzymes capable of successive glycosylation at the C-3 position of quillaic acid. The invention further relates to systems, methods and products employing the same.

Figure 1:
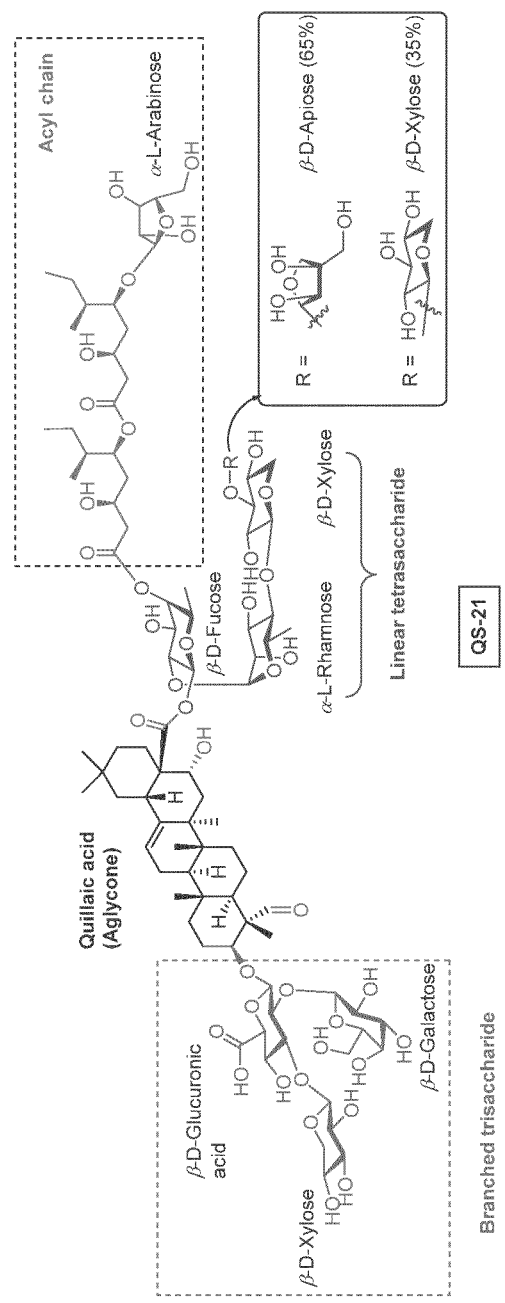

33 Claims, 18 Drawing Sheets
Specification includes a Sequence Listing.

(56) References Cited

FOREIGN PATENT DOCUMENTS

WO      WO-2020263524 A1 *   12/2020   ............. C12P 5/007

OTHER PUBLICATIONS

Meesapyodsuk, D., et al. Plant Physiology (2007) vol. 143, pp. 959-969. (Year: 2007).*

Meesapyodsuk et al., "Saponin Biosynthesis in Saponaria vaccaria. cDNAs Encoding b-Amyrin Synthase and a Triterpene Carboxylic Acid Glucosyltransferase", Plant Physiology, Feb. 2007, 143: 959-969.

Ragupathi et al., "Natural and synthetic saponin adjuvant QS-21 for vaccines against cancer", Expert Rev Vaccines, Apr. 2011, 10(4): 463-470.

Database EMBL [Online], Feb. 14, 2018, Gupta, K.D.: "*Fagus sylvatica* (European beech) hypothetical protein", XP055719466, Database accession No. SPD01343.

Database EMBL [Online], Apr. 25, 2018, "SubName: Full= Uncharacterized protein {ECO: 0000313 | EMBL: SPD01343.1};", XP055719470, retrieved from EBI accession No. UNIPROT:A0A2N9GPE3, Database accession No. A0A2N9GPE3.

Database EMBL [Online], Feb. 14, 2018, Gupta, K.D.: "*Fagus sylvatica* (European beech) hypothetical protein", XP055719484, Database accession No. SPC85424.

Database EMBL [Online], Apr. 25, 2018, "RecName: Full= Glycosyltransferase {ECO: 0000256 | RuleBase: RU362057}; EC=2.4.1.- {ECO: 0000256 | RuleBase: RU362057};", XP055719482, retrieved from EBI accession No. UNIPROT:A0A2N9FF75, Database accession No. A0A2N9FF75.

Jozwiak et al., "Plant terpenoid metabolism co-opts a component of the cell wall biosynthesis machinery", Nature Chemical Biology, Jul. 2020, 16: 740-748.

Kim et al., "A Novel Multifunctional C-23 Oxidase, CYP714E19, is Involved in Asiaticoside Biosynthesis", Plant & Cell Physiology, 2018, 59(6): 1200-1213.

Li et al., "De Novo Biosynthesis of the Oleanane-Type Triterpenoids of Tunicosaponins in Yeast", ACS Synthetic Biology, 2021, 10: 1874-1881.

Reed et al., "Engineering terpenoid production through transient expression in Nicotiana benthamiana", Plant Cell Reports, 2018, 37: 1431-1441.

Shibuya et al., "Identification and characterization of glycosyltransferases involved in the biosynthesis of soyasaponin in Glycine max", FEBS Letters, 2010, 584: 2258-2264.

Xu et al., "A novel glucuronosyltransferase has an unprecedented ability to catalyse continuous two-step glucuronosylation of glycyrrhetinic acid to yield glycyrrhizin", New Phytologist, 2016, 212: 123-135.

Zeng et al., "Chemical synthesis of quillaic acid, the aglycone of QS-21", Organic Chemistry Frontiers, 2021, 8: 748-753.

Genebank, cellulose synthase-like protein G1 [Olea europaea var. sylvestris], XP_022851692.1, Nov. 19, 2017.

* cited by examiner

TRANSFERASE ENZYMES

CROSS-REFERENCE TO RELATED APPLICATIONS

This application is a § 371 national phase of International Application No. PCT/EP2020/067866, filed on Jun. 25, 2020, which claims the benefit of United Kingdom Application No. 1909104.0, filed on Jun. 25, 2019, which applications are incorporated by reference herein.

TECHNICAL FIELD

The present invention relates generally to genes and polypeptides which have utility in modifying quillaic acid in host cells. The invention further relates to systems, methods and products employing the same.

BACKGROUND TO THE INVENTION

Plants produce a wide variety of cyclic triterpenes, such as sterols and triterpenoids, which are the major products of the mevalonate pathway.

QS-21 is a complex triterpenoid saponin synthesised by the Chilean tree *Quillaja saponaria* (order Fabales) (FIG. 1). QS-21 is a potent immunostimulatory agent capable of enhancing antibody responses and boosting specific T-cell responses, giving it significant adjuvant potential [1, 2]. The AS01 adjuvant is a liposomal formulation of QS-21 and 3-O-desacyl-4'-monophosphoryl lipid A and is currently licensed as part of the GlaxoSmithKline 'Shingrix' vaccine against herpes zoster and 'Mosquirix' against malaria [1, 3]. As these represent the first licensed human vaccines to utilise QS-21, demand for this molecule is expected to increase substantially over the coming years.

Currently, QS-21 is naturally sourced. Engineering production of QS-21 (or a suitable intermediate for semi-synthesis) in a heterologous host would provide an alternative or addition to current production methods. Presently however, little is known about the biosynthesis of this QS-21 which provides a significant barrier to realising this objective.

Biochemically, QS-21 consists of a C-30 triterpenoid backbone known as quillaic acid. This scaffold is decorated with a branched trisaccharide at the C-3 position and a linear tetrasaccharide at the C-28 position. The terminal sugar of the tetrasaccharide may be either β-D-apiose or β-D-xylose. Finally, the β-D-fucose sugar within the tetrasaccharide also features a C-18 acyl chain which is glycosylated with an arabinose sugar (FIG. 1).

Figure 2:
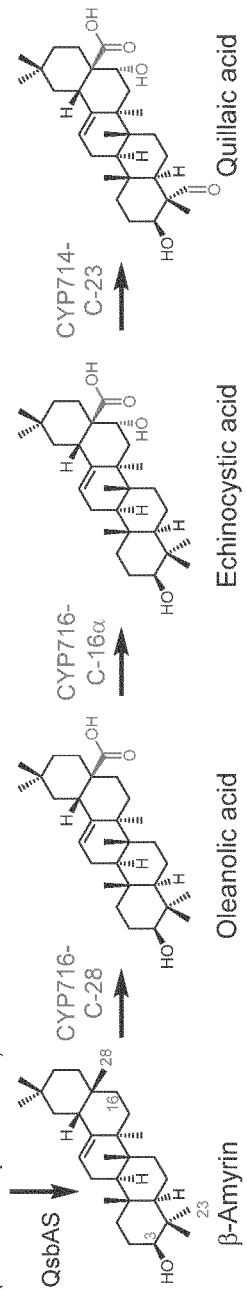

Biosynthesis of quillaic acid proceeds from β-Amyrin which is synthesised through cyclisation of the universal linear precursor 2,3-oxidosqualene (OS) by oxidosqualene cyclases (OSCs) (FIG. 2). The β-amyrin scaffold is further oxidised with a carboxylic acid, alcohol and aldehyde at the C-28, C-16α and C-23 positions, respectively, to form quillaic acid (QA). A proposed biosynthetic pathway for this is given in FIG. 2.

Prior-filed unpublished PCT/EP2018/086430 (subsequently published as WO 2019/122259) describes the identification of enzymes participating in QA production. Candidate enzymes were cloned from leaf cDNA. Enzymes were tested by transient co-expression in *Nicotiana benthamiana*, allowing for the identification of one OSC and three cytochrome P450s (P450s) required for synthesis of β-amyrin and oxidation to quillaic acid (FIG. 2). These enzymes may be referred to herein as QsbAS (β-amyrin synthase) and QsCYP716-C-28, OsCYP716-C-16α and OsCYP714-C-23 oxidases.

Figure 3:
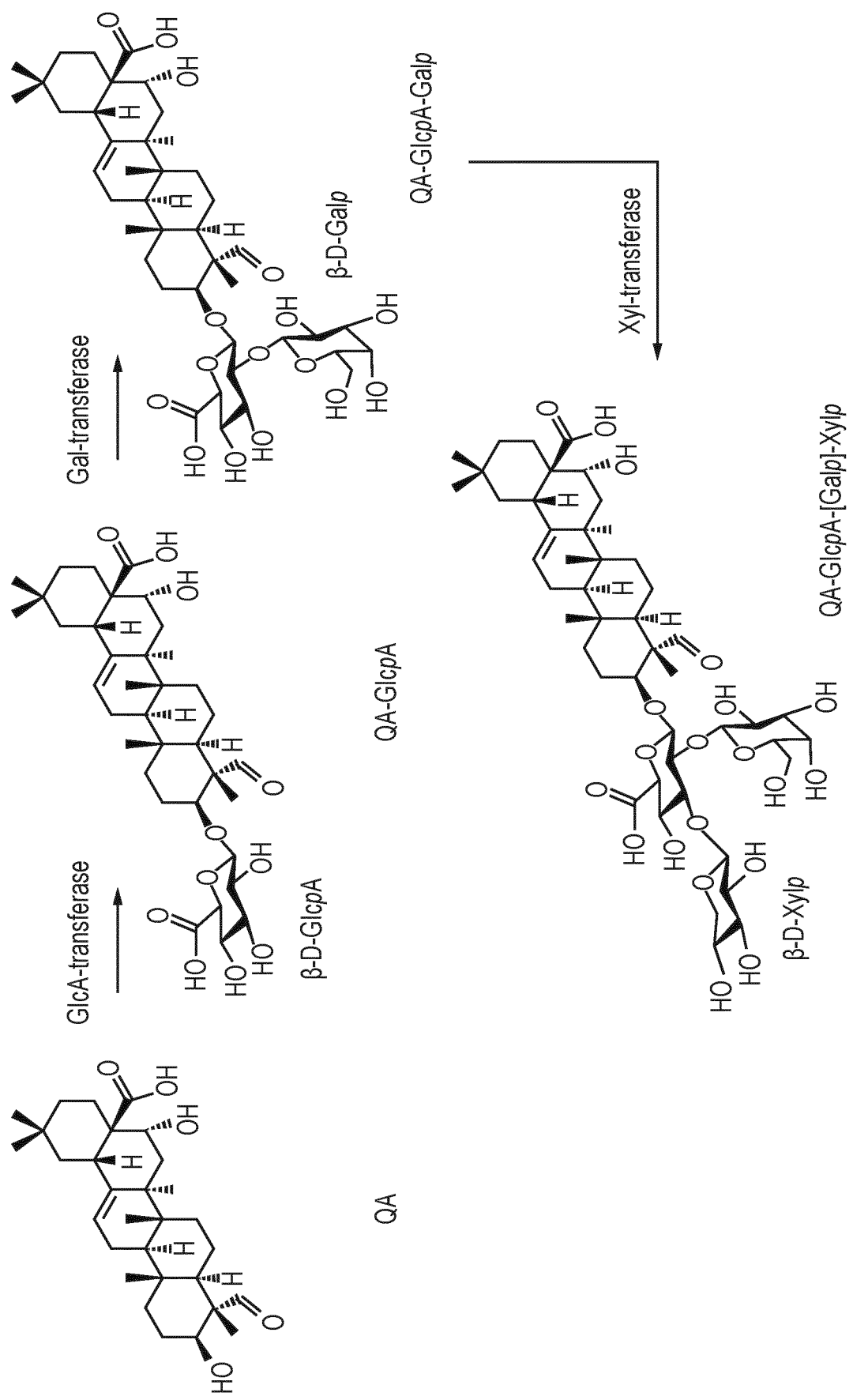

A proposed scheme for the glycosylation of quillaic acid to 3β-{[[β-D-xylopyranosyl-(1->3)-[β-D-galactopyranosyl-(1->2)]-β-D-glucopyranosiduronic acid]oxy}-quillaic acid (QA-GlcpA-[Galp]-Xylp) is shown in FIG. 3.

Some enzymes reported to be capable of glycosylating triterpenes have previously been obtained from plants other than *Q. saponaria*, including a C-3 glucuronic acid (GlcA) transferase from licorice [Xu, G., et al., *A novel glucuronosyltransferase has an unprecedented ability to catalyse continuous two-step glucuronosylation of glycyrrhetinic acid to yield glycyrrhizin*. New Phytologist, 2016. 212(1): p. 123-135.] and a C-3-GlcA galactosyltransferase from soybean [Shibuya, M., et al., *Identification and characterization of glycosyltransferases involved in the biosynthesis of soyasaponin I in Glycine max*. FEBS Lett, 2010. 584(11): p. 2258-64].

US20190059314 and WO/2020/049572 relate to genes reported to be useful in the biosynthesis of steroidal alkaloids and saponins, including regulatory genes and enzyme-encoding genes, and the use thereof for altering the content of steroidal (glyco)alkaloids or phytosterols in plants. US20190059314 discusses the use of a gene encoding a cellulose synthase like protein in this context.

However, glycosyltransferases (GTs) responsible for glycosylation or successive glycosylation at the C-3 position of QA have not been previously reported. In the light of the above it can be seen that the provision of such GTs would provide a contribution to the art.

DISCLOSURE OF THE INVENTION

The present invention concerns the identification of the glycosyltransferases (GTs) responsible for successive glycosylation at the C-3 position of QA.

As depicted in FIG. 3, the branched trisaccharide chain at the C-3 position in QS-21 is initiated with a β-D-glucuronic acid (GlcpA) residue attached at the 3-O position of QA. The GlcpA residue is then linked to a D-Galactose (Galp) via a β-1->2 linkage and to a D-Xylose (Xylp) via a β-1,3 linkage.

Note that these latter two steps (Galp and Xylp linkage to GlcpA) are shown in FIG. 3 in a linear fashion for simplicity, but may occur in either order.

Additionally, as explained below, the β-D-Xylp residue may be replaced in certain circumstances with an α-L-Rhamnose residue.

Specifically, the inventors have characterised from *Quillaja saponaria* two glucuronosyl transferases, a galactosyl transferase, and Rhamnosyl, Xylosyl, and dual Rhamnosyl/Xylosyl transferases which permit glycosylation of the 3-O position of QA with the respective saccharide within the 3-O branched trisaccharide. Accordingly, in the sense of the present invention, in the term "3-O branched trisaccharide", the number "3" is to be understood as the position C-3 of QA (as depicted in FIG. 2).

They have termed these enzymes "QsCSL1" and "QsCSLG2" (glucuronosyl transferases), "Qs-3-O-GalT" (galactosyl transferase), "Qs_0283850", "DN20529_c0_g2_i8", "Qs_0283870" and "Qs-3-O-RhaT/XylT" (rhamnosyl and/or xylosyl transferases), as provided in Table 5.

Surprisingly, the glucuronosyl transferase enzymes are "cellulose synthase-like" enzymes. Cellulose synthases are generally associated with cell wall biosynthesis, and the functions of most members are unknown [13].

The present disclosure thus provides new uses (in vivo or in vitro) for such enzymes in QA-glycosylation. The terms "QA-glycosylation" and the like as used herein are used broadly to include also successive glycosylations of QA which has already been glycosylated.

The galactosyl transferase, and the Rhamnosyl/Xylosyl transferase enzymes are Family 1 UDP-dependent glycosyltransferases (UGTs). This class of enzymes has been previously identified as being involved in plant specialised glycosylation, although other enzyme classes have been found to play a role in plant specialised metabolite biosynthesis [8-12].

Figure 9:
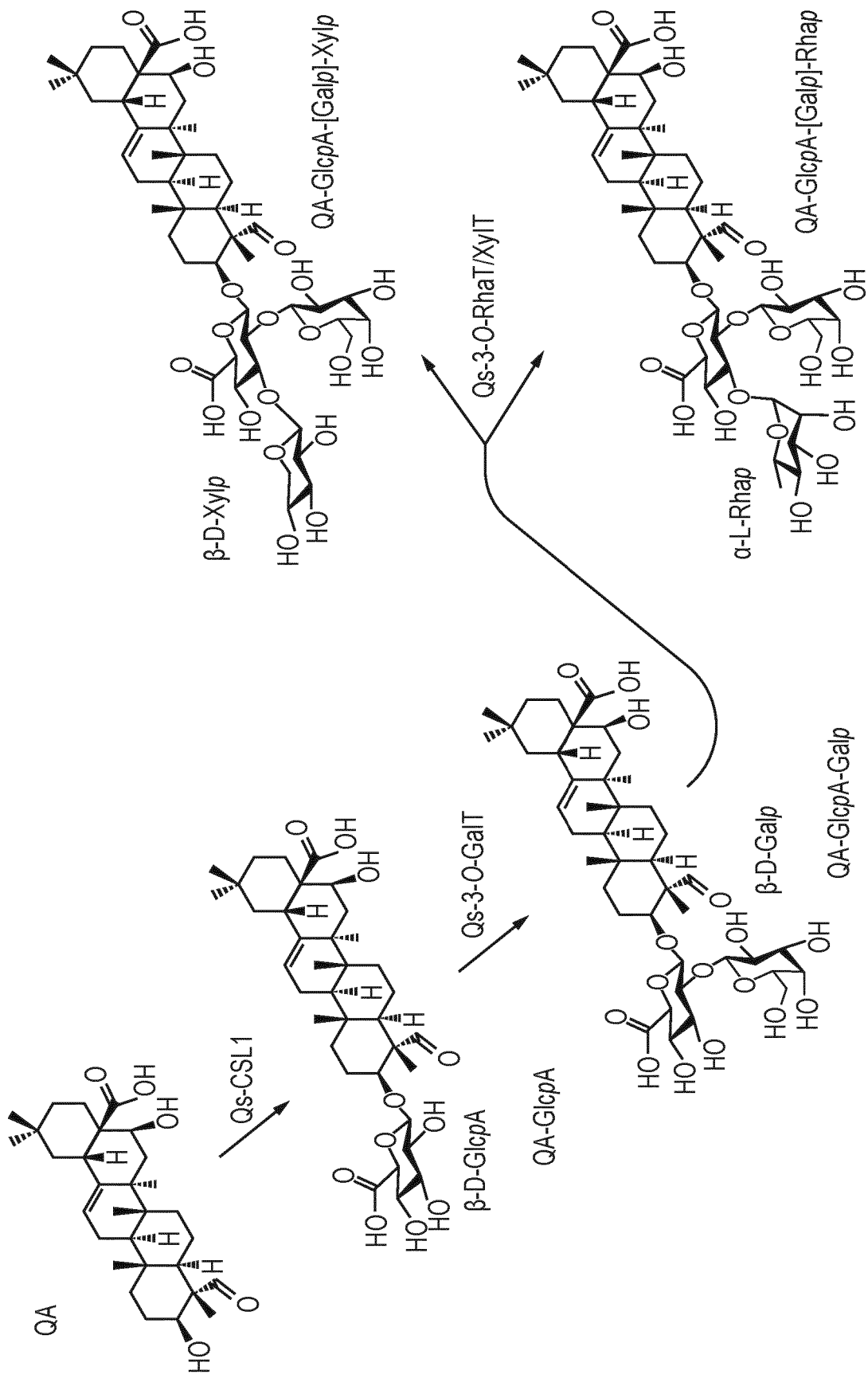

The operation of the enzymes in concert is shown in FIG. 9 (again depicted in linear fashion for simplicity).

The present invention thus provides for the engineering into host cells or organisms (for example plants or microorganisms) of the ability to perform the biosynthesis of glycosylated QA, for example the 3-O branched trisaccharide quillaic acid (QA) derivative ("QA-3-O-TriS"). Alternatively, the enzymes may be used in vitro to perform the respective activities reported in Table 5.

They may advantageously be used in combination with enzymes permitting the synthesis of QA from OS, such as are characterised in Prior-filed unpublished PCT/EP2018/086430 (subsequently published as WO 2019/122259), the entire disclosure of which is specifically incorporated herein by cross-reference for this purpose. Examples of such enzymes (defined as "QA polypeptides") are shown in Table 8.

Thus, in one aspect of the invention, there is provided a method of converting a host from a phenotype whereby the host is unable to perform the biosynthesis of the 3-O branched trisaccharide quillaic acid ("QA") derivative ("QA-3-O-TriS"), which QA-3-O-TriS is 3β-{[β-D-xylopyranosyl-(1->3)-[β-D-galactopyranosyl-(1->2)]-β-D-glucopyranosiduronic acid]oxy}-quillaic acid (QA-GlcpA-[Galp]-Xylp) or (3β-{[α-L-rhamnopyranosyl-(1->3)-[β-D-galactopyranosyl-(1->2)]-β-D-glucopyranosiduronic acid]oxy}-quillaic acid) (QA-GlcpA-[Galp]-Rhap),
by glycosylation of the 3-O position of QA, to a phenotype whereby the host is able to carry out said QA-3-O-TriS biosynthesis,
which method comprises the step of expressing a heterologous nucleic acid within the host or one or more cells thereof, following an earlier step of introducing the nucleic acid into the host or an ancestor of either,
wherein the heterologous nucleic acid comprises a plurality of nucleotide sequences each of which encodes a polypeptide which in combination have said QA-3-O-TriS biosynthesis activity.

By way of example, using the illustrative scheme of FIG. 3, the encoded polypeptides (enzymes) could comprise any one or more of the following:

(i) a QA 3-O glucuronosyl transferase ("QA-GlcAT") capable of transferring D-glucuronic acid ("GlcpA") at the 3-O position of quillaic acid to form 3β-{[β-D-glucopyranosiduronic acid]oxy}-quillaic acid ("QA-GlcpA");

(ii) a QA-GlcpA galactosyl transferase ("QA-GalT") capable of transferring D-Galactose ("Galp") via a β-1->2 linkage to QA-GlcpA to form 3β-{[β-D-galactopyranosyl-(1->2)-β-D-glucopyranosiduronic acid]oxy}-quillaic acid ("QA-GlcpA-Galp");

(iii) a QA-GlcpA-Galp Rhamnosyl/Xylosyl transferase ("QA-RhaT/XylT") capable of transferring L-Rhamnose ("Rhap") and/or D-Xylose ("Xylp") via a 1->3 linkage to QA-GlcpA-Galp to form (3β-{[α-L-rhamnopyranosyl-(1->3)-[β-D-galactopyranosyl-(1->2)]-β-D-glucopyranosiduronic acid]oxy}-quillaic acid) ("QA-GlcpA-[Galp]-Rhap") and/or
3β-{[β-D-xylopyranosyl-(1->3)-[β-D-galactopyranosyl-(1->2)]-β-D-glucopyranosiduronic acid]oxy}-quillaic acid ("QA-GlcpA-[Galp]-Xylp") respectively.

In one embodiment, the QA-GlcpA-Galp Rhamnosyl/Xylosyl transferase may be a dual QA-GlcpA-Galp Rhamnosyl/Xylosyl transferase.

Each of the polypeptide or nucleotide sequences is optionally obtained or derived from Q. saponaria.

By way of non-limiting example, the QA-GlcAT, QA-GalT, and QA-RhaT/XylT are selected from the respective enzymes in Table 5 or 6, or substantially homologous variants or fragments of any of said polypeptides in Tables 5 or 6.

The nucleic acid may include polynucleotide sequences encoding the respective enzymes in Table 5 or 6, or substantially homologous variants or fragments of any of said polynucleotides.

Regarding the QA-RhaT/XylT enzymes in Table 5, as explained in the Examples below, Qs-3-O-RhaT/XylT is believed to be a dual Rhamnosyl/Xylosyl transferase.

Both Qs_0283850 and DN20529_c0_g2_i8 are believed to be primarily Rhamnosyl transferases, while Qs_0283870 is believed to be primarily a Xylosyl transferase. It will be appreciated, however, that some level of cross-activity may be present. For brevity, all these types of enzymes may be referred to herein as being Qs-3-O-RhaT/XylT enzymes or having QA-RhaT/XylT activity.

Preferably, all three types of enzymes (QA-GlcAT, QA-GalT, and QA-RhaT/XylT) are provided as part of the method of the invention.

Preferred genes or polypeptides for use in the practice of the invention in relation to QA-GlcAT, QA-GalT, QA-RhaT/XylT activities are shown in Table 5 or 6 herein (and the Sequence Annex) or are substantially homologous variants or fragments of these sequences, having or retaining or encoding the requisite biological activity.

For example, QA-GalT activity may be provided by Qs-3-O-GalT, or alternatively by GmUGT73P2, which has been demonstrated herein to share that activity, or by substantially homologous variants or fragments of either of these sequences, retaining that biological activity.

In preferred embodiments, the one, two, or three polypeptides (i), (ii) or (iii) are selected from the respective amino acid sequences listed in Table 5.

In one embodiment, the respective polypeptides are selected from the list consisting of:

(i) the QA-GlcAT shown in SEQ ID: No 2 or 26, most preferably 2;

(ii) the QA-GalT shown in SEQ ID: No 4;

(iii) the QA-RhaT/XylT shown in SEQ ID: No 6, 28, 30, or 32, most preferably 6;

or substantially homologous variants or fragments of any of said polypeptides.

For brevity, in the context of the present invention, and in particular the methods and uses described herein, the polypeptide or nucleotide sequences of any of Tables 5 and 6 may be referred to herein as "QA-3-O-TriS biosynthetic sequences" or "QA-3-O-TriS sequences" e.g. QA-3-O-TriS genes and QA-3-O-TriS polypeptides.

Variants

In addition to the use of these QA-3-O-TriS genes (and polypeptides), the invention encompasses use of variants of these genes (and polypeptides).

A "variant" QA-3-O-TriS nucleic acid or QA-3-O-TriS polypeptide molecule shares homology with, or is identical to, all or part of the QA-3-O-TriS genes or polypeptides sequences discussed herein.

A variant polypeptide shares the relevant biological activity of the native QA-3-O-TriS polypeptide. A variant nucleic acid encodes the relevant variant polypeptide.

In this context, the "biological activity" of the QA-3-O-TriS polypeptide is the ability to catalyse the respective reaction shown in FIG. 3 and described above and/or the activity set out in the respective Table e.g. Table 5 or 6. The relevant biological activities may be assayed based on the reactions shown in Table 5 in vitro. Alternatively, they can be assayed by activity in vivo as described in the Examples i.e. by introduction of a plurality of heterologous constructs to generate the respective product into a host, which can be assayed by LC-MS or the like.

Variants of Qs-3-O-RhaT/XylT may include those preferentially catalysing D-Xylose (Xylp) or L-Rhamnose (Rhap).

Alignments for the purpose of assessing homology may be obtained e.g. using Clustal Omega (version 1.2.4—accessed through https://www.ebi.ac.uk; see e.g. Sievers F, et al. (2011) Fast, scalable generation of high-quality protein multiple sequence alignments using Clustal Omega. *Molecular Systems Biology* 7(1):539.

Variants of the sequences disclosed herein preferably share at least 50%, 55%, 56%, 57%, 58%, 59%, 60%, 65%, or 70%, or 80% identity, most preferably at least about 90%, 95%, 96%, 97%, 98% or 99% identity with a reference polypeptide or polynucleotide sequence. Such variants may be referred to herein as "substantially homologous". Preferred variants share at least 80% identity.

Preferred variants may be:

(i) Naturally occurring nucleic acids such as alleles (which will include polymorphisms or mutations at one or more bases) or pseudoalleles (which may occur at closely linked loci to the QA-3-O-TriS genes of the invention). Also included are paralogues, isogenes, or other homologous genes belonging to the same families as the QA-3-O-TriS genes of the invention, for example sharing clades or subclades. Also included are orthologues or homologues from other plant species.

Homology may be at the nucleotide sequence and/or amino acid sequence level, as discussed below.

(ii) Artificial nucleic acids, which can be prepared by the skilled person in the light of the present disclosure. Such derivatives may be prepared, for instance, by site directed or random mutagenesis, or by direct synthesis. Preferably the variant nucleic acid is generated either directly or indirectly (e.g. via one or more amplification or replication steps) from an original nucleic acid having all or part of the sequence of a QA-3-O-TriS gene of the invention.

Also included are nucleic acids corresponding to those above, but which have been extended at the 3' or 5' terminus.

The term "QA-3-O-TriS variant nucleic acid" as used herein encompasses all of these possibilities. When used in the context of polypeptides or proteins it indicates the encoded expression product of the variant nucleic acid.

In each case, the preferred QA-3-O-TriS-biosynthesis modifying nucleic acids are any of SEQ ID Nos 1, 3, 5, or 25, 27, 29 or 31, or substantially homologous variants thereof. In one embodiment (of this, or other aspects of the invention concerning these sequences) they are any of SEQ ID Nos 1, 3, 5, or substantially homologous variants thereof.

The preferred QA-3-O-TriS-biosynthesis modifying polypeptides are any of SEQ ID Nos 2, 4, 6, 26, 28, 30 or 32, or substantially homologous variants thereof. In one embodiment (of this, or other aspects of the invention concerning these sequences), they are any of SEQ ID Nos 2, 4, 6, or substantially homologous variants thereof.

Other preferred QA-3-O-TriS-biosynthesis modifying nucleic acids for use in the invention are SEQ ID No 19, or substantially homologous variants or fragments thereof. Other preferred QA-3-O-TriS-biosynthesis modifying polypeptides are polypeptides encoded by any of these sequences or variants or fragments e.g. SEQ ID No 20.

Supplementary Genes

In embodiments of the invention, in addition to the QA-3-O-TriS genes and variant nucleic acids of the invention described herein, it may be preferable to introduce additional genes which may affect flux of QA-3-O-TriS production.

As explained in prior-filed unpublished PCT/EP2018/086430 (subsequently published as WO 2019/122259), the core aglycone of QS-21 (i.e. QA) is a derivative of the simple triterpene, β-amyrin, which is in turn synthesised by cyclisation of the universal linear precursor 2,3-oxidosqualene (OS) by oxidosqualene cyclases (OSCs).

The β-amyrin scaffold is further oxidised with an alcohol, aldehyde and carboxylic acid at the C-16α, C-23 and C-28 positions, respectively, to form quillaic acid.

QA biosynthesis from OS thus includes at least four different enzymatic steps. The enzymes involved include:
an oxidosqualene cyclase;
an enzyme capable of oxidising β-amyrin or an oxidised derivative thereof at the C-28 position to a carboxylic acid;
an enzyme capable of oxidising β-amyrin or an oxidised derivative thereof such as oleanolic acid at the C-16α position to an alcohol;
an enzyme capable of oxidising β-amyrin or an oxidised derivative thereof such as echinocystic acid at the C-23 position to an aldehyde.

For example:
(i) a β-amyrin synthase (bAS) for cyclisation of 2,3-oxidosqualene (OS) to a triterpene;
(ii) an enzyme capable of oxidising β-amyrin or an oxidised derivative thereof at the C-28 position to a carboxylic acid ("C-28 oxidase");
(iii) an enzyme capable of oxidising β-amyrin or an oxidised derivative thereof at the C-16α position to an alcohol ("C-16α oxidase"); and
(iv) an enzyme capable of oxidising β-amyrin or an oxidised derivative thereof at the C-23 position to an aldehyde ("C-23 oxidase"), For brevity, these enzymes may be referred to as "bAS", "C-28 oxidase", "C-16α oxidase", and "C-23 oxidase" respectively herein.

For further brevity, these enzymes may be referred to collectively as "QA polypeptides" herein.

The present invention may be advantageously applied in conjunction with these QA polypeptides and encoding-nucleic acids.

Thus it will be appreciated that the use of the aforementioned QA polypeptides and genes in conjunction with the QA-3-O-TriS polypeptides and genes is expressly envisaged in relation to the any aspects of the invention relating to the materials or methods of QA-3-O-TriS biosynthesis.

In one embodiment:
The C-28 oxidase is a CYP716
The C-16α is a CYP716 or CYP87
The C-23 oxidase is a CYP714, CYP72 or CYP94

Preferred QA genes or QA polypeptides are shown in the Table 8, or biologically active fragments or variants of these. Variants may be homologues, alleles, or artificial derivatives etc. as discussed in relation to QA-3-O-TriS genes or polypeptides as described above.

For example, the QA polypeptides may be any one or more (preferably all) of:
(i) the β-amyrin synthase (bAS) shown in SEQ ID: No 12;
(ii) the C-28 oxidase shown in SEQ ID: No 14;
(iii) the C-16α oxidase shown in SEQ ID: No 16;
(iv) the C-23 oxidase shown in the SEQ ID: No 18;
or substantially homologous variants or fragments of any of said polypeptides.

Mevalonic acid (MVA) is an important intermediate in triterpenoid synthesis. Therefore, it may be desirable to express rate-limiting MVA pathway genes into the host, to maximise yields of QA.

HMG-CoA reductase (HMGR) is believed to be a rate-limiting enzyme in the MVA pathway.

The use of a recombinant feedback-insensitive truncated form of HMGR (tHMGR) has been demonstrated to increase triterpene (β-amyrin) content upon transient expression in *N. benthamiana* [19].

Thus one embodiment of the invention comprises the use of a heterologous HMGR (e.g. a feedback-insensitive HMGR) along with the QA-3-O-TriS genes described herein. Examples of HMGR encoding or polypeptide sequences include SEQ ID Nos 7 to 10, or variants or fragments of these. Variants may be homologues, alleles, or artificial derivatives etc. as discussed in relation to QA-3-O-TriS genes or polypeptides as described above. For example an HMGR native to the host being utilised may be preferred—for example a yeast HMGR in a yeast host, and so on. HMGR genes are known in the art and may be selected, as appropriate in the light of the present disclosure.

It has also been reported that squalene synthase (SQS) is a potential rate-limiting step [19].

Thus one embodiment of the invention comprises the use of a heterologous SQS along with the QA-3-O-TriS genes and optionally HMGR described herein.

Examples of SQS encoding or polypeptide sequences include SEQ ID Nos 21 to 22, or variants or fragments of these. Variants may be homologues, alleles, or artificial derivatives etc. as discussed in relation to QA-3-O-TriS genes or polypeptides as described above. For example an SQS native to the host being utilised may be preferred—for example a yeast SQS in a yeast host, and so on. SQS genes are known in the art and may be selected, as appropriate in the light of the present disclosure.

When using certain hosts (for example yeasts) it may be desirable to introduce additional genes to improve the flux of QA production. Examples may include one or more plant cytochrome P450 reductases (CPRs) to serve as the redox partner to the introduced P450s. Thus one embodiment of the invention comprises the use of a heterologous cytochrome P450 reductase such as AtATR2 (*Arabidopsis thaliana* cytochrome P450 reductase 2) along with the QA polypeptides and QA-3-O-TriS genes described herein. Examples of AtATR2 encoding or polypeptide sequences include SEQ ID Nos 23 to 24, or variants or fragments of these. Variants may be homologues, alleles, or artificial derivatives etc. as discussed in relation to QA-3-O-TriS genes or polypeptides as described above.

Thus in one embodiment the nucleic acid utilised in the invention further encodes one or more of the following polypeptides:
(i) an HMG-CoA reductase (HMGR);
(ii) a squalene synthase (SQS)

wherein the HMGR or SQS are optionally selected from the respective polypeptides in Table 7 or substantially homologous variants or fragments of any of said polypeptides, or are encoded by the respective polynucleotides in Table 7, or substantially homologous variants or fragments of any of said polynucleotides.

It will be understood by those skilled in the art, in the light of the present disclosure, that additional genes may be utilised in the practice of the invention, to provide additional activities and\or improve expression or activity. These include those expressing co-factor or helper proteins, or other factors.

For brevity, unless context demands otherwise, any of these nucleic acid sequences (the "QA-3-O-TriS genes of the invention", plus other genes effecting QA-3-O-TriS synthesis, or secondary modifications to QA-3-O-TriS) may be referred to herein as "QA-3-O-TriS-biosynthesis modifying nucleic acid". Likewise the encoded polypeptides may be referred to herein as "QA-3-O-TriS-biosynthesis modifying polypeptides".

It will be appreciated that where these generic terms are used in relation to any aspect or embodiment, the meaning or disclosure will be taken to apply mutatis mutandis to any of these sequences individually.

Vectors

As one aspect of the invention, there is disclosed a method employing the co-infiltration of a plurality of *Agrobacterium tumefaciens* strains each carrying one or more of the QA-3-O-TriS nucleic acids discussed above for concerted expression thereof in a biosynthetic pathway discussed above.

In some embodiments, at least 2 or 3 different *Agrobacterium tumefaciens* strains are co-infiltrated e.g. each carrying a QA-3-O-TriS nucleic acid.

The genes may be present from transient expression vectors.

A preferred expression system utilises the called "'Hyper-Translatable' Cowpea Mosaic Virus ('CPMV-HT') system, described in WO2009/087391 the disclosure of which is specifically incorporated herein in support of the embodiments using the CPMV-HT system—for example vectors based on pEAQ-HT expression plasmids.

Thus the vectors (typically binary vectors) for use in the present invention will typically comprise an expression cassette comprising:
(i) a promoter, operably linked to
(ii) an enhancer sequence derived from the RNA-2 genome segment of a bipartite RNA virus, in which a target initiation site in the RNA-2 genome segment has been mutated;
(iii) a QA-3-O-TriS nucleic acid sequence as described above;
(iv) a terminator sequence; and optionally
(v) a 3' UTR located upstream of said terminator sequence.

Further examples of vectors and expression systems useful in the practice of the invention are described in more detail hereinafter.

Hosts

In aspects of the invention, a host may be converted from a phenotype whereby the host is unable to carry out effective QA-3-O-TriS biosynthesis from OS to a phenotype whereby the host is able to carry out said QA-3-O-TriS-biosynthesis, such that QA-3-O-TriS can be recovered therefrom or utilised in vivo to synthesize downstream products.

As explained above, QA biosynthesis can also be engineered into plants based on the disclosure of prior-filed unpublished PCT/EP2018/086430 (subsequently published as WO 2019/122259). Since the QA precursor (2,3-oxidosqualene) is ubiquitous in higher plants due to its role in sterol biosynthesis, the present invention has wide applicability in plant hosts. As discussed herein, additional activities may be employed when practising the invention in microorganisms.

Examples of hosts include plants such as *Nicotiana benthamiana* and microorganisms such as yeast. These are discussed in more detail below.

The invention may comprise transforming the host with heterologous nucleic acid as described above by introducing the QA-3-O-TriS nucleic acid into the host cell via a vector and causing or allowing recombination between the vector and the host cell genome to introduce a nucleic acid according to the present invention into the genome.

In another aspect of the invention, there is provided a host cell transformed with a heterologous nucleic acid which comprises a plurality of nucleotide sequences each of which encodes a polypeptide which in combination have said QA-3-O-TriS-biosynthesis activity,
wherein expression of said nucleic acid imparts on the transformed host the ability to carry out QA-3-O-TriS-biosynthesis from OS, or improves said ability in the host.

The invention further encompasses a host cell transformed with nucleic acid or a vector as described above (e.g. comprising the QA-3-O-TriS-biosynthesis modifying nucleotide sequences) especially a plant or a microbial cell. In the transgenic host cell (i.e. transgenic for the nucleic acid in question) the transgene may be on an extra-genomic vector or incorporated, preferably stably, into the genome. There may be more than one heterologous nucleotide sequence per haploid genome.

The methods and materials described herein can be used, inter alia, to generate stable crop-plants that accumulate QA-3-O-TriS. Examples of plants include row crops such as sunflower, potato, canola, dry bean, field pea, flax, safflower, buckwheat, cotton, maize, soybeans, and sugar beets. Major crop-plants such as corn, wheat, oilseed rape and rice may also be preferred hosts.

Plants which include a plant cell according to the invention are also provided.

Production of Products

The methods described above may be used to generate glycosylated QA, such as QA-3-O-TriS, in a heterologous host. The glycosylated QA, such as QA-3-O-TriS, will generally be non-naturally occurring in the species into which they are introduced.

Glycosylated QA, such as QA-3-O-TriS, from the plants or methods of the invention may be isolated and commercially exploited.

The methods above may form a part of, possibly one step in, a method of producing downstream products, such as QS-21 in a host. The method may comprise the steps of culturing the host (where it is a microorganism) or growing the host (where it is a plant) and then harvesting it and purifying the glycosylated QA, such as QA-3-O-TriS, or a downstream product or derivative (e.g. QS-21) product therefrom. The product thus produced forms a further aspect of the present invention. The utility of QS-21 is described above.

Alternatively, glycosylated QA, such as QA-3-O-TriS, may be recovered to allow for further chemical synthesis of downstream compounds.

Novel Genes of the Invention

In support of the present invention, the present inventors have newly characterised or identified sequences from *Q. saponaria* which are believed to be involved in the synthesis of glycosylated compounds (see SEQ. ID: Nos 1-6; also 25-32).

In one embodiment (of this, or other aspects of the invention concerning these sequences), the sequences are selected from any of SEQ ID Nos 1-6.

In preferred embodiments, the methods of the present invention will include the use of one or more of these newly characterised QA-3-O-TriS nucleic acids of the invention (e.g. one, two, or three such QA-3-O-TriS nucleic acids) optionally in conjunction with the manipulation of other genes affecting QA biosynthesis known in the art.

These newly characterised QA-3-O-TriS sequences from *Q. saponaria* (SEQ. ID: Nos 1-6 also 25-32) form aspects of the invention in their own right, as do derived variants and materials of these sequences, and methods of using them.

Some aspects and embodiments of the present invention will now be described in more detail.

DETAILED DESCRIPTION OF THE INVENTION

The present inventors utilised a variety of genome and transcriptome approaches with *Q. saponaria* to begin to elucidate biosynthetic pathways associated with glycosylation of QA. Functional characterisation of candidate genes by transient expression in *Nicotiana benthamiana* has led to the identification of three enzymes from *Q. saponaria* which together are capable of biosynthesis of QA-3-O-TriS from QA.

In different embodiments, the present invention provides means for manipulation of total levels of glycosylated QAs in host cells such as microorganisms or plants.

In one aspect of the present invention, the QA-3-O-TriS modifying nucleic acid described above is in the form of a recombinant and preferably replicable vector.

"Vector" is defined to include, inter alia, any plasmid, cosmid, phage or *Agrobacterium* binary vector in double or single stranded linear or circular form which may or may not be self-transmissible or mobilizable, and which can transform a prokaryotic or eukaryotic host either by integration into the cellular genome or exist extrachromosomally (e.g. autonomous replicating plasmid with an origin of replication).

As is well known to those skilled in the art, a "binary vector" system includes (a) border sequences which permit the transfer of a desired nucleotide sequence into a plant cell genome; (b) desired nucleotide sequence itself, which will generally comprise an expression cassette of (i) a plant active promoter, operably linked to (ii) the target sequence and\or enhancer as appropriate. The desired nucleotide sequence is situated between the border sequences and is capable of being inserted into a plant genome under appropriate conditions. The binary vector system will generally require other sequence (derived from *A. tumefaciens*) to effect the integration. Generally this may be achieved by use of so called "agro-infiltration" which uses *Agrobacterium*-mediated transient transformation. Briefly, this technique is based on the property of *Agrobacterium tumefaciens* to transfer a portion of its DNA ("T-DNA") into a host cell where it may become integrated into nuclear DNA. The T-DNA is defined by left and right border sequences which are around 21-23 nucleotides in length. The infiltration may be achieved e.g. by syringe (in leaves) or vacuum (whole plants). In the present invention the border sequences will generally be included around the desired nucleotide sequence (the T-DNA) with the one or more vectors being introduced into the plant material by agro-infiltration.

Generally speaking, those skilled in the art are well able to construct vectors and design protocols for recombinant gene expression (e.g. for expressing a heterologous nucleic acid within a host or one or more cells of a host). Suitable vectors can be chosen or constructed, containing appropriate regulatory sequences, including promoter sequences, terminator fragments, polyadenylation sequences, enhancer sequences, marker genes and other sequences as appropriate. For further details see, for example, *Molecular Cloning: a Laboratory Manual:* 2nd edition, Sambrook et al, 1989, Cold Spring Harbor Laboratory Press or *Current Protocols in Molecular Biology*, Second Edition, Ausubel et al. eds., John Wiley & Sons, 1992.

Specifically included are shuttle vectors by which is meant a DNA vehicle capable, naturally or by design, of replication in two different host organisms, which may be selected from actinomycetes and related species, bacteria and eucaryotic (e.g. higher plant, mosses, yeast or fungal cells).

A vector including nucleic acid according to the present invention need not include a promoter or other regulatory sequence, particularly if the vector is to be used to introduce the nucleic acid into cells for recombination into the genome.

Preferably the nucleic acid in the vector is under the control of, and operably linked to, an appropriate promoter or other regulatory elements for transcription in a host cell such as a microbial, e.g. yeast and bacterial, or plant cell. The vector may be a bi-functional expression vector which functions in multiple hosts. In the case of genomic DNA, this may contain its own promoter or other regulatory elements (optionally in combination with a heterologous enhancer, such as the 35S enhancer discussed in the Examples below). The advantage of using a native promoter is that this may avoid pleiotropic responses. In the case of cDNA this may be under the control of an appropriate promoter or other regulatory elements for expression in the host cell By "promoter" is meant a sequence of nucleotides from which transcription may be initiated of DNA operably linked downstream (i.e. in the 3' direction on the sense strand of double-stranded DNA).

"Operably linked" means joined as part of the same nucleic acid molecule, suitably positioned and oriented for transcription to be initiated from the promoter. DNA operably linked to a promoter is "under transcriptional initiation regulation" of the promoter.

In a preferred embodiment, the promoter is an inducible promoter.

The term "inducible" as applied to a promoter is well understood by those skilled in the art. In essence, expression under the control of an inducible promoter is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus.

Thus nucleic acid according to the invention may be placed under the control of an externally inducible gene promoter to place expression (expressing the heterologous sequence) under the control of the user. An advantage of introduction of a heterologous gene into a plant cell, particularly when the cell is comprised in a plant, is the ability to place expression of the gene under the control of a promoter of choice, in order to be able to influence gene expression, and therefore QA-3-O-TriS biosynthesis, according to preference. Furthermore, mutants and derivatives of the wild-type gene, e.g. with higher or lower activity than wild-type, may be used in place of the endogenous gene.

Thus this aspect of the invention provides a gene construct, preferably a replicable vector, comprising a promoter (optionally inducible) operably linked to a nucleotide sequence provided by the present invention, such as the QA-3-O-TriS-biosynthesis modifying gene, most preferably one of the QA-3-O-TriS nucleic acids which are described herein, or a derivative thereof.

Particularly of interest in the present context are nucleic acid constructs which operate as plant vectors. Specific procedures and vectors previously used with wide success upon plants are described by Guerineau and Mullineaux (1993) (Plant transformation and expression vectors. In: Plant Molecular Biology Labfax (Croy RRD ed.) Oxford, BIOS Scientific Publishers, pp 121-148). Suitable vectors may include plant viral-derived vectors (see e.g. EP-A-194809).

Preferably the vectors of the present invention which are for use in plants comprise border sequences which permit the transfer and integration of the expression cassette into the plant genome. Preferably the construct is a plant binary vector. Preferably the binary transformation vector is based on pPZP (Hajdukiewicz, et al. 1994). Other example constructs include pBin19 (see Frisch, D. A., L. W. Harris-Haller, et al. (1995). "Complete Sequence of the binary vector Bin 19." Plant Molecular Biology 27: 405-409).

Suitable promoters which operate in plants include the Cauliflower Mosaic Virus 35S (CaMV 35S). Other examples are disclosed at pg. 120 of Lindsey & Jones (1989) "Plant Biotechnology in Agriculture" Pub. OU Press, Milton Keynes, UK. The promoter may be selected to include one or more sequence motifs or elements conferring developmental and/or tissue-specific regulatory control of expression. Inducible plant promoters include the ethanol induced promoter of Caddick et al (1998) Nature Biotechnology 16: 177-180.

If desired, selectable genetic markers may be included in the construct, such as those that confer selectable phenotypes such as resistance to antibiotics or herbicides (e.g. kanamycin, hygromycin, phosphinotricin, chlorsulfuron, methotrexate, gentamycin, spectinomycin, imidazolinones and glyphosate). Positive selection system such as that described by Haldrup et al. 1998 Plant molecular Biology 37, 287-296, may be used to make constructs that do not rely on antibiotics.

As explained above, a preferred vector is a 'CPMV-HT' vector as described in WO2009/087391. The Examples below demonstrate the use of these pEAQ-HT expression plasmids.

These vectors (typically binary vectors) for use in the present invention will typically comprise an expression cassette comprising:

(i) a promoter, operably linked to (ii) an enhancer sequence derived from the RNA-2 genome segment of a bipartite RNA virus, in which a target initiation site in the RNA-2 genome segment has been mutated;

(iii) a QA-3-O-TriS nucleic acid sequence as described above;

(iv) a terminator sequence; and optionally (v) a 3' UTR located upstream of said terminator sequence.

"Enhancer" sequences (or enhancer elements), as referred to herein, are sequences derived from (or sharing homology with) the RNA-2 genome segment of a bipartite RNA virus, such as a comovirus, in which a target initiation site has been mutated. Such sequences can enhance downstream expression of a heterologous ORF to which they are attached. Without limitation, it is believed that such sequences when present in transcribed RNA, can enhance translation of a heterologous ORF to which they are attached.

A "target initiation site" as referred to herein, is the initiation site (start codon) in a wild-type RNA-2 genome segment of a bipartite virus (e.g. a comovirus) from which the enhancer sequence in question is derived, which serves as the initiation site for the production (translation) of the longer of two carboxy coterminal proteins encoded by the wild-type RNA-2 genome segment.

Typically, the RNA virus will be a comovirus as described hereinbefore.

Most preferred vectors are the pEAQ vectors of WO2009/087391 which permit direct cloning version by use of a polylinker between the 5' leader and 3' UTRs of an expression cassette including a translational enhancer of the invention, positioned on a T-DNA which also contains a suppressor of gene silencing and an NPTII cassettes.

The presence of a suppressor of gene silencing in such gene expression systems is preferred but not essential. Suppressors of gene silencing are known in the art and described in WO/2007/135480. They include HcPro from Potato virus Y, He-Pro from TEV, P19 from TBSV, rgsCam, B2 protein from FHV, the small coat protein of CPMV, and coat protein from TCV. A preferred suppressor when producing stable transgenic plants is the P19 suppressor incorporating a R43W mutation.

The present invention also provides methods comprising introduction of such a construct into a plant cell or a microbial (e.g. bacterial, yeast or fungal) cell and/or induction of expression of a construct within a plant cell, by application of a suitable stimulus e.g. an effective exogenous inducer.

As an alternative to microorganisms, cell suspension cultures of engineered glycosylated QA-producing plant species, including also the moss *Physcomitrella patens*, may be cultured in fermentation tanks (see e.g. Grotewold et al. (Engineering Secondary Metabolites in Maize Cells by Ectopic Expression of Transcription Factors, Plant Cell, 10, 721-740, 1998).

In a further aspect of the invention, there is disclosed a host cell containing a heterologous construct according to the present invention, especially a plant or a microbial cell.

The discussion of host cells above in relation to reconstitution of QA-3-O-TriS biosynthesis in heterologous organisms applies mutatis mutandis here.

Thus a further aspect of the present invention provides a method of transforming a plant cell involving introduction of a construct as described above into a plant cell and causing or allowing recombination between the vector and the plant cell genome to introduce a nucleic acid according to the present invention into the genome.

The invention further encompasses a host cell transformed with nucleic acid or a vector according to the present invention (e.g. comprising the QA-3-O-TriS-biosynthesis modifying nucleotide sequence) especially a plant or a microbial cell. In the transgenic plant cell (i.e. transgenic for the nucleic acid in question) the transgene may be on an extra-genomic vector or incorporated, preferably stably, into the genome. There may be more than one heterologous nucleotide sequence per haploid genome.

Yeast has seen extensive employment as a triterpene-producing host and is therefore potentially well adapted for QA and then QA-3-O-TriS biosynthesis.

Therefore, in one embodiment, the host is a yeast. For such hosts, it may be desirable to introduce additional genes to improve the flux of QA, and hence QA-3-O-TriS production as described above. Examples may include one or more plant cytochrome P450 reductases (CPRs) to serve as the redox partner to the introduced P450s, as well as an HMGR. It may likewise be desirable to introduce additional genes to contribute other elements of the QA or improve QA-3-O-TriS pathways. These may include enzymes providing UDP-sugar donors and the like (see e.g. Ohashi T, Hasegawa Y, Misaki R, Fujiyama K (2016) "Substrate preference of citrus naringenin rhamnosyltransferases and their application to flavonoid glycoside production in fission yeast". (2016). Applied Microbiology and Biotechnology. 100(2): 687-696.); Oka T, Jigami Y. (2006). "Reconstruction of de novo pathway for synthesis of UDP-glucuronic acid and UDP-xylose from intrinsic UDP-glucose in *Saccharomyces cerevisiae*". FEBS J. 273(12):2645-57). In the light of the present disclosure, those skilled in the art can provide such ancillary activities as required.

Plants, which include a plant cell transformed as described above, form a further aspect of the invention.

If desired, following transformation of a plant cell, a plant may be regenerated, e.g. from single cells, callus tissue or leaf discs, as is standard in the art. Almost any plant can be entirely regenerated from cells, tissues and organs of the plant. Available techniques are reviewed in Vasil et al., *Cell Culture and Somatic Cell Genetics of Plants, Vol I, II and III, Laboratory Procedures and Their Applications*, Academic Press, 1984, and Weissbach and Weissbach, *Methods for Plant Molecular Biology*, Academic Press, 1989.

In addition to the regenerated plant, the present invention embraces all of the following: a clone of such a plant, seed, selfed or hybrid progeny and descendants (e.g. F1 and F2 descendants). The invention also provides a plant propagule from such plants, that is any part which may be used in reproduction or propagation, sexual or asexual, including cuttings, seed and so on. In all cases these plants or parts include the plant cell or heterologous QA-3-O-TriS-biosynthesis modifying DNA described above, for example as introduced into an ancestor plant.

It also provides any part of these plants (e.g. leaf, stem, dried or ground product, edible portion etc.), which in all cases include the plant cell or heterologous QA-3-O-TriS-biosynthesis modifying DNA described above.

The present invention also encompasses the expression product of any of the coding QA-3-O-TriS-biosynthesis modifying nucleic acid sequences disclosed and methods of making the expression product by expression from encoding nucleic acid therefore under suitable conditions, which may be in suitable host cells.

As described below, plant backgrounds such as those above may be natural or transgenic e.g. for one or more other genes relating to glycosylated QA, such as QA-3-O-TriS, biosynthesis, or otherwise affecting that phenotype or trait.

In modifying the host phenotypes, the QA-3-O-TriS nucleic acids described herein may be used in combination with any other gene, such as transgenes affecting the rate or yield of QA-3-O-TriS, or its modification, or any other phenotypic trait or desirable property.

By use of a combination of genes, plants or microorganisms (e.g. bacteria, yeasts or fungi) can be tailored to enhance production of desirable precursors, or reduce undesirable metabolism.

As an alternative, down-regulation of genes in the host may be desired e.g. to reduce undesirable metabolism or fluxes which might impact on QA-3-O-TriS yield.

Such down regulation may be achieved by methods known in the art, for example using anti-sense technology.

In using anti-sense genes or partial gene sequences to down-regulate gene expression, a nucleotide sequence is placed under the control of a promoter in a "reverse orientation" such that transcription yields RNA which is complementary to normal mRNA transcribed from the "sense" strand of the target gene. See, for example, Rothstein et al, 1987; Smith et al, (1988) *Nature* 334, 724-726; Zhang et al, (1992) *The Plant Cell* 4, 1575-1588, English et al., (1996) *The Plant Cell* 8, 179-188. Antisense technology is also reviewed in Bourque, (1995), *Plant Science* 105, 125-149, and Flavell, (1994) *PNAS USA* 91, 3490-3496.

An alternative to anti-sense is to use a copy of all or part of the target gene inserted in sense, that is the same, orientation as the target gene, to achieve reduction in expression of the target gene by co-suppression. See, for example, van der Krol et al., (1990) *The Plant Cell* 2, 291-299; Napoli et al., (1990) *The Plant Cell* 2, 279-289; Zhang et al., (1992) *The Plant Cell* 4, 1575-1588, and U.S. Pat. No. 5,231,020. Further refinements of the gene silencing or co-suppression technology may be found in WO95/34668 (Biosource); Angell & Baulcombe (1997) The EMBO Journal 16, 12:3675-3684; and Voinnet & Baulcombe (1997) Nature 389: pg 553.

Double stranded RNA (dsRNA) has been found to be even more effective in gene silencing than both sense or antisense strands alone (Fire A. et al Nature, Vol 391, (1998)). dsRNA mediated silencing is gene specific and is often termed RNA interference (RNAi) (See also Fire (1999) *Trends Genet.* 15: 358-363, Sharp (2001) *Genes Dev.* 15: 485-490, Hammond et al. (2001) *Nature Rev. Genes* 2: 1110-1119 and Tuschl (2001) *Chem. Biochem.* 2: 239-245).

RNA interference is a two-step process. First, dsRNA is cleaved within the cell to yield short interfering RNAs (siRNAs) of about 21-23 nt length with 5' terminal phosphate and 3' short overhangs (~2 nt) The siRNAs target the corresponding mRNA sequence specifically for destruction (Zamore P. D. Nature Structural Biology, 8, 9, 746-750, (2001) Another methodology known in the art for down-regulation of target sequences is the use of "microRNA" (miRNA) e.g. as described by Schwab et al 2006, Plant Cell 18, 1121-1133.

This technology employs artificial miRNAs, which may be encoded by stem loop precursors incorporating suitable oligonucleotide sequences, which sequences can be generated using well defined rules in the light of the disclosure herein.

Thus in one aspect, the invention provides a method for influencing or affecting glycosylated QA biosynthesis in a host, which method comprises any of the following steps of:

(i) causing or allowing transcription from a nucleic acid comprising the complement sequence of a QA-3-O-TriS nucleotide sequence such as to reduce the respective encoded polypeptide activity by an antisense mechanism;

(ii) causing or allowing transcription from a nucleic acid encoding a stem loop precursor comprising 20-25 nucleotides, optionally including one or more mismatches, of a QA-3-O-TriS nucleotide sequence such as to reduce the respective encoded polypeptide activity by an miRNA mechanism;

(iii) causing or allowing transcription from nucleic acid encoding double stranded RNA corresponding to 20-25 nucleotides, optionally including one or more mismatches, of a QA-3-O-TriS nucleotide sequence such as to reduce the respective encoded polypeptide activity by an siRNA mechanism.

The methods of the present invention embrace both the in vitro and in vivo production, or manipulation, of one or more glycosylated QAs. For example, QA-3-O-TriS polypeptides may be employed in fermentation via expression in microorganisms such as e.g. *E. coli*, yeast and filamentous fungi and so on. In one embodiment, one or more newly characterised QA-3-O-TriS sequences of the present invention may be used in these organisms in conjunction with one or more other biosynthetic genes.

In vivo methods are described extensively above, and generally involve the step of causing or allowing the transcription of, and then translation from, a recombinant nucleic acid molecule encoding the QA-3-O-TriS polypeptides.

In other aspects of the invention, the QA-3-O-TriS polypeptides (enzymes) may be used in vitro, for example in isolated, purified, or semi-purified form. Optionally they may be the product of expression of a recombinant nucleic acid molecule.

Newly Characterised Sequences from *Q. saponaria*

As noted above, in support of the present invention, the inventors have identified genes from *Q. saponaria* which are believed to encode polypeptides which affect QA-3-O-TriS biosynthesis (see SEQ. ID: Nos 1-6 and 25-32 in Table 5).

The above newly characterised QA-3-O-TriS biosynthetic genes from *Q. saponaria* thus form aspects of the present invention in their own right.

In a further aspect of the present invention, there are disclosed nucleic acids which are variants of the QA-3-O-TriS nucleic acid derived from *Q. saponaria* discussed above.

Such variants, as with the native genes discussed herein, may be used to alter the glycosylated QA (e.g. QA-3-O-TriS) content of a plant, as assessed by the methods disclosed herein. For instance, a variant nucleic acid may include a sequence encoding a variant QA-3-O-TriS polypeptide sharing the relevant biological activity of the native QA-3-O-TriS polypeptide, as discussed above. Examples include variants of any of SEQ ID Nos 2, 4, 6, 26, 28, 30, or 32.

Derivatives

Described herein are methods of producing a derivative nucleic acid comprising the step of modifying any of the QA-3-O-TriS genes of the present invention disclosed above, particularly the QA-3-O-TriS sequences from *Q. saponaria.*

Changes may be desirable for a number of reasons. For instance, they may introduce or remove restriction endonuclease sites or alter codon usage. This may be particularly desirable where the QA-3-O-TriS genes are to be expressed in alternative hosts e.g. microbial hosts such as yeast. Methods of codon optimizing genes for this purpose are known in the art (see e.g. Elena, Claudia, et al. "Expression of codon optimized genes in microbial systems: current industrial applications and perspectives." *Frontiers in microbiology* 5 (2014)). Thus sequences described herein including codon modifications to maximise yeast expression represent specific embodiments of the invention.

Alternatively, changes to a sequence may produce a derivative by way of one or more (e.g. several) of addition, insertion, deletion or substitution of one or more nucleotides in the nucleic acid, leading to the addition, insertion, deletion or substitution of one or more (e.g. several) amino acids in the encoded polypeptide.

Such changes may modify sites which are required for post translation modification such as cleavage sites in the encoded polypeptide; motifs in the encoded polypeptide for phosphorylation etc. Leader or other targeting sequences (e.g. membrane or golgi locating sequences) may be added to the expressed protein to determine its location following expression if it is desired to isolate it from a microbial system.

Other desirable mutations may be random or site-directed mutagenesis in order to alter the activity (e.g. specificity) or stability of the encoded polypeptide. Changes may be by way of conservative variation, i.e. substitution of one hydrophobic residue such as isoleucine, valine, leucine or methionine for another, or the substitution of one polar residue for another, such as arginine for lysine, glutamic for aspartic acid, or glutamine for asparagine. As is well known to those skilled in the art, altering the primary structure of a polypeptide by a conservative substitution may not significantly alter the activity of that peptide because the side-chain of the amino acid which is inserted into the sequence may be able to form similar bonds and contacts as the side chain of the amino acid which has been substituted out. This is so even when the substitution is in a region which is critical in determining the peptides conformation. Also included are variants having non-conservative substitutions. As is well known to those skilled in the art, substitutions to regions of a peptide which are not critical in determining its conformation may not greatly affect its activity because they do not greatly alter the peptide's three dimensional structure. In regions which are critical in determining the peptides conformation or activity such changes may confer advantageous properties on the polypeptide. Indeed, changes such as those described above may confer slightly advantageous properties on the peptide e.g. altered stability or specificity.

Fragments

The present invention may utilise fragments of the genes encoding the QA-3-O-TriS polypeptides of the present invention disclosed above, particularly the QA-3-O-TriS sequences from Q. saponaria.

Thus the present invention provides for the production and use of fragments of the full-length QA-3-O-TriS polypeptides of the invention disclosed herein, especially active portions thereof. An "active portion" of a polypeptide means a peptide which is less than said full length polypeptide, but which retains its essential biological activity e.g. in relation to glycosylation of QA (see e.g. Table 5).

A "fragment" of a polypeptide means a stretch of amino acid residues of at least about five to seven contiguous amino acids, often at least about seven to nine contiguous amino acids, typically at least about nine to 13 contiguous amino acids and, most preferably, at least about 20 to 30 or more contiguous amino acids. Fragments of the polypeptides may include one or more epitopes useful for raising antibodies to a portion of any of the amino acid sequences disclosed herein. Preferred epitopes are those to which antibodies are able to bind specifically, which may be taken to be binding a polypeptide or fragment thereof of the invention with an affinity which is at least about 1000× that of other polypeptides.

For brevity, and of these QA-3-O-TriS sequences from the Q. saponaria, or variants (e.g. derivatives such as fragments thereof) may be referred to as "Qs QA-3-O-TriS sequences (or nucleic acid, or polypeptide)". These Qs QA-3-O-TriS polypeptides, and nucleic acids encoding them, form one aspect of the invention.

It will be appreciated that, where this term is used generally, it also applies to any of these sequences individually.

Thus in one aspect of the invention, there is disclosed isolated nucleic acid encoding any of these polypeptides (2, 4, 6, 26, 28, 30, or 32). Preferably, this may have the sequence of 1, 3, 5, 25, 27, 29, or 31. Other nucleic acids of the invention include those which are degeneratively equivalent to these, or homologous variants (e.g. derivatives) of these.

Aspects of the invention further embrace isolated nucleic acid comprising a sequence which is complementary to any of those discussed hereinafter.

In vitro or in vivo use of a QA-3-O-TriS sequence to catalyse its respective biological activity (QA-glycosylation, for example as described in FIG. 3 or FIG. 9 or Table 5) forms another aspect of the invention.

Thus the invention further provides a method of influencing or affecting glycosylated QA (e.g. QA-3-O-TriS) biosynthesis in a host such as a plant, the method including causing or allowing transcription of a heterologous Qs QA-3-O-TriS nucleic acid as discussed above within the cells of the plant. The step may be preceded by the earlier step of introduction of the QsQA-3-O-TriS nucleic acid into a cell of the plant or an ancestor thereof.

Such methods will usually form a part of, possibly one step in, a method of producing a glycosylated QA (e.g. QA-3-O-TriS) in a host such as a plant. Preferably the method will employ a Qs QA-3-O-TriS polypeptide of the present invention (e.g. in Table 5) or derivative thereof, as described above, or nucleic acid encoding either.

In a further embodiment, there are provided antibodies raised to a Qs QA-3-O-TriS polypeptide or peptide of the invention Some aspects of the invention as it relates to heterologous reconstitution of the biosynthetic pathways discussed above will now be discussed in more detail.

"Nucleic acid" according to the present invention may include cDNA, RNA, genomic DNA and modified nucleic acids or nucleic acid analogs (e.g. peptide nucleic acid). Where a DNA sequence is specified, e.g. with reference to a figure, unless context requires otherwise the RNA equivalent, with U substituted for T where it occurs, is encompassed. Nucleic acids may include more than one nucleic acid molecule. Nucleic acid molecules according to the present invention may be provided isolated and/or purified from their natural environment, in substantially pure or homogeneous form, or free or substantially free of other nucleic acids of the species of origin, and double or single stranded. Where used herein, the term "isolated" encompasses all of these possibilities. The nucleic acid molecules may be wholly or partially synthetic. In particular they may be recombinant in that nucleic acid sequences which are not found together in nature (do not run contiguously) have been ligated or otherwise combined artificially. Nucleic acids may comprise, consist, or consist essentially of, any of the sequences discussed hereinafter.

The "complement" of a nucleic acid described herein means the complementary sequence of the or a nucleotide sequence comprised by the nucleic acid. Optionally complementary sequences are full length compared to the reference nucleotide sequence.

The term "heterologous" is used broadly herein to indicate that the gene/sequence of nucleotides in question (e.g. encoding QA-3-O-TriS-biosynthesis modifying polypeptides) have been introduced into said cells of the host or an ancestor thereof, using genetic engineering, i.e. by human intervention. Nucleic acid heterologous to a host cell will be non-naturally occurring in cells of that type, variety or species. Thus the heterologous nucleic acid may comprise a coding sequence of or derived from a particular type of plant cell or species or variety of plant, placed within the context of a plant cell of a different type or species or variety of plant. A further possibility is for a nucleic acid sequence to be placed within a cell in which it or a homologue is found naturally, but wherein the nucleic acid sequence is linked and/or adjacent to nucleic acid which does not occur naturally within the cell, or cells of that type or species or variety of plant, such as operably linked to one or more regulatory sequences, such as a promoter sequence, for control of expression.

"Transformed" in this context means that the nucleotide sequences of the heterologous nucleic acid alter one or more of the cell's characteristics and hence phenotype e.g. with respect to glycosylated QA e.g. QA-3-O-TriS biosynthesis. Such transformation may be transient or stable.

"Unable to carry out QA-3-O-TriS biosynthesis" means that the host, prior to the conversion, does not, or is not believed to, naturally produce detectable or recoverable levels of QA-3-O-TriS under normal metabolic circumstances of that host. Following the application of the invention it is able to produce detectable or recoverable levels of QA-3-O-TriS.

The nucleotide sequence information provided herein may be used to design probes and primers for probing or amplification. An oligonucleotide for use in probing or PCR may be about 30 or fewer nucleotides in length (e.g. 18, 21 or 24). Generally specific primers are upwards of 14 nucleotides in length. For optimum specificity and cost effectiveness, primers of 16-24 nucleotides in length may be preferred. Those skilled in the art are well versed in the design of primers for use in processes such as PCR. If required, probing can be done with entire restriction fragments of the gene disclosed herein which may be 100's or even 1000's of nucleotides in length. Small variations may be introduced into the sequence to produce 'consensus' or 'degenerate' primers if required.

Probing may employ the standard Southern blotting technique. For instance DNA may be extracted from cells and digested with different restriction enzymes. Restriction fragments may then be separated by electrophoresis on an agarose gel, before denaturation and transfer to a nitrocellulose filter. Labelled probe may be hybridised to the single stranded DNA fragments on the filter and binding determined. DNA for probing may be prepared from RNA preparations from cells. Probing may optionally be done by means of so-called 'nucleic acid chips' (see Marshall & Hodgson (1998) Nature Biotechnology 16: 27-31, for a review).

In one embodiment, a variant encoding a QA-3-O-TriS-biosynthesis modifying polypeptide in accordance with the present invention is obtainable by means of a method which includes:

(a) providing a preparation of nucleic acid, e.g. from plant cells. Test nucleic acid may be provided from a cell as genomic DNA, cDNA or RNA, or a mixture of any of these, preferably as a library in a suitable vector. If genomic DNA is used the probe may be used to identify untranscribed regions of the gene (e.g. promoters etc.), such as are described hereinafter, (b) providing a nucleic acid molecule which is a probe or primer as discussed above, (c) contacting nucleic acid in said preparation with said nucleic acid molecule under conditions for hybridisation of said nucleic acid molecule to any said gene or homologue in said preparation, and, (d) identifying said gene or homologue if present by its hybridisation with said nucleic acid molecule. Binding of a probe to target nucleic acid (e.g. DNA) may be measured using any of a variety of techniques at the disposal of those skilled in the art. For instance, probes may be radioactively, fluorescently or enzymatically labelled. Other methods not employing labelling of probe include amplification using PCR (see below), RN'ase cleavage and allele specific oligonucleotide probing. The identification of successful hybridisation is followed by isolation of the nucleic acid which has hybridised, which may involve one or more steps of PCR or amplification of a vector in a suitable host.

Preliminary experiments may be performed by hybridising under low stringency conditions. For probing, preferred conditions are those which are stringent enough for there to be a simple pattern with a small number of hybridisations identified as positive which can be investigated further.

For example, hybridizations may be performed, according to the method of Sambrook et al. (below) using a hybridization solution comprising: 5×SSC (wherein 'SSC'=0.15 M sodium chloride; 0.15 M sodium citrate; pH 7), 5×Denhardt's reagent, 0.5-1.0% SDS, 100 µg/ml denatured, fragmented salmon sperm DNA, 0.05% sodium pyrophosphate and up to 50% formamide. Hybridization is carried out at 37-42° C. for at least six hours. Following hybridization, filters are washed as follows: (1) 5 minutes at room temperature in 2×SSC and 1% SDS; (2) 15 minutes at room temperature in 2×SSC and 0.1% SDS; (3) 30 minutes-1 hour at 37° C. in 1×SSC and 1% SDS; (4) 2 hours at 42-65° C. in 1×SSC and 1% SDS, changing the solution every 30 minutes.

One common formula for calculating the stringency conditions required to achieve hybridization between nucleic acid molecules of a specified sequence homology is (Sambrook et al., 1989): $T_m=81.5°$ C.$+16.6$ Log [Na+]$+0.41$ (% G+C)$-0.63$ (% formamide)$-600/\#bp$ in duplex As an illustration of the above formula, using [Na+]= [0.368] and 50-% formamide, with GC content of 42% and an average probe size of 200 bases, the $T_m$ is 57° C. The $T_m$ of a DNA duplex decreases by 1-1.5° C. with every 1% decrease in homology. Thus, targets with greater than about 75% sequence identity would be observed using a hybridization temperature of 42° C. Such a sequence would be considered substantially homologous to the nucleic acid sequence of the present invention.

It is well known in the art to increase stringency of hybridisation gradually until only a few positive clones remain. Other suitable conditions include, e.g. for detection of sequences that are about 80-90% identical, hybridization overnight at 42° C. in 0.25M Na₂HPO₄, pH 7.2, 6.5% SDS, 10% dextran sulfate and a final wash at 55° C. in 0.1×SSC, 0.1% SDS. For detection of sequences that are greater than about 90% identical, suitable conditions include hybridization overnight at 65° C. in 0.25M Na₂HPO₄, pH 7.2, 6.5% SDS, 10% dextran sulfate and a final wash at 60° C. in 0.1×SSC, 0.1% SDS.

In a further embodiment, hybridization of a nucleic acid molecule to a variant may be determined or identified indirectly, e.g. using a nucleic acid amplification reaction, particularly the polymerase chain reaction (PCR). PCR requires the use of two primers to specifically amplify target nucleic acid, so preferably two nucleic acid molecules with sequences characteristic of a QA-3-O-TriS gene of the present invention are employed. Using RACE PCR, only one such primer may be needed (see "PCR protocols; A Guide to Methods and Applications", Eds. Innis et al, Academic Press, New York, (1990)).

Thus a method involving use of PCR in obtaining nucleic acid according to the present invention may include:

(a) providing a preparation of plant nucleic acid, e.g. from a seed or other appropriate tissue or organ, (b) providing a pair of nucleic acid molecule primers useful in (i.e. suitable for) PCR, at least one of said primers being a primer according to the present invention as discussed above, (c) contacting nucleic acid in said preparation with said primers under conditions for performance of PCR, (d) performing PCR and determining the presence or absence of an amplified PCR product.

The presence of an amplified PCR product may indicate identification of a variant.

In all cases above, if need be, clones or fragments identified in the search can be extended. For instance if it is suspected that they are incomplete, the original DNA source (e.g. a clone library, mRNA preparation etc.) can be revisited to isolate missing portions e.g. using sequences, probes or primers based on that portion which has already been obtained to identify other clones containing overlapping sequence.

Purified protein (polypeptide, enzyme), or a fragment, mutant, derivative or variant thereof, e.g. produced recombinantly by expression from encoding nucleic acid therefor, forms one aspect of the invention.

Such purified polypeptides may be used to raise antibodies employing techniques which are standard in the art. Antibodies and polypeptides comprising antigen-binding fragments of antibodies may be used in identifying homologues from other species as discussed further below.

Methods of producing antibodies include immunising a mammal (e.g. human, mouse, rat, rabbit, horse, goat, sheep or monkey) with the protein or a fragment thereof. Antibodies may be obtained from immunised animals using any of a variety of techniques known in the art, and might be screened, preferably using binding of antibody to antigen of interest. For instance, Western blotting techniques or immunoprecipitation may be used (Armitage et al, 1992, Nature 357: 80-82). Antibodies may be polyclonal or monoclonal.

As an alternative or supplement to immunising a mammal, antibodies with appropriate binding specificity may be obtained from a recombinantly produced library of expressed immunoglobulin variable domains, e.g. using lambda bacteriophage or filamentous bacteriophage which display functional immunoglobulin binding domains on their surfaces; for instance see WO92/01047.

Antibodies raised to a polypeptide or peptide can be used in the identification and/or isolation of homologous polypeptides, and then the encoding genes.

Antibodies may be modified in a number of ways. Indeed the term "antibody" should be construed as covering any specific binding substance having a binding domain with the required specificity. Thus, this term covers antibody fragments, derivatives, functional equivalents and homologues of antibodies, including any polypeptide comprising an immunoglobulin binding domain, whether natural or synthetic.

A number of patents and publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

Any sub-titles herein are included for convenience only, and are not to be construed as limiting the disclosure in any way.

The invention will now be further described with reference to the following non-limiting Figures and Examples. Other embodiments of the invention will occur to those skilled in the art in the light of these.

ABBREVIATIONS

Compound 1—3β-{[α-L-rhamnopyranosyl-(1->3)-[β-D-galactopyranosyl-(1->2)]-β-D-glucopyranosiduronic acid]oxy}-quillaic acid Compound 2—3β-{[β-D-xylopyranosyl-(1->3)-[β-D-galactopyranosyl-(1->2)]-β-D-glucopyranosiduronic acid]oxy}-quillaic acid Galp—D-Galactopyranose GlcpA—D-Glucopyranuronic acid (Additional numbers denote specific carbons i.e. GlcA-1)

GmSGT2/GmUGT73P2 —*Glycine max* (soybean) Soyasaponin β-D-galactosyltransferase

GTs—Glycosyltransferases

QA—Quillaic acid

QA-GlcpA—3β-{[β-D-glucopyranosiduronic acid]oxy}-quillaic acid

QA-GlcpA-Galp—3β-{[β-D-galactopyranosyl-(1->2)-β-D-glucopyranosiduronic acid]oxy}-quillaic acid QA-GlcpA-[Galp]-Rhap—3β-{[α-L-rhamnopyranosyl-(1->3)-[β-D-galactopyranosyl-(1->2)]-β-D-glucopyranosiduronic acid]oxy}-quillaic acid QA-GlcpA-[Galp]-Xylp—3β-{[β-D-xylopyranosyl-(1->3)-[β-D-galactopyranosyl-(1->2)]-β-D-glucopyranosiduronic acid]oxy}-quillaic acid QA-3-O-TriS—QA glycosylated at 3-O position with a branched trisaccharide which is either QA-GlcpA-[Galp]-Rhap or QA-GlcpA-[Galp]-Xylp OS—2,3-oxidosqualene QA-GlcAT—QA 3-O glucuronosyl transferase QA-GalT—QA-GlcpA galactosyl transferase QA-RhaT/XylT—QA-GlcpA-Galp Rhamnosyl and/or Xylosyl transferase
QsbAS—*Q. saponaria* β-amyrin synthase
Qs-3-O-GalT—*Q. saponaria* QA-GlcpA β-1,2-D-galactosyltransferase
QsCSL1—*Q. saponaria* cellulose synthase-like enzyme (quillaic acid 3-O-glucuronosyltransferase)
QsCslG2—*Q. saponaria* cellulose synthase-like enzyme (quillaic acid 3-O-glucuronosyltransferase)
Qs-3-O-RhaT/XylT—*Q. saponaria* QA-GlcpA-Galp dual β-1,3-D-xylosyltransferase/α-1,3-L-rhamnosyltransferase
Qs_0283850—*Q. saponaria* QA-GlcpA-Galp α-1,3-L-rhamnosyltransferase
DN20529_c0_g2_i8—*Q. saponaria* QA-GlcpA-Galp α-1,3-L-rhamnosyltransferase
Qs 0283870—*Q. saponaria* QA-GlcpA-Galp β-1,3-D-xylosyltransferase
QsCYP716-C-28—*Q. saponaria* quillaic acid C-28 oxidase
QsCYP716-C-16α—*Q. saponaria* quillaic acid C-16α oxidase
QsCYP714-C-23—*Q. saponaria* quillaic acid C-23 oxidase
Rhap—L-Rhamnopyranose
tHMGR—*Avena strigosa* (diploid oat) truncated 3-hydroxy, 3-methylbutyryl-CoA reductase
Family 1 UGT—Family 1 UDP-dependent glycosyltransferase
Xylp—D-Xylopyranose
Qs_2073886_D6—synonymous with Qs-3-O-GalT
Qs_2015879_D7—synomymous with Qs-3-O-RhaT/XylT

FIGURES

FIG. 1: QS-21. The major structural features are highlighted, including the quillaic acid triterpene aglycone, a branched trisaccharide at C-3, linear tetrasaccharide at C-28 and an arabinosylated 18-carbon acyl chain attached to the β-D-fucose at C-28.

FIG. 2: Production of quillaic acid from 2,3-oxidosqualene via β-amyrin. Numbering of important β-amyrin carbons referred to herein are labelled in red. The pathway from β-amyrin requires oxidation at three (C-28, C-23 and C-16α) positions. These oxidation steps are shown in a linear fashion for simplicity, however they could occur in any order.

FIG. 3: Production of quillaic acid trisaccharide derivative (QA-3-O-TriS) from quillaic acid. The pathway (showed in linear sequential form for simplicity) entails a 3-step glycosylation at C-3 of quillaic acid beginning with D-Glucuronic acid (GlcpA). GlcpA is further glycosylated with a β-1,2-D-Galactose (Galp) and with a β-1,3-D-Xylose (Xylp), in one or other order.

Figure 4:
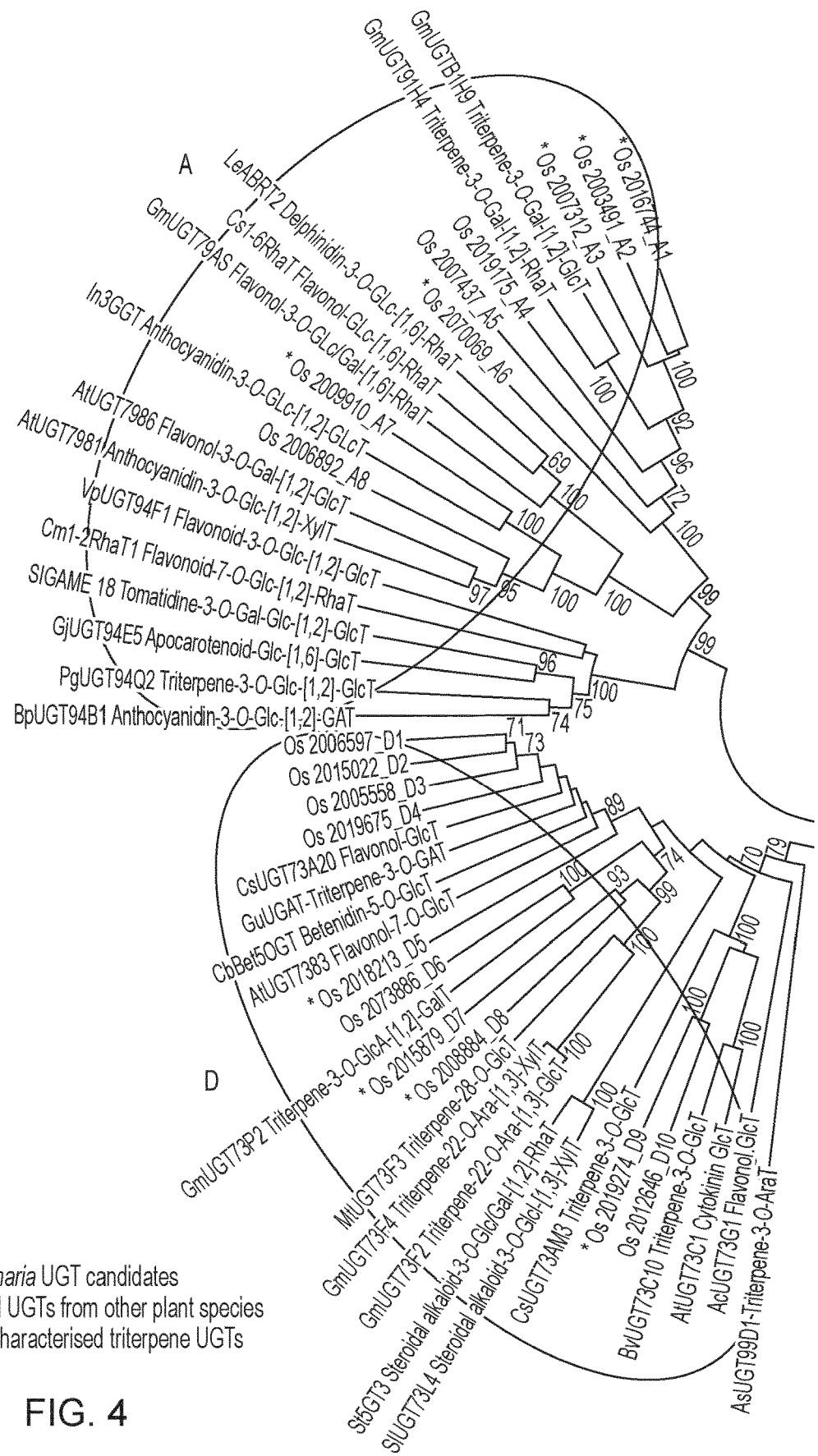
Figure 4:
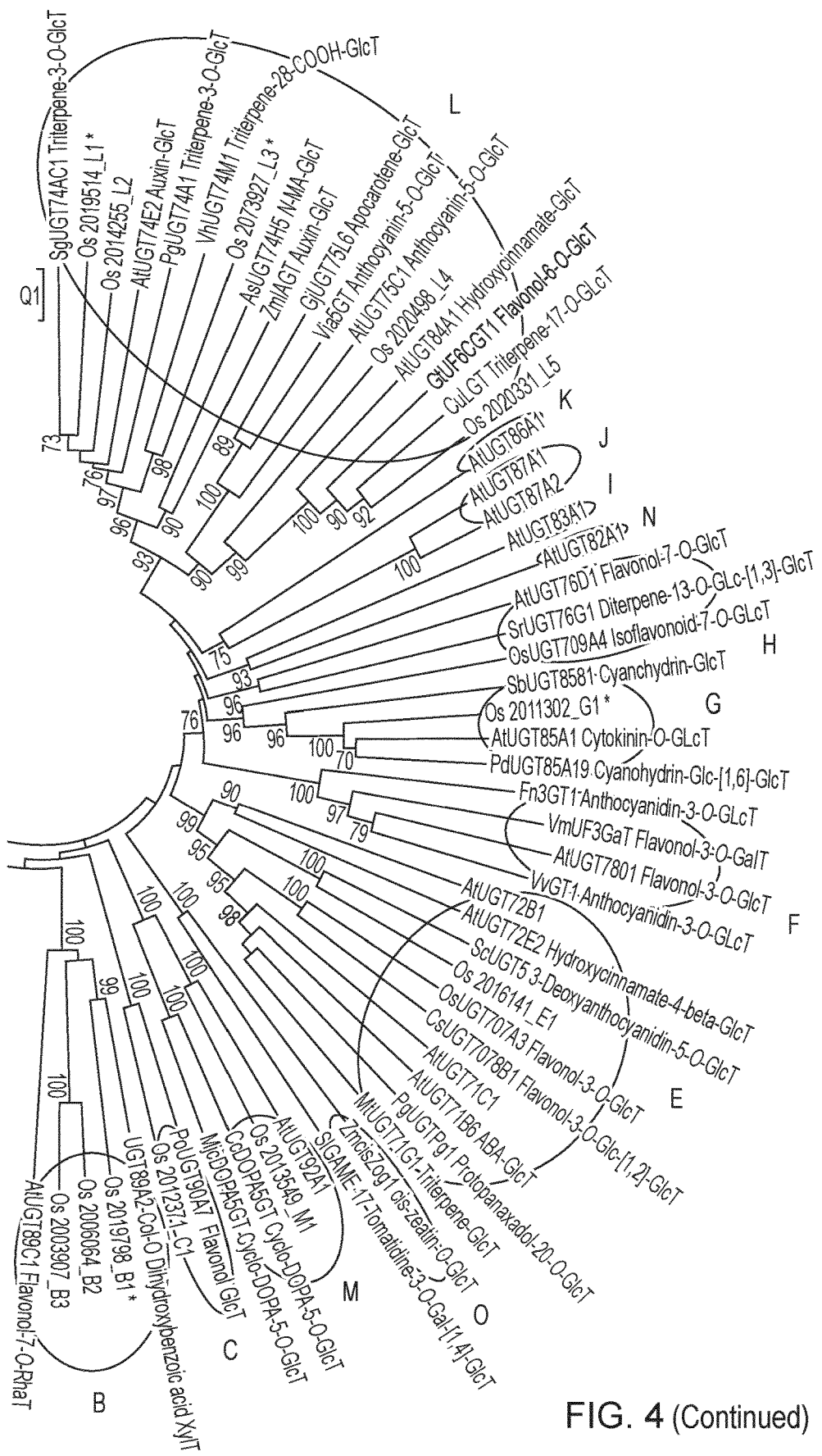

FIG. 4: Mining for candidate QS-21 UDP-dependent glycosyltransferases (UGTs). Phylogenetic tree of *Quillaja saponaria* UGT candidates (red) with characterised UGTs from other plant species (black) (listed in Table 3). Functionally characterised triterpene UGTs are indicated in blue. *Q. saponaria* UGTs whose genes are predicted to be within biosynthetic gene clusters (BCGs) are indicated by asterisks. The UGT phylogenetic groups (Groups A-P) are labelled as described in Ross, J., Li, Y., Lim, E., and Bowles, D. J. (2001). "Higher plant glycosyltransferases". Genome Biol., 2: REVIEWS 3004, and Caputi, L., Malnoy, M., Goremykin, V., Nikiforova, S., and Martens, S. (2012). "A genome-wide phylogenetic reconstruction of family 1 UDP-glycosyltransferases revealed the expansion of the family during the adaptation of plants to life on land". Plant J., 69:1030-42]. The tree was constructed using the Neighbour Joining method with 1000 bootstrap replicates (% support for branch points is shown). The scale bar shows 0.1 substitutions per site at the amino acid level. The *Q. saponaria* contigs in the 1 KP database consist of a 4-letter code (OQHZ) followed by seven digits; this seven digit code is included in the name for the candidate UGT genes.

Figure 5:
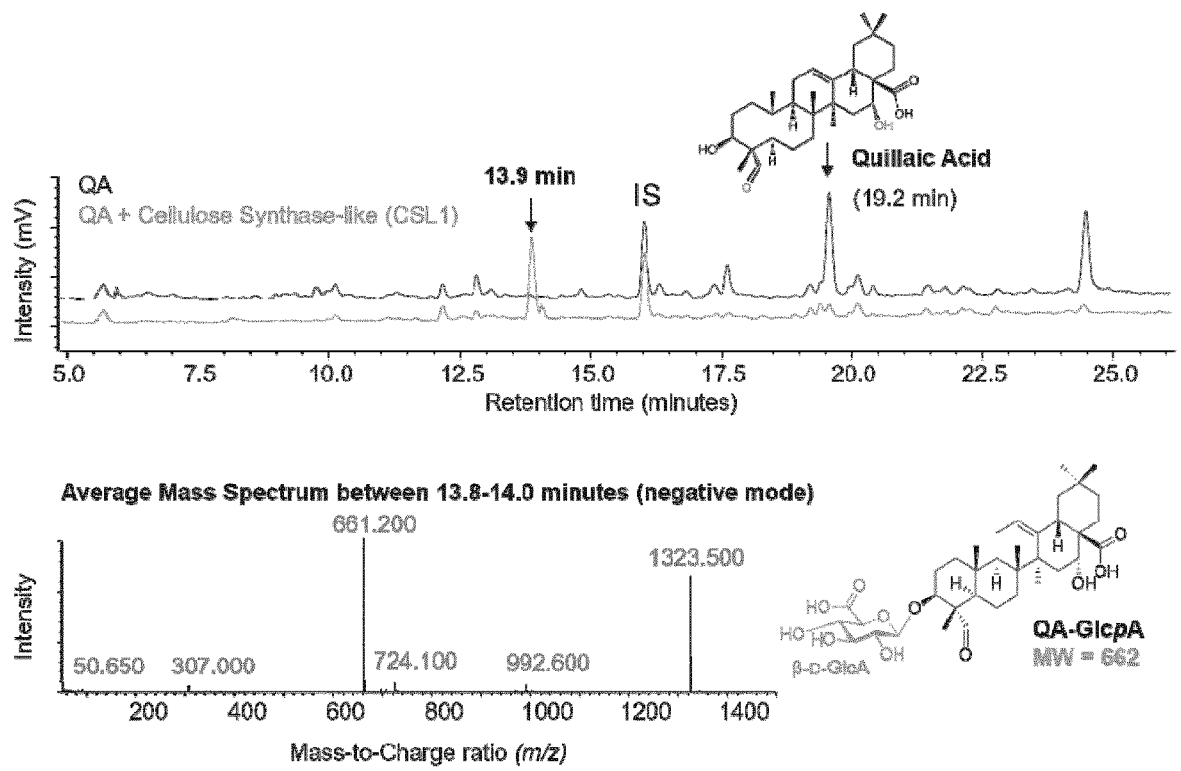

FIG. 5: Conversion of quillaic acid by QsCSL1. Accumulation of quillaic acid was detected in leaves expressing QsbAS and C-28/C-23/C-16α oxidases. The addition of *Q. saponaria* Cellulose Synthase-like (QsCSL1) resulted in lower levels of quillaic acid and the accumulation of a new peak with the mass of quillaic acid with the addition of a glucuronide residue [m/z=661, retention time=13.9 min]. IS=internal standard (digitoxin).

Figure 6:
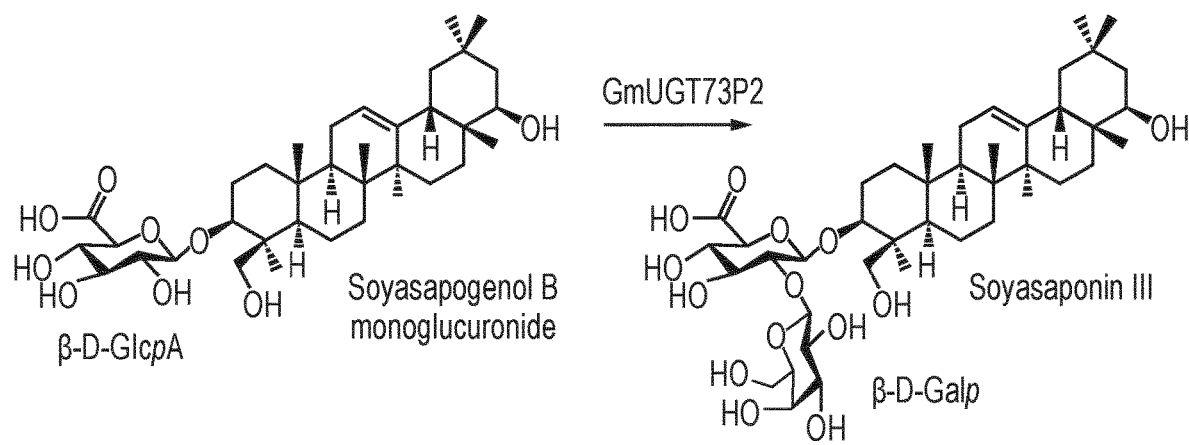

FIG. 6: GmUGT73P2 (accession number: BA199584) from Glycine maxcatalyses the addition of D-galactose to soyasapogenol B monoglucuronide with a β-1,2-linkage to form soyasaponin III (Shibuya et al., 2010).

Figure 7:
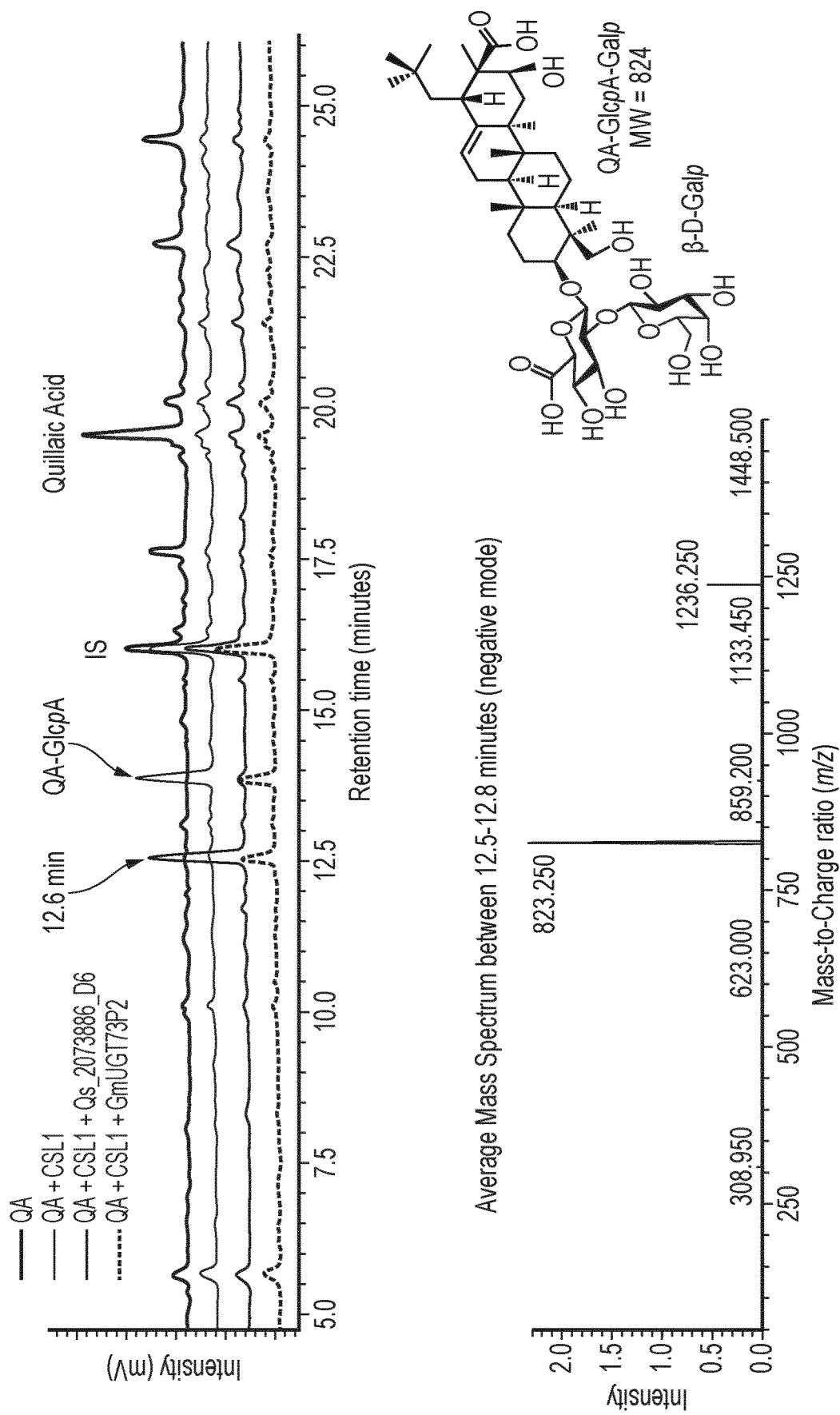

FIG. 7: Conversion of QA-GlcpA by Qs_2073886_D6 (Qs-3-O-GalT). Co-expression of Qs_2073886_D6 with genes required for production of the putative QA-GlcpA (tHMGR/QsbAS/CYP716-C-28/CYP716-C-16α/CYP714-C23/QsCSL1) resulted in the appearance of a more polar peak with the expected mass of QA-GlcpA with the addition of a hexose [m/z=823, retention time=12.6 min]. The average mass spectrum of this peak is shown. Co-expression of genes required for production of the putative QA-GlcpA with GmUGT73P2 resulted in a new peak with the same retention time as the Qs_2073886_D6 product. IS=internal standard (digitoxin).

Figure 8:
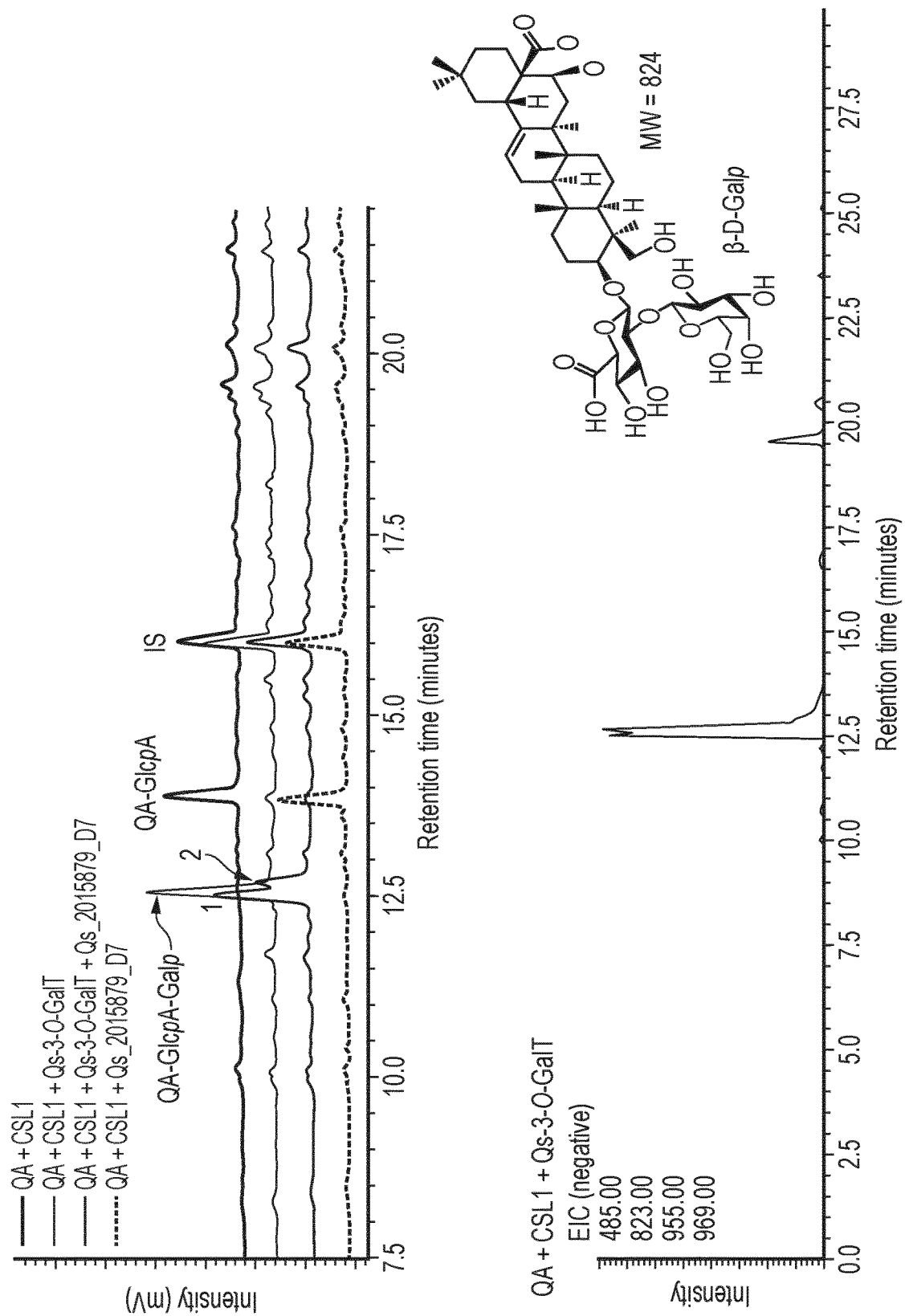
Figure 8:
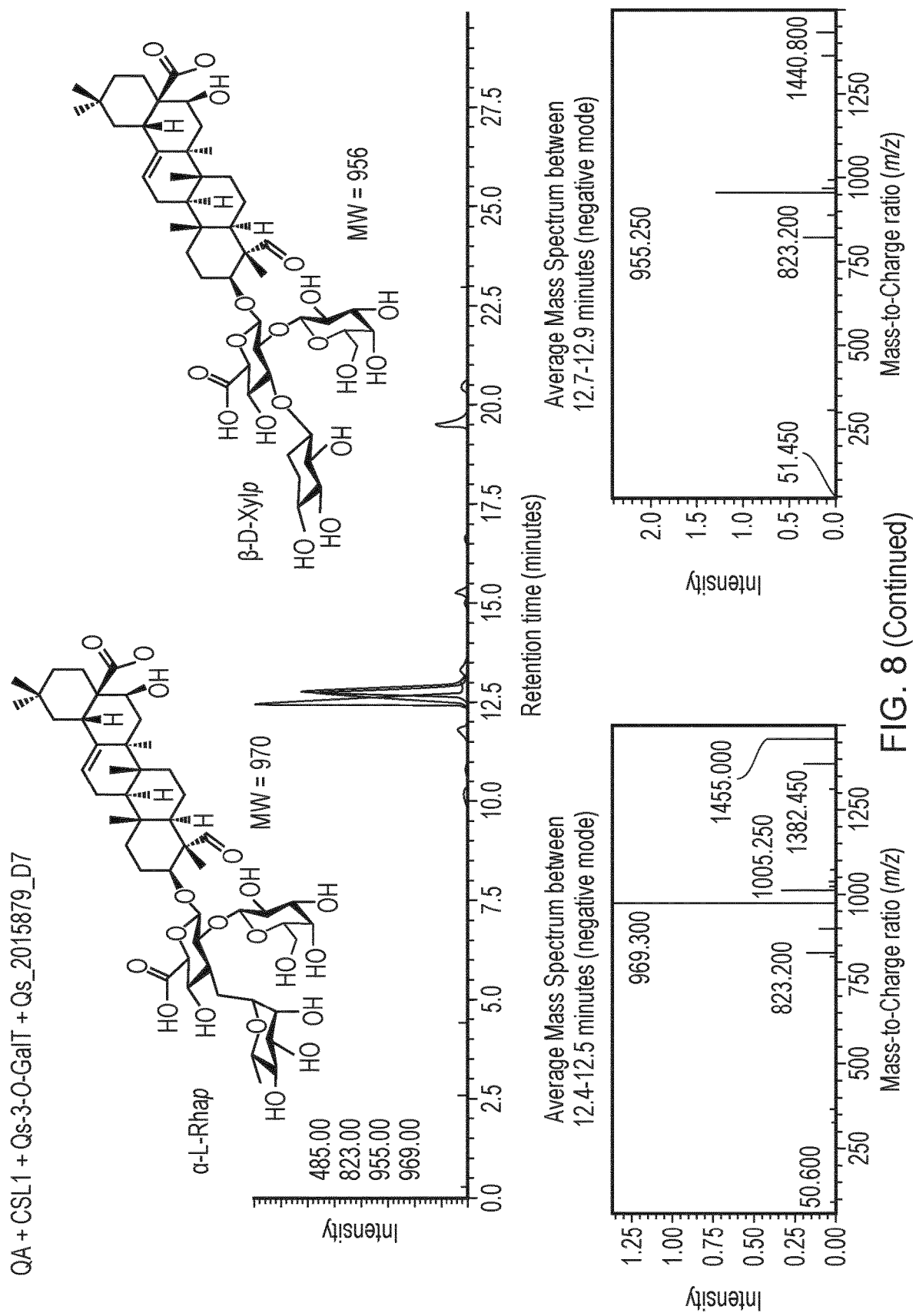

FIG. 8: Co-expression of Qs_2015879_D7 with genes required for production of the putative QA-GlcpA-Galp (tHMGR/QsbAS/CYP716-C-28/CYP716-C-16α/CYP714-C23/QsCSL1/Qs-3-O-GalT) resulted in the appearance of two peaks that co-eluted with similar retention times as the putative QA-GlcpA-Galp peak. The more polar peak had the expected mass of QA-GlcpA-Galp with the addition of a deoxyhexose [m/z=869, retention time=12.5 min] and the less polar peak had the expected mass of QA-GlcpA-Galp with the addition of a pentose [m/z=855, retention time=12.75 min]. The average mass spectrum of each peak and predicted structures are shown. Co-expression of a combination without the Qs-3-O-GalT gene did not result in any new peaks suggesting that Qs_2015879_D7 is dependent on Qs-3-O-GalT activity. IS=internal standard (digitoxin).

FIG. 9: Proposed biosynthesis of QA-GlcpA-[Galp]-Rhap and QA-GlcpA-[Galp]-Xylp from quillaic acid with the enzymes characterised herein.

Figure 10:
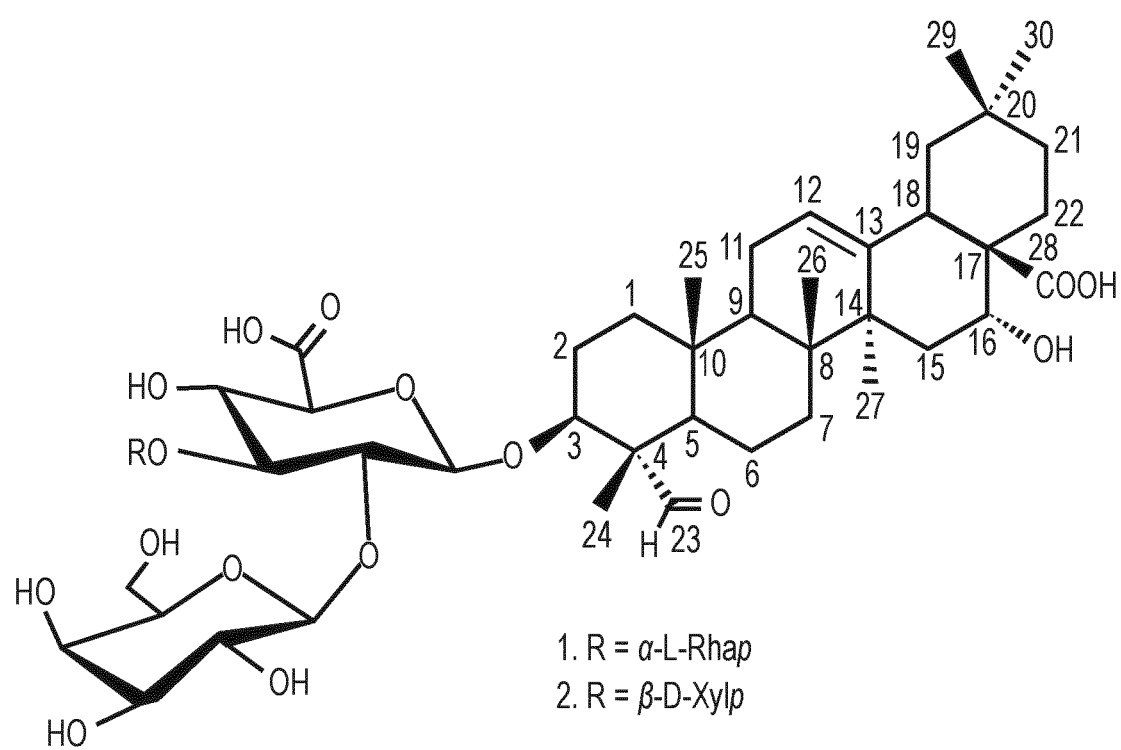

FIG. 10: Structure of isolated compounds 1 and 2.

Figure 11:
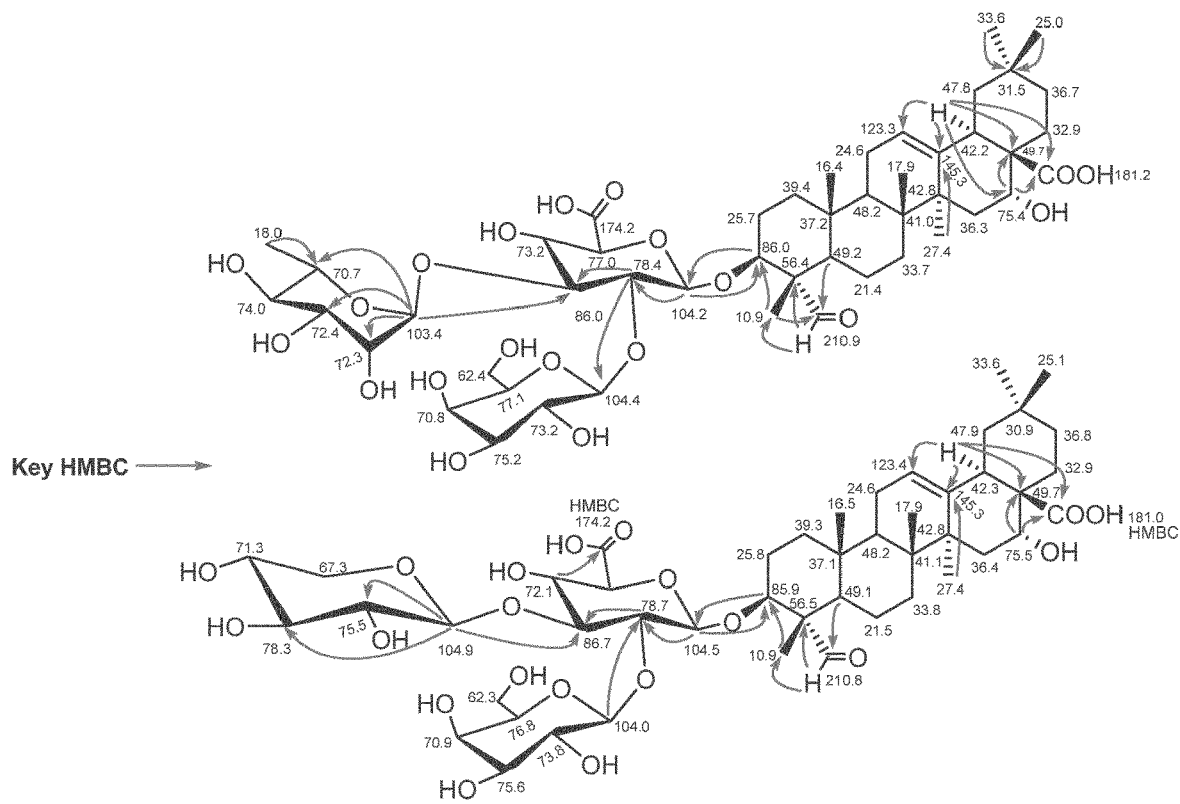

FIG. 11: Full $^{13}$C NMR assignment and Key HMBC (H→C) reported for compounds 1 and 2

Figure 12:
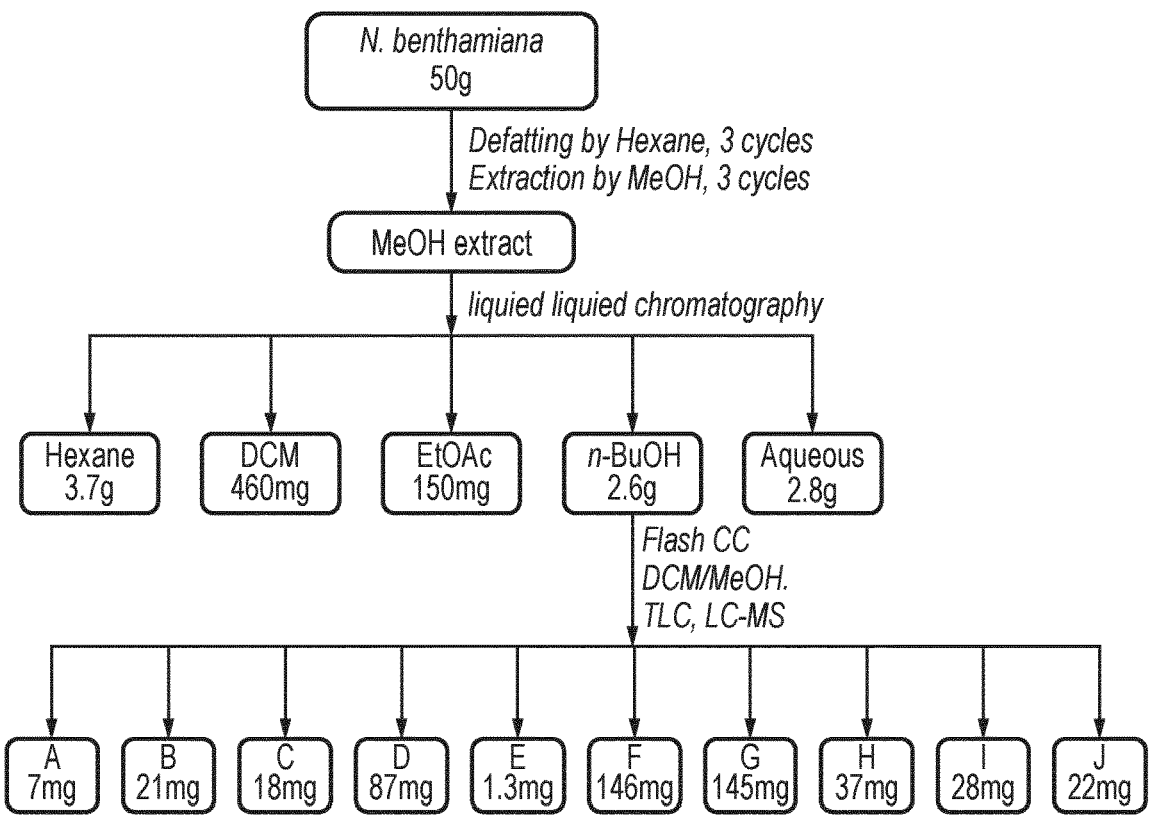

FIG. 12: Schematic for isolation of the trisaccharides from *N. benthamiana* leaf material.

Figure 13:
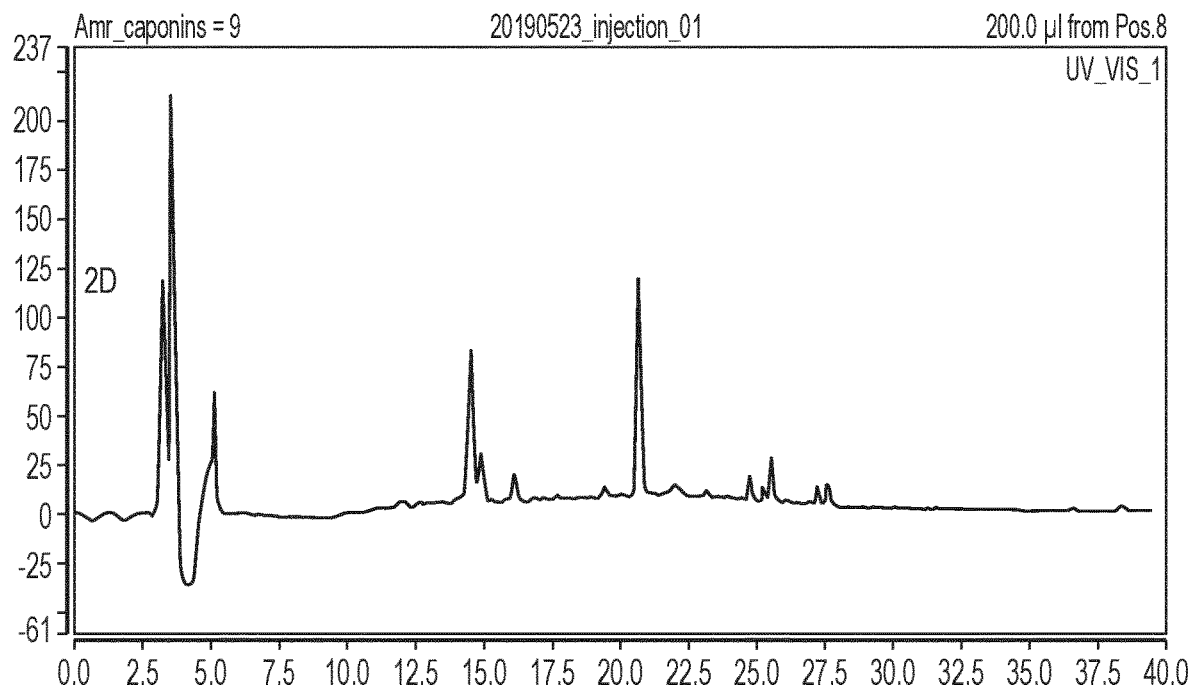

FIG. 13: Semi-preparative HPLC chromatogram for purification of compounds 1 and 2.

Figure 14:
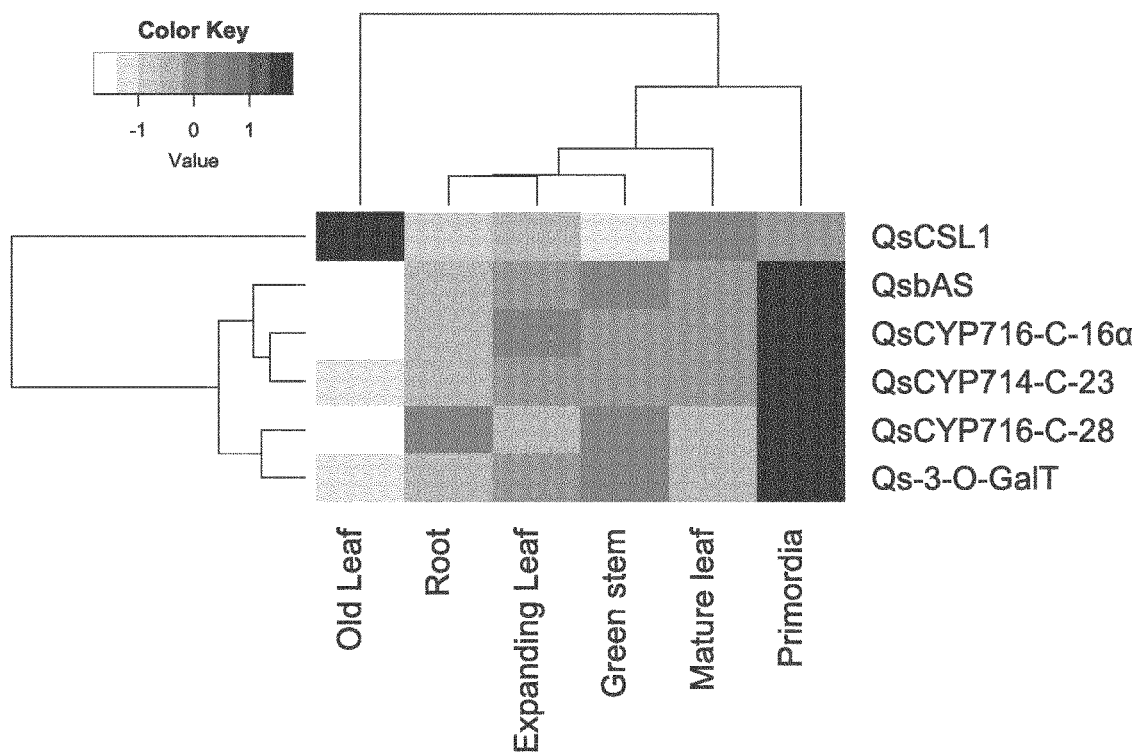

FIG. 14: Heatmap showing the expression profiles of the previously characterised QS-21 biosynthetic genes.

Figure 15:
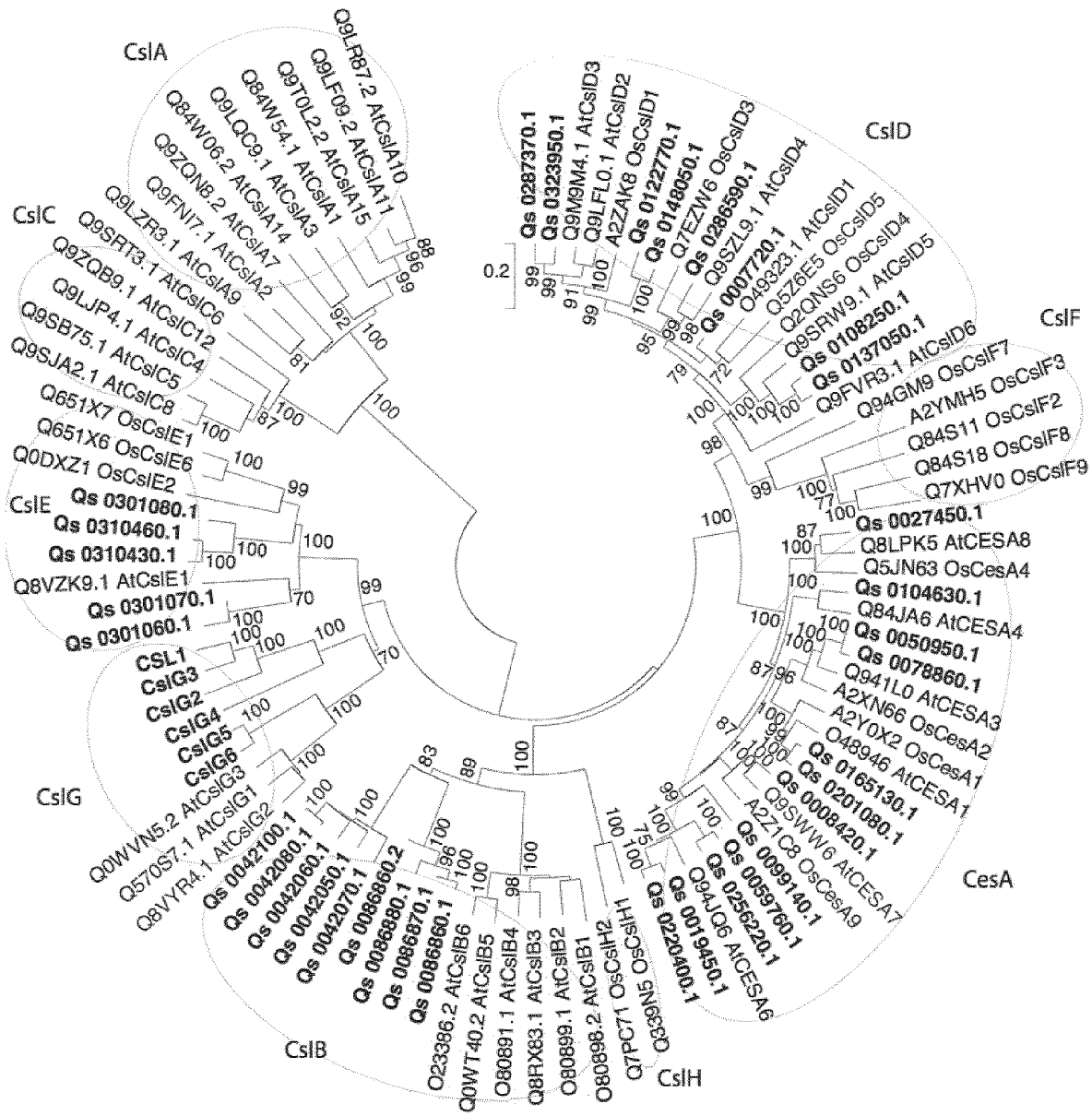

FIG. 15: Phylogenetic tree of *Quillaja saponaria* cellulose synthase superfamily proteins (bold) with cellulose synthase superfamily proteins from *Oryza sativa* and *Arabidopsis thaliana*. The tree was constructed using the Neighbour Joining method with 1000 bootstrap replicates (% support for branch points is shown). The *Q. saponaria* genes in the genomic database consist of a code (QUISA32244_Elv1_) followed by seven digits; this seven-digit code is included in the name for the *Q. saponaria* proteins; *Q. saponaria* proteins in the same subfamily (CslG) as CSL1 have been renamed CslG2-6.

Figure 16:
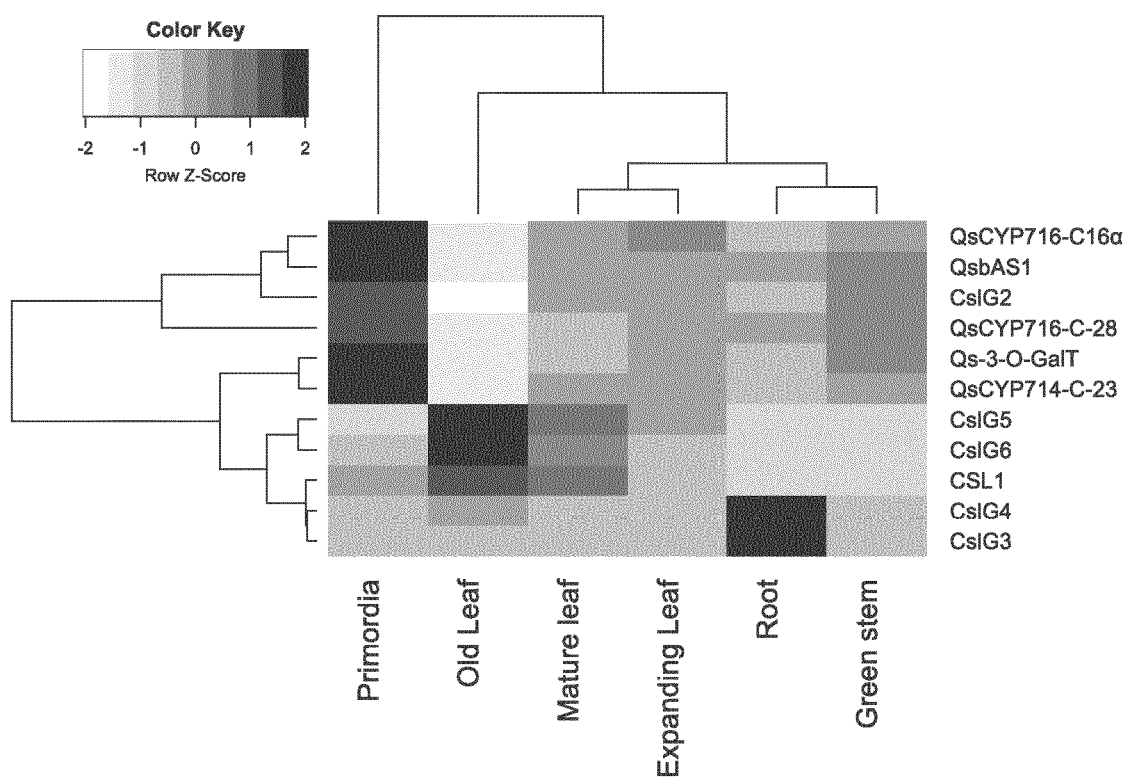

FIG. 16: Heatmap showing the expression profiles of the previously characterised QS-21 biosynthetic genes and CslG2-CslG6.

Figure 17:
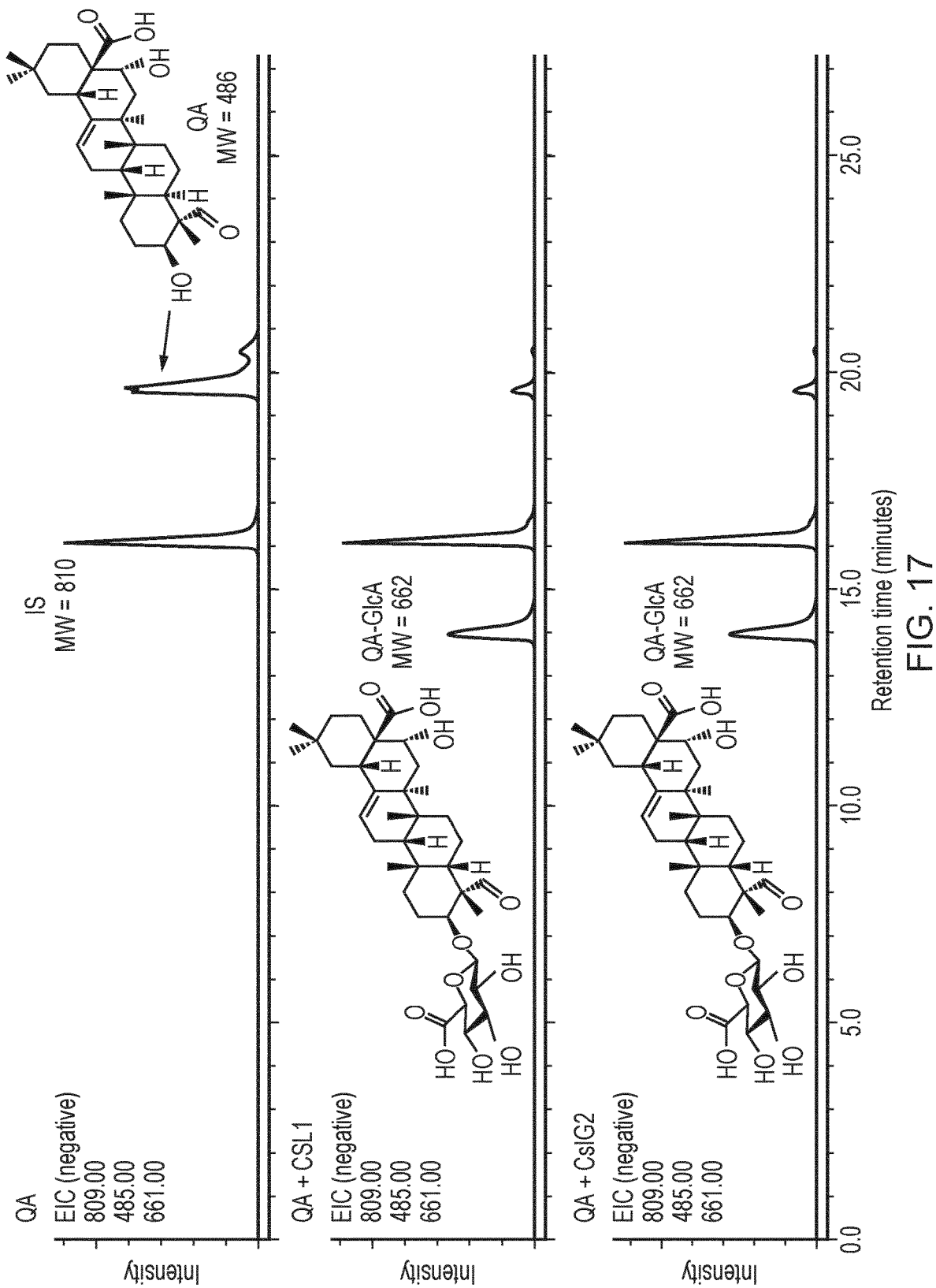

FIG. 17: Co-expression of CslG2 with genes r used for production of quillaic acid (tHMGR/QsbAS/CYP716-C-28/CYP716-C-16α/CYP714-C23) resulted in the reduction of the quillaic acid peak [m/z=485, retention time=19.6 min] and the appearance of a more polar peak with the expected mass of quillaic acid with the addition of a glucuronide residue and the same retention time as the CSL1 product [m/z=661, retention time=14.0 min]. IS=internal standard (digitoxin).

Figure 18:
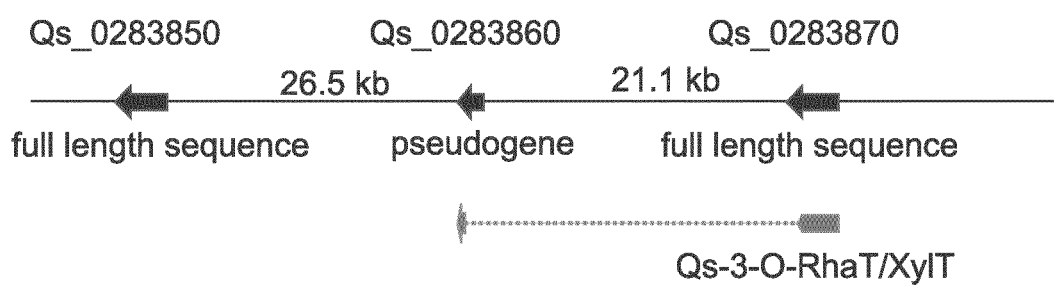

FIG. 18: Qs-3-O-RhaT/XylT is a chimera between two adjacent genes, Qs_0283860 and Qs_0283870 in the *Quillaja saponaria* genome. The *Q. saponaria* genes in the genome database consist of a code (QUISA32244_Elv1) followed by seven digits; this seven-digit code is included in the name for the *Q. saponaria* genes.

Figure 19:
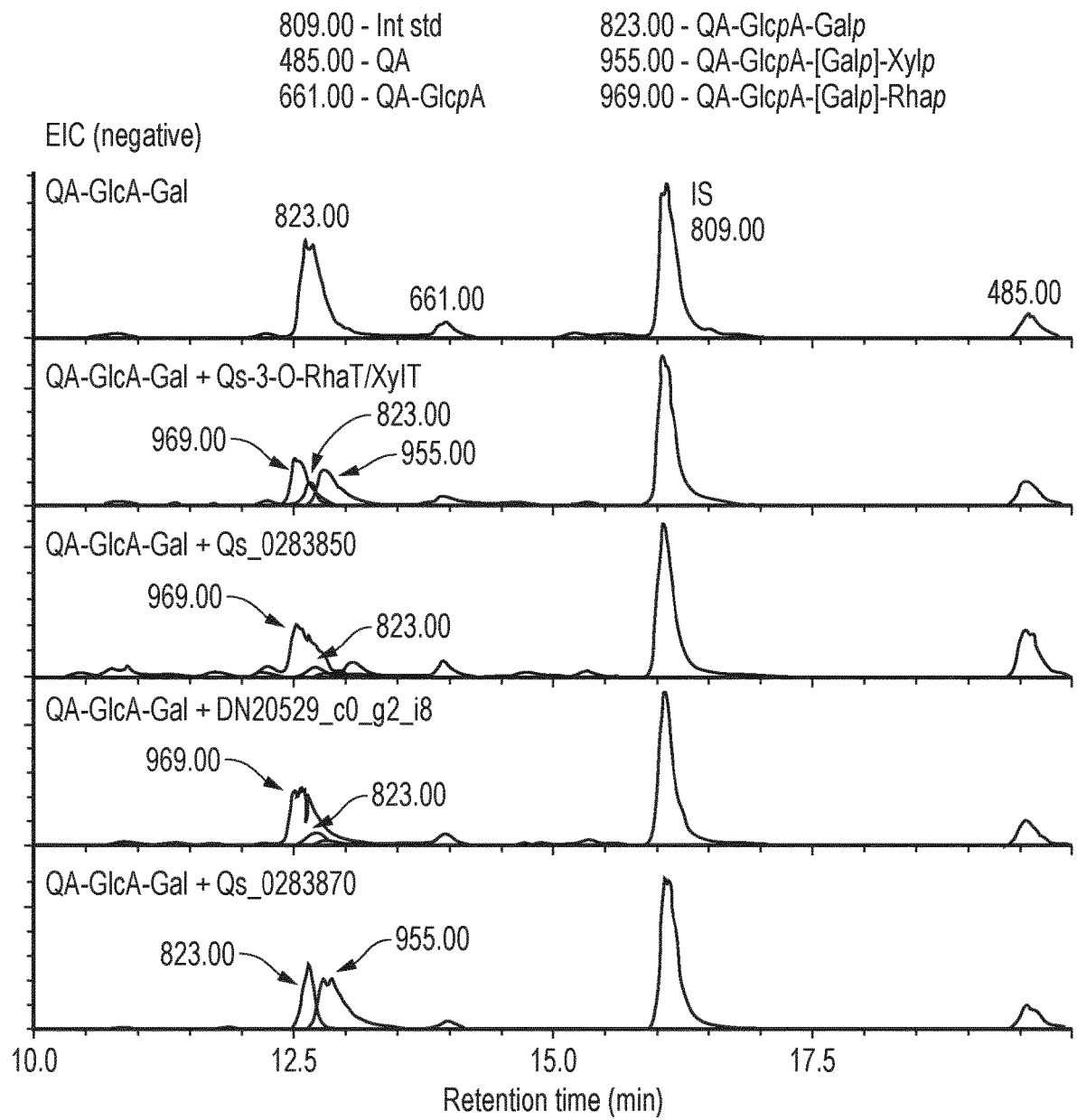
Figure 19:
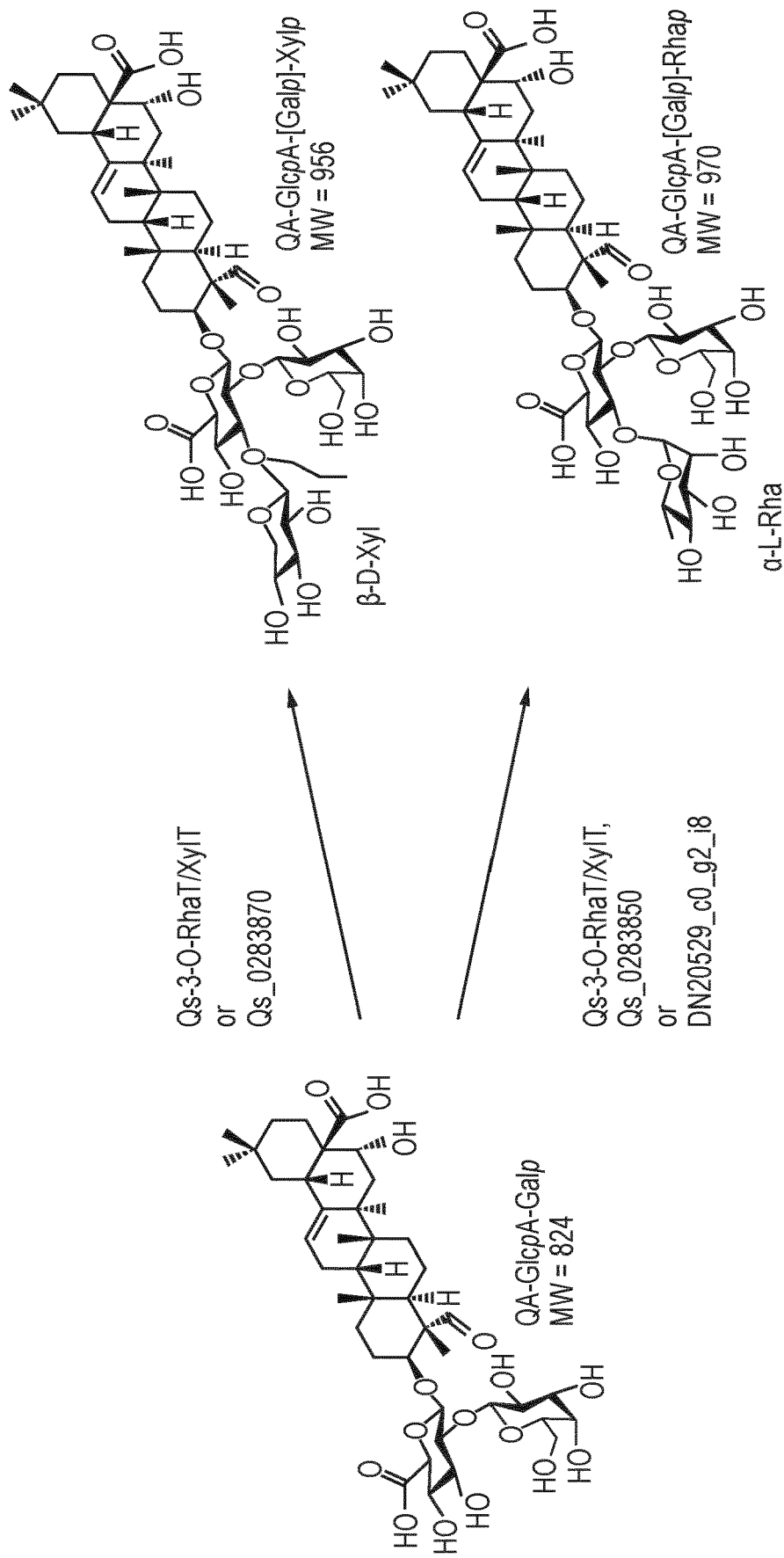

FIG. 19: Conversion of QA-GlcpA-Galp by Qs_0283850, DN20529_c0_g2_i8 and Qs_0283870. Co-expression of the dual function Qs-3-O-RhaT/XylT with the genes used for production of QA-GlcpA-Galp (tHMGR/QsbAS/CYP716-C-28/CYP716-C-16α/CYP714-C23/QsCSL1/Qs-3-O-GalT) results in the conversion of QA-GlcpA-Galp (retention time=12.6 min, MW=824) to QA-GlcpA-[Galp]-Rhap (retention time=12.5 min, MW=970) and QA-GlcpA-[Galp]-Xylp (retention time=12.75 min, MW=956). Co-expression of Qs_0283850 or DN20529_c0_g2_i8 with the genes required for production of QA-GlcpA-Galp resulted in the reduction of the QA-GlcpA-Galp peak at 12.6 minutes and the appearance of a single new peak, with the same retention time (12.5 min) and molecular weight (MW=970) as QA-GlcpA-[Galp]-Rhap. Co-expression of Qs_0283870 with the genes required for production of QA-GlcpA-Galp resulted in the reduction of the QA-GlcpA-Galp peak at 12.6 min and the accumulation of a new single peak with the same retention time (12.75 min) and molecular weight (MW=956) as QA-GlcpA-[Galp]-Xylp.

EXAMPLES

Example 1—Identification and Cloning of Glycosyltransferases from *Q. saponaria*

In order to augment the publicly available transcriptome, we generated genome sequence data (PacBio sequencing performed by the Earlham Institute, Norwich, Norfolk). The genome sequence was annotated using publicly available data (including the '1 KP' leaf transcriptomic data from *Q. saponaria* [4]) and proteins from related plant species in Phytozome.

From this data, we shortlisted a series of sequences which were annotated as putative Family 1 UDP-dependent glycosyltransferases (UGTs)—an important class of enzymes which are known to participate in biosynthesis of many plant natural products, including triterpenes [5, 6]. We refined the initial list (containing ~200 sequences) down to sequences which were also represented in the 1 KP database from which the original QA biosynthetic enzymes were found. The *Q. saponaria* contigs consist of a 4-letter code (OQHZ) followed by seven digits. Where possible, this seven digit code is included for all of the candidate genes below. To further refine this list, we performed phylogenetic analysis using a series of characterised GTs from other plant species (Table 3). This allowed us to prioritise the enzymes which fell into the same phylogenetic groups as currently characterised triterpene UGTs from other plant species (Groups A, D and L) and UGTs with relevant sugar-donor specificity (Group B).

Finally, in recent years it has been proposed that a number of chemically-diverse plant natural products are synthesised by enzymes encoded by physically co-localised genes. These so-called 'biosynthetic gene clusters' (BCGs) could facilitate identification of additional candidate genes. We therefore deployed the 'PlantiSMASH' genome mining tool [7] to predict possible BCGs within the *Q. saponaria* genome. This combination of approaches resulted in a final list of 30 candidate *Q. saponaria* UGTs (FIG. 4) plus one other non-UGT candidate gene.

As described above, the genes for quillaic acid biosynthesis appear to be expressed in leaf tissue and were previously amplified by PCR from leaf cDNA. The same approach was therefore utilised for amplification of the GT candidates. A series of oligonucleotide primers were designed which incorporated 5' attB sites upstream of the target sequence to allow for Gateway® cloning. From this, genes were successfully amplified and cloned into pDONR 207. The clones were sequenced before transfer into the plant expression vector pEAQ-HT-DEST1 [14]. Finally, the expression constructs were transformed individually into *Agrobacterium tumefaciens* (LBA4404) for transient expression in *N. benthamiana*.

Screening of the 31 candidate GTs was performed using transient expression in *N. benthamiana*. All infiltrations included the four *A. tumefaciens* strains carrying the constructs for QA biosynthesis (QsbAS and C-28/C-23/C-16α oxidases) along with a strain carrying tHMGR, a key yield-enhancing enzyme for triterpene production.

Example 2—Identification of Quillaic Acid 3-O Glucuronosyl Transferase

Following LC-MS analysis of the samples, it was discovered that, unexpectedly, one candidate, a predicted 'cellulose synthase-like' (CSL) enzyme (named herein QsCSL1) was active upon quillaic acid. Co-expression of this enzyme with the five *A. tumefaciens* strains for QA-production resulted in significant depletion of the QA peak at 19.2 minutes, accompanied by the appearance of a new peak at 13.9 minutes (FIG. 5). The shift in retention of the peak suggested a significant increase in polarity as would be expected by addition of a sugar. Furthermore, MS analysis of the peak suggested a mass of 662, consistent with the predicted molecular weight of a quillaic acid glucuronoside (FIG. 5). We performed a large scale infiltration of *N. benthamiana* as previously described [19] to purify sufficient amounts of the compound (68.1 g) to assign its structure by NMR. This confirmed it to be 3β-{[β-D-glucopyranosiduronic acid]oxy}-quillaic acid (QA-GlcpA) (Table 11).

Example 3—Identification of QA-GlcpA Galactosyl Transferase

Following the identification of a putative glucuronosyl transferase, the next proposed step was the addition of the β-D-galactose residue.

A triterpene 3-O-glucuronoside-β-1,2-galactosyltransferase, GmUGT73P2 has been previously identified in soybean (*Glycine max*) (Shibuya et al, 2010). This enzyme catalyses the addition of D-galactose to soyasapogenol B monoglucuronide to form soyasaponin III (FIG. 6).

Interestingly, the phylogenetic analysis of the *Q. saponaria* UGT enzymes showed that one candidate, Qs_2073886_D6, is closely related to GmUGT73P2 (FIG. 4). Analysis of the predicted protein sequence of this candidate also revealed that it had a histidine residue characteristic of galactosyl- or arabinosyltransferases (Table 4) (Kubo et al., 2004; Han et al., 2014; Louveau et al., 2018). Therefore Qs_2073886_D6 was prioritised as the possible galactosyltransferase.

Qs_2073886_D6 was coexpressed with the six genes required for production of the putative QA-GlcpA (tHMGR/QsbAS/CYP716-C-28/CYP716-C-16α/CYP714-C23/QsCSL1). HPLC-MS analysis revealed that Qs_2073886_D6 appeared to convert the putative QA-GlcpA product to a new, more polar product at 12.6 minutes (FIG. 7, top). MS analysis of this product suggested a mass of 824 which is consistent with the addition of a hexose, such as galactose (FIG. 7, bottom).

To establish further evidence for the identity of the new product, we utilised the soybean (*Glycine max*) triterpene 3-O-glucuronoside-β-1,2-galactosyltransferase enzyme, GmUGT73P2. It was reasoned that this enzyme may show similar galactosyltransferase activity towards the putative QA-GlcpA product. An infiltration was thus also performed with coexpression of the six enzymes necessary for synthesis of the QA-GlcpA and GmUGT73P2. LC-MS analysis of the infiltrated leaf extracts revealed that a peak could indeed be observed in the GmSGT2-expressing samples which had a matching retention time and mass spectrum to the product seen at 12.6 minutes in the *Q. saponaria* galactosyltransferase-expressing samples (FIG. 7, top). This provides substantial evidence that the *Q. saponaria* enzyme has triterpene 3-O-glucuronoside-β-1,2-galactosyltransferase activity, to form the quillaic acid disaccharide QA-GlcpA-Galp. The enzyme is therefore herein named Qs-3-O-GalT. Qs-3-O-GalT and GmUGT73P2 share 68% sequence identity at the nucleotide level and 57% at the protein level.

We additionally performed a large scale infiltration of tHMGR/QsbAS/CYP716-C-28/CYP716-C-16α/CYP714-C23/QsCSL1/Qs-3-O-GalT in *N. benthamiana* as previously described [19] to purify this compound (32.1 g) to assign its structure by NMR. This confirmed it to be 3β-{[β-D-galactopyranosyl-(1->2)-β-D-glucopyranosiduronic acid]oxy}-quillaic acid (QA-GlcpA-Galp) (Table 13).

Example 4—Identification of QA-GlcpA-Galp Dual Rhamnosyl/Xylosyl Transferase

We next repeated the process of screening the remaining GT candidates against the QA-GlcpA-Galp product. As before, GT candidates were screened by co-expression with the seven genes required to make QA-GlcpA-Galp (tHMGR/QsbAS/CYP716-C-28/CYP716-C-16α/CYP714-C23/QsCSL1/Qs-3-O-GalT). With this strategy we identified a UGT enzyme which resulted in depletion of the QA-GlcpA-Galp product. However, rather than a single new product, we observed the appearance of two new products with very close retention times to the former QA-GlcpA-Galp (FIG. 8). The mass spectra of each of these products was unique, with the first (retention time 12.50 min, FIG. 8 bottom left) suggesting a mass of 970, while the second (retention time 12.8 min, FIG. 8 bottom right) suggesting a mass of 956. Compared to the QA-GlcpA-Galp product (MW=824), peaks 1 and 2 would be consistent with addition of a deoxyhexose and a pentose, respectively.

*Q. saponaria* is known to produce in excess of 100 different saponins [16]. Within these saponins, the 3-O-GlcpA-β-1,2-D-Galp disaccharide of QA is well conserved [17], while there is variation of the terminal sugar attached at the C3 position of GlcpA within the QA branched trisaccharide. The variations are the addition of α-L-rhamnose (Rhap—a deoxyhexose) or β-D-xylose (Xylp—a pentose) [17], with the latter observed in QS-21 (FIG. 1). Therefore, the new compounds observed in *N. benthamiana* are consistent with addition of either Rhap or Xylp at the GlcA 3-O position of the QA-Glcp-Galp disaccharide. These compounds are named QA-GlcpA-[Galp]-Rhap (3β-{[α-L-rhamnopyranosyl-(1->3)-β-D-galactopyranosyl-(1->2)]-β-D-glucopyranosiduronic acid]oxy}-quillaic acid) and QA-GlcpA-[Galp]-Xylp (3β-{[[β-D-xylopyranosyl-(1->3)-[β-D-galactopyranosyl-(1->2)]-β-D-glucopyranosiduronic acid]oxy}-quillaic acid). The isolation and structural verification of these compounds are described below. The sugar transferase is referred to as Qs-3-O-RhaT/XylT and a schematic for the biosynthesis of the two trisaccharides QA-GlcpA-[Galp]-Rhap and QA-GlcpA-[Galp]-Xylp are shown in FIG. 9.

Previously, chemical profiling of *Q. saponaria* trees has demonstrated the existence of distinct 'chemotypes' which vary in their ability to produce saponins containing either Rhap or Xylp attached to GlcpA-3-O (see WO 2018/057031). One explanation for these observations is the presence of two distinct alleles of the terminal sugar transferase with differing sugar specificity as previously demonstrated for soybean [18]. Notwithstanding this, the present disclosure provides an enzyme which is capable of catalysing addition of two distinct sugars at the same position.

Example 5—Purification and NMR Validation of the Trisaccharide Produced in *N. benthamiana*

To verify the structures of the compounds 1 and 2 (FIG. 10), we performed a large scale infiltration of *N. benthamiana* plants as previously described [19]. Plants were infiltrated with the *A. tumefaciens* strains carrying the eight pEAQ-HT-DEST1 constructs for production of the two trisaccharides (tHMGR, QsbAS, CYP716-C-28, CYP716-C-16α, CYP714-C-23, QsCSL1, Qs-3-O-GalT and Qs-3-O-RhaT/XylT). After harvesting and subsequent isolation of the compounds, we successfully obtained 1.8 and 0.9 mg of purified 1 and 2, respectively. Subsequent $^1$H and $^{13}$C NMR analysis was performed and validated the identity of the compound 1 (3β-{[α-L-rhamnopyranosyl-(1->3)-[β-D-galactopyranosyl-(1->2)]-β-D-glucopyranosiduronic acid] oxy}-quillaic acid) and compound 2 as (3β-{[[β-D-xylopyranosyl-(1->3)-[β-D-galactopyranosyl-(1->2)]-β-D-glucopyranosiduronic acid]oxy}-quillaic acid) (FIG. 10). NMR assignments are given in Table 1 and FIG. 11.

Example 6—Use of QA-3-O-TriS Genes, Optionally in Combination with QA Genes, for Production of Stably Transformed Plants Triterpenes have previously been produced using engineered transgenic plant lines (e.g. *Arabidopsis*, Wheat). A series of Golden Gate [23] vectors which allows for construction of multigene vectors and allows integration of an entire pathway into a single locus have been reported. These can be applied analogously to the present invention, in the light of the disclosure herein.

The QA-3-O-TriS genes described herein, optionally in conjunction with QA genes of prior-filed unpublished PCT/EP2018/086430 (subsequently published as WO 2019/122259), may thus be used to produce stable transgenic plants in the light of the present disclosure in combination with known transgenic technologies.

Example 7—Identification of Quillaic Acid 3-O Glucuronosyl Transferase CSLG2 (QsCSLG2)

As described in the preceding Examples, the '1 KP' *Q. saponaria* leaf transcriptome was used to identify genes involved in the biosynthesis of quillaic acid (QsbAS, QsCYP716-C-16α, QsCYP714-C-23 and QsCYP716-C-28) and the trisaccharide at the C-3 position of QS-21 (QsCSL1, Qs-3-O-GalT and Qs-3-O-RhaT/XylT).

Genes involved in triterpene glycoside biosynthesis are typically co-expressed [25]. In order to investigate the expression pattern of the characterised QS-21 biosynthetic genes across multiple tissues, RNA-seq data were generated for six *Q. saponaria* tissues (primordia, expanding leaf, mature leaf, old leaf, green stem and root). The gene expression profiles for QsbAS, QsCYP716-C-16α, QsCYP714-C-23, QsCYP716-C-28 and Qs-3-O-GalT showed a pattern of low expression in old leaf and high expression in primordia, with some variability in expression levels in root, expanding leaf, green stem and mature leaf (FIG. 14). In contrast, the expression profile for QsCSL1 had the highest expression level in old leaf (FIG. 14). Qs-3-O-RhaT/XylT was not included in this analysis (see Example 8 below).

As the expression profile for QsCSL1 did not follow the general pattern seen for the other characterised QS-21 genes, it was investigated whether there might be genes related to QsCSL1 that did have the QS-21 gene expression pattern and which therefore might be involved in QS-21 biosynthesis. QsCSL1 was used in a BLASTp search to identify cellulose synthase-like genes in the *Q. saponaria* annotated genome. This identified 39 additional cellulose synthase superfamily genes, of which five (named CslG2 to CslG6) were in the same subfamily as QsCSL1 (FIG. 15).

Analysis of the expression profile of these genes show that CslG3-CslG6 are expressed most highly in old leaf or in the root (FIG. 16). Interestingly, one gene, CslG2, shared the same expression profile as the other QS-21 biosynthetic genes, with high relative expression in primordia and low relative expression in old leaves (FIG. 16). This gene shares 78% DNA sequence identity and 70% protein sequence identity with QsCSL1. To investigate potential quillaic acid glucuronosyltransferase activity, CslG2 was amplified from leaf cDNA, cloned into the plant expression vector pEAQ-HT-DEST1 and transformed into *A. tumefaciens* for transient expression in *Nicotiana benthamiana*. QsbAS, QsCYP716-C-16α, QsCYP714-C-23, QsCYP716-C-28 and CslG2 were transiently co-expressed in *Nicotiana benthamiana*. This revealed that CslG2 has the same activity as CSL1: a reduction of the quillaic acid peak and the formation of a more polar peak with the mass of quillaic acid with the addition of a glucuronide residue (FIG. 17). We performed a large scale infiltration of *N. benthamiana* as described previously [19], to purify 2.1 mg of the target molecule. This was confirmed by NMR to be 3β-{[β-D-glucopyranosiduronic acid]oxy}-quillaic acid (QA-GlcpA) (Table 12).

Example 8—Identification of QA-GlcpA-Galp Xylosyltransferase and Rhamnosyltransferases As explained in Example 4, the DNA sequence for the dual glycosyltransferase Qs-3-O-RhaT/XylT was not identified in the *Quillaja saponaria* genomic dataset. Instead, this gene appeared to be a chimera between two adjacent genes, Qs_0283860 (a pseudogene) and Qs_0283870 (FIG. 18). The section of the Qs_0283860 pseudogene that is incorporated into the Qs-3-O-RhaT/XylT sequence has high sequence similarity to a further adjacent gene, Qs_0283850 (FIG. 18, Table 9).

It is theoretically possible that there are alleles of these genes that are not represented in the genomic *Q. saponaria* dataset or that this region was incorrectly resolved. As an alternative database, a de novo transcriptome assembly was generated from the *Q. saponaria* primordia RNA-seq reads [26]. A BLASTn search using the three genomic genes and Qs-3-O-RhaT/XylT as queries identified two full-length transcripts: DN20529_c0_g2_i6, which was identical to the sequence of Qs_0283870, corroborating the sequence of this gene; and DN20529_c0_g2_i8, which had 99% DNA sequence identity to the Qs_0283860 pseudogene and 98% DNA sequence identity to Qs_0283850 (Table 9).

To investigate the presence and function of these genes, we attempted to amplify the sequences from *Q. saponaria* leaf cDNA. Qs_0283850 and Qs_0283870 were successfully amplified. Primers designed to amplify the pseudogene Qs_0283860 amplified a full-length sequence with 100% sequence identity in the coding region of the gene predicted by the de novo transcriptome, DN20529_c0_g2_i8. This amplified sequence is subsequently referred to as DN20529_c0_g2_i8. These three amplified genes (Qs_0283850, Qs_0283870 and DN20529_c0 g2_i8) were cloned into the plant expression vector pEAQ-HT-DEST1 and transformed into *A. tumefaciens* for transient expression in *Nicotiana benthamiana*.

As described above, co-expression of Qs-3-O-RhaT/XylT with the seven genes able to make QA-GlcpA-Galp (tHMGR/QsbAS/CYP716-C-28/CYP716-C-16α/CYP714-C23/QsCSL1/Qs-3-O-GalT) resulted in the appearance of trisaccharides QA-GlcpA-[Galp]-Rhap (retention time=12.5 min, MW=970) and QA-GlcpA-[Galp]-Xylp (retention time=12.75 min, MW=956), which have very close retention times to the former QA-GlcpA-Gal (retention time=12.6 min, MW=824) (FIG. 19).

Similarly, co-expression of either Qs_0283850, Qs_0283870 or DN20529_c0 g2_i8 with the genes required to make QA-GlcpA-Galp revealed that all three enzymes were able to convert QA-GlcpA-Galp, but resulted in the production of one new product each (FIG. 19). Qs_0283850 and DN20529_c0_g2_i8 shared the same activity, reducing the QA-GlcpA-Galp peak and accumulating a more polar peak with the same retention time (12.5 min) and molecular weight (MW=970) as QA-GlcpA-[Galp]-Rhap (FIG. 19). This suggests that Qs_0283850 and DN20529_c0_g2_i8 have rhamnosyltransferase activity and can produce QA-GlcpA-[Galp]-Rhap as a single product without producing QA-GlcpA-[Galp]-Xylp. A large scale infiltration of *N. benthamiana* [19] to transiently express QsbAS, QsCYP716-C-16α, QsCYP714-C-23, QsCYP716-C-28, CslG2, Qs-3-O-GalT and Qs_0283850 was carried out. Purification of the product (43.3 mg) and structural analysis by NMR confirmed its structure to be 3β-{[α-L-rhamnopyranosyl-(1->3)-[β-D-galactopyranosyl-(1->2)]-β-D-glucopyranosiduronic acid]oxy}-quillaic acid (QA-GlcpA-[Galp]-Rhap) (Table 14).

Co-expression of Qs_0283870 with the genes required to make QA-GlcpA-Galp also reduced the QA-GlcpA-Galp peak, however it accumulated a less polar compound with the same retention time (12.75 min) and molecular weight (MW=956) as QA-GlcpA-[Galp]-Xylp (FIG. 6). A large scale infiltration of *N. benthamiana* plants [19] to co-express tHMGR/QsbAS/CYP716-C-28/CYP716-C-16α/CYP714-C23/QsCskG2/Qs-3-O-GalT/Qs_0283870 was carried out. Purification of the resulting compound (21.6 mg) and structural analysis by NMR confirmed its structure to be 3β-{[β-D-xylopyranosyl-(1->3)-[β-D-galactopyranosyl-(1->2)]-β-D-glucopyranosiduronic acid]oxy}-quillaic acid (QA-GlcpA-[Galp]-Xylp) (Table 15).

This suggests that Qs_0283870 is primarily a xylosyltransferase and can produce QA-GlcpA-[Galp]-Xylp without producing significant amounts of QA-GlcpA-[Galp]-Rhap.

Materials and Methods

Phylogenetic Analysis of UGT Candidates

Amino acid sequences were deduced from the predicted full-length coding sequences of the Q. saponaria UGTs. Representative amino acid sequences of characterised glycosyltransferase family 1 UGTs from other plant species (Table 3) were obtained from the NCBI database and incorporated into the phylogenetic analysis. Protein sequences were aligned using MAFFT (https://mafft.cbrc.jp/alignment/software/). The unrooted trees were constructed in MEGA7 by the Neighbor-Joining method with 1000 bootstrap replicates [20, 21].

Primers and Cloning

The genes encoding the enzymes described herein (QsCSL1, Qs-3-O-GalT, Qs-3-O-RhaT/XylT, QsCslG2, Qs_0283850, DN20529_c0_g2_i8 and Qs_0283870) were amplified by PCR from cDNA derived from leaf tissue of Q. saponaria. PCR was performed using the primers detailed in Tables 2 and 10, using iProof polymerase with thermal cycling according to the manufacturer's recommendations. The resultant PCR products were purified (Qiagen PCR cleanup kit) and each cloned into the pDONR207 vector using BP clonase according to the manufacturer's instructions. The BP reaction was transformed into E. coli and the resulting transformants were cultured and the plasmids isolated by miniprep (Qiagen). The isolated plasmids were sequenced (Eurofins) to verify the presence of the correct genes. Next each of the three genes were further subcloned into the pEAQ-HT-DEST1 expression vector using LR clonase. The resulting vectors were used to transform A. tumefaciens LBA4404 by flash freezing in liquid $N_2$.

Agroinfiltration of N. benthamiana Leaves

Agroinfiltration was performed using a needleless syringe as previously described [19]. All genes were expressed from pEAQ-HT-DEST1 binary expression vectors [14] in A. tumefaciens LBA4404 as described above. Cultivation of bacteria and plants is as described in [19].

Preparation of N. benthamiana Leaf Extracts for LC-MS Analysis

Leaves were harvested 5 days after agroinfiltration and freeze-dried. Freeze-dried leaf material (10 mg per sample) was ground at 1000 rpm for 1 min (Geno/Grinder 2010, Spex SamplePrep). Extractions were carried out in 550 μL 80% methanol with 20 μg/mL of digitoxin (internal standard; Sigma) for 20 min at 40° C., with shaking at 1400 rpm (Thermomixer Comfort, Eppendorf). The sample was partitioned twice with 400 μL hexane. The aqueous phase was dried under vacuum at 40° C. (EZ-2 Series Evaporator, Genevac). Dried material was resuspended in 75 μL of 100% methanol and filtered at 12, 500 g for 30 sec (0.2 μm, Spin-X, Costar). Filtered samples were transferred to glass vials and analysed as detailed below.

LC-MS Analysis of N. benthamiana Leaf Extracts

Analysis was carried out using a Prominence HPLC system with single quadrupole mass spectrometer LCMS-2020 (Shimadzu) and Corona Veo RS Charged Aerosol Detector (CAD) (Dionex). Detection: MS (dual ESI/APCI ionization, DL temp 250° C., neb gas flow 15 L·min−1, heat block temp 400° C., spray voltage Pos 4.5 kV, Neg −3.5 kV) CAD: data collection rate 10 Hz, filter constant 3.6 s, 925 evaporator temp. 35° C., ion trap voltage 20.5 V. Method: Solvent A: [$H_2O$+0.1% formic acid] Solvent B: [acetonitrile ($CH_3CN$)+0.1% formic acid. Injection volume: 10 μL. Gradient: 15% [B] from 0 to 1.5 min, 15% to 60% [B] from 1.5 to 26 min, 60% to 100% [B] from 26 to 26.5 min, 100% [B] from 26.5 to 28.5 min, 100% to 15% [B] from 28.5 to 29 min, 35% [B] from 29 to 30 min. Method was performed using a flow rate of 0.3 mL·min-1 and a Kinetex column 2.6 μm XB-C18 100 Å, 50×2.1 mm (Phenomenex). Analysis was performed using LabSolutions software (Shimadzu).

Large Scale Vacuum Infiltration of N. benthamiana

A total of 198 plants were infiltrated by vacuum as previously described [19, 22] with the A. tumefaciens strains carrying the pEAQ-HT-DEST1 constructs for tHMGR, QsbAS, CYP716-C-28, CYP716-C-16α, CYP714-C-23, QsCSL1, Qs-3-O-GalT and Qs-3-O-RhaT/XylT. Plants were harvested after 4 days and freeze dried, resulting in a total of 175.25 g dry leaf material.

Purification of Compounds from Large Scale Infiltrations of N. benthamiana

General Procedures

Organic solvents used for extraction and flash chromatography were reagent grade and used directly without further distillation. HPLC mobile phases were prepared using HPLC grade solvents. LC-MS spectral data were recorded on SHIMADZU-2020, single quad, using Kinetex-XB-$C_{18}$ (50×10 mm i.d.; 2.6 μm; USA), (JIC, UK). 1D and 2D NMR spectra were recorded on Bruker Avance 600 MHz spectrometer equipped with a BBFO Plus Smart probe and a triple resonance TCI cryoprobe, respectively (JIC, UK). The chemical shifts are relative to the residual signal solvent (MeOH-$d_4$: $δ_H$ 3.31; $δ_C$ 49.15). Preparative HPLC experiments were performed on Ultimate 3000 using Luna $C_{18}$ column (250×10 mm i.d.; 5 μm; USA). Flash column chromatography (FCC) was performed using an Isolera One (Biotage), using SNAP Ultra 50 g columns. Analytical TLC experiments were performed on silica gel precoated aluminium plates (F254, 20×20 cm, Merck KGaA, Germany). TLC plates were visualized under UV light (254 nm) followed by staining with p-anisaldehyde (2% v/v p-anisaldehyde, 2% v/v, Conc. $H_2SO_4$).

Extraction and Isolation

Dried N. benthamiana powder was mixed with quartz sand (0.3-0.9 mm). This mixture was layered on top of a bottom layer of quartz sand (0.3-0.9 mm) 3 cm in depth within a 120 mL extraction cell. Extraction was performed using a Speed Extractor E-914 (Büchi) with three cycles at 100° C. and a pressure of 130 bar. Cycle one had zero hold time, and cycles two and three had 5 min hold times. The run finished with a 1 min solvent flush and 12 min $N_2$ flush. The dried leaves were initially extracted by hexane for defatting, followed by subsequent exhaustive extraction using methanol. Organic layers were combined together and evaporated under reduced pressure. The crude methanolic extract was dissolved in the least amount of methanol and diluted with equivalent volume of water, then it was successfully partitioned using separation funnel against hexane, dichloromethane, ethyl acetate and n-butanol. The butanol layer was recollected and dried over anhydrous $NaSO_4$, evaporated under reduced pressure and subjected to a normal phase silica-gel flash chromatography (35-70 μm), using a long gradient of DCM/MeOH [100/0-0/100] along 30 min. The column was further washed with ethyl acetate/acetone/ water/formic acid (5/3/0.5/0.5). All fractions were monitored by TLC using different eluent systems and combined together according to their polarities. Based on the LC-MS profiling and $^1$H NMR as well, promising fractions were introduced for further reparative chromatographic purifications by reversed phase (preparative/semipreparative $C_{18}$-HPLC) using the eluent system water/acetonitrile containing 0.1% formic acid, to finally afford pure saponins. The detailed isolation scheme of the isolated compounds for the purification of compounds 1 and 2 (see Examples 4 and 5) and their quantities is given (FIG. 12). The same method was used to purify trisaccharide compounds described in Example 8. For mono- and disaccharide compounds described in Examples 2, 3 and 7, extraction and isolation were carried out as above, with the following changes: the liquid-liquid partition was carried out against ethyl acetate, the organic layer was dried over anhydrous $MgSO_4$ and the saponin fractions were subsequently purified by reverse-phase C18 HPLC.

NMR Analysis

NMR spectra were recorded in Fourier transform mode at a nominal frequency of 600 MHz for $^1$H NMR and 150 MHz for $^{13}$C NMR in deuterated methanol unless otherwise indicated. Chemical investigation of the n-butanol fraction of *N. benthamiana* leaves (Examples 4 and 5) afforded the isolation of two previously reported triterpene saponins, namely 3β-{[α-L-rhamnopyranosyl-(1->3)-[β-D-galactopyranosyl-(1->2)]-β-D-glucopyranosiduronic acid]oxy}-quillaic acid (1) and 3β-{[β-D-xylopyranosyl-(1->3)-[β-D-galactopyranosyl-(1->2)]-β-D-glucopyranosiduronic acid]oxy}-quillaic acid (2) (FIG. 10). Their structures were resolved based on a combination of spectral tools including extensive full set of 2D-NMR, mass spectroscopy and reported literature [23] (Table 1 and FIG. 11).

Alignment of RNA Sequences and Heatmaps

RNA-seq data (Illumina-sequenced reads) were aligned to the *Q. saponaria* genome using the STAR package (version 2.5) [27] and quantified using the featureCounts program (http://subread.sourceforge.net/, version 1.6.0). The heatmaps were drawn in R using heatmap.2, https://CRAN.R-proiect.org/packaae=gplots).

REFERENCES

1. Del Giudice, G., R. Rappuoli, and A. M. Didierlaurent, *Correlates of adjuvanticity: A review on adjuvants in licensed vaccines*. Seminars in Immunology, 2018. 39: p. 14-21.
2. Marciani, D. J., *Elucidating the Mechanisms of Action of Saponin-Derived Adjuvants*. Trends in Pharmacological Sciences, 2018. 39(6): p. 573-585.
3. FDA. Available from: https://www.fda.qov/vaccines-blood-biologics/vaccines/shinqrix.
4. Johnson, M. T. J., et al., *Evaluating Methods for Isolating Total RNA and Predicting the Success of Sequencing Phylogenetically Diverse Plant Transcriptomes*. PLOS ONE, 2012. 7(11): p. e50226.
5. Bowles, D., et al., *Glycosyltransferases of lipophilic small molecules*. Annu Rev Plant Biol, 2006. 57: p. 567-97.
6. Louveau, T. and A. Osbourn, *The Sweet Side of Plant-Specialized Metabolism*. Cold Spring Harb Perspect Biol (In Press), 2019.
7. Kautsar, S. A., et al., *plantiSMASH: automated identification, annotation and expression analysis of plant biosynthetic gene clusters*. Nucleic Acids Res, 2017.
8. Luang, S., et al., *Rice Os9BGlu31 is a transglucosidase with the capacity to equilibrate phenylpropanoid, flavonoid, and phytohormone glycoconjugates*. J Biol Chem, 2013. 288(14): p. 10111-23.
9. Matsuba, Y., et al., *A novel glucosylation reaction on anthocyanins catalyzed by acyl—glucose-dependent glucosyltransferase in the petals of carnation and delphinium*. Plant Cell, 2010. 22(10): p. 3374-89.
10. Miyahara, T., et al., *Isolation of an acyl-glucose-dependent anthocyanin 7-O-glucosyltransferase from the monocot Agapanthus africanus*. J Plant Physiol, 2012. 169(13): p. 1321-6.
11. Miyahara, T., et al., *Isolation of anthocyanin 7-O-glucosyltransferase from Canterbury bells (Campanula medium)*. Plant Biotechnology, 2014. advpub.
12. Nishizaki, Y., et al., *p-Hydroxybenzoyl-glucose is a zwitter donor for the biosynthesis of 7-polyacylated anthocyanin in Delphinium*. Plant Cell, 2013. 25(10): p. 4150-65.
13. Song, X., et al., *Genome-wide characterization of the cellulose synthase gene superfamily in Solanum lycopersicum*. Gene, 2019. 688: p. 71-83.
14. Sainsbury, F., E. C. Thuenemann, and G. P. Lomonossoff, *pEAQ: versatile expression vectors for easy and quick transient expression of heterologous proteins in plants*. Plant Biotechnol J, 2009. 7(7): p. 682-93.
15. Louveau, T., et al., *Analysis of two new arabinosyltransferases belonging to the carbohydrate-active enzyme (CAZY) glycosyl transferase family 1 provides insights into disease resistance and sugar donor specificity*. The Plant Cell, 2018: p. tpc.00641.2018.
16. Kite, G. C., M. J. Howes, and M. S. Simmonds, *Metabolomic analysis of saponins in crude extracts of Quillaja saponaria by liquid chromatography/mass spectrometry for product authentication*. Rapid Commun Mass Spectrom, 2004. 18(23): p. 2859-70.
17. Fleck, J. D., et al., *Saponins from Quillaja saponaria and Quillaja brasiliensis: Particular Chemical Characteristics and Biological Activities*. Molecules, 2019. 24(1).
18. Sayama, T., et al., *The Sg-1 glycosyltransferase locus regulates structural diversity of triterpenoid saponins of soybean*. Plant Cell, 2012. 24(5): p. 2123-38.
19. Reed, J., et al., *A translational synthetic biology platform for rapid access to gram-scale quantities of novel drug-like molecules*. Metab Eng, 2017. 42: p. 185-193.
20. Kumar, S., G. Stecher, and K. Tamura, *MEGA7: Molecular Evolutionary Genetics Analysis Version 70 for Bigger Datasets*. Mol Biol Evol, 2016. 33(7): p. 1870-4.
21. Saitou, N. and M. Nei, *The neighbor-joining method: a new method for reconstructing phylogenetic trees*. Mol Biol Evol, 1987. 4(4): p. 406-25.
22. Stephenson, M. J., et al., *Transient Expression in Nicotiana Benthamiana Leaves for Triterpene Production at a Preparative Scale*. Journal of visualized experiments: JoVE, 2018(138): p. 58169.
23. Guo, S., et al., *Triterpenoid saponins from Quillaja saponaria*. Phytochemistry, 1998. 48(1): p. 175-180.
24. Miettinen, K., et al., *The ancient CYP716 family is a major contributor to the diversification of eudicot triterpenoid biosynthesis*. Nat Commun, 2017. 8: p. 14153.
25. Thimmappa, R., Geisler, K., Louveau, T., O'Maille, P., and Osbourn, A. (2014). Triterpene biosynthesis in plants. *Annu. Rev. Plant Biol.*, 65:225-257.
26. Grabherr, M. G., et al. (2011). Full-length transcriptome assembly from RNA-seq data without a reference genome. *Nat. Biotechnol.*, 29:644-652.
27. Dobin, A., et al. (2013). STAR: ultrafast universal RNA-seq aligner. *Bioinformatics*, 29:15-21.

Tables and Sequences

TABLE 1

$^1$H, $^{13}$C NMR spectral data for compounds 1 and 2 in MeOH-d4, (600, 150 MHz)

| | QA-GlcpA-[Galp]-Rhap (1) | | QA-GlcpA-[Galp]-Rhap (2) | |
|---|---|---|---|---|
| Position No. | $\delta_C$, Type | $\delta_H$ mult, (J in Hz) | $\delta_C$, Type | $\delta_H$ mult, (J in Hz) |
| 1 | 39.4, CH$_2$ | 1.71/1.13, m | 39.3, CH$_2$ | 1.69/1.10, m |
| 2 | 25.7, CH$_2$ | 2.02/1.79, m | 25.8, CH$_2$ | 2.05/1.77, m |
| 3 | 86.0, CH | 3.85, dd, (11.9, 4.55) | 85.9, CH | 3.86, m |
| 4 | 56.4, Cq | — | 56.5, Cq | — |
| 5 | 49.2, CH | 1.35, m | 49.1, CH | 1.32, m |
| 6 | 21.4, CH$_2$ | 1.50/0.90, m | 21.5, CH$_2$ | 1.47/0.90, m |
| 7 | 33.7, CH$_2$ | 1.57/1.25, m | 33.8, CH$_2$ | 1.55/1.23, m |
| 8 | 41.0, Cq | — | 41.1, Cq HMBC | — |
| 9 | 48.2, CH | 1.77, m | 48.2, CH | 1.75, m |
| 10 | 37.2, Cq | — | 37.1, Cq | — |
| 11 | 24.6, CH$_2$ | 1.93/1.93, m | 24.6, CH$_2$ | 1.92/1.92 |
| 12 | 123.3, CH | 5.30, br t (3.7) | 123.4, CH | 5.30, bd s |
| 13 | 145.3, Cq | — | 145.3, Cq HMBC | — |
| 14 | 42.8, Cq | — | 42.8, Cq | — |
| 15 | 36.3, CH$_2$ | 1.84/1.34, m | 36.4, CH$_2$ | 1.84/1.33, m |
| 16 | 75.4, CH | 4.45, m | 75.5, CH | 4.44, br s |
| 17 | 49.7, Cq | — | 49.7, Cq | — |
| 18 | 42.2, CH | 3.01, dd, (14.3, 4.4) | 42.3, CH | 3.01, d (14.3, 4.4) |
| 19 | 47.8, CH$_2$ | 2.30, t (13.6)/1.04, m | 47.9, CH$_2$ | 2.29, t (13.6)/1.03, m |
| 20 | 31.5, Cq | — | 30.9, Cq | — |
| 21 | 36.7, CH$_2$ | 1.96/1.16, m | 36.8, CH$_2$ | 195/1.14, m |
| 22 | 32.9, CH$_2$ | 1.91/1.78, m | 32.9, CH$_2$ | 1.89/1.76, m |
| 23 | 210.9, CH | 9.44, s | 210.8, CH | 9.43, s |
| 24 | 10.9, CH$_3$ | 1.15, s | 10.9, CH$_3$ | 1.13, s |
| 25 | 16.4, CH$_3$ | 1.00, s | 16.5, CH$_3$ | 1.00, s |
| 26 | 17.9, CH$_3$ | 0.79, s | 17.9, CH$_3$ | 0.80, s |
| 27 | 27.4, CH$_3$ | 1.40, s | 27.4, CH$_3$ | 1.39, s |
| 28 | 181.2, Cq | — | 181.0, Cq HBMC | — |
| 29 | 33.6, CH$_3$ | 0.88, s | 33.6, CH$_3$ | 0.88, s |
| 30 | 25.0, CH$_3$ | 0.97, s | 25.1, CH$_3$ | 0.97, s |
| GlcA-1 | 104.2, CH | 4.46, m | 104.5, CH | 4.36, d (7) |
| GlcA-2 | 78.4, CH | 3.63, m | 78.7, CH | 3.65, m |
| GlcA-3 | 86.0, CH | 3.63, m | 86.7, CH | 3.67, m |
| GlcA-4 | 73.2, CH | 3.48, m | 72.1, CH | 3.55, m |
| GlcA-5 | 77.0, CH | 3.73, m | Not detected | Not detected |
| GlcA-6 | 174.2, Cq | — | 176.3 Cq, HMBC | — |
| Gal-1 | 104.4, CH | 4.45, m | 104.0, CH | 4.78, d (6) |
| Gal-2 | 73.2, CH | 3.48, m | 73.8, CH | 3.45, m |
| Gal-3 | 75.2, CH | 3.47, m | 75.6, CH | 3.43, m |
| Gal-4 | 70.8, CH | 3.81, m | 70.9, CH | 3.80, m |
| Gal-5 | 77.1, CH | 3.47, m | 76.8, CH | 3.48, m |
| Gal-6 | 62.4, CH$_2$ | 3.78/3.73, m | 62.3, CH$_2$ | 3.75/3.72, m |
| Rha-1 | 103.4, CH | 5.03, d (1.8) | | |
| Rha-2 | 72.3, CH | 4.01, dd (3.4, 1.8) | | |
| Rha-3 | 72.4, CH | 3.65, m | | |
| Rha-4 | 74.0, CH | 3.40, m | | |
| Rha-5 | 70.7, CH | 3.96, m | | |
| Rha-6 | 18.0, CH$_3$ | 1.24, d (6.1) | | |
| Xyl-1 | | | 104.9, CH | 4.61, d (7.7) |
| Xyl-2 | | | 75.5, CH | 3.23, m |
| Xyl-3 | | | 78.3, CH | 3.31, m |
| Xyl-4 | | | 71.3, CH | 3.49, m |
| Xyl-5 | | | 67.3, CH$_2$ | 3.89/3.21, m |

TABLE 2

Primers used to clone the three glycosyltransferases required for biosynthesis of the trisaccharide at C-3 of quillaic acid. Gene specific sequences are shown in black, while the attB sites required for Gateway ® cloning are shown in red.

| Name | Sequence |
|---|---|
| QsCSL1_attB1F | GGGGACAAGTTTGTACAAAAAAGCAGGCTTA ATGAAATCCCCTCTAACCCAAATC (SEQ ID NO.: 33) |
| QsCSL1_attB2R | GGGGACCACTTTGTACAAGAAAGCTGGGTA TCAGACCATTTTCTTGCTGATTCAG (SEQ ID NO.: 34) |
| Qs-3-O-GalT_attB1F | GGGGACAAGTTTGTACAAAAAAGCAGGCTTA ATGGTGGAGTCTCCAGCAGATC (SEQ ID NO.: 35) |

TABLE 2-continued

Primers used to clone the three glycosyltransferases required for biosynthesis of the trisaccharide at C-3 of quillaic acid. Gene specific sequences are shown in black, while the attB sites required for Gateway ® cloning are shown in red.

| Name | Sequence |
|---|---|
| Qs-3-O-GalT_attB2R | GGGGACCACTTTGTACAAGAAAGCTGGGTA TCAGACACCCTGAATTCTTGATTTC (SEQ ID NO.: 36) |
| Qs-3-O-RhaT/ XylT_attB1F | GGGGACAAGTTTGTACAAAAAAGCAGGCTTA ATGGTCTCCGGCGACGACGATG (SEQ ID NO.: 37) |
| Qs-3-O-RhaT/ XylT_attB2R | GGGGACCACTTTGTACAAGAAAGCTGGGTA TCACGATTCATGATCTTGTGCAGCC (SEQ ID NO.: 38) |

TABLE 4

Alignment of UGT protein sequences in the region of the Family 1 UGT 44-amino acid Plant Secondary Product Glycosyltransferase (PSPG) motif. Qs_2073886_D6 ("Qs-3-O-GalT") shares the histidine residue conserved in UGTs that transfer β-D-galactose or α-L-arabinose. Figure adapted from Louveau, Orme [15]. Accession numbers: AsUGT99A6 (AZQ26916), MtUGT73K1 (AAW56091), AtUGT78D2 (NP_197207), GmSSAT (XP_003532274), AtUGT78D3 (NP_197205), AeGaT (BAD06514), GmUGT73P2 (BAI99584).

| | | | |
|---|---|---|---|
| GlcT | AsUGT99A6 | WAPQALILSHRAAGAFVTHCGWNSTLEAVAAGLPVVTWPHFTD | Q |
| | MtUGT73K1 | WVPQALILDHPSIGGFLTHCGWNATVEAISSGVPMVTMPGFGD | Q |
| | AtUGT78D2 | WAPQVELLKHEATGVFVTHCGWNSVLESVSGGVPMICRPFFGD | Q |
| AraT/ GalT | Qs_2073886_D6 | WAPQLLILDHPAIGGLLNHSGWNSVLEGATAGLPMITWPLYAE | H |
| | GmSSAT | WVPQGLILKHDAIGGFLTHCGANSVVEAICEGVPLITMPRFGD | H |
| | AtUGT78D3 | WAPQVELLNHEAMGVFVSHGGWNSVLESVSAGVPMICRPIFGD | H |
| | AcGaT | WAPQIQVLSHDAVGVVITHGGWNSVVESIAAGVPVICRPFFGD | H |
| | GmUGT73P2 | WAPQLLILENPAIGGLVTHCGWNTVVESVNAGLPMATWPLFAE | H |

(SEQ ID NOs.: 39-46)

TABLE 5

Glycosyltransferases identified herein ("Qs QA-3-O-TriS sequences"):

| Enzyme | Biological activity | Nucleotide Sequence CDS - SEQ ID NOs | AA sequence - SEQ ID NOs |
|---|---|---|---|
| QsCSL1 | QA-GlcAT Capable of transferring D-glucuronic acid (GlcpA) at the 3-O position of quillaic acid to form 3β-{[β-D-glucopyranosiduronic acid]oxy}-quillaic acid (QA-GlcpA). | 1 | 2 |
| QsCSLG2 | | 25 | 26 |
| Qs-3-O-GalT | QA-GalT Capable of transferring D-Galactose (Galp) via a β-1->2 linkage to QA-GlcpA to form =>3β-{[β-D-galactopyranosyl-(1->2)-β-D-glucopyranosiduronic acid]oxy}-quillaic acid (QA-GlcpA-Galp) | 3 | 4 |

TABLE 5-continued

Glycosyltransferases identified herein ("Qs QA-3-O-TriS sequences"):

| Enzyme | Biological activity | Nucleotide Sequence CDS - SEQ ID NOs | AA sequence - SEQ ID NOs |
|---|---|---|---|
| Qs-3-O-RhaT/XylT | QA-RhaT/XylT | 5 | 6 |
| Qs_0283850 | | 27 | 28 |
| DN20529_c0_g2_i8 | | 29 | 30 |
| Qs_0283870 | The enzymes are capable of transferring D-Xylose (Xylp)or L-Rhamnose via a 1,3 linkage to QA-GlcpA-Galp to form 3β-{[β-D-xylopyranosyl-(1–>3)-[β-D-galactopyranosyl-(1–>2)]-β-D-glucopyranosiduronic acid]oxy}-quillaic acid (QA-GlcpA-[Galp]-Xylp) and/or (3β-{[α-L-rhamnopyranosyl-(1–>3)-[β-D-galactopyranosyl-(1–>2)]-β-D-glucopyranosiduronic acid]oxy}-quillaic acid) (QA-GlcpA-[Galp]-Rhap) respectively | 31 | 32 |

TABLE 6

Other GTs which may be used in QA-glycosylation ("QA-3-O-TriS sequences")

| Enzyme | Activity | Nucleotide Sequence CDS - SEQ ID NOs | AA Sequence - SEQ ID NOs |
|---|---|---|---|
| GmUGT73P2 | QA-GalT: a triterpene 3-O-glucuronoside-β-1,2-D-galactosyltransferase | 19 | 20 |

TABLE 7

Ancillary activities

| Enzyme | Activity | CDS - SEQ ID NOs | AA Sequence - SEQ ID NOs |
|---|---|---|---|
| AsHMGR | HMG-CoA reductase (HMGR); | 7 | 8 |
| tHMGR | HMG-CoA reductase (HMGR); | 9 | 10 |
| AsSQS (*Avena strigosa* squalene synthase) | squalene synthase (SQS) | 21 | 22 |
| AtATR2 (*Arabidopsis thaliana* cytochrome P450 reductase 2) | cytochrome P450 reductase | 23 | 24 |

TABLE 8

QA biosynthesis activities

| Enzyme ("QA polypeptides") | Activity | CDS - SEQ ID NOs | AA Sequence - SEQ ID NOs |
|---|---|---|---|
| QsbAS (β-amyrin synthase) | cyclisation of 2,3-oxidosqualene (OS) to a triterpene | 11 | 12 |
| QsCYP716-C-28 | enzyme capable of oxidising β-amyrin or an oxidised derivative thereof at the C-28 position to a carboxylic acid | 13 | 14 |

TABLE 8-continued

QA biosynthesis activities

| Enzyme ("QA polypeptides") | Activity | CDS - SEQ ID NOs | AA Sequence - SEQ ID NOs |
|---|---|---|---|
| QsCYP716-C-16α | enzyme capable of oxidising β-amyrin or an oxidised derivative thereof at the C-16α position to an alcohol | 15 | 16 |
| QsCYP714-C-23 | enzyme capable of oxidising β-amyrin or an oxidised derivative thereof at the C-23 position to an aldehyde | 17 | 18 |

TABLE 9

DNA (top right) and protein (bottom left) sequence identity between the gene and protein sequences of the three UGT sequences identified in the *Q. saponaria* genome, the new sequence DN20529_c0_g2_i8 identified in the de novo transcriptome and Qs-3-O-RhaT/XylT. Qs_0283860 region corresponds to the genomic region of the Qs_0283860 pseudogene starting from the predicted start codon and the predicted stop codon.

| | NA identity | | | | |
|---|---|---|---|---|---|
| Protein identity | Qs_0283850 | Qs_0283860 region | Qs_0283870 | DN20529_c0_g2_i8 | Qs-3-O-RhaT/XylT |
| Qs_0283850 | | 97% | 90% | 98% | 92% |
| Qs_0283860 region | N/A | | 89% | 99% | 92% |
| Qs_0283870 | 86% | N/A | | 89% | 97% |
| DN20529_c0_g2_i8 | 98% | N/A | 86% | | 92% |
| Qs-3-O-RhaT/XylT | 90% | N/A | 96% | 90% | |

TABLE 10

Primers used to clone the four glycosyltransferases. Gene specific sequences are shown in black, while the attB sites required for Gateway ® cloning are shown in grey.

| Name | Sequence |
|---|---|
| CslG2_attB1F | GGGGACAAGTTTGTACAAAAAAGCAGGCTTA ATGGCGACCGTCTCCTCCCT (SEQ ID NO.: 47) |
| CslG2_attB2R | GGGGACCACTTTGTACAAGAAAGCTGGGTA TTAGGCCTTTCCCTTGCCTTT (SEQ ID NO.: 48) |
| Qs_0283870_attB1F | GGGGACAAGTTTGTACAAAAAAGCAGGCTTA ATGGTCTCCGGCGACGACGATG (SEQ ID NO.: 49) |
| Qs_0283870_attB2R | GGGGACCACTTTGTACAAGAAAGCTGGGTA TCACGATTCATGATCTTGTGCAGCC (SEQ ID NO.: 50) |
| Qs_0283850_attB1F | GGGGACAAGTTTGTACAAAAAAGCAGGCTTA ATGGTCTCCGGCGACGACGACG (SEQ ID NO.: 51) |
| Qs_0283850_attB2R | GGGGACCACTTTGTACAAGAAAGCTGGGTA TCATGCAACCTTGCCATTGTTAGCCCT (SEQ ID NO.: 52) |
| Qs_0283860_attB1F | GGGGACAAGTTTGTACAAAAAAGCAGGCTTA ATGGTCTCCGGCGACGACGAC (SEQ ID NO.: 53) |
| Qs_0283860_attB2R | GGGGACCACTTTGTACAAGAAAGCTGGGTA TCATGATTTCATTGCAGCCTTGCCA (SEQ ID NO.: 54) |

TABLE 11

Full NMR data for quillaic acid 3-O-β-D-glucopyranosiduronic acid (QsbAS/QsCYP716-C-16α/QsCYP714-C-23/QsCYP716-C-28/QsCSL1 product) in MeOH-d$_4$ (600, 150 MHz)

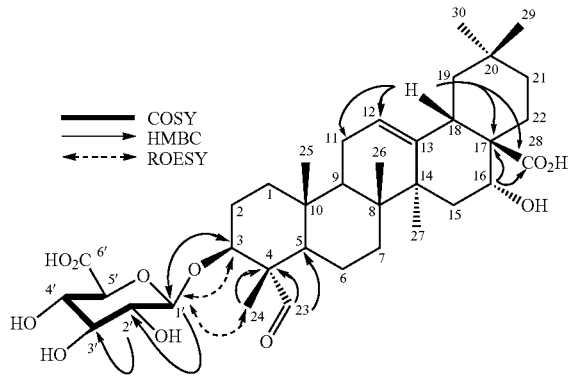

| No. | $\delta_C$, Type | $\delta_H$ mult, (J in Hz) |
|---|---|---|
| 1 | 39.4, CH$_2$ | 1.70, d (13.3)/1.13, m |
| 2 | 25.8, CH$_2$ | 2.03/1.78, m |
| 3 | 83.0, CH | 3.94, dd (12, 4.4) |
| 4 | 56.4, Cq | — |
| 5 | 49.1, CH | 1.35, m |
| 6 | 21.6, CH$_2$ | 1.50/0.90, m |
| 7 | 33.7, CH$_2$ | 1.58/1.26, m |
| 8 | 41.1, Cq | — |
| 9 | 48.2, CH | 1.77, m |
| 10 | 37.2, Cq | — |
| 11 | 24.6, CH$_2$ | 1.94/1.94, m |
| 12 | 123.3, CH | 5.31, t (3.3) |
| 13 | 145.3, Cq | — |
| 14 | 42.9, Cq | — |
| 15 | 36.3, CH$_2$ | 1.84/1.34, m |
| 16 | 75.4, CH | 4.45, t (3.5) |
| 17 | 50.0, Cq | — |
| 18 | 42.2, CH | 3.01, dd (14.0, 4.3) |
| 19 | 47.8, CH$_2$ | 2.30/1.04, m |
| 20 | 31.6, Cq | — |
| 21 | 36.7, CH$_2$ | 1.96/1.15, m |
| 22 | 32.9, CH$_2$ | 1.91/1.77, m |
| 23 | 209.3, CH | 9.42, s |
| 24 | 10.5, CH$_3$ | 1.11, s |
| 25 | 16.3, CH$_3$ | 1.01, s |
| 26 | 17.9, CH$_3$ | 0.80, s |
| 27 | 27.4, CH$_3$ | 1.40, s |
| 28 | 181.3, Cq | — |
| 29 | 33.6, CH$_3$ | 0.89, s |
| 30 | 25.0, CH$_3$ | 0.97, s |
| GlcA-1 | 104.8, CH | 4.20, d (7) |
| GlcA-2 | 75.3, CH | 3.11, t (8.3) |
| GlcA-3 | 77.9, CH | 3.32, overlapped with methanol |
| GlcA-4 | 73.7, CH | 3.42, m |
| GlcA-5 | 76.6, CH | 3.57, br s |
| GlcA-6 | Not observed | — |

TABLE 12

Full NMR data for quillaic acid 3-O-β-D-glucopyranosiduronic acid (QsbAS/QsCYP716-C-16α/QsCYP714-C-23/QsCYP716-C-28/CslG2 product) in MeOH-d$_4$ (600, 150 MHz)

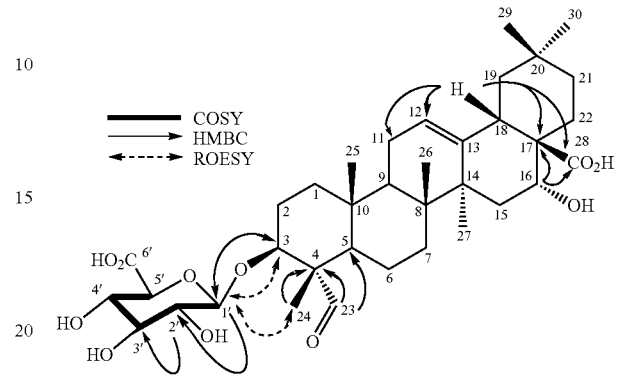

| No. | $\delta_C$, Type | $\delta_H$ mult, (J in Hz) |
|---|---|---|
| 1 | 39.4, CH$_2$ | 1.70, d (13.3)/1.12, m |
| 2 | 25.9, CH$_2$ | 1.97/1.78, m |
| 3 | 83.6, CH | 3.89, dd (11.5, 3.8) |
| 4 | 56.3, Cq | — |
| 5 | 49.2, CH, overlapped | 1.34, m |
| 6 | 21.5, CH$_2$ | 1.52/0.91, m |
| 7 | 33.7, CH$_2$ | 1.57/1.25, m |
| 8 | 41.1, Cq | — |
| 9 | 48.2, CH | 1.76, m |
| 10 | 37.2, Cq | — |
| 11 | 24.6, CH$_2$ | 1.93/1.93, m |
| 12 | 123.3, CH | 5.30, t (3.3) |
| 13 | 145.3, Cq | — |
| 14 | 42.9, Cq | — |
| 15 | 36.3, CH$_2$ | 1.84/1.34, m |
| 16 | 75.4, CH | 4.45, br s |
| 17 | 50.0, Cq | — |
| 18 | 42.2, CH | 3.01, dd (14.3, 4.2) |
| 19 | 47.9, CH$_2$ | 2.30/1.02, m |
| 20 | 31.6, Cq | — |
| 21 | 36.7, CH$_2$ | 1.96/1.15, m |
| 22 | 32.9, CH$_2$ | 1.90/1.76, m |
| 23 | 209.2, CH | 9.41, s |
| 24 | 10.6, CH$_3$ | 1.11, s |
| 25 | 16.3, CH$_3$ | 1.01, s |
| 26 | 17.9, CH$_3$ | 0.80, s |
| 27 | 27.4, CH$_3$ | 1.40, s |
| 28 | 181.2, Cq | — |
| 29 | 33.6, CH$_3$ | 0.88, s |
| 30 | 25.0, CH$_3$ | 0.97, s |
| GlcA-1 | 104.8, CH | 4.24, d (7.6) |
| GlcA-2 | 75.1, CH | 3.12, t (8.2) |
| GlcA-3 | 77.7, CH | 3.31, overlapped with methanol |
| GlcA-4 | 73.3, CH | 3.46, m |
| GlcA-5 | 76.7, CH | 3.72, br s |
| GlcA-6 | Not observed | — |

TABLE 13

Full NMR data for quillaic acid 3-O-{-β-D-galactopyranosyl-(1→2)-β-D-glucopyranosiduronic acid} (QsbAS/QsCYP716-C-16α/QsCYP714-C-23/QsCYP716-C-28/QsCSL1/Qs-3-O-GalT product) in MeOH-d$_4$ (600, 150 MHz)

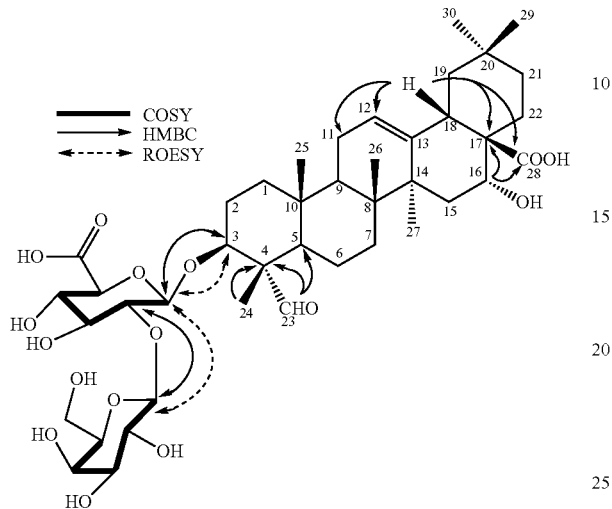

| No. | $\delta_C$, Type | $\delta_H$ mult, (J in Hz) |
|---|---|---|
| 1 | 39.4, CH$_2$ | 1.70, d (13.1)/1.10, m |
| 2 | 25.6, CH$_2$ | 2.00/1.78, m |
| 3 | 84.9, CH | 3.91, dd (11.2, 2.3) |
| 4 | 56.4, Cq | — |
| 5 | 49.2, CH | 1.33, m |
| 6 | 21.4, CH$_2$ | 1.48/0.91, m |
| 7 | 33.7, CH$_2$ | 1.55/1.24, m |
| 8 | 41.1, Cq | — |
| 9 | 48.2, CH | 1.75, m |
| 10 | 37.3, Cq | — |
| 11 | 24.6, CH$_2$ | 1.92/1.92, m |
| 12 | 123.3, CH | 5.30, br s |
| 13 | 145.3, Cq | — |
| 14 | 42.9, Cq | — |
| 15 | 36.3, CH$_2$ | 1.83/1.33, m |
| 16 | 75.4, CH | 4.45, br s |
| 17 | 49.7, Cq | — |
| 18 | 42.2, CH | 3.01, dd (14.2, 3.1) |
| 19 | 47.8, CH$_2$ | 2.29/1.02, m |
| 20 | 31.6, Cq | — |
| 21 | 36.7, CH$_2$ | 1.94/1.13, m |
| 22 | 32.9, CH$_2$ | 1.90/1.76, m |
| 23 | 201.9, CH | 9.46, s |
| 24 | 10.9, CH$_3$ | 1.13, s |
| 25 | 16.4, CH$_3$ | 1.0, s |
| 26 | 17.9, CH$_3$ | 0.80, s |
| 27 | 27.4, CH$_3$ | 1.40, s |
| 28 | 181.3, Cq | — |
| 29 | 33.6, CH$_3$ | 0.88, s |
| 30 | 25.0, CH$_3$ | 0.97, s |
| GlcA-1 | 103.7, CH | 4.36, d (6.1) |
| GlcA-2 | 81.4, CH | 3.46, m |
| GlcA-3 | 78.1, CH | 3.54, m |
| GlcA-4 | Not observed | 3.47, m |
| GlcA-5 | 77.0, CH | 3.74, m |
| GlcA-6 | Not observed | — |
| Gal-1 | 105.4, CH | 4.49, d (7.3) |
| Gal-2 | 74.0, CH | 3.53, m |
| Gal-3 | 75.0, CH | 3.46, m |
| Gal-4 | 70.6, CH | 3.82, m |
| Gal-5 | 77.1, CH | 3.51, m |
| Gal-6 | 62.5, CH$_2$ | 3.80/3.73, dd (10.9, 5.5) |

TABLE 14

¹H, ¹³C NMR spectral data for QA-GlcpA-[Galp]-Rhap (QsbAS/QsCYP716-C-16α/QsCYP714-C-23/QsCYP716-C-28/QsCslG2/Qs-3-O-GalT/Qs_0283850 product) in MeOH-d₄, (400, 100 MHz)

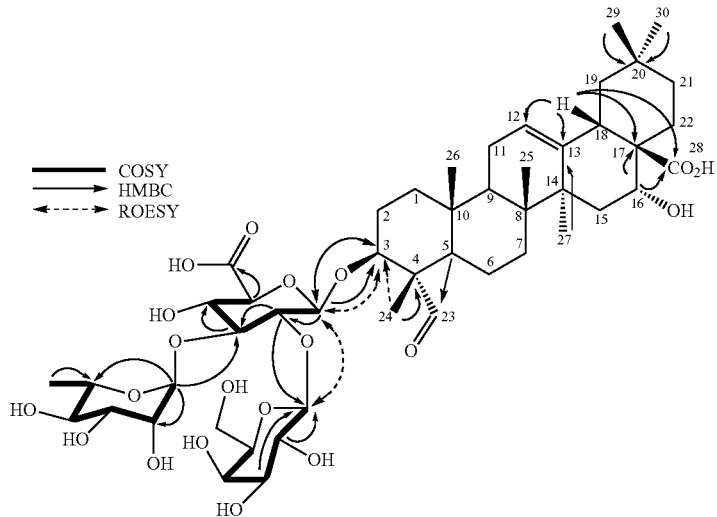

| No. | $\delta_C$, Type | $\delta_H$ mult, (J in Hz) |
|---|---|---|
| 1 | 39.4, CH$_2$ | 1.70/1.11, m |
| 2 | 25.9, CH$_2$ | 1.98/1.77, m |
| 3 | 86.2, CH | 3.87, dd (12.3, 7.7) |
| 4 | 56.4, Cq | — |
| 5 | 49.2, CH, overlapped | 1.33, m |
| 6 | 21.5, CH$_2$ | 1.51/0.91, m |
| 7 | 33.7, CH$_2$ | 1.54/1.24, m |
| 8 | 41.1, Cq | — |
| 9 | 48.2, CH | 1.75, m |
| 10 | 37.2, Cq | — |
| 11 | 24.6, CH$_2$ | 1.93/1.93, m |
| 12 | 123.3, CH | 5.30, t (3.3) |
| 13 | 145.3, Cq | — |
| 14 | 42.9, Cq | — |
| 15 | 36.3, CH$_2$ | 1.83/1.33, m |
| 16 | 75.4, CH | 4.45, d (1.6) |
| 17 | 50.0, Cq | — |
| 18 | 42.2, CH | 3.00, dd (14.3, 4.1) |
| 19 | 47.9, CH$_2$ | 2.29/1.02 |
| 20 | 31.6, Cq | — |
| 21 | 36.7, CH$_2$ | 1.94/1.14, m |
| 22 | 32.9, CH$_2$ | 1.91/1.76, m |
| 23 | 210.9, CH | 9.44, s |
| 24 | 11.0, CH$_3$ | 1.16, s |
| 25 | 16.4, CH$_3$ | 1.00, s |
| 26 | 18.0, CH$_3$ | 0.79, s |
| 27 | 27.4, CH$_3$ | 1.40, s |
| 28 | 181.2, Cq | — |
| 29 | 33.6, CH$_3$ | 0.88, s |
| 30 | 25.0, CH$_3$ | 0.97, s |
| GlcA-1 | 104.3, CH | 4.48, d (6.8) |
| GlcA-2 | 78.3, CH | 3.64, m |
| GlcA-3 | 85.9, CH | 3.65, m |
| GlcA-4 | 73.2, CH | 3.49, m |
| GlcA-5 | 76.7, CH | 3.83, m |
| GlcA-6 | 172.6, Cq | — |
| Gal-1 | 104.4, CH | 4.46, d (1.6) |
| Gal-2 | 73.2, CH | 3.48, m |
| Gal-3 | 75.2, CH | 3.48, m |
| Gal-4 | 70.8, CH | 3.81, m |
| Gal-5 | 77.2, CH | 3.48, m |
| Gal-6 | 62.5, CH$_2$ | 3.79/3.73, m |
| Rha-1 | 103.5, CH | 5.03, d (1.6) |
| Rha-2 | 72.2, CH | 4.02, dd (3.3, 1.8) |
| Rha-3 | 72.3, CH | 3.65, m |
| Rha-4 | 73.9, CH | 3.49, m |

TABLE 14-continued $^1$H, $^{13}$C NMR spectral data for QA-GlcpA-[Galp]-Rhap (QsbAS/QsCYP716-C-16α/QsCYP714-C-23/QsCYP716-C-28/QsCslG2/Qs-3-O-GalT/Qs_0283850 product) in MeOH-$d_4$, (400, 100 MHz)

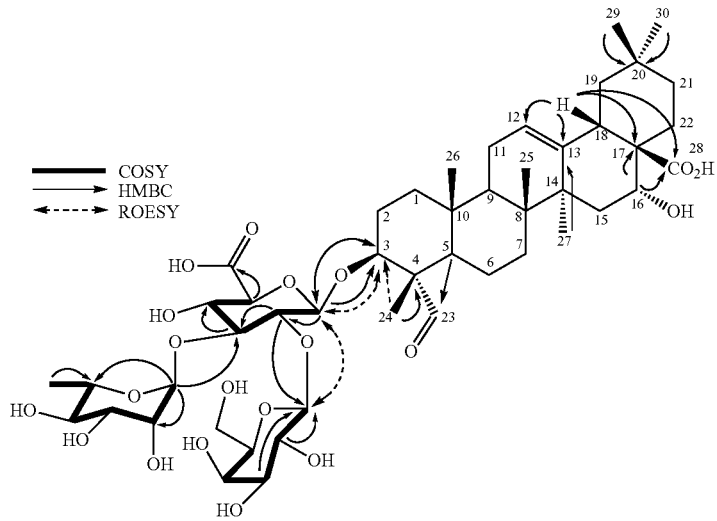

| No. | $\delta_C$, Type | $\delta_H$ mult, (J in Hz) |
|---|---|---|
| Rha-5 | 70.7, CH$_2$ | 3.92, m |
| Rha-6 | 17.9, CH$_3$ | 1.24, d (6.2) |

TABLE 15

$^1$H, $^{13}$C NMR spectral data for QA-GlcpA-[Galp]-Xylp (QsbAS/QsCYP716-C-16α/QsCYP714-C-23/QsCYP716-C-28/QsCslG2/Qs-3-O-GalT/Qs_0283870 product) in MeOH-$d_4$, (400, 100 MHz)

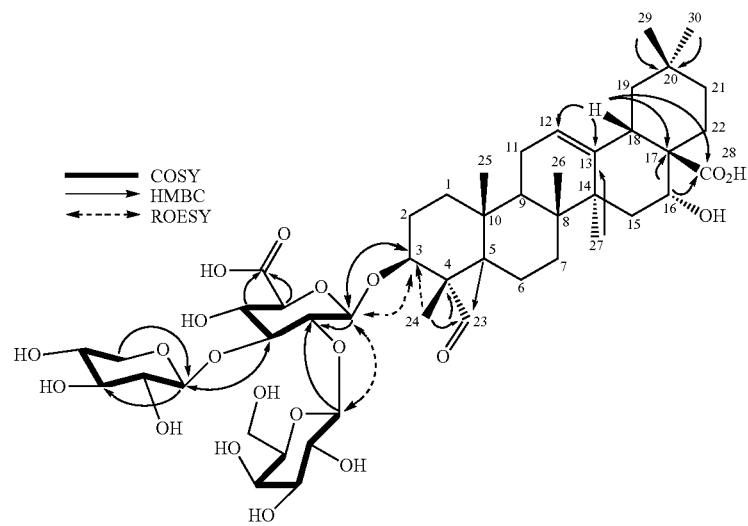

| No. | $\delta_C$, Type | $\delta_H$ mult, (J in Hz) |
|---|---|---|
| 1 | 39.4, CH$_2$ | 1.70, d (13.3)/1.12, m |
| 2 | 25.9, CH$_2$ | 1.97/1.78, m |
| 3 | 86.5, CH | 3.87, dd (11.7, 4.9) |
| 4 | 56.4, Cq | — |
| 5 | 49.2, CH, overlapped | 1.32, m |
| 6 | 21.4, CH$_2$ | 1.51/0.91, m |
| 7 | 33.7, CH$_2$ | 1.54/1.23, m |
| 8 | 41.1, Cq | — |
| 9 | 48.2, CH | 1.75, m |

TABLE 15-continued $^1$H, $^{13}$C NMR spectral data for QA-GlcpA-[Galp]-Xylp (QsbAS/QsCYP716-C-16α/QsCYP714-C-23/QsCYP716-C-28/QsCslG2/Qs-3-O-GalT/Qs_0283870 product) in MeOH-d$_4$, (400, 100 MHz)

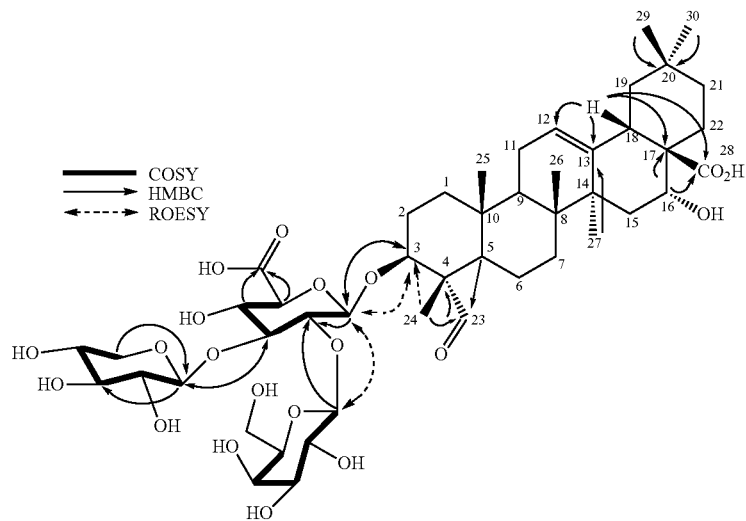

| No. | $\delta_C$, Type | $\delta_H$ mult, (J in Hz) |
|---|---|---|
| 10 | 37.3, Cq | — |
| 11 | 24.6, CH$_2$ | 1.92/1.92, m |
| 12 | 123.3, CH | 5.30, t (3.3) |
| 13 | 145.3, Cq | — |
| 14 | 42.9, Cq | — |
| 15 | 36.3, CH$_2$ | 1.82/1.33, m |
| 16 | 75.3, CH | 4.45, d (3.2) |
| 17 | 50.0, Cq | — |
| 18 | 42.2, CH | 3.01, dd (14.3, 4.2) |
| 19 | 47, 8, CH$_2$ | 2.29, t (13.6)/1.02 |
| 20 | 31.6, Cq | — |
| 21 | 36.7, CH$_2$ | 1.94/1.14, m |
| 22 | 32.9, CH$_2$ | 1.90/1.76, m |
| 23 | 210.8, CH | 9.44, s |
| 24 | 10.9, CH$_3$ | 1.15, s |
| 25 | 16.4, CH$_3$ | 1.00, s |
| 26 | 17.9, CH$_3$ | 0.79, s |
| 27 | 27.4, CH$_3$ | 1.39, s |
| 28 | 181.2, Cq | — |
| 29 | 33.6, CH$_3$ | 0.88, s |
| 30 | 25.0, CH$_3$ | 0.97, s |
| GlcA-1 | 104.6, CH | 4.48, d (2.9) |
| GlcA-2 | 78.3, CH | 3.64, m |
| GlcA-3 | 86.7, CH | 3.69, m |
| GlcA-4 | 71.5, CH | 3.56, m |
| GlcA-5 | 76.6, CH | 3.80, m |
| GlcA-6 | 172.3, Cq | — |
| Gal-1 | 103.9, CH | 4.79, d (7.3) |
| Gal-2 | 73.7, CH | 3.44, m |
| Gal-3 | 75.5, CH | 3.41, m |
| Gal-4 | 70.9, CH | 3.80, m |
| Gal-5 | 76.9, CH | 3.48, m |
| Gal-6 | 62.4, CH$_2$ | 3.76/3.69, m |
| Xyl-1 | 105.1, CH | 4.58, d (7.6) |
| Xyl-2 | 75.4, CH | 3.24, m |
| Xyl-3 | 78.4, CH | 3.30, overlapped |
| Xyl-4 | 71.2, CH | 3.53, m |
| Xyl-5 | 67.3, CH$_2$ | 3.90/3.25, m |

TABLE 3

Family 1 UDP-dependent glycosyltransferases (UGT) used in phylogenetic analysis. UGTs believed to be active on triterpenes are highlighted in bold.

| Enzyme | Accession number | UGT family | UGT Group | Plant species | Reported activity | Reference |
|---|---|---|---|---|---|---|
| AtUGT79B1 | Q9LVW3 | UGT79 | A | Arabidopsis thaliana | Anthocyanidin 3-O-glucoside [1,2]-xylosyltransferase | Yonekura-Sakakibara et al. (2012) |
| AtUGT79B6 | Q9FN26 | UGT79 | A | Arabidopsis thaliana | Flavonol 3-O-galactoside [1,2]-glucosyltransferase | Yonekura-Sakakibara et al. (2014) |
| Cs1-6RhaT | ABA18631 | UGT79 | A | Citrus sinensis | Flavonoid 7-O/3-O-glucoside [1,6]-rhamnosyltransferase | Frydman et al. (2013) |
| GmUGT79A6 | BAN91401 | UGT79 | A | Glycine max | Flavonol 3-O-glucoside/galactoside [1,6]-rhamnosyltransferase | Rojas Rodas et al. (2014) |
| LeABRT2 | BAU68118 | UGT79 | A | Lobelia erinus | Delphinidin 3-O-glucoside [1,6]-rhamnosyltransferase | Hsu et al. (2017) |
| GmUGT91H4 | BAI99585 | UGT91 | A | Glycine max | Triterpene 3-O-galactoside [1,2]-rhamnosyltransferase | Shibuya et al. (2010) |
| GmUGT91H9 | NP_001348424 | UGT91 | A | Glycine max | Triterpene 3-O-galactoside [1,2]-glucosyltransferase | Yano et al. (2018) |
| In3GGT | Q53UH4 | UGT91 | A | Ipomoea nil | Anthocyanidin 3-O-glucoside [1,2]-glucosyltransferase | Morita et al. (2005) |
| GjUGT94E5 | F8WKW8 | UGT94 | A | Gardenia jasminoides | Apocarotenoid glucoside [1,6]-glucosyltransferase | Nagatoshi et al. (2012) |
| BpUGT94B1 | Q5NTH0 | UGT94 | A | Bellis perennis | Anthocyanidin 3-O-glucoside [1,2]-glucuronosyltransferase | Sawada et al. (2005) |
| Cm1-2RhaT1 | AAL06646 | UGT94 | A | Citrus maxima | Flavonoid 7-O-glucoside [1,2]-rhamnosyltransferase | Frydman et al. (2013) |
| PgUGT94Q2 | AGR44632 | UGT94 | A | Panax ginseng | Triterpene 3-O-glucoside [1,2]-glucosyltransferase | Jung et al. (2014) |
| SlGAME18 | XP_004243636 | UGT94 | A | Solanum lycopersicum | Steroidal alkaloid 3-O-glucoside [1,2]-glucosyltransferase | Itkin et al. (2013) |
| VpUGT94F1 | BAI44133 | UGT94 | A | Veronica persica | Flavonoid 3-O-glucoside [1,2]-glucosyltransferase | Ono et al. (2010) |
| AtUGT89C1 | AAF80123 | UGT89 | B | Arabidopsis thaliana | Flavonol 7-O-rhamnosyltransferase | Yonekura-Sakakibara et al. (2007) |
| UGT89A2-Col-0 | Q9LZD8 | UGT89 | B | Arabidopsis thaliana | Dihydroxybenzoic acid xylosyltransferase | Chen and Li (2017) |
| PoUGT90A7 | ACB56926 | UGT90 | C | Pilosella officinarum | Flavonol glucosyltransferase | Witte et al. (2009) |
| AcUGT73G1 | AAP88406 | UGT73 | D | Allium cepa | Flavonoid-7-O-glucosyltransferase | Kramer et al. (2003) |
| AtUGT73B3 | AAM47999 | UGT73 | D | Arabidopsis thaliana | Flavonol-7-O-glucosyltransferase | Kim et al. (2006) |
| AtUGT73C1 | AEC09294 | UGT73 | D | Arabidopsis thaliana | Cytokinin glucosyltransferase 1 | Gandia-Herrero et al. (2008) |
| AsUGT99D1 | AZQ26921 | UGT99 | D | Avena strigosa | Triterpene-3-O-arabinosyltransferase | Louveau et al. (2018) |
| BvUGT73C10 | AFN26666 | UGT73 | D | Barbarea vulgaris | Triterpene-3-O-glucosyltransferase | Augustin et al. (2012) |
| CbBet5OGT | CAB56231 | UGT73 | D | Cleretum bellidiforme | Betanidin-5-O-glucosyltransferase | Vogt et al. (1999) |
| CsUGT73A20 | ALO19886 | UGT73 | D | Camellia sinensis | Flavonoid 7-O/3-O-glucosyltransferase | Zhou et al. (2017) |
| CsUGT73AM3 | KGN59015 | UGT73 | D | Cucumis sativus | Triterpene-3-O-glucosyltranferase | Zhong et al. (2017) |
| GmUGT73F2 | BAM29362 | UGT73 | D | Glycin max | Triterpene 22-O-arabinoside [1,3]-glucosyltransferase | Sayama et al. (2012) |
| GmUGT73F4 | BAM29363 | UGT73 | D | Glycin max | Triterpene 22-O-arabinoside [1,3]-xylosyltransferase | Sayama et al. (2012) |
| GmUGT73P2 (GmSGT2) | BAI99584 | UGT73 | D | Glycin max | Triterpene 3-O-glucuronide [1,2]-galactosyltransferase | Shibuya et al. (2010) |
| GuUGAT | ANJ03631 | UGT73 | D | Glycyrrhiza uralensis | Triterpene 3-O-glucuronosyltransferase/Triterpene 3-O-glucuronide [1,2]-glucuronosyltransferase | Xu et al. (2016) |
| MtUGT73F3 | ACT34898 | UGT73 | D | Medicago trunctula | Triterpene 28-O-glucuronosyltransferase | Naoumkina et al. (2010) |
| SlUGT73L4 | ADQ37966 | UGT73 | D | Solanum lycopersicum | Steroidal alkaloid 3-O-glucoside [1,3]-xylosyltransferase | Itkin et al. (2013) |
| StSGT3 | ABB84472 | UGT73 | D | Solanum tuberosum | Steroidal alkaloid 3-O-glucoside/galactoside [1,2]-rhamnosyltransferase | McCue et al. (2007) |
| CsUGT707B1 | CCG85331 | UGT707 | E | Crocus sativus | Flavonol 3-O-glucoside [1,2]-glucosyltransferase | Trapero et al. (2012) |
| AtUGT71B6 | NP_188815 | UGT71 | E | Arabidopsis thaliana | Abscisate β-glucosyltransferase | Priest et al. (2006) |
| AtUGT71C1 | NP_180536 | UGT71 | E | Arabidopsis thaliana | UDP-glucosyl transferase 71C1 | Lim et al. (2008) |
| OsUGT707A3 | BAC83989 | UGT71 | E | Oryza sativa | Flavonol 3-O-glycosyltransferase | Ko et al. (2008) |
| AtUGT72B1 | Q9M156 | UGT72 | E | Arabidopsis thaliana | UDP-glycosyltransferase 72B1 | Brazier-Hicks et al. (2007) |
| AtUGT72E2 | AED98252 | UGT72 | E | Arabidopsis thaliana | Hydroxycinnamate 4-β-glucosyltransferase | Lanot et al. (2006) |
| MtUGT71G1 | AAW56092 | UGT71 | E | Medicago trunctula | Triterpenoid-O-glucosyltransferase | Achnine et al. (2005) |
| PgUGTPg1 | AIE12479 | UGT71 | E | Panax ginseng | Protopanaxadiol-20-O-glucosyltransferase | Yan et al. (2014) |
| ScUGT5 | BAJ11653 | UGT88 | F | Sinningia cardinalis | 3-Deoxyanthocyanidin 5-O-glucosyltransferase | Nakatsuka and Nishihara (2010) |
| AtUGT78D1 | Q9S9P6 | UGT78 | F | Arabidopsis thaliana | Flavonol 3-O-glucosyltransferase | Jones et al. (2003) |
| Fh3GT1 | ADK75021 | UGT78 | F | Freesia hybrid cultivar | Anthocyanidin 3-O-glucosyltransferase | Sun et al. (2016) |
| VmUF3GaT | BAA36972 | UGT78 | F | Vigna mungo | Flavonol 3-O-galactosyltransferase | Mato et al. (1998) |
| VvGT1 | AAB81683 | UGT78 | F | Vitis vinifera | Anthocyanidin 3-O-glucosyltransferase | Ford et al. (1998) |
| AtUGT85A1 | AAF18537 | UGT85 | G | Arabidopsis thaliana | Cytokinin-O-glucosyltransferase 2 | Hou et al. (2004) |

TABLE 3-continued

Family 1 UDP-dependent glycosyltransferases (UGT) used in phylogenetic analysis. UGTs believed to be active on triterpenes are highlighted in bold.

| Enzyme | Accession number | UGT family | UGT Group | Plant species | Reported activity | Reference |
|---|---|---|---|---|---|---|
| PdUGT85A19 | ABV68925 | UGT85 | G | Prunus dulcis | Cyanohydrin glucoside [1,6]-glucosyltransferase | Franks et al. (2008) |
| SbUGT85B1 | AAF17077 | UGT85 | G | Sorghum bicolor | Cyanohydrin glycosyltransferase UGT85B1 | Hansen et al. (2003) |
| AtUGT76D1 | AEC07843 | UGT76 | H | Arabidopsis thaliana | Flavonoid-7-O-glucosyltransferase | Lim et al. (2004) |
| SrUGT76G1 | AAR06912 | UGT76 | H | Stevia rebaudiana | Diterpenoid 13-O-glucoside [1,3]-glucosyltransferase | Richman et al. (2005) |
| AtUGT83A1 | Q9SGA8 | UGT83 | I | Arabidopsis thaliana | Unknown | Ross et al. (2001) |
| AtUGT87A1 | O64732 | UGT87 | J | Arabidopsis thaliana | Unknown | Ross et al. (2001) |
| AtUGT87A2 | NP_001077979 | UGT87 | J | Arabidopsis thaliana | Unknown | Wang et al. (2012) |
| AtUGT86A1 | Q9SIL0 | UGT86 | K | Arabidopsis thaliana | Unknown | Ross et al. (2001) |
| AtUGT74E2 | NP_172059 | UGT74 | L | Arabidopsis thaliana | Auxin (IBA) glycosyltransferase | Tognetti et al. (2010) |
| AsUGT74H5 | ACD03250 | UGT74 | L | Avena strigosa | N-Methylanthranilate O-glucosyltransferase | Owatworakit et al. (2012) |
| PgUGT74A1 | AGR44631 | UGT74 | L | Panax ginseng | Triterpene-3-O-glucosyltransferase | Jung et al. (2014) |
| SgUGT74AC1 | AEM42999 | UGT74 | L | Siraitia grosvenorii | Triterpene (PPD)-3-O-glucosyltransferase | Dai et al. (2015) |
| VhUGT74M1 | ABK76266 | UGT74 | L | Vaccaria hispanica | Triterpene carboxylic acid 28-O-glucosyltransferase | Meesapyodsuk et al. (2007) |
| ZmIAGT | AAA59054 | UGT74 | L | Zea mays | Auxin glucosyltransferase | Szerszen et al. (1994) |
| AtUGT75C1 | Q0WW21 | UGT75 | L | Arabidopsis thaliana | Anthocyanin 5-O-glucosyltransferase | Yamazaki et al (1999) |
| GjUGT75L6 | F8WKW0 | UGT75 | L | Gardenia jasminoides | Apocarotenoid glucosyltransferase | Nagatoshi et al. (2012) |
| Via5GT | AHL68667 | UGT75 | L | Vitis amurensis Rupr. cv. 'Zuoshanyi' | Anthocyanin 5-O-glucosyltransferase | He et al. (2015) |
| AtUGT84A1 | Q5XF20 | UGT84 | L | Arabidopsis thaliana | Hydroxycinnamate glucosyltransferase 2 | Milkowski et al. (2000) |
| GtUf6CGT1 | BAQ19550 | UGT84 | L | Gentiana triflora | Flavonoid 6-C-glucosyltransferase | Sasaki et al. (2015) |
| CuLGT | BAA93039 | UGT84 | L | Citrus unshui | Triterpene (limonoid)-17-O-glucosyltransferase | Kita et al. (2000) |
| AtUGT92A1 | Q9LXV0 | UGT92 | M | Arabidopsis thaliana | Unknown | Ross et al. (2001) |
| CcDOPA5GT | BAD91804 | UGT92 | M | Celosia cristata | Cyclo-DOPA 5-O-glucosyltransferase | Sasaki et al. (2005) |
| MjDOPA5GT | BAD91803 | UGT92 | M | Mirabilis jalapa | Cyclo-DOPA 5-O-glucosyltransferase | Sasaki et al. (2005) |
| AtUGT82A1 | Q9LH12 | UGT82 | N | Arabidopsis thaliana | Unknown | Ross et al. (2001) |
| SlGAME17 | XP_004243637 | UGT93 | O | Solanum lycopersicum | Steroidal alkaloid 3-O-galactoside [1,4]-glucosyltransferase | Itkin et al. (2013) |
| ZmcisZog1 | AAK53551 | UGT93 | O | Zea mays | cis-zeatin O-glucosyltransferase | Martin et al. (2001) |
| OsUGT709A4 | BAC80066 | UGT709A4 | P | Oryza sativa | Isoflavonoid-7-O-glucosyltransferase | Ko et al. (2008) |

References for Table 3

Achnine, L., Huhman, D. V., Farag, M. A., Sumner, L. W., Blount, J. W., and Dixon, R. A. (2005). Genomics-based selection and functional characterization of triterpene glycosyltransferases from the model legume *Medicago truncatula*. Plant J., 41:875-87.

Augustin, J. M., Drok, S., Shinoda, T., Sanmiya, K., Nielsen, J. K., Khakimov, B., Olsen, C. E., Hansen, E. H., Kuzina, V., Ekstrom, C. T., Hauser, T., and Bak, S. (2012). UDP-glycosyltransferases from the UGT73C subfamily in *Barbarea vulgaris* catalyze sapogenin 3-O-glucosylation in saponin-mediated insect resistance. Plant Physiol., 160:1881-95.

Brazier-Hicks, M., Offen, W. A., Gershater, M. C., Revett, T. J., Lim, E.-K., Bowles, D. J., Davies, G. J., and Edwards, R. (2007). Characterization and engineering of the bifunctional N- and O-glucosyltransferase involved in xenobiotic metabolism in plants. Proc. Natl. Acad. Sci. U.S.A., 104:20238-43.

Chen, H.-Y. and Li, X. (2017). Identification of a residue responsible for UDP-sugar donor selectivity of a dihydroxybenzoic acid glycosyltransferase from *Arabidopsis* natural accessions. Plant J., 89:195-203.

Dai, L., Liu, C., Zhu, Y., Zhang, J., Men, Y., Zeng, Y., and Sun, Y. (2015). Functional characterization of cucurbitadienol synthase and triterpene glycosyltransferase involved in biosynthesis of mogrosides from *Siraitia grosvenorii*. Plant Cell Physiol., 56:1172-82.

Ford, C. M., Boss, P. K., and Hoj, P. B. (1998). Cloning and characterization of *Vitis vinifera* UDP-glucose:flavonoid 3-O-glucosyltransferase, a homologue of the enzyme encoded by the maize Bronze-1 locus that may primarily serve to glucosylate anthocyanidins in vivo. J. Biol. Chem., 273:9224-33.

Franks, T. K., Yadollahi, A., Wirthensohn, M. G., Guerin, J. R., Kaiser, B. N., Sedgley, M., and Ford, C. M. (2008). A seed coat cyanohydrin glucosyltransferase is associated with bitterness in almond (*Prunus dulcis*) kernels. Funct. Plant Biol., 35(3):236-246.

Frydman, A., Liberman, R., Huhman, D. V., Carmeli-Weissberg, M., Sapir-Mir, M., Ophir, R., W Sumner, L., and Eyal, Y. (2013). The molecular and enzymatic basis of bitter/non-bitter flavor of citrus fruit: evolution of branch-forming rhamnosyltransferases under domestication. Plant J., 73:166-78.

Gandia-Herrero, F., Lorenz, A., Larson, T., Graham, I. A., Bowles, D. J., Rylott, E. L., and Bruce, N. C. (2008). Detoxification of the explosive 2,4,6-trinitrotoluene in *Arabidopsis*: discovery of bifunctional O- and C-glucosyltransferases. Plant J., 56:963-74.

Hansen, K. S., Kristensen, C., Tattersall, D. B., Jones, P. R., Olsen, C. E., Bak, S., and Moller, B. L. (2003). The in vitro substrate regiospecificity of recombinant UGT85B1, the cyanohydrin glucosyltransferase from *Sorghum bicolor*. Phytochemistry, 64:143-51.

He, F., Chen, W.-K., Yu, K.-J., Ji, X.-N., Duan, C.-Q., Reeves, M. J., and Wang, J. (2015). Molecular and biochemical characterization of the UDP-glucose: Anthocyanin 5-O-glucosyltransferase from *Vitis amurensis*. Phytochemistry, 117:363-72.

Hou, B., Lim, E.-K., Higgins, G. S., and Bowles, D. J. (2004). N-glucosylation of cytokinins by glycosyltransferases of *Arabidopsis thaliana*. J. Biol. Chem., 279: 47822-32.

Hsu, Y.-H., Tagami, T., Matsunaga, K., Okuyama, M., Suzuki, T., Noda, N., Suzuki, M., and Shimura, H. (2017). Functional characterization of UDP-rhamnose-dependent rhamnosyltransferase involved in anthocyanin modification, a key enzyme determining blue coloration in *Lobelia erinus*. Plant J., 89:325-337.

Itkin, M., Heinig, U., Tzfadia, O., Bhide, A. J., Shinde, B., Cardenas, P. D., Bocobza, S. E., Unger, T., Malitsky, S., Finkers, R., Tikunov, Y., Bovy, A., Chikate, Y., Singh, P., Rogachev, I., Beekwilder, J., Giri, A. P., and Aharoni, A. (2013). Biosynthesis of antinutritional alkaloids in solanaceous crops is mediated by clustered genes. Science, 341:175-9.

Jones, P., Messner, B., Nakajima, J.-I., Schaffner, A. R., and Saito, K. (2003). UGT73C6 and UGT78D1, glycosyltransferases involved in flavonol glycoside biosynthesis in *Arabidopsis thaliana*. J. Biol. Chem., 278:43910-8.

Jung, S.-C., Kim, W., Park, S. C., Jeong, J., Park, M. K., Lim, S., Lee, Y., Im, W.-T., Lee, J. H., Choi, G., and Kim, S. C. (2014). Two ginseng UDP-glycosyltransferases synthesize ginsenoside Rg3 and Rd. Plant Cell Physiol., 55:2177-88.

Kim, J. H., Kim, B. G., Park, Y., Ko, J. H., Lim, C. E., Lim, J., Lim, Y., and Ahn, J.-H. (2006). Characterization of flavonoid 7-O-glucosyltransferase from *Arabidopsis thaliana*. Biosci. Biotechnol. Biochem., 70:1471-7.

Kita, M., Hirata, Y., Moriguchi, T., Endo-Inagaki, T., Matsumoto, R., Hasegawa, S., Suhayda, C. G., and Omura, M. (2000). Molecular cloning and characterization of a novel gene encoding limonoid UDP-glucosyltransferase in *Citrus*. FEBS Lett., 469:173-8.

Ko, J. H., Kim, B. G., Kim, J. H., Kim, H., Lim, C. E., Lim, J., Lee, C., Lim, Y., and Ahn, J.-H. (2008). Four glucosyltransferases from rice: cDNA cloning, expression, and characterization. J. Plant Physiol., 165:435-44.

Kramer, C. M., Prata, R. T. N., Willits, M. G., De Luca, V., Steffens, J. C., and Graser, G. (2003). Cloning and regiospecificity studies of two flavonoid glucosyltransferases from *Allium cepa*. Phytochemistry, 64:1069-76.

Lanot, A., Hodge, D., Jackson, R. G., George, G. L., Elias, L., Lim, E.-K., Vaistij, F. E., and Bowles, D. J. (2006). The glucosyltransferase UGT72E2 is responsible for monolignol 4-O-glucoside production in *Arabidopsis thaliana*. Plant J., 48:286-95.

Lim, C. E., Choi, J. N., Kim, I. A., Lee, S. A., Hwang, Y.-S., Lee, C. H., and Lim, J. (2008). Improved resistance to oxidative stress by a loss-of-function mutation in the *Arabidopsis* UGT71C1 gene. Mol. Cells, 25:368-75.

Lim, E.-K., Ashford, D. A., Hou, B., Jackson, R. G., and Bowles, D. J. (2004). *Arabidopsis* glycosyltransferases as biocatalysts in fermentation for regioselective synthesis of diverse quercetin glucosides. Biotechnol. Bioeng., 87:623-31.

Louveau, T., Orme, A., Pfalzgraf, H., Stephenson, M. J., Melton, R., Saalbach, G., Hemmings, A. M., Leveau, A., Rejzek, M., Vickerstaff, R. J., Langdon, T., Field, R. A., and Osbourn, A. (2018). Analysis of two new arabinosyltransferases belonging to the carbohydrate-active enzyme (CAZY) glycosyl transferase family 1 provides insights into disease resistance and sugar donor specificity. Plant Cell, 30(12):3038-3057.

Martin, R. C., Mok, M. C., Habben, J. E., and Mok, D. W. (2001). A maize cytokinin gene encoding an O-glucosyltransferase specific to cis-zeatin. Proc. Natl. Acad. Sci. U.S.A., 98:5922-6.

Mato, M., Ozeki, Y., Itoh, Y., Higeta, D., Yoshitama, K., Teramoto, S., Aida, R., Ishikura, N., and Shibata, M. (1998). Isolation and characterization of a cDNA clone of UDP-galactose: flavonoid 3-O-galactosyltransferase (UF3GaT) expressed in *Vigna mungo* seedlings. *Plant Cell Physiol.*, 39:1145-55.

McCue, K. F., Allen, P. V., Shepherd, L. V. T., Blake, A., Maccree, M. M., Rockhold, D. R., Novy, R. G., Stewart, D., Davies, H. V., and Belknap, W. R. (2007). Potato glycosterol rhamnosyltransferase, the terminal step in triose side-chain biosynthesis. *Phytochemistry*, 68:327-34.

Meesapyodsuk, D., Balsevich, J., Reed, D. W., and Covello, P. S. (2007). Saponin biosynthesis in *Saponaria vaccaria*. cDNAs encoding β-amyrin synthase and a triterpene carboxylic acid glucosyltransferase. *Plant Physiol.*, 143:959-69.

Milkowski, C., Baumert, A., and Strack, D. (2000). Identification of four *Arabidopsis* genes encoding hydroxycinnamate glucosyltransferases. *FEBS Lett.*, 486:183-4.

Morita, Y., Hoshino, A., Kikuchi, Y., Okuhara, H., Ono, E., Tanaka, Y., Fukui, Y., Saito, N., Nitasaka, E., Noguchi, H., and Iida, S. (2005). Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2″-O-glucosyltransferase, due to 4-bp insertions in the gene. *Plant J.*, 42:353-63.

Nagatoshi, M., Terasaka, K., Owaki, M., Sota, M., Inukai, T., Nagatsu, A., and Mizukami, H. (2012). UGT75L6 and UGT94E5 mediate sequential glucosylation of crocetin to crocin in *Gardenia* jasminoides. FEBS Lett., 586:1055-61.

Nakatsuka, T. and Nishihara, M. (2010). UDP-glucose:3-deoxyanthocyanidin 5-O-glucosyltransferase from *Sinningia cardinalis*. *Planta*, 232:383-92.

Naoumkina, M. A., Modolo, L. V., Huhman, D. V., Urbanczyk-Wochniak, E., Tang, Y., Sumner, L. W., and Dixon, R. A. (2010). Genomic and coexpression analyses predict multiple genes involved in triterpene saponin biosynthesis in *Medicago truncatula*. *Plant Cell*, 22:850-66.

Ono, E., Ruike, M., Iwashita, T., Nomoto, K., and Fukui, Y. (2010). Co-pigmentation and flavonoid glycosyltransferases in blue *Veronica persica* flowers. *Phytochemistry*, 71:726-35.

Owatworakit, A., Townsend, B., Louveau, T., Jenner, H., Rejzek, M., Hughes, R. K., Saalbach, G., Qi, X., Bakht, S., Roy, A. D., Mugford, S. T., Goss, R. J. M., Field, R. A., and Osbourn, A. (2013). Glycosyltransferases from oat (*Avena*) implicated in the acylation of avenacins. *J. Biol. Chem.*, 288(6):3696-3704.

Priest, D. M., Ambrose, S. J., Vaistij, F. E., Elias, L., Higgins, G. S., Ross, A. R. S., Abrams, S. R., and Bowles, D. J. (2006). Use of the glucosyltransferase UGT71 B6 to disturb abscisic acid homeostasis in *Arabidopsis thaliana*. *Plant J.*, 46:492-502.

Richman, A., Swanson, A., Humphrey, T., Chapman, R., McGarvey, B., Pocs, R., and Brandle, J. (2005). Functional genomics uncovers three glucosyltransferases involved in the synthesis of the major sweet glucosides of *Stevia rebaudiana*. *Plant J.*, 41:56-67.

Rojas Rodas, F., Rodriguez, T. O., Murai, Y., Iwashina, T., Sugawara, S., Suzuki, M., Nakabayashi, R., Yonekura-Sakakibara, K., Saito, K., Kitajima, J., Toda, K., and Takahashi, R. (2014). Linkage mapping, molecular cloning and functional analysis of soybean gene Fg2 encoding flavonol 3-O-glucoside (1->6) rhamnosyltransferase. *Plant Mol. Biol.*, 84:287-300.

Ross, J., Li, Y., Lim, E., and Bowles, D. J. (2001). Higher plant glycosyltransferases. *Genome Biol.*, 2: REVIEWS3004.

Sasaki, N., Nishizaki, Y., Yamada, E., Tatsuzawa, F., Nakatsuka, T., Takahashi, H. and Nishihara, M. (2015). Identification of the glucosyltransferase that mediates direct flavone C-glucosylation in *Gentiana triflora*. *FEBS Lett.*, 589:182-187.

Sasaki, N., Wada, K., Koda, T., Kasahara, K., Adachi, T., and Ozeki, Y. (2005). Isolation and characterization of cDNAs encoding an enzyme with glucosyltransferase activity for cyclo-DOPA from four o'clocks and feather cockscombs. *Plant Cell Physiol.*, 46:666-70.

Sawada, S., Suzuki, H., Ichimaida, F., Yamaguchi, M.-A., Iwashita, T., Fukui, Y., Hemmi, H., Nishino, T., and Nakayama, T. (2005). UDP-glucuronic acid:anthocyanin glucuronosyltransferase from red daisy (*Bellis perennis*) flowers. Enzymology and phylogenetics of a novel glucuronosyltransferase involved in flower pigment biosynthesis. *J. Biol. Chem.*, 280:899-906.

Sayama, T., Ono, E., Takagi, K., Takada, Y., Horikawa, M., Nakamoto, Y., Hirose, A., Sasama, H., Ohashi, M., Hasegawa, H., Terakawa, T., Kikuchi, A., Kato, S., Tatsuzaki, N., Tsukamoto, C., and Ishimoto, M. (2012). The Sg-1 glycosyltransferase locus regulates structural diversity of triterpenoid saponins of soybean. *Plant Cell*, 24:2123-38.

Shibuya, M., Nishimura, K., Yasuyama, N., and Ebizuka, Y. (2010). Identification and characterization of glycosyltransferases involved in the biosynthesis of soyasaponin i in *Glycine max*. FEBS Lett., 584:2258-64.

Sun, W., Liang, L., Meng, X., Li, Y., Gao, F., Liu, X., Wang, S., Gao, X., and Wang, L. (2016). Biochemical and molecular characterization of a flavonoid 3-O-glycosyltransferase responsible for anthocyanins and flavonols biosynthesis in *Freesia hybrida*. *Front. Plant Sci.*, 7:410.

Szerszen, J. B., Szczyglowski, K., and Bandurski, R. S. (1994). iaglu, a gene from *Zea mays* involved in conjugation of growth hormone indole-3-acetic acid. *Science*, 265:1699-701.

Tognetti, V. B., Van Aken, O., Morreel, K., Vandenbroucke, K., van de Cotte, B., De Clercq, I., Chiwocha, S., Fenske, R., Prinsen, E., Boerjan, W., Genty, B., Stubbs, K. A., Inze, D., and Van Breusegem, F. (2010). Perturbation of indole-3-butyric acid homeostasis by the UDP-glucosyltransferase UGT74E2 modulates *Arabidopsis* architecture and water stress tolerance. *Plant Cell*, 22:2660-79.

Trapero, A., Ahrazem, O., Rubio-Moraga, A., Jimeno, M. L., Gomez, M. D., and Gomez-Gomez, L. (2012). Characterization of a glucosyltransferase enzyme involved in the formation of kaempferol and quercetin sophorosides in *Crocus sativus*. *Plant Physiol.*, 159:1335-54.

Vogt, T., Grimm, R., and Strack, D. (1999). Cloning and expression of a cDNA encoding betanidin 5-O-glucosyltransferase, a betanidin- and flavonoid-specific enzyme with high homology to inducible glucosyltransferases from the Solanaceae. *Plant J.*, 19:509-19.

Wang, B., Jin, S.-H., Hu, H.-Q., Sun, Y.-G., Wang, Y.-W., Han, P., and Hou, B.-K. (2012). UGT87A2, an *Arabidopsis* glycosyltransferase, regulates flowering time via FLOWERING LOCUS C. *New Phytol.*, 194:666-75.

Witte, S., Moco, S., Vervoort, J., Matern, U., and Martens, S. (2009). Recombinant expression and functional characterisation of regiospecific flavonoid glucosyltransferases from *Hieracium pilosella* L. *Planta*, 229:1135-46.

Xu, G., Cai, W., Gao, W., and Liu, C. (2016). A novel glucuronosyltransferase has an unprecedented ability to catalyse continuous two-step glucuronosylation of glycyrrhetinic acid to yield glycyrrhizin. *New Phytol.,* 212:123-35.

Yamazaki, M., Gong, Z., Fukuchi-Mizutani, M., Fukui, Y., Tanaka, Y., Kusumi, T., and Saito, K. (1999). Molecular cloning and biochemical characterization of a novel anthocyanin 5-O-glucosyltransferase by mRNA differential display for plant forms regarding anthocyanin. *J. Biol. Chem.,* 274:7405-11.

Yan, X., Fan, Y., Wei, W., Wang, P., Liu, Q., Wei, Y., Zhang, L., Zhao, G., Yue, J., and Zhou, Z. (2014). Production of bioactive ginsenoside compound K in metabolically engineered yeast. *Cell Res,* 24:770-3.

Yano, R., Takagi, K., Tochigi, S., Fujisawa, Y., Nomura, Y., Tsuchinaga, H., Takahashi, Y., Takada, Y., Kaga, A., Anai, T., Tsukamoto, C., Seki, H., Muranaka, T., and Ishimoto, M. (2018) Isolation and characterization of the soybean Sg-3 gene that is involved in genetic variation in sugar chain composition at the C-3 position in soyasaponins. *Plant Cell Physiol.,* 59:792-805.

Yonekura-Sakakibara, K., Fukushima, A., Nakabayashi, R., Hanada, K., Matsuda, F., Sugawara, S., Inoue, E., Kuromori, T., Ito, T., Shinozaki, K., Wangwattana, B., Yamazaki, M., and Saito, K. (2012). Two glycosyltransferases involved in anthocyanin modification delineated by transcriptome independent component analysis in *Arabidopsis thaliana. Plant J.,* 69:154-67.

Yonekura-Sakakibara, K., Nakabayashi, R., Sugawara, S., Tohge, T., Ito, T., Koyanagi, M., Kitajima, M., Takayama, H., and Saito, K. (2014). A flavonoid 3-O-glucoside:2"-O-glucosyltransferase responsible for terminal modification of pollen-specific flavonols in *Arabidopsis thaliana. Plant J.,* 79:769-82.

Yonekura-Sakakibara, K., Tohge, T., Niida, R., and Saito, K. (2007). Identification of a flavonol 7-O-rhamnosyltransferase gene determining flavonoid pattern in *Arabidopsis* by transcriptome coexpression analysis and reverse genetics. *J. Biol. Chem.,* 282:14932-41.

Zhong, Y., Xue, X., Liu, Z., Ma, Y., Zeng, K., Han, L., Qi, J., Ro, D.-K., Bak, S., Huang, S., Zhou, Y., and Shang, Y. (2017). Developmentally regulated glucosylation of bitter triterpenoid in cucumber by the UDP-glucosyltransferase UGT73AM3. *Mol. Plant,* 10:1000-1003.

Zhao, X., Wang, P., Li, M., Jiang, X., Cui, L., Qian, Y., Zhuang, J., Gao, L., and Xia, T. (2017). Functional characterization of a new tea (*Camellia sinensis*) flavonoid glycosyltransferase. *J. Agric. Food Chem.* 65:2074-2083.

| Sequences |
|---|
| SEQ ID NO: 1-*Q. saponaria* quillaic acid 3-O-glucuronosyltransferase (cellulose synthase-like enzyme QsCSL1) coding sequence (2142 bp)<br>ATGAAATCCCCTCTAACCCAAATCAGAAACCCATCCTCCACACTTGTACAATTCAGCAGCCTCGT<br>GCTACCCTTAACAAAATTCATAGTCTTATTCATTTCTCAGCCATACTTGTCCTATTTTATTACCGG<br>ATAACCCGTCTATTCTTCACCGACGATTTCAAGGTACCCAAGTTACTATGGACTCTAATGACAATC<br>TCCGAGTTCATTCTTGCCTTCATTTGGGTTCTCATCCAACCTTTCCGGTGGCGACCGGTGTCCCGT<br>TCCGTCATACCAGAGAATATGCCGAAGGACATCAGTTTGCCGGCGGTGGACGTGTTTGTATGCACA<br>GCTGACCCTCAAAAAGAACCCACAGTGGAGGTGATGAACACAATTTTATCAGCCATGGCTTTAGAC<br>TACCCGGCGGAGAAGCTCGCCGTGTATCTTTCCGATGATGGGGGTTCTGCTGTCACCTTATATGCT<br>ATAAAAGAAGCTTGTTGTTTTGCTAAGATGTGGCTTCCGTTTTGTAACAAGTATGGGATCAAATCA<br>AGGTGTCCCGAGGCTTATTTTTCAAAGCTTGCCGCTGACGAGTGGCTTCACCGGAGTGTGGAATTC<br>GTGGCAGAAGAAAAGGAGGTCAAGGCTAATTATGAAGAGTTCAAGAGAAATGTGCAGAAATTTGGT<br>GAGCAACAAGAAAACAGTCGTGTTGTGCATGATCGTCACCCTCATGTTGAGATTATACACAATAAT<br>TGGAATAACGAAGACCAAGCTCATGAGATGCCACTCCTTGTTTATGTCTCTCGTGAAAGAAGACCA<br>TCTCACCATCCTCGATTCAAAGCTGGAGCTCTTAACACCCTTCTTCGAGTTTCTGGCATCATCAGC<br>AACAGCCCCTACATACTGGTTCTAGACTGTGACATGTACTGCAATGACCCAACCTCAGCTAGACAA<br>GCAATGTGCTTCCATCTTGATCCCCAACTGTCTAAAAATCTTGCTTTTGTACAATTCCCTCAAATA<br>TTCTATAACGCTAGTAAGAATGACGTCTATGATGCCCAAGTCAGGGCGGCATACCAGACAAAGTGG<br>CAGGGTATGGATGGACTTCAAGGACCAATTTTTTCTGGCACTGGCTTTTACTTAAAGAGGAAGGCA<br>ATGTATGGAAACCCTGATCAAGATGATAATTGTCTACTCAAGCCATATAAGAAATTTGGCATGTCT<br>GGAGAATTTGTAGAATCACTTAAGGTCCTTAACGAACAAGATGGTACCCAGAAGAAATTATTGGAT<br>GGATTTTTACAAGAGGCCAAACTATTGGCCTCGTGTGCCTATGAAACAAAGACAAGTTGGGGTAAA<br>GAGATTGGATTCTCATATGACTGTTTAATAGAGAGCACTTTCACTGGTTATCTTTTGCACTGCAGA<br>GGGTGGATATCTGTTTATCTTTATCCCAAGAGACCATGTTTTTAGGATGCTGTCCTACTGATATG<br>AAGGATGCCATGGTTCAATATACCAAGTGGATGTCTGAGCTATTTTCAATTGCTATCTCAAGATTC<br>AATCCTCTGCTCTATGGGGTGGCAAGAATGTCCATTCTTCAAAGCCTGTGTTATGGATCCTTTACA<br>CTGGCGCCTATTTTGTCATTTCCTTTGTTCTTATATGGAACGGTTCCTCAATTATGCCTCTTGAAA<br>GGCATATCTTTGTTTCCAAAGGTTTCGGACCCATGGTTTGCTGTGTTTGCAGCTATCTTTGTATCC<br>TCCCTGTGTCAACACTGGTTCGAGGTCCTCTCTTGTGATGGTACATTTACGACTTGGTGTAATGAA<br>CAGCGGAGTTGGCTTATAAAGTCGGTTTCCGGTAGTTTGTTTGGAGTTGTGGGCGCAATCTTGCAG<br>CGGCTAGGCTTGAAGACAAAGTTTAGTTTATCAAACAAAGCCATGGACAAAGAAAAGCTGGAGAAA<br>TATGAAAAGGGTAAATTTAATTTCCAAGGGGCTGCCATGTTCATGGTTCCTGTGTCTATTTTAGTC<br>ATACTGAACACATTTTGCTTCCTCGGTGGGTTTTGGAAAGTGATCATAATGAAGAATATCCTGGAC<br>ATGTTTGGACAACTTTCTCTCTCTGCCTACGTTCTGGTTCTCAGTTGTCCAGTTCTTGAAGGGATG<br>TTAACTAGAATCAGCAAGAAAATGGTCTGA |
| SEQ ID NO: 2-*Q. saponaria* quillaic acid 3-O-glucuronosyltransferase (cellulose synthase-like enzyme QsCSL1) translated nucleotide sequence (713 aa):<br>MKSPSNPNQKPILHTCTIQQPRATLNKIHSLIHFSAILVLFYYRITRLFFTDDFKVPKLLWTLMTI<br>SEFILAFIWVLIQPFRWRPVSRSVIPENMPKDISLPAVDVFVCTADPQKEPTVEVMNTILSAMALD<br>YPAEKLAVYLSDDGGSAVTLYAIKEACCFAKMWLPFCNKYGIKSRCPEAYFSKLAADEWLHRSVEF<br>VAEEKEVKANYEEFKRNVQKFGEQQENSRVVHDRHPHVEIIHNNWNNEDQAHEMPLLVYVSRERRP<br>SHHPRFKAGALNTLLRVSGIISNSPYILVLDCDMYCNDPTSARQAMCFHLDPQLSKNLAFVQFPQI<br>FYNASKNDVYDAQVRAAYQTKWQGMDGLQGPIFSGTGFYLKRKAMYGNPDQDDNCLLKPYKKFGMS<br>GEFVESLKVLNEQDGTQKKLLDGFLQEAKLLASCAYETKTSWGKEIGFSYDCLIESTFTGYLLHCR<br>GWISVYLYPKRPCFLGCCPTDMKDAMVQYTKWMSELFSIAISRFNPLLYGVARMSILQSLCYGSFT |

```
LAPILSFPLFLYGTVPQLCLLKGISLFPKVSDPWFAVFAAIFVSSLCQHWFEVLSCDGTFTTWCNE
QRSWLIKSVSGSLFGVVGAILQRLGLKTKFSLSNKAMDKEKLEKYEKGKFNFQGAAMFMVPVSILV
ILNTFCFLGGFWKVIIMKNILDMFGQLSLSAYVLVLSCPVLEGMLTRISKKMV*

SEQ ID NO: 3-Q. saponaria QA-GlcpA β-1,2-D-galactosyltransferase (Qs-3-O-GalT)
coding sequence (1479 bp)
ATGGTGGAGTCTCCAGCAGATCATGATGTGCTCAAAATCATTGTCCTTCCATGGG -continued Sequences Part 2-Other biosynthetic enzymes:
SEQ ID NO: 7-AsHMGR (Avena strigosa HMG-CoA reductase) coding sequence
(1689 bp):
The full-length HMGR sequence is provided below. The 5' region (underlined) can
be removed to generate a truncated feedback-insensitive form (tHMGR). The
sequence for tHMGR is also given separately below.
<u>ATGGCTGTGGAGGTTCACCGCCGGGCTCCCGCGCCCCATGGCCGGGGCACCGGGGAGAAGGGCCGC
GTGCAGGCCGGGGACGCGCTGCCGCTGCCGATCCGCCACACCAACCTCATCTTCTCGGCGCTCTTC
GCCGCCTCCCTCGCATACCTCATGCGCCGCTGGAGGGAGAAGATCCGCAACTCCACGCCGCTCCAC
GTCGTGGGGCTCACCGAGATCTTCGCCATCTGCGGCCTCGTCGCCTCCCTCATCTACCTCCTCAGC
TTCTTCGGCATCGCCTTCGTGCAGTCCGTCGTATCCAACAGCGACGACGAGGACGAGGACTTCCTC
ATCGCGGCTGCAGCATCCCAGGCCCCCCCGCCGCCCTCCTCAAGCCCGCGCCGCAGCAGTGCGCC
CTGCTGCAGAGCGCGGAGTCGCGCCCGAGAAAATGCCCGAGGAGGACGAGGAAATCGTCGCCGGG</u>
GTCGTCGCAGGGAAGATCCCCTCCTACGTGCTCGAGACCAGGCTAGGCGACTGCCGCAGGGCAGCC
GGGATCCGCCGCGAGGCGCTGCGCCGGATCACCGGCAGGGAGATCGACGGCCTTCCCCTCGACGGC
TTCGACTACGACTCGATTCTCGGACAGTGCTGCGAGATGCCCGTCGGGTACGTGCAGCTGCCGGTC
GGCGTCGCGGGGCCGCTCGTCCTCGACGGCCGCCGCATATACGTCCCGATGGCCACCACGGAGGGC
TGCCTAATCGCCAGCACCAACCGCGGATGCAAGGCCATTGCCGAGTCCGGAGGCGCATCCAGCGTC
GTGTACCGCGACGGGATGACCCGCGCCCCCGTAGCCCGCTTCCCCTCCGCACGACGCGCCGCAGAG
CTCAAGGGCTTCCTGGAGAATCCGGCCAACTACGACACCCTGTCCGTGGTCTTTAACAGATCAAGC
AGATTTGCAAGGCTGCAGGGGGTCAAGTGCGCCATGGCTGGGAGGAACTTGTACATGAGGTTCACC
TGCAGCACCGGGGATGCCATGGGGATGAACATGGTCTCCAAGGGCGTCCAAAATGTGCTCGACTAT
CTGCAGGAGGACTTCCCTGACATGGACGTTGTCAGCATCTCAGGCAACTTTTGTTCCGACAAGAAA
TCAGCTGCTGTAAACTGGATTGAAGGCCGTGGAAAGTCCGTGGTTTGTGAGGCAGTAATCAGAGAG
GAAGTTGTCCACAAGGTTCTCAAGACCAACGTTCAGTCACTCGTGGAGTTGAATGTGATCAAGAAC
CTTGCTGGCTCAGCAGTTGCTGGTGCTCTTGGGGGTTTCAACGCCCACGCAAGCAACATCGTAACG
GCTATCTTCATTGCCACTGGTCAGGATCCTGCACAGAATGTGGAGAGCTCACAGTGTATCACTATG
TTGGAAGCTGTAAATGATGGCAGAGACCTTCACATCTCCGTTACAATGCCATCTATCGAGGTGGGC
ACAGTTGGTGGAGGCACGCAGCTGGCCTCACAGTCGGCCTGCTTGGACCTACTGGGCGTCAAAGGC
GCCAACAGGGAATCTCCGGGGTCGAACGCTAGGCTGCTGGCCACGGTGGTGGCTGGTGCCGTCCTA
GCTGGGGAGCTGTCCCTCATCTCCGCCCAAGCTGCCGGCCATCTGGTCCAGAGCCACATGAAATAC
AACAGATCCAGCAAGGACATGTCCAAGATCGCCTGCTGA SEQ ID NO: 8-AsHMGR (Avena strigosa HMG-CoA reductase) translated
nucleotide sequence (562 aa):
<u>MAVEVHRRAPAPHGRGTGEKGRVQAGDALPLPIRHTNLIFSALFAASLAYLMRRWREKIRNSTPLH
VVGLTEIFAICGLVASLIYLLSFFGIAFVQSVVSNSDDEDEDFLIAAAASQAPPPPSSKPAPQQCA
LLQSAGVAPEK</u>MPEEDEEIVAGVVAGKIPSYVLETRLGDCRRAAGIRREALRRITGREIDGLPLDG
FDYDSILGQCCEMPVGYVQLPVGVAGPLVLDGRRIYVPMATTEGCLIASTNRGCKAIAESGGASSV
VYRDGMTRAPVARFPSARRAAELKGFLENPANYDTLSVVFNRSSRFARLQGVKCAMAGRNLYMRFT
CSTGDAMGMNMVSKGVQNVLDYLQEDFPDMDVVSISGNFCSDKKSAAVNWIEGRGKSVVCEAVIRE
EVVHKVLKTNVQSLVELNVIKNLAGSAVAGALGGFNAHASNIVTAIFIATGQDPAQNVESSQCITM
LEAVNDGRDLHISVTMPSIEVGTVGGGTQLASQSACLDLLGVKGANRESPGSNARLLATVVAGAVL
AGELSLISAQAAGHLVQSHMKYNRSSKDMSKIAC*

SEQ ID NO: 9-AstHMGR (Avena strigosa truncated HMG-CoA reductase) coding
sequence (1275 bp):
ATGGCGCCCGAGAAAATGCCCGAGGAGGACGAGGAAATCGTCGCCGGGGTCGTCGCAGGGAAGATC
CCCTCCTACGTGCTCGAGACCAGGCTAGGCGACTGCCGCAGGGCAGCCGGGATCCGCCGCGAGGCG
CTGCGCCGGATCACCGGCAGGGAGATCGACGGCCTTCCCCTCGACGGCTTCGACTACGACTCGATT
CTCGGACAGTGCTGCGAGATGCCCGTCGGGTACGTGCAGCTGCCGGTCGGCGTCGCGGGGCCGCTC
GTCCTCGACGGCCGCCGCATATACGTCCCGATGGCCACCACGGAGGGCTGCCTAATCGCCAGCACC
AACCGCGGATGCAAGGCCATTGCCGAGTCCGGAGGCGCATCCAGCGTCGTGTACCGCGACGGGATG
ACCCGCGCCCCCGTAGCCCGCTTCCCCTCCGCACGACGCGCCGCAGAGCTCAAGGGCTTCCTGGAG
AATCCGGCCAACTACGACACCCTGTCCGTGGTCTTTAACAGATCAAGCAGATTTGCAAGGCTGCAG
GGGGTCAAGTGCGCCATGGCTGGGAGGAACTTGTACATGAGGTTCACCTGCAGCACCGGGGATGCC
ATGGGGATGAACATGGTCTCCAAGGGCGTCCAAAATGTGCTCGACTATCTGCAGGAGGACTTCCCT
GACATGGACGTTGTCAGCATCTCAGGCAACTTTTGTTCCGACAAGAAATCAGCTGCTGTAAACTGG
ATTGAAGGCCGTGGAAAGTCCGTGGTTTGTGAGGCAGTAATCAGAGAGGAAGTTGTCCACAAGGTT
CTCAAGACCAACGTTCAGTCACTCGTGGAGTTGAATGTGATCAAGAACCTTGCTGGCTCAGCAGTT
GCTGGTGCTCTTGGGGGTTTCAACGCCCACGCAAGCAACATCGTAACGGCTATCTTCATTGCCACT
GGTCAGGATCCTGCACAGAATGTGGAGAGCTCACAGTGTATCACTATGTTGGAAGCTGTAAATGAT
GGCAGAGACCTTCACATCTCCGTTACAATGCCATCTATCGAGGTGGGCACAGTTGGTGGAGGCACG
CAGCTGGCCTCACAGTCGGCCTGCTTGGACCTACTGGGCGTCAAAGGCGCCAACAGGGAATCTCCG
GGGTCGAACGCTAGGCTGCTGGCCACGGTGGTGGCTGGTGCCGTCCTAGCTGGGGAGCTGTCCCTC
ATCTCCGCCCAAGCTGCCGGCCATCTGGTCCAGAGCCACATGAAATACAACAGATCCAGCAAGGAC
ATGTCCAAGATCGCCTGCTGA SEQ ID NO: 10-AstHMGR (Avena strigosa truncated HMG-CoA reductase)
translated nucleotide sequence (424 aa):
MAPEKMPEEDEEIVAGVVAGKIPSYVLETRLGDCRRAAGIRREALRRITGREIDGLPLDGFDYDSI
LGQCCEMPVGYVQLPVGVAGPLVLDGRRIYVPMATTEGCLIASTNRGCKAIAESGGASSVVYRDGM
TRAPVARFPSARRAAELKGFLENPANYDTLSVVFNRSSRFARLQGVKCAMAGRNLYMRFTCSTGDA
MGMNMVSKGVQNVLDYLQEDFPDMDVVSISGNFCSDKKSAAVNWIEGRGKSVVCEAVIREEVVHKV
LKTNVQSLVELNVIKNLAGSAVAGALGGFNAHASNIVTAIFIATGQDPAQNVESSQCITMLEAVND GRDLHISVTMPSIEVGTVGGGTQLASQSACLDLLGVKGANRESPGSNARLLATVVAGAVLAGELSL
ISAQAAGHLVQSHMKYNRSSKDMSKIAC SEQ ID NO: 11-*Q. saponaria* β-amyrin synthase, QsbAS (OQHZ-2074321) coding
sequence (2277 bp):
ATGTGGAGGCTGAAGATAGCAGAAGGTGGTTCCGATCCATATCTGTTCAGCACAAACAACTTCGTG
GGTCGCCAGACATGGGAGTTCGAACCGGAGGCCGGCACACCTGAGGAGCGAGCAGAGGTCGAAGCT
GCCCGCCAAAACTTTTACAACAACCGTTACCAGGTCAAGCCCTGTGACGACCTCCTTTGGAGATAT
CAGTTCCTGAGAGAGAAGAATTTCAAACAAACAATACCGCCTGTCAAGGTTGAAGATGGCCAAGAA
ATTACTTATGAGATGGCCACAACCTCAATGCAGAGGGCGGCCCGTCACCTATCAGCCTTGCAGGCC
AGCGATGGCCATTGGCCAGCTCAAATTGCTGGCCCCTTGTTCTTCATGCCACCCTTGGTCTTTTGT
GTGTACATTACTGGGCATCTTAATACAGTATTCCCATCTGAACATCGCAAAGAAATCCTTCGTTAC
ATGTACTATCACCAGAACGAAGATGGTGGGTGGGGACTGCACATAGAGGGTCACAGCACCATGTTT
TGCACAGCACTCAACTACATTTGTATGCGTATCCTTGGGGAAGGACCAGAGGGGGGTCAAGACAAT
GCTTGTGCCAGAGCACGAATGTGGATTCTTGATCATGGTGGTGTAACACATATTCCATCTTGGGGA
AAGACCTGGCTTTCGATACTTGGTCTATTTGAGTGGTCTGGAAGCAATCCAATGCCTCCAGAGTTT
TGGATCCTTCCTTCATTTCTTCCTATGCATCCAGCAAAAATGTGGTGCTATTGCCGGATGGTTTAC
ATGCCCATGTCTTATTTATATGGGAAAAGGTTTGTTGGCCCAATCACGCCTCTCATTGTTCAGTTA
AGAGAGGAAATACACACTCAAAATTACCATGAAATCAACTGGAAGTCAGTCCGCCATCTATGTGCA
AAGGAGGATATCTACTATCCCCATCCACTCATCCAAGATTTGATTTGGGACAGTTTGTACATACTA
ACGGAGCCTCTTTCTCACTCGCTGGCCCTTGAACAAGTTGGTGCGGGAGAGGGCTCTCCAAGTAACA
ATGAAGCATATCCACTATGAAGATGAAATAGTCGATACATAACCATTGGATGTGTGGAAAAGGTG
TTATGTATGCTTGCTTGTTGGGTTGATGATCCAAATGGAGATGCTTTCAAGAAGCACCTTGCTCGA
GTCCCAGATTACGTATGGGTCTCTGAAGATGGAATTACTATGCAGAGTTTTGGTAGTCAAGAATGG
GATGCTGGCTTTGCCGTCCAGGCTCTGCTTGCTTCTAATCTTACCGAGGAACTTGGCCCTGCTCTT
GCCAAAGGACATGACTTCATAAAGCAATCTCAGGTTAAGGACAATCCTTCAGGTGACTTCAAAAGC
ATGTATCGTCACATTTCTAGAGGATCATGGACCTTCTCTGACCAAGATCATGGATGGCAAGTTTCT
GATTGCACTGCAGAAGGTCTGAAGTGTTGCCTGCTTTTGTCGATGTTGCCACCAGAAATTGTTGGT
GAAAAAATGGAACCACAAAGGCTATTTGATTCTGTCAATGTGCTGCTCTCTCTACAGAGCAAAAAA
GGTGGTTTAGCTGCCTGGGAGCCAGCAGGGGCGCAAGATTGGTTGGAATTACTCAATCCCACAGAA
TTTTTTTGCGGACATTGTCGTTGAGCATGAATATGTTGAATGTACTGGATCAGCAATTCAGGCATTA
GTTTTGTTCAAGAAGCTGTATCCGGGGCACAGGAAAAAAGAGATTGACAGTTTCATTACAAATGCT
GTCCGGTTCCTTGAGAATACACAAACGGCAGATGGCTCTTGGTATGGAAACTGGGGAGTTTGCTTC
ACCTATGGTTGTTGGTTCGCACTGGGAGGGCTAGCAGCAGCTGGCAAGACTTACAACAACTGTCCT
GCAATACGCAAAGCTGTTAATTTCCTACTTACAACACAAAGAGAAGACGGTGGTTGGGGAGAAAGC
TATCTTTCAAGCCCAAAAAAGATATATGTACCCCTGGAAGGAAGCCGATCAAATGTGGTACATACT
GCATGGGCTATGATGGGTCTAATTCATGCTGGGCAGGCTGAAAGAGACTCAACTCCTCTTCATCGT
GCAGCAAAGTTGATCATCAATTATCAACTAGAAAATGGCGATTGGCCGCAACAGGAAATCACTGGA
GTATTCATGAAAAACTGCATGTTACATTACCCTATGTACAGAAACATCTACCCAATGTGGGCTCTT
GCAGAATACCGGAGGCGGGTTCCATTGCCTTAA SEQ ID NO: 12-QsbAS (OQHZ-2074321) translated nucleotide sequence (758 aa):
MWRLKIAEGGSDPYLFSTNNFVGRQTWEFEPEAGTPEERAEVEAARQNFYNNRYQVKPCDDLLWRY
QFLREKNFKQTIPPVKVEDGQEITYEMATTSMQRAARHLSALQASDGHWPAQIAGPLFFMPPLVFC
VYITGHLNTVFPSEHRKEILRYMYYHQNEDGGWGLHIEGHSTMFCTALNYICMRILGEGPEGGQDN
ACARARMWILDHGGVTHIPSWGKTWLSILGLFEWSGSNPMPPEFWILPSFLPMHPAKMWCYCRMVY
MPMSYLYGKRFVGPITPLIVQLREEIHTQNYHEINWKSVRHLCAKEDIYYPHPLIQDLIWDSLYIL
TEPLLTRWPLNKLVRERALQVTMKIHYEDENSRYITIGCVEKVLCMLACWVDDPNGDAFKKHLAR
VPDYVWVSEDGITMQSFGSQEWDAGFAVQALLASNLTEELGPALAKGHDFIKQSQVKDNPSGDFKS
MYRHISRGSWTFSDQDHGWQVSDCTAEGLKCCLLLSMLPPEIVGEKMEPQRLFDSVNVLLSLQSKK
GGLAAWEPAGAQDWLELLNPTEFFADIVVEHEYVECTGSAIQALVLFKKLYPGHRKKEIDSFITNA
VRFLENTQTADGSWYGNWGVCFTYGCWFALGGLAAAGKTYNNCPAIRKAVNFLLTTQREDGGWGES
YLSSPKKIYVPLEGSRSNVVHTAWAMMGLIHAGQAERDSTPLHRAAKLIINYQLENGDWPQQEITG
VFMKNCMLHYPMYRNIYPMWALAEYRRRVPLP*

SEQ ID NO: 13-QsCYP716-C-28 (OQHZ-2073932) (C-28 oxidase, named previously
as CYP716A224 [24]) coding sequence (1443 bp):
ATGGAGCACTTGTATCTCTCCCTTGTGCTCCTGTTTGTTTCCTCAATCTCCCTCTCCCTCTTCTTC
CTGTTCTACAAACACAAATCTATGTTCACCGGGGCCAACCTACCACCTGGTAAAATCGGTTACCCA
TTGATCGGAGAGAGCTTGGAGTTCTTGTCCACGGGATGGAAGGGCCACCCGGAGAAATTCATCTTC
GATCGCATGAGCAAGTACTCATCCCAAATCTTCAAGACCTCGATTTTAGGGGAACCAACGGCGGTG
TTCCCGGGAGCCGTATGCAACAAGTTCCTCTTCTCCAACGAGAACAAGCTGGTGAATGCATGGTGG
CCTGCCTCCGTGGACAAGATCTTTCCTTCCTCACTCCAGACATCCTCCAAAGAAGAGGCCAAGAAG
ATGAGGAAGTTGCTTCCTCAGTTTCTCAAGCCCGAAGCTCTGCACCGCTACATTGGTATTATGGAT
TCTATTGCCCAGAGACACTTTGCCGATAGCTGGGAAAACAAAACCAAGTCATTGTCTTTCCTCTA
GCAAAGAGGTATACTTTCTGGCTGGCTTGCCGTTGTTCATTAGCGTCGAGGATCCGACCCACGTA
TCCAGATTTGCTGACCCGTTCCAACTTTTGGCCGCCGGAATCATATCAATCCCAATCGACTTGCCA
GGGCACACCGTTCCGCAAGGCAATCAATGCGTCCCAGTTCATCAGGAAGGAATTGTTGGCCATCATC
AGGCAGAGAAAGATCGATTGGGTGAAGGGAAGGCATCTCCGACGCAGGACATACTGTCTCACATG
TTGCTCACATGCGACGAGAACGGACAATACATGAATGAATTGGACATTGCCGACAAGATTCTTGGC
TTGTTGGTCGGCGGACATGACACTGCCAGTGCCGCTTGCACTTTCATTGTCAAGTTCCTCGCTGAG
CTTCCCCACATTTATGAACAAGTCTACAAGGAGCAAATGGAGATTGCAAATCAAAGTGCCAGGA
GAGTTGTTGAATTGGAGGACATCCAAAAGATGAAATATTCGTGGAACGTAGCTTGTGAAGTGATG
AGACTTGCCCCTCCACTCCAAGGAGCTTTCAGGGAAGCCATTACTGACTTCGTCTTCAACGTTTC
TCCATTCCAAAAGGCTGGAAGTTGTACTGGAGCGCAAATTCCACCCACAAAAGTCCGGATTATTTC
CCTGAGCCCGACAAGTTCGACCCAACTAGATTCGAAGGAAATGGACCTGCGCCTTACACCTTTGTT
CCATTTGGGGGAGGACCCAGGATGTGCCCGGGCAAAGAGTATGCCCGATTGGAAATACTTGTGTTC

```
ATGCATAACTTGGTGAAGAGGTTCAAGTGGGAGAAATTGGTTCCTGATGAAAAGATTGTGGTTGAT
CCAATGCCCATTCCAGCAAAGGGTCTTCCTGTTCGCCTTTATCCTCACAAAGCTTGA
```

SEQ ID NO: 14-QsCYP716-C-28 (OQHZ-2073932) translated nucleotide sequence (480 aa):
```
MEHLYLSLVLLFVSSISLSLFFLFYKHKSMFTGANLPPGKIGYPLIGESLEFLSTGWKGHPEKFIF
DRMSKYSSQIFKTSILGEPTAVFPGAVCNKFLFSNENKLVNAWWPASVDKIFPSSLQTSSKEEAKK
MRKLLPQFLKPEALHRYIGIMDSIAQRHFADSWENKNQVIVFPLAKRYTFWLACRLFISVEDPTHV
SRFADPFQLLAAGIISIPIDLPGTPFRKAINASQFIRKELLAIIRQRKIDLGEGKASPTQDILSHM
LLTCDENGQYMNELDIADKILGLLVGGHDTASAACTFIVKFLAELPHIYEQVYKEQMEIAKSKVPG
ELLNWEDIQKMKYSWNVACEVMRLAPPLQGAFREAITDFVFNGFSIPKGWKLYWSANSTHKSPDYF
PEPDKFDPTRFEGNGPAPYTFVPFGGGPRMCPGKEYARLEILVFMHNLVKRFKWEKLVPDEKIVVD
PMPIPAKGLPVRLYPHKA*
```

SEQ ID NO: 15-QsCYP716-C-16α (OQHZ-2012090) (C-16α oxidase) coding sequence (1506 bp/1443 bp):
Long and short isoforms as described herein are distinguished by the presence of the first 63 nucleotides, underlined in the sequences below (21 amino acids).
```
ATGATATATAATAATGATAGTAATGATAATGAATTAGTAATCAGCTCAGTTCAGCAACCATCCATG
GATCCTTTCTTCATTTTTGGCTTACTTCTCTTGGCTCTCTTTCTCTGTTTCTTTTCTTCTCTAC
CTTTCCCGTAGAGCCTATGCTTCTCTCCCCAACCCTCCGCCGGGGAAGCTCGGCTTCCCGTCGTC
GGCGAGAGTCTCGAATTTCTCTCCACCCGACGCAAAGGTGTTCCTGAGAAATTCGTCTTCGACAGA
ATGGCCAAATACTGTCGGGATGTCTTTAAGACATCAATATTGGGAGCAACCACCGCCGTCATGTGC
GGCACCGCCGGTAACAAATTCTTGTTCTCCAACGAGAAAAAACACGTCACTGGTTGGTGGCCGAAA
TCTGTAGAGCTGATTTTCCCAACCTCACTTGAGAAATCATCCAACGAAGAATCCATCATGATGAAA
CAATTCCTTCCCAACTTCTTGAAACCAGAACCTTTGCAGAAGTACATACCCGTTATGGACATAATT
ACCCAAAGACACTTCAATACAAGCTGGGAAGGACGCAACGTGGTCAAAGTGTTTCCTACGGCTGCC
GAATTCACCACGTTGCTGGCTTGTCGGGTATTCCTCAGTGTTGAGGATCCCATTGAAGTAGCCAAG
ATTTCAGAGCCATTTGAAATCTTAGCTGCTGGGTTTCTTTCAATACCCATAAATCTTCCGGGTACC
AAATTAAATAAAGCGGTTAAGGCAGCGGATCAGATTAGAGACGCAATTGTACAGATTTTGAAACGG
AGAAGGGTTGAAATTGCGGAGAATAAAGCAAATGGAATGCAAGATATAGCGTCCATGTTGTTGACG
ACACCAACTAATGCTGGGTTTTATATGACCGAGGCTCACATTTCTGAGAAAATTTTGGGTATGATT
GTTGGTGGCCGTGATACTGCTAGTACTGTTATCACCTTCATCATCAAGTATTTGGCAGAGAATCCT
GAAATTTATAATAAGGTCTATGAGGAGCAAATGGAAGTGGTAAAGTCAAAGAAACCAGGTGAGTTG
CTGAACTGGGAAGATGTGCAGAAAATGAAGTACTCTTGGTGCGTAGCATGTGAAGCTATGCGACTT
GCTCCTCCTGTTCAAGGTGGTTTCAAGGTGGCCATTAATGACTTTGTGTATTCTGGGTTCAACATT
CGCAAGGGTTGGAAGTTATATTGGAGTGCCATTGCAACACACATGAATCCAGAATATTTCCCAGAA
CCTGAGAAATTCAACCCCTCAAGGTTTGAAGGGAAGGGACCAGTACCTTACAGCTTCGTACCCTTC
GGAGGCGGACCTCGGATGTGTCCCGGGAAGAGTATTCCCGGCTGGAAACACTTGTTTTCATGCAT
CATTTGGTGACGAGGTACAATTGGGAGAAAGTGTATCCCACAGAAGATAACAGTGGATCCAATG
CCATTCCCTGTCAACGGCCTCCCCATTCGCCTTATTCCTCACAAGCACCAATGA
```

SEQ ID NO: 16-QsCYP716-C-16α translated nucleotide sequence (501 aa/480 aa):
```
MIYNNDSNDNELVISSVQQPSMDPFFIFGLLLLALFLSVSFLLYLSRRAYASLPNPPPGKLGFPVV
GESLEFLSTRRKGVPEKFVFDRMAKYCRDVFKTSILGATTAVMCGTAGNKFLFSNEKKHVTGWWPK
SVELIFPTSLEKSSNEESIMMKQFLPNFLKPEPLQKYIPVMDIITQRHFNTSWEGRNVVKVFPTAA
EFTTLLACRVFLSVEDPIEVAKISEPPFEILAAGFLSIPINLPGTKLNKAVKAADQIRDAIVQILKR
RRVEIAENKANGMQDIASMLLTTPTNAGFYMTEAHISEKILGMIVGGRDTASTVITFIIKYLAENP
EIYNKVYEEQMEVVKSKKPGELLNWEDVQKMKYSWCVACEAMRLAPPVQGGFKVAINDFVYSGFNI
RKGWKLYWSAIATHMNPEYFPEPEKFNPSRFEGKGPVPYSFVPFGGGPRMCPGKEYSRLETLVFMH
HLVTRYNWEKVYPTEKITVDPMPFPVNGLPIRLIPHKHQ*
```

SEQ ID NO: 17-QsCYP714-C-23 (C-23 oxidase) coding sequence (1524 bp):
```
ATGTGGTTCACAGTAGGATTGGTCTTGGTTTTCGCCCTATTCATACGTCTCTACAGCAGTCTGTGG
TTGAAGCCTCGTGCAACTCGGATTAAGCTTAGCAATCAAGGAATTAAAGGTCCAAAACCAGCATTT
CTTCTGGGTAATGTTGCAGAGATGAGAAGATTTCAATCTAAGCTTCCAAAATCTGAACTCAAACAA
GGCCAAGTTTCTCATGATTGGGCTTCTAAATCTCTGTTTCCATTTTTCAGTCTTTGGTCCCAGAAA
TACGGAAATACGTTCGTGTTCTCATTGGGGAACATACAGGTGCTCTATGTTCTGATCATGAGTTG
GTGAAAGAAATTAATCAGAATACCTCTTTAGATTTGGGCAAACCCAAGTACCTGCAGAAGGAGCGT
GGCCCTTTGCTGGGACAAGGTATTTTGACCTCCAATGGACAGTTTGGGCGTACCAGAGAAAATC
ATGACTCCTGAACTCTACAAGGAGAAAATCAAGGGCATGTGCGAGTTGATGGTGGAATCTGTAGCT
TGGTTGGTTGAGGAATGGGAACGAAGATCCAAGCTGAGGGTGGGGCAGCAGACATTAGAATAGAC
GAGGATCTTAGAAGCTTCTCTGGTGATGTAATTTCAAAAGCTTGTTTTGGGAGCTGCTATGCCGA
GGGAGGGAAATCTTTCTTAGGCTCAGAGCTCTTCAACACCAAATTGCTTCCAAAGCCTTACTCATG
GGCTTCCCTGGATTAAAGTACCTGCCCATTAAGAGCAACAGAGAGATATGGAGATTGGAGAAGGAG
ATCTTCCAGCTGATTATGAAGCTGGCTGAAGATAGAAAAAAAGAACACATGAGAGAGACCTATTA
CAGATTATAATTGAGGGAGCTAAAAGTAGTGATCTGAGTTCGGAAGCAATGGCAAAATTCATTGTG
GACAACTGCAAGAATGTCTACTTGGCTGGCCATGAAACTACTGCAATGTCTGCTGGTTGGACTTTG
CTTCTCTTGGCTAATCATCCTGAGTGGCAAGCCCGTGTCCGTGATGAGATTTTACAAGTCACCGAG
GGCCGCAATCCTGATTTGACATGCTGCACAAGATGAAACTGTTAACAATGGTAATTCAGGAGGCA
CTGCGACTCTACCCAACAGTCATATTCATGTCAAGAGAAGCATTGGAAGATATTAATGTTGGAAAC
ATCCAAGTTCCAAAAGGTGTTAACATATGGATACCTGTGGTAAATCTTCAAAGGGACACAACGGTA
TGGGGTGCAGACGCAAACGAGTTTAATCCTGAAAGGTTTGCCAATGGAGTTAACAATTCATGCAAG
GTTCCACAACTTTACCTACCATTTGGAGCTGGACCTCGCATTTGTCCTGGAATTAACTCGGCCATG
ACTGAGATCAAGATACTTCTGTGTATCCTGCTCACCAAGTTTTCGTTTTCAGTTTCACCCAACTAT
CGCCACTCACCGGTGTTTAAATTGGTGCTTGAGCCTGAAAATGGAATCAATGTCATCATGAAGAAG
CTCTAA
```

-continued

Sequences

SEQ ID NO: 18-QsCYP714-C-23 translated nucleotide sequence (507 aa):
MWFTVGLVLVFALFIRLYSSLWLKPRATRIKLSNQGIKGPKPAFLLGNVAEMRRFQSKLPKSELKQ
GQVSHDWASKSLFPFFSLWSQKYGNTFVFSLGNIQVLYVSDHELVKEINQNTSLDLGKPKYLQKER
GPLLGQGILTSNGQLWAYQRKIMTPELYKEKIKGMCELMVESVAWLVEEWGTKIQAEGGAADIRID
EDLRSFSGDVISKACFGSCYAGGREIFLRLRALQHQIASKALLMGFPGLKYLPIKSNREIWRLEKE
IFQLIMKLAEDRKKEQHERDLLQIIIEGAKSSDLSSEAMAKFIVDNCKNVYLAGHETTAMSAGWTL
LLLANHPEWQARVRDEILQVTEGRNPDFDMLHKMKLLTMVIQEALRLYPTVIFMSREALEDINVGN
IQVPKGVNIWIPVVNLQRDTTVWGADANEFNPERFANGVNNSCKVPQLYLPFGAGPRICPGINLAM
TEIKILLCILLTKFSFSVSPNYRHSPVFKLVLEPENGINVIMKKL*

SEQ ID NO: 19-GmSGT2 (GmUGT73P2) (Glycine max (soybean) β-D-
galactosyltransferase) coding sequence (1488 bp):
ATGTGGTTCACAGTAGGATTGGTCTTGGTTTTCGCCCTATTCATACGTCTCTACAGCAGTCTGTGG
TTGAAGCCTCGTGCAACTCGGATTAAGCTTAGCAATCAAGGAATTAAAGGTCCAAAACCAGCATTT
CTTCTGGGTAATGTTGCAGAGATGAGAAGATTTCAATCTAAGCTTCCAAAATCTGAACTCAAACAA
GGCCAAGTTTCTCATGATTGGGCTTCTAAATCTCTGTTTCCATTTTTCAGTCTTTGGTCCCAGAAA
TACGGAAATACGTTCGTGTTCTCATTGGGGAACATACAGGTGCTCTATGTTTCTGATCATGAGTTG
GTGAAAGAAATTAATCAGAATACCTCTTTAGATTTGGGCAAACCCAAGTACCTGCAGAAGGAGCGT
GGCCCTTTGCTGGGACAAGGTATTTTGACCTCCAATGGACAGCTTTGGGCGTACCAGAGAAAAATC
ATGACTCCTGAACTCTACAAGGAGAAAATCAAGGGCATGTGCGAGTTGATGGTGGAATCTGTAGCT
TGGTTGGTTGAGGAATGGGGAACGAAGATCCAAGCTGAGGGTGGGCAGCAGACATTAGAATAGAC
GAGGATCTTAGAAGCTTCTCTGGTGATGTAATTTCAAAAGCTTGTTTTGGGAGCTGCTATGCCGGA
GGGAGGGAAATCTTTCTTAGGCTCAGAGCTCTTCAACACCAAATTGCTTCCAAAGCCTTACTCATG
GGCTTCCCTGGATTAAAGTACCTGCCCATTAAGAGCAACAGAGAGATATGGAGATTGGAGAAGGAG
ATCTTCCAGCTGATTATGAAGCTGGCTGAAGATAGAAAAAAAGAACAACATGAGAGAGACCTATTA
CAGATTATAATTGAGGGAGCTAAAAGTAGTGATCTGAGTTCGGAAGCAATGGCAAAATTCATTGTG
GACAACTGCAAGAATGTCTACTTGGCTGGCCATGAAACTACTGCAATGTCTGCTGGTTGGACTTTG
CTTCTCTTGGCTAATCATCCTGAGTGGCAAGCCCGTGTCCGTGATGAGATTTTACAAGTCACCGAG
GGCCGCAATCCTGATTTTGACATGCTGCACAAGATGAAACTGTTAACAATGGTAATTCAGGAGGCA
CTGCGACTCTACCCAACAGTCATATTCATGTCAAGAGAAGCATTGGAAGATATTAATGTTGGAAAC
ATCCAAGTTCCAAAGGTGTTAACATATGGATACCTGTGGTAAATCTTCAAAGGGACACAACGGTA
TGGGGTGCAGACGCAAACGAGTTTAATCCTGAAAGGTTTGCCAATGGAGTTAACAATTCATGCAAG
GTTCCACAACTTTACCTACCATTTGGAGCTGGACCTCGCATTTGTCCTGGAATTAATCTGGCCATG
ACTGAGATCAAGATACTTCTGTGTATCCTGCTCACCAAGTTTTCGTTTTCAGTTTCACCCAACTAT
CGCCACTCACCGGTGTTTAAATTGGTGCTTGAGCCTGAAAATGGAATCAATGTCATCATGAAGAAG
CTCTAA SEQ ID NO: 20-GmSGT2 (GmUGT73P2) (Glycine max (soybean) β-D-
galactosyltransferase) translated nucleotide sequence (495 aa):
MEKKKGELKSIFLPFLSTSHIIPLVDMARLFALHDVTIITTAHNATVFQKSIDLDASRGRPIRT
HVVNFPAAQVGLPVGIEAFNVDTPREMTPRIYMGLSLLQQVFEKLFHDLQPDFIVTDMFHPWSVDA
AAKLGIPRIMFHGASYLARSAAHSVEQYAPHLEAKFDTDKFVLPGLPDNLEMTRLQLPDWLRSPNQ
YTELMRTIKQSEKKSYGSLFNSFYDLESAYYEHYKSIMGTKSWGIGPVSLWANQDAQDKAARGYAK
EEEEKEGWLKWLNSKAESSVLYVSFGSINKFPYSQLVEIARALEDSGHDFIWVVRKNDGGEGDNFL
EEFEKRMKESNKGYLIWGWAPQLLILENPAIGGLVTHCGWNTVVESVNAGLPMATWPLFAEHFFNE
KLVVDVLKIGVPVGAKEWRNWNEFGSEVVKREEIGNAIASLMSEEEEDGGMRKRAKELSVAAKSAI
KVGGSSHNNMKELIRELKEIKLSKEAQETAPNP*

SEQ ID NO: 21-AsSQS (Avena strigosa squalene synthase) coding sequence
(1212 bp):
ATGGGGGCGCTGTCGCGGCCGGAGGAGGTGGTGGCGCTGGTCAAGCTGAGGGTGGCGGCGGGGCAG
ATCAAGCGCCAGATCCCGGCCGAGGAACACTGGGCCTTCGCCTACGACATGCTCCAGAAGGTCTCC
CGCAGCTTCGCGCTCGTCATCCAGCAGCTCGGACCCGAACTCCGCAATGCCGTGTGCATCTTCTAC
CTCGTGCTCCGGGCCCTGGACACCGTCGAGGACGACACCAGCATCCCCAACGACGTGAAGCTGCCC
ATCCTTCGGGATTTCTACCGCCATGTCTACAACCCCGACTGGCGTTATTCATGTGGAACAAACCAC
TACAAGGTGCTGATGGATAAGTTCAGACTCGTCTCCACGGCTTTCCTGGAGCTAGGCGAAGGATAT
CAAAAGGCAATTGAAGAAATCACTAGGCGAATGGGAGCAGGAATGGCAAAATTTATATGCCAGGAG
GTTGAAACGATTGATGACTATAATGAGTACTGCCACTATGTAGCAGGGCTAGTAGGCTATGGACTT
TCCAGGCTCTTTCATGCTGCTGGGACAGAAGATCTGGCTTCAGATCAACTTTCGAATTCAATGGGT
TTGTTTCTTCAGAAAACCAATATAATAAGGGATTATTTGGAGGATATAAATGAGATACCAAAGTGC
CGTATGTTTTGGCCTCGAGAAATATGGAGTAAATATGCAGATAAACTTGAGGACCTCAAGTATGAG
GAAAATTCAGAAAAAGCAGTCAATGCTTAATGATATGGTGACTAATGCTTTGGTCCACGCCGAA
GACTGTCTTAATACATGTCTGCGTTGAAGGATAATACTAATTTTCGGTTTTGTGCAATACCTCAG
ATAATGGCAATTGGGACATGTGCTATTTGCTACAATAATGTGAAAGTCTTTAGAGGAGTTGTTAAG
ATGAGGCGTGGGCTCACTGCACGAATAATTGATGAGACAAAATCAATGTCAGATGTCTATTCTGCT
TTCTATGAGTTCTCTTCATTGCTAGAGTCAAAGATTGACGATAACGACCCAAGTTCTGCACTAACA
CGGAAGCGTGTAGAGGCAATAAAGAGGACTTGCAAGTCATCCGGTTTACTAAAGAGAAGGGGATAC
GACCTGGAAAAGTCAAAGTATAGGCATATGTTGATCATGCTTGCACTTCTGTTGGTGGCTATTATC
TTCGGTGTACTGTACGCCAAGTGA SEQ ID NO: 22-AsSQS (Avena strigosa squalene synthase) translated nucleotide
sequence (403 aa):
MGALSRPEEVVALVKLRVAAGQIKRQIPAEEHWAFAYDMLQKVSRSFALVIQQLGPELRNAVCIFY
LVLRALDTVEDDTSIPNDVKLPILRDFYRHVYNPDWRYSCGTNHYKVLMDKFRLVSTAFLELGEGY
QKAIEEITRRMGAGMAKFICQEVETIDDYNEYCHYVAGLVGYGLSRLFHAAGTEDLASDQLSNSMG
LFLQKTNIIRDYLEDINEIPKCRMFWPREIWSKYADKLEDLKYEENSEKAVQCLNDMVTNALVHAE DCLQYMSALKDNTNFRFCAIPQIMAIGTCAICYNNVKVFRGVVKMRRGLTARIIDETKSMSDVYSA
FYEFSSLLESKIDDNDPSSALTRKRVEAIKRTCKSSGLLKRRGYDLEKSKYRHMLIMLALLLVAII
FGVLYAK*

SEQ ID NO: 23-AtATR2 (*Arabidopsis thaliana* cytochrome P450 reductase 2)
coding sequence (2325 bp):
ATGAAAAACATGATGAATTATAAATTAAAACTCTGTTCTGTCTCAAAAAACTCAAAAGGAGTCTCT
CTCTCACCTACACCACACCTAACCAAACCCCCTACGATTCACACAGAGAGAGATCTTCTTCTTCCT
TCTTCTTCCTTCTTCTTTCTTCTTTCTTCTTCTAGCTACAACATCTACAACGCCATGTCCTCT
TCTTCTTCTTCGTCAACCTCCATGATCGATCTCATGGCAGCAATCATCAAAGGAGAGCCTGTAATT
GTCTCCGACCCAGCTAATGCCTCCGCTTACGAGTCCGTAGCTGCTGAATTATCCTCTATGCTTATA
GAGAATCGTCAATTCGCCATGATTGTTACCACTTCCATTGCTGTTCTTATTGGTTGCATCGTTATG
CTCGTTTGGAGGAGATCCGGTTCTGGGAATTCAAAACGTGTCGAGCCTCTTAAGCCTTTGGTTATT
AAGCCTCGTGAGGAAGAGATTGATGATGGGCGTAAGAAAGTTACCATCTTTTTCGGTACACAAACT
GGTACTGCTGAAGGTTTTGCAAAGGCTTTAGGAGAAGAAGCTAAAGCAAGATATGAAAAGACCAGA
TTCAAAATCGTTGATTTGGATGATTACGCGGCTGATGATGAGTATGAGGAGAAATTGAAGAAA
GAGGATGTGGCTTTCTTCTTCTTAGCCACATATGGAGATGGTGAGCCTACCGACAATGCAGCGAGA
TTCTACAAATGGTTCACCGAGGGGAATGACAGAGGAGAATGGCTTAAGAACTTGAAGTATGGAGTG
TTTGGATTAGGAAACAGACAATATGAGCATTTTAATAAGGTTGCCAAAGTTGTAGATGACATTCTT
GTCGAACAAGGTGCACAGCGTCTTGTACAAGTTGGTCTTGGAGATGATGACCAGTGTATTGAAGAT
GACTTTACCGCTTGGCGAGAAGCATTGTGGCCCGAGCTTGATACAATACTGAGGGAAGAAGGGGAT
ACAGCTGTTGCCACACCATACACTGCAGCTGTGTTAGAATACAGAGTTTCTATTCACGACTCTGAA
GATGCCAAATTCAATGATATAAACATGGCAAATGGGAATGGTTACACTGTGTTTGATGCTCAACAT
CCTTACAAAGCAAATGTCGCTGTTAAAAGGGAGCTTCATCTCCCGAGTCTGATCGTTCTTGTATC
CATTTGGAATTTGACATTGCTGGAAGTGGACTTACGTATGAAACTGGAGATCATGTTGGTGTACTT
TGTGATAACTTAAGTGAAACTGTAGATGAAGCTCTTAGATTGCTGGATATGTCACCTGATACTTAT
TTCTCACTTCACGCTGAAAAAGAAGACGGCACACCAATCAGCAGCTCACTGCCTCCTCCCTTCCCA
CCTTGCAACTTGAGAACAGCGCTTACACGATATGCATGTCTTTTGAGTTCTCCAAAGAAGTCTGCT
TTAGTTGCGTTGGCTGCTCATGCATCTGATCCTACCGAAGCAGAACGATTAAAACACCTTGCTTCA
CCTGCTGGAAAGGATGAATATTCAAAGTGGGTAGTAGAGAGTCAAAGAAGTCTACTTGAGGTGATG
GCCGAGTTTCCTTCAGCCAAGCCACCACTTGGTGTCTTCTTCGCTGGAGTTGCTCCAAGGTTGCAG
CCTAGGTTCTATTCGATATCATCATCGCCCAAGATTGCTGAAACTAGAATTCACGTCACATGTGCA
CTGGTTTATGAGAAAATGCCAACTGGCAGGATTCATAAGGGAGTGTGTTCCACTTGGATGAAGAAT
GCTGTGCCTTACGAGAAGAGTGAAAACTGTTCCTCGGCGCCGATATTTGTTAGGCAATCCAACTTC
AAGCTTCCTTCTGATTCTAAGGTACCGATCATCATGATCGGTCCAGGGACTGGATTAGCTCCATTC
AGAGGATTCCTTCAGGAAAGACTAGCGTTGGTAGAATCTGGTGTTGAACTTGGGCCATCAGTTTTG
TTCTTTGGATGCAGAAACCGTAGAATGGATTTCATCTACGAGGAAGAGCTCCAGCGATTTGTTGAG
AGTGGTGCTCTCGCAGAGCTAAGTGTCGCCTTCTCTCGTGAAGGACCCACCAAAGAATACGTACAG
CACAAGATGATGGACAAGGCTTCTGATATCTGGAATATGATCTCTCAAGGAGCTTATTTATATGTT
TGTGGTGACGCCAAAGGCATGGCAAGAGATGTTCACAGATCTCTCCACACAATAGCTCAAGAACAG
GGGTCAATGGATTCAACTAAAGCAGAGGGCTTCGTGAAGAATCTGCAAACGAGTGGAAGATATCTT
AGAGATGTATGGTAA SEQ ID NO: 24-AtATR2 (*Arabidopsis thaliana* cytochrome P450 reductase 2)
translated nucleotide sequence (774 aa):
MKNMMNYKLKLCSVSKNSKGVSLSPTPHLTKPPTIHTERDLLLPSSSFFFLLLSSSSYNIYNAMSS
SSSSSTSMIDLMAAIIKGEPVIVSDPANASAYESVAAELSSMLIENRQFAMIVTTSIAVLIGCIVM
LVWRRSGSGNSKRVEPLKPLVIKPREEEIDDGRKKVTIFFGTQTGTAEGFAKALGEEAKARYEKTR
FKIVDLDDYAADDDEYEEKLKKEDVAFFFLATYGDGEPTDNAARFYKWFTEGNDRGEWLKNLKYGV
FGLGNRQYEHFNKVAKVVDDILVEQGAQRLVQVGLGDDDQCIEDDFTAWREALWPELDTILREEGD
TAVATPYTAAVLEYRVSIHDSEDAKFNDINMANGNGYTVFDAQHPYKANVAVKRELHTPESDRSCI
HLEFDIAGSGLTYETGDHVGVLCDNLSETVDEALRLLDMSPDTYFSLHAEKEDGTPISSSLPPPFP
PCNLRTALTRYACLLSSPKKSALVALAAHASDPTEAERLKHLASPAGKDEYSKWVVESQRSLLEVM
AEFPSAKPPLGVFFAGVAPRLQPRFYSISSSPKIAETRIHVTCALVYEKMPTGRIHKGVCSTWMKN
AVPYEKSENCSSAPIFVRQSNFKLPSDSKVPIIMIGPGTGLAPFRGFLQERLALVESGVELGPSVL
FFGCRNRRMDFIYEEELQRFVESGALAELSVAFSREGPTKEYVQHKMMDKASDIWNMISQGAYLYV
CGDAKGMARDVHRSLHTIAQEQGSMDSTKAEGFVKNLQTSGRYLRDVW*

SEQ ID NO: 25-*Q. saponaria* quillaic acid 3-O-glucuronosyltransferase (cellulose
synthase-like enzyme QsCslG2) coding sequence (2124 bp):
ATGGCGACCGTCTCCTCCCTCCACACTTGCACTGTACAGCAACCCCGTGCAGCCATTAATCGAATT
CACATTTTCTTACACTTTATTGCCATACTTTTCCTCTTTTACTACCGGGTCACCGGTCTTTTCTAT
GACAATGCAGTACCCACTTTAGCTTGGTCTCAATGACCTTAGCTGAGTTGATTTTCGCCTTCGTT
TGGGTGCTCAGCCAAGCCTTCCGGTGGCGCCCGGTGTTGCGTTCAGTTATTCCTGAGAGGATTCCC
AAAGATGTACGATTGCCCGCGGTGGATATCTTAATTTGTACGGCTGACCCATTAAAGGAACCGACG
GTGGAGGTGATGAACACTGTCTTGTCCGCCATGGCATTGGACTATTCCTGCGGAGAATCTGGCTGTA
TATCTTTCTGATGACGGGGGTTCTCCGGTCACCTTATTTGCTATGAAGCAAGTGGGTCCGTTTGCT
AAGCTGTGGCTTCCGTTTTGCAACAAGTACGGAATCAAAACAAGGCATCCTGAGTCTTTTTTCTCG
GCATTTGCGGATGACGAAAGGCTTCACCGGAGTGATGAATTCAGGGCAGAGGAGGAGGCGATCAAG
GACAAATATGAAGAATTTAAGAGAACTATAGAGAAATATGGTGGAGAAGGAAAAAATAGTCATGTT
GTACAAGACCGGCCTCCTCATGTGGAGATTATACATGACACTGGAGATTAGAGAGAATGTGAA
GACCAAGCTGTGCCTCTTCTTGTCTACGTCTCTCGTGAGAAAAGACCATCCTACAATTCTCGGTTC
AAAGCAGGAGCTCTGAACACCCTTCTTCGAGTTTCTGGGGTAATCAGCAATAGCCCATATGTATTG
GTGTTAGACTGTGACATGTACTGCAATGATCCAACATCAGCTAGACAAGCAATGTGCTTCCATCTT
GATCCACAAATGTCTCGCACTCTCTCTTTTGTACAATTCCCCCAGGTTTTCTACAATGTTAGTAAA
AATGATATCTATGATGGCCAAGCTAGGGCAGCCTTTAAGACAAAGTGGCAAGGTATGGATGGACTA
CGTGGGCCACTGCTTTCTGGTACTGGCTTTTATTTGAAGAGGAAGTCCTTGTATGGAAGTCCAAAC

```
CAAGAAGATGATTGTTTACTTGAGCCCCATAAGAATTTTGGAAAGTGTGACAAGCTCATAGAATCA
GTAAAGGTCATTTATGAACGTGATGTTTCAATAAAGGCAGATTCATCAGATGCCATTTTGCAAGAT
GCCAACAATTAGCATCTTGTCCCTATGAAACAAACACAAGCTGGGGCAAAGAGGTTGGGTTCTCG
TATGACTGCTTATTAGAGAGTACATTCACAGGTTATCTGTTGCACTGCAGAGGGTGGACATCAGTT
TATCTTTATCCAAGAAGCCATGTTTCTTAGGGTGTACTCCAGTTGATATGAAGGAAGCCATGGTT
CAGTATACGAAGTGGATTTCTGAATTATTTTTACTTGCTATCTCAAGATTCAACCCTCTGACATTT
GGGATATCCAGAATGTCCATTCTCCAGAGCATGTGTTACGGATACCTTACAATCATGCCCATTTTA
TCTGTTGCTATGATCTTCTATGCCACAGTTCCTCAATTGTGCCTCTTGAGAGGCGTACCTCTGTTT
CCCAAGGTTTCAGACCCATGGTTTGCAGTGTTCCTAGCAATATTTGTGTCCTCCCTCTGTCAGCAC
TTAATTGAAGTCCTCACGAGTGATGGCACGCTCAAGACTTGGTGGAATGAACAAAGAAATTGGGTG
ATAAAGTCTGGTTCCGGTAGCGTATTTGGAGCTCTGAGTGGAATATTGAAGTGGTTTGGCATGAAG
ATTAAATTTGGTTTATCAAACAAAGCCGTGGACAAAGAAAAGCTTGAGAAATATGAAAAGGGTAAG
TTTGATTTCCAAGGGGCTGCCATGTTTATGGTTCCCTTAACTATATCAGTCATCTTGAACACATTA
TGCCTTATCGGTGGTTTATGGAGAGTAATCACACTTAAAAACTTCGAAGAGATGTCAGGGCAGTTC
ATCATCTCCTTGTACTTTCTAGCTCTCAGCTATCCAATTCTTGAAGGGTTACTAAGAAAAGGCAAG
GGAAAGGCCTAA
```

SEQ ID NO: 26-*Q. saponaria* quillaic acid 3-O-glucuronosyltransferase (cellulose
synthase-like enzyme QsCslG2) translated nucleotide sequence (707 aa):
```
MATVSSLHTCTVQQPRAAINRIHIFLHFIAILFLFYYRVTGLFYDNAVPTLAWSLMTLAELIFAFV
WVLSQAFRWRPVLRSVIPERIPKDVRLPAVDILICTADPLKEPTVEVMNTVLSAMALDYPAENLAV
YLSDDGGSPVTLFAMKQVGPFAKLWLPFCNKYGIKTRHPESFFSAFADDERLHRSDEFRAEEEAIK
DKYEEFKRTIEKYGGEGKNSHVVQDRPPHVEIIHDTRKIRENSEDQAVPLLVYSREKRPSYNSRF
KAGALNTLLRVSGVISNSPYVLVLDCDMYCNDPTSARQAMCFHLDPQMSRTLSFVQPPQVFYNVSK
NDIYDGQARAAFKTKWQGMDGLRGPLLSGTGFYLKRKSLYGSPNQEDDCLLEPHKNFGKCDKLIES
VKVIYERDVSIKADSSDAILQDAKQLASCPYETNTSWGKEVGFSYDCLLESTFTGYLLHCRGWTSV
YLYPKKPCFLGCTPVDMKEAMVQYTKWISELFLLAISRFNPLTFGISRMSILQSMCYGYLTIMPIL
SVAMIFYATVPQLCLLRGVPLFPKVSDPWFAVFLAIFVSSLCQHLIEVLTSDGTLKTWWNEQRNWV
IKSGSGSVFGALSGILKWFGMKIKFGLSNKAVDKEKLEKYEKGKFDFQGAAMFMVPLTISVILNTL
CLIGGLWRVITLKNFEEMSGQFIISLYFLALSYPILEGLLRKGKGKA
```

SEQ ID NO: 27-*Q. saponaria* QA-GlcpA-Galp α-1,3-L-rhamnosyltransferase
(Qs_0283850) coding sequence (1485 bp):
```
ATGGTCTCCGGCGACGACGACGTTTCTCGTCGGCCACTGAAAGTTTACTTTATTGCACACCCCTCA
CCTGGCCATATTGCCCCTCTAACCAAAATAGCCCAACTCTTTGCTGCACGTGGTGAGCACGTGACT
ATTCTTACTACTCCCGCCAATGTCCACTTCCATGAGAAATCCATCGACAAAGGAAAGACTTCCGGC
TATCATGTTAACATCCACGCCGTTAAATTTCCTTCTAAAGAGGTCGGTCTCCCCGACGGCATCGAA
AACTTCTCTCACGCCTCCGATAATGAAACAGCAGCCAAAATTTGGGCCGGATTCTCCATGCTTCAA
ACTGAAATGGAGCAATATATGGAACAAAACCCACCCGATTGCATTGTTGCCGACATGTTCAACCGC
TGGACTTCCGACTTCGCTATCAAATTGGGAATCCCGAGAATAGTTTTCAACGTCTACTGTATTTTC
ACACGCTGTTTGGAAGAAGCAATCAGATCACCTGACTCGCCCACACTTGAAACTAAACTCCGATAAT
GAACAGTTTATTATTCCGGGTCTACCCGACCCCATAACAATTACCCGAGCTCAACTGCCCGACGGT
GCCTTTTCTGTCGTCAAAGAACAAGTTAGTGAAGCTGAGTTGAAAAGCTTCGGAATGGTGATCAAC
GGGTTTTCCGAACTCGAAACCGAATACATCGAGTATTACAAGAATATCATGGGTCGAAAACGGATT
TGGCATGTCGGACCCCTTCAGCTCATTTACCAAAACGATGACCCCAAAGTTCAGAGGAGCCAGAAG
ACAGCGGTCGTGAGTGACAACGAGTTAGTGAGTTGGCTTGACTCGAAGAAACCCGACTCAGTGATT
TACATTTCCTTCGGTAGTGCAATTCGTTTCTCTAATAAGCAGCTCTATGAAATAGCATGTGGATTA
GAAGCTTCCGGCTACCCATTTTTGTGGGCCTTACTTTGGGTGCCAGAAGATGACGACGACGTGGGC
AACAAATGGTTGCCTGATTTCGAAGAAAGAATAAAAAGAGAAAATAAGGGAATAATTTTCAGGGGG
TGGGCCCCACAGATGTTAATCTTAAACCACCCGGCGATCGGTGGTTTCATGACGCATTGTGGTTGG
AATGCGGTGGTGGAAGCGCTTTCTTTCGGTGTTCCGACTATTACGCTTCCGGTTTTCTCGGAGCAG
TTTTATACTGAGAGACTGATATCACAAGTGCTCAAGACTGGTGTCGAGGTCGGTGCAGAAGTGG
ACCTATGCATTTGATGCGGGGAAATATCCGGTGAGTCGGGAAAGATAGCGCGGTGAAGAAG
ATATTAGACTGTGGAGAAGAGGCAGAAGGAATGAGAAAGCGGGCCAGGGAGATGAAAGAAAAGCC
CAAAAAAGTGTTGAAGAAGGTGGGTCCTCTTATAATAATTTAACGGCTATGATTGAAGATCTTAAA
GAATTTAGGGCTAACAATGGCAAGGTTGCATGA
```

SEQ ID NO: 28-*Q. saponaria* QA-GlpA-Galp α-1,3-L-rhamnosyltransferase
(Qs_0283850) translated nucleotide sequence (494 aa):
```
MVSGDDDVSRRPLKVYFIAHPSPGHIAPLTKIAQLFAARGEHVTILTTPANVHFHEKSIDKGKTSG
YHVNIHAVKFPSKEVGLPDGIENFSHASDNETAAKIWAGFSMLQTEMEQYMEQNPPDCIVADMFNR
WTSDFAIKLGIPRIVFNVYCIFTRCLEEAIRSPDSPHLKLNSDNEQFIIPGLPDPITITRAQLPDG
AFSVVKEQVSEAELKSFGMVINGFSELETEYIEYYKNIMGRKRIWHVGPLQLIYQNDDPKVQRSQK
TAVVSDNELVSWLDSKKPDSVIYISFGSAIRFSNKQLYEIACGLEASGYPFLWALLWVPEDDDDVG
NKWLPDFEERIKRENKGIIFRGWAPQMLILNHPAIGGFMTHCGWNAVVEALSFGVPTITLPVFSEQ
FYTERLISQVLKTGVEVGAEKWTYAFDAGKYPVSREKIATAVKKILDCGEEAEGMRKRAREMKEKA
QKSVEEGGSSYNNLTAMIEDLKEFRANNGKVA
```

SEQ ID NO: 29-*Q. saponaria* QA-GlcpA-Galp α-1,3-L-rhamnosyltransferase
(TRINITY_DN20529_c0_g2_i8) coding sequence (1491 bp):
```
ATGGTCTCCGGCGACGATACCGTTTCACGGCCACTGATAGTTTACTTTATTGCACACCCCTCACCT
GGCCATATTGCCCCTCTAACCAAAATAGCCCAACTCTTCGCTGCACGTGGTGAGCACGTCACTATT
CTTACTACTCCCGCCAATGTCCACTTCCATGAGAAATCCATCGACAAAGAAAGAATTCCGGCTAT
CATGTTAACATCCACACCGTTAAATTTCCTTCTAAAGAGGTCGGTCTCCCTGACGGCATCGAAAAC
TTCTCTCACGCCTCCGATAATGAAACAGCAGCCAAAATTTGGGCCGGATTCTCCATGCTTCAAACT
GAAATGGAGCAATATATGGAACAAAACCCACCCGATTGCATTGTTGCCGACATGTTCAACCGCTGG
ACTTCCGACTTCGCTATCAAATTGGGAATCCCGAGAATAGTTTTCAACGTCTACTGTATTTTCACA
```

```
CGCTGTTTGGAAGAAGCAATCAGATCACCTGACTCGCCACACTTGAAACTAAACTCCGATAATGAA
CAGTTTATTATTCCCGGTCTACCCGACCCCATAACAATTACCCGAGCTCAACTCCCCGACGGTGCC
TTTTCTGTCGTCAAAGAACAAGTTAGTGAAGCTGAGTTGAAAAGCTTCGGAATGGTGATCAACGGG
TTTTCCGAACTCGAAACTGAATACATCGAGTATTACAAGAATATCATGGGTCGCAAACGGATTTGG
CATGTCGGACCCCTTCAGCTAATTTACCAAAACGACGACCCCAAAGTTCAGAGGAGCCAGAAGACA
GCGGTCTTGAGTGACAACGAGTTAGTGAGTTGGCTTGACTCGAAGAAACCCGACTCAGTGATTTAC
ATTTCCTTCGGTAGTGCAATTCGTTTCTCTAATAAGCAGCTCTATGAAATCGCATGTGGATTAGAA
GCTTCCGGCTACCCATTTTTGTGGGCCTTACTTTGGGTGCCAGAAGATGATGACGACGTGGGCAAC
AAATGGTTGCCGGGTTTCGAAGAAAGAATAAAAAGAGAAATAAGGGAATAATTTTCAGGGGGTGG
GCCCCACAGATGTTAATCTTAAACCACCCGGCGATCGGTGGTTTCATGACGCATTGTGGTTGGAAT
GCGGTGGTGGAAGCACTTTCATTCGGTGTTCCGACTATTACGCTTCCAGTTTTCTCGGAGCAGTTT
TATACTGAGAGACTGATATCACAAGTGCTCAAGACTGGTGTGGAGGTTGGTGCAGAGAAGTGGACC
TATGCATTTGATGCGGGGAAATATCCGGTGAGTAGGGAAAAGATAGCGACGGCGGTGAAGAAGATA
TTAGACGATGGAGAAGAGGCAGAAGGAATGAGAAAGCGGGCCAGGGAGATGAAAGAAAAAGCCCAA
AAAAGTGTTGAAGAAGGTGGATCCTCTTATAATAATTTAACGGCTATGATTGAAGATCTTAAAGAA
TTTAGGGCTAACAATGGCAAGGCTGCAATGAAATCATGA

SEQ ID NO: 30-Q. saponaria QA-GlcpA-Galp α-1,3-L-rhamnosyltransferase
(TRINITY_DN20529_c0_g2_i8) translated nucleotide sequence (496 aa):
MVSGDDTVSRPLIVYFIAHPSPGHIAPLTKIAQLFAARGEHVTILTTPANVHFHEKSIDKRKNSGY
HVNIHTVKFPSKEVGLPDGIENFSHASDNETAAKIWAGFSMLQTEMEQYMEQNPPDCIVADMFNRW
TSDFAIKLGIPRIVFNVYCIFTRCLEEAIRSPDSPHLKLNSDNEQFIIPGLPDPITITRAQLPDGA
FSVVKEQVSEAELKSFGMVINGFSELETEYIEYYKNIMGRKRIWHVGPLQLIYQNDDPKVQRSQKT
AVLSDNELVSWLDSKKPDSVIYISFGSAIRFSNKQLYEIACGLEASGYPFLWALLWVPEDDDDVGN
KWLPGFEERIKRENKGIIFRGWAPQMLILNHPAIGGFMTHCGWNAVVEALSFGVPTITLPVFSEQF
YTERLISQVLKTGVEVGAEKWTYAFDAGKYPVSREKIATAVKKILDDGEEAEGMRKRAREMKEKAQ
KSVEEGGSSYNNLTAMIEDLKEFRANNGKAAMKS SEQ ID NO: 31-Q. saponaria QA-GlcpA-Galp β-1,3-D-xylosyltransferase
(Qs_0283870) coding sequence (1515 bp):
ATGGTCTCCGGCGACGACGATGTTTCTCGTCGGCCACTGAAAGTTTACTTCATTGCACACCCCTCA
CCTGGCCATATTGCCCCTCTGACCAAAATAGCCCATCTCTTCGCTGCCTCGGTGAGCACGTGACT
ATTCTCACTACTCCCGCCAATGTCCACTTCCATGAGAAATCCATCGACAAAGGAAAGGCTTCCGGC
TATCATGTTAACATCCACACCGTTAAATTTCCTTCTAAAGAGGTCGGTCTCCCTGACGGCATCGAA
AACTTCTCTTACGCCTCCGATGTTGAAACAGCAGCTAAAATTTGGGCTGGATTCGCCATGCTACAA
ACTGAAATGGAGCAATATATGGAGCTTAACCCACCCGATTGCATCGTTGCCGACATGTTCACCTCC
TGGACCTCCGACTTTGCTATCAAATTGGGAATCACAAGAATCGTTTTCAACGTCTATTGTATTTTC
ACACGCTGTTTGGAAGAAGCCATCCGATCACCGGACTCGCCACACTTGAACAAAGAAATCTCTGAT
AATGAACCGTTTGTTATCCCGGGTCTACCAGACCCCATAACAATTACCCGAGCTCAACTGCCCGAC
GGTACCTTTTCTCCCATGAAAGAACTAGCTAGAACAGCTGAGTTGAAGAGCTTTGGAATGGTGATC
AACGGGTTTTCCGAACTCGAAACCGATTACATCGAGCATTACAAGAAAATCATGGGTCACAAACGG
ATTTGGCATGTCGGACCCCTTCAGCTAATCCACCGTAACGATGAAGACAAAATTCAGAGGAGCCAC
AAGACAGCGGTGCTGAGTGATAACGATAACGAGTTAGTGAGTTGGCTTAACTCGAAGAAACCCGAC
TCAGTTATTTACATTTGCTTCGGTAGTGCAACTCGTTTCTCTAATCACCAGCTCTATGAAATCGCC
TGTGGATTAGAAGCTTCCGGGCACCCATTTTTGTGGGGCCTACTTTGGGTGCCAGAAGATGAAGAT
AACGATGACGTGGGCAACAAATGGTTGCCAGCTTTCGAAGAAAGAATTAAAAAGGAAAATAAGGGA
ATGATTTTAAGGGGTGGGCTCCACAGATGTTAATCTTGAATCACCCGGCGATCGGTGGTTTCATG
ACGCATTGTGGTTGGAATGCGCGGTGGAGGCGCTTTCTTCCGGTGTTCCGATTATTACATTTCCG
GTTTTCTCGGATCAGTTTTATAATGAAAGGCTGATATCACAAGTGCATAAGTGTGGGGTGGGGTT
GGTACGGAGGCGTGGAGCTATGCATTCGATGCCGGGAAGAATCCGGTGGGTCGGGAAAGATAATG
ACGGCGGTGAAGAAGATATTAGACGGTGGAGAAGAGGCGAAGGAATGAGAAAGAGGGCCCGGGAG
CTGAAAGAAATAGCTAAAAGAAGTGTGGAAGAAGGTGGGTCCTCTTATAATAATTTAACGGCTATG
ATTCAAGATCTGAAAGAATTTAGAGCTAACAATGGCAAGGCTGCACAAGATCATGAATCGTGA SEQ ID NO: 32-Q. saponaria QA-GlcpA-Galp β-1,3-D-xylosyltransferase
(Qs_0283870) translated nucleotide sequence (504 aa):
MVSGDDDVSRRPLKVYFIAHPSPGHIAPLTKIAHLFAALGEHVTILTTPANVHFHEKSIDKGKASG
YHVNIHTVKFPSKEVGLPDGIENFSYASDVETAAKIWAGFAMLQTEMEQYMELNPPDCIVADMFTS
WTSDFAIKLGITRIVFNVYCIFTRCLEEAIRSPDSPHLNKEISDNEPFVIPGLPDPITITRAQLPD
GTFSPMKELARTAELKSFGMVINGFSELETDYIEHYKKIMGHKRIWHVGPLQLIHRNDEDKIQRSH
KTAVLSDNDNELVSWLNSKKPDSVIYICFGSATRFSNHQLYEIACGLEASGHPFLWGLLWVPEDED
NDDVGNKWLPAFEERIKKENKGMILRGWAPQMLLLNHPAIGGFMTHCGWNAAVEALSSGVPIITFP
VFSDQFYNERLISQVHKCGVGVGTEAWSYAFDAGKNPVGREKIMTAVKKILDGGEEAEGMRKRARE
LKEIAKRSVEEGGSSYNNLTAMIQDLKEFRANNGKAAQDHES

The invention claimed is:

1. A method of converting a host from a phenotype whereby the host is unable to perform the biosynthesis of the 3-O branched trisaccharide quillaic acid ("QA") derivative ("QA-3-O-TriS"), which QA-3-O-TriS is 3β-{[β-D-xylopyranosyl-(1->3)-[β-D-galactopyranosyl-(1->2)]-β-D-glucopyranosiduronic acid]oxy}-quillaic acid (QA-GlcpA-[Galp]-Xylp) or (3β-{[α-L-rhamnopyranosyl-(1->3)-[β-D-galactopyranosyl-(1->2)]-β-D-glucopyranosiduronic acid]oxy}-quillaic acid) (QA-GlcpA-[Galp]-Rhap), by glycosylation of the 3-O position of QA, to a phenotype whereby the host is able to carry out said QA-3-O-TriS biosynthesis, which method comprises the step of expressing a heterologous nucleic acid within the host or one or more cells thereof, following an earlier step of introducing the nucleic acid into the host or an ancestor of either, wherein the heterologous nucleic acid comprises nucleotide sequences each of which encodes a polypeptide which in combination have said QA-3-O-TriS biosynthesis activity, wherein the heterologous nucleic acid encodes two or three of the following types of polypeptide (i), (ii) or (iii):

(i) a QA 3-O glucuronosyl transferase ("QA-GlcAT") capable of transferring D-glucuronic acid ("GlcpA") at the 3-O position of quillaic acid to form 3β-{[β-d-glucopyranosiduronic acid]oxy}-quillaic acid ("QA-GlcpA");

(ii) a QA-GlcpA galactosyl transferase ("QA-GalT") capable of transferring D-Galactose ("Galp") via a β-1->2 linkage to QA-GlcpA to form 3β-{[β-d-galactopyranosyl-(1->2)-β-d-glucopyranosiduronic acid]oxy}-quillaic acid ("QA-GlcpA-Galp");

(iii) a QA-GlcpA-Galp Rhamnosyl/Xylosyl transferase ("QA-RhaT/XylT"), capable of transferring 1-Rhamnose ("Rhap") and/or d-Xylose ("Xylp") via a 1,3 linkage to QA-GlcpA-Galp to form (3β-{[α-l -rhamnopyranosyl-(1->3)-[β-d-galactopyranosyl-(1->2)]-β-d-glucopyranosiduronic acid]oxy}-quillaic acid) ("QA-GlcpA-[Galp]-Rhap") and/or 3β-{[β-d-xylopyranosyl-(1->3)-[β-d-galactopyranosyl-(1->2)]-β-d-glucopyranosiduronic acid]oxy}-quillaic acid ("QA-GlcpA-[Galp]-Xylp") respectively;

wherein:

the QA-GlcAT of (i) comprises the amino acid sequence of SEQ ID: No 2 or 26, or an amino acid sequence that is at least 80% identical to SEQ ID: No 2 or 26;

the QA-GalT of (ii) comprises the amino acid sequence of SEQ ID: No 4, or an amino acid sequence that is at least 80% identical to SEQ ID: No 4; and the QA-RhaT/XylT of (iii) comprises the amino acid sequence of SEQ ID: No 6, 28, 30, or 32, or an amino acid sequence that is at least 80% identical to SEQ ID: No 6, 28, 30, or 32 therewith.

2. The method of claim 1, wherein the heterologous nucleic acid encodes all three types of polypeptide.

3. The method of claim 1, wherein the nucleotide sequences are from *Q. saponaria*.

4. The method of claim 3, wherein:
the QA-GlcAT of (i) comprises the amino acid sequence of SEQ ID: No 2 or 26;
the QA-GalT of (ii) comprises the amino acid sequence of SEQ ID: No 4;
the QA-RhaT/XylT of (iii) comprises the amino acid sequence of SEQ ID: No 6, 28, 30, or 32.

5. The method of claim 1, wherein the heterologous nucleic acid further comprises a plurality of nucleotide sequences each of which encodes a polypeptide which in combination have QA biosynthesis activity ("QA polypeptide"), wherein the nucleic acid encodes all of the following QA polypeptides:
(i) a β-amyrin synthase (bAS) for cyclisation of 2,3-oxidosqualene (OS) to a triterpene;
(ii) an enzyme capable of oxidising β-amyrin or an oxidised derivative thereof at the C-28 position to a carboxylic acid ("C-28 oxidase");
(iii) an enzyme capable of oxidising β-amyrin or an oxidised derivative thereof at the C-16α position to an alcohol ("C-16α oxidase"); and
(iv) an enzyme capable of oxidising β-amyrin or an oxidised derivative thereof at the C-23 position to an aldehyde ("C-23 oxidase").

6. The method of claim 5, wherein the C-28 oxidase, C-16α oxidase, and C-23 oxidase are all CYP450 enzymes.

7. The method of claim 6, wherein
(i) the C-28 oxidase is a CYP716;
(ii) the C-16α oxidase is a CYP716 or CYP87;
(iii) the C-23 oxidase is a CYP714, CYP72, or CYP94.

8. The method of claim 5, wherein:
the β-amyrin synthase (bAS) comprises the amino acid sequence of SEQ ID: No 12 or an amino acid sequence that is least 80% identical to SEQ ID: No 12;
the C-28 oxidase comprises the amino acid sequence of SEQ ID: No 14 or an amino acid sequence that is least 80% identical to SEQ ID: No 14;
the C-16α oxidase comprises the amino acid sequence of SEQ ID: No 16 or an amino acid sequence that is least 80% identical to SEQ ID: No 16; and
the C-23 oxidase comprises the amino acid sequence of the SEQ ID: No 18 or an amino acid sequence that is least 80% identical to SEQ ID: No 18.

9. The method of claim 1, wherein the nucleic acid further comprises a plurality of nucleotide sequences encoding one or more of the following polypeptides:
(i) an HMG-CoA reductase (HMGR);
(ii) a squalene synthase (SQS).

10. The method of claim 1, wherein the nucleotide sequences are present on two or more different nucleic acid molecules.

11. The method of claim 10, wherein the host is a plant and the nucleic acid molecules are introduced by co-infiltration with a plurality of *Agrobacterium tumefaciens* strains each carrying one or more of the nucleic acid molecules.

12. The method of claim 11, wherein the nucleic acid molecules are transient expression vectors, wherein each of the transient expression vectors comprises an expression cassette comprising:
(i) a promoter, operably linked to
(ii) an enhancer sequence derived from the RNA-2 genome segment of a bipartite RNA virus, in which a target initiation site in the RNA-2 genome segment has been mutated;
(iii) a nucleotide sequence encoding one of the polypeptides which in combination have said QA-3-O-TriS biosynthesis activity;
(iv) a terminator sequence; and optionally
(v) a 3' UTR located upstream of said terminator sequence.

13. The method of claim 1, wherein the host is a plant which that has modified QA-3-O-TriS content.

14. A genetically engineered host cell comprising a a heterologous nucleic acid that is not native to the cell, wherein the heterologous nucleic acid comprises a plurality of nucleotide sequences each of which encodes a polypeptide which in combination have QA-3-O-TriS biosynthesis activity,
wherein expression of said nucleic acid imparts on the host cell the ability to carry out QA-3-O-TriS biosynthesis,
wherein the nucleic acid encodes two or three of the following types of polypeptide (i), (ii) or (iii):
(i) a QA-GlcAT capable of GlcpA at the 3-O position of quillaic acid to form QA-GlcpA;
(ii) a QA-GalT capable of transferring Galp via a β-1->2 linkage to QA-GlcpA to form QA-GlcpA-Galp;
(iii) a QA-RhaT/XylT, capable of transferring Rhap and/or Xylp via a 1,3 linkage to QA-GlcpA-Galp to form QA-GlcpA-[Galp]-Rhap and/or GlcpA-[Galp]-Xylp respectively;
wherein:
the QA-GlcAT of (i) comprises the amino acid sequence of SEQ ID: No 2 or 26, or an amino acid sequence that is at least 80% identical to SEQ ID: No 2 or 26;
the QA-GalT of (ii) comprises the amino acid sequence of SEQ ID: No 4, or an amino acid sequence that is at least 80% identical to SEQ ID: No 4; and
the QA-RhaT/XylT of (iii) comprises the amino acid sequence of SEQ ID: No 6, 28, 30, or 32, or an amino acid sequence that is at least 80% identical to SEQ ID: No 6, 28, 30, or 32.

15. The genetically engineered host cell of claim 14, further comprising a plurality of nucleotide sequences each of which encodes a polypeptide which in combination have QA biosynthesis activity, wherein the nucleic acid encodes all of the following QA polypeptides:
(i) a β-amyrin synthase (bAS) for cyclisation of 2,3-oxidosqualene (OS) to a triterpene;

(ii) an enzyme capable of oxidising β-amyrin or an oxidised derivative thereof at the C-28 position to a carboxylic acid ("C-28 oxidase");

(iii) an enzyme capable of oxidising β-amyrin or an oxidised derivative thereof at the C-16α position to an alcohol ("C-16α oxidase"); and (iv) an enzyme capable of oxidising β-amyrin or an oxidised derivative thereof at the C-23 position to an aldehyde ("C-23 oxidase").

16. A method for producing the host cell of claim 14, comprising co-infiltrating a plurality of recombinant constructs comprising the heterologous nucleic acid into the cell for transient expression thereof.

17. The method for producing the host cell of claim 14, comprising transforming a cell with the heterologous nucleic acid by introducing said nucleic acid into the cell via a vector and causing or allowing recombination between the vector and the cell genome to introduce the heterologous nucleic acid into the genome.

18. The method of claim 17, wherein the cell is a plant cell and the method further comprises regenerating a plant from the transformed cell.

19. A transgenic plant made by the method of claim 18, or a clone or descendant of said transgenic plant that comprises the heterologous nucleic acid, wherein expression of said heterologous nucleic acid imparts an increased ability to carry out QA-3-O-TriS synthesis compared to a wild-type plant otherwise corresponding to said transgenic plant except that is does not comprise the heterologous nucleic acid.

20. A transgenic plant comprising a heterologous nucleic acid that is not native to the plant, wherein the nucleic acid encodes one or more of:

(i) a QA 3-O glucuronosyl transferase ("QA-GlcAT") capable of transferring D-glucuronic acid ("GlcpA") at the 3-O position of quillaic acid to form 3β-{[β-D-glucopyranosiduronic acid]oxy}-quillaic acid ("QA-GlcpA");

(ii) a QA-GlcpA galactosyl transferase ("QA-GalT") capable of transferring D-Galactose ("Galp") via a β-1->2 linkage to QA-GlcpA to form 3β-{[β-D-galactopyranosyl-(1->2)-β-D-glucopyranosiduronic acid]oxy}-quillaic acid ("QA-GlcpA-Galp");

(iii) a QA-GlcpA-Galp Rhamnosyl/Xylosyl transferase ("QA-RhaT/XylT"), capable of transferring L-Rhamnose ("Rhap") and/or D-Xylose ("Xylp") via a 1,3 linkage to QA-GlcpA-Galp to form (3β-{[α-L-rhamnopyranosyl-(1->3)-[β-D-galactopyranosyl-(1->2)]-β-D-glucopyranosiduronic acid]oxy}-quillaic acid) ("QA-GlcpA-[Galp]-Rhap") and/or 3β-{[β-D-xylopyranosyl-(1->3)-[β-D-galactopyranosyl-(1->2)]-β-D-glucopyranosiduronic acid]oxy}-quillaic acid ("QA-GlcpA-[Galp]-Xylp") respectively;

wherein:
the QA-GlcAT of (i) comprises the amino acid sequence of SEQ ID: No 2 or 26, or an amino acid sequence that is at least 80% identical to SEQ ID: No 2 or 26;
the QA-GalT of (ii) comprises the amino acid sequence of SEQ ID: No 4, or an amino acid sequence that is at least 80% identical to SEQ ID: No 4;
the QA-RhaT/XylT of (iii) comprises the amino acid sequence of SEQ ID: No 6, 28, 30, or 32, or an amino acid sequence that is at least 80% identical to SEQ ID: No 6, 28, 30, or 32.

21. A recombinant vector comprising a nucleic acid encoding:

(i) a QA 3-O glucuronosyl transferase ("QA-GlcAT") capable of transferring D-glucuronic acid ("GlcpA") at the 3-O position of quillaic acid to form 3β-{[β-D-glucopyranosiduronic acid]oxy}-quillaic acid ("QA-GlcpA");

(ii) a QA-GlcpA galactosyl transferase ("QA-GalT") capable of transferring D-Galactose ("Galp") via a β-1->2 linkage to QA-GlcpA to form 3β-{[β-D-galactopyranosyl-(1->2)-β-D-glucopyranosiduronic acid]oxy}-quillaic acid ("QA-GlcpA-Galp"); and/or (iii) a QA-GlcpA-Galp Rhamnosyl/Xylosyl transferase ("QA-RhaT/XylT"), capable of transferring L-Rhamnose ("Rhap") and/or D-Xylose ("Xylp") via a 1,3 linkage to QA-GlcpA-Galp to form (3β-{[α-L-rhamnopyranosyl-(1->3)-[β-D-galactopyranosyl-(1->2)]-β-D-glucopyranosiduronic acid]oxy}-quillaic acid) ("QA-GlcpA-[Galp]-Rhap") and/or 3β-{[β-D-xylopyranosyl-(1->3)-[β-D-galactopyranosyl-(1->2)]-β-D-glucopyranosiduronic acid]oxy}-quillaic acid ("QA-GlcpA-[Galp]-Xylp") respectively;

wherein:
the QA-GlcAT of (i) comprises the amino acid sequence of SEQ ID: No 2 or 26, or an amino acid sequence that is at least 80% identical to SEQ ID: No 2 or 26;
the QA-GalT of (ii) comprises the amino acid sequence of SEQ ID: No 4, or an amino acid sequence that is at least 80% identical to SEQ ID: No 4;
the QA-RhaT/XylT of (iii) comprises the amino acid sequence of SEQ ID: No 6, 28, 30, or 32, or an amino acid sequence that is at least 80% identical to SEQ ID: No 6, 28, 30, or 32, and
wherein the nucleic acid is operably linked to a promoter that is heterologous to the nucleic acid.

22. The vector of claim 21 wherein the promoter is an inducible promoter.

23. A method comprising the step of a vector of claim 21 into a host cell to transform the host cell.

24. A host cell comprising a vector according to claim 21.

25. The host cell of claim 24, wherein the host cell is microbial.

26. The host cell of claim 25, further comprising a nucleic acid which comprises one or more nucleotide sequences each of which encodes a cytochrome P450 reductase (CPR).

27. The method of claim 23, wherein the host cell is a plant cell, and the method further comprises regenerating a plant from the transformed host cell.

28. A transgenic plant made by the method of claim 27, or a clone or descendant of said transgenic plant that comprises the vector.

29. The method of claim 1, further comprising isolating QA-3-O-TriS, or a downstream product thereof from the host.

30. A method comprising culturing the host cell of claim 14 and isolating QA-3-O-TriS, or a downstream product thereof.

31. A method comprising isolating QA-3-O-TriS, or a derivative thereof from a plant of claim 20.

32. The method of claim 1, wherein:
the QA-GlcAT of (i) comprises the amino acid sequence of SEQ ID: No 2 or 26, or an amino acid sequence that is at least 90% identical to SEQ ID: No 2 or 26;
the QA-GalT of (ii) comprises the amino acid sequence of SEQ ID: No 4, or an amino acid sequence that is at least 90% identical to SEQ ID: No 4; and the QA-RhaT/XyIT of (iii) comprises the amino acid sequence of SEQ ID: No 6, 28, 30, or 32, or an amino acid sequence that is at least 90% identical to SEQ ID: No 6, 28, 30, or 32.

33. The method of claim 1, wherein
the QA-GlcAT of (i) comprises the amino acid sequence of SEQ ID: No 2 or 26, or an amino acid sequence that is at least 95% identical to SEQ ID: No 2 or 26;
the QA-GalT of (ii) comprises the amino acid sequence of SEQ ID: No 4, or an amino acid sequence that is at least 95% identical to SEQ ID: No 4; and
the QA-RhaT/XyIT of (iii) comprises the amino acid sequence of SEQ ID: No 6, 28, 30, or 32, or an amino acid sequence that is at least 95% identical to SEQ ID: No 6, 28, 30, or 32.

* * * * *

```

SEQUENCE LISTING

<160> NUMBER OF SEQ ID NOS: 54

<210> SEQ ID NO 1
<211> LENGTH: 2142
<212> TYPE: DNA
<213> ORGANISM: Quillaja saponaria

<400> SEQUENCE: 1

```
atgaaatccc cctctaaccc aaatcagaaa cccatcctcc acacttgtac aattcagcag        60
cctcgtgcta cccttaacaa aattcatagt cttattcatt tctcagccat acttgtccta       120
ttttattacc ggataacccg tctattcttc accgacgatt tcaaggtacc caagttacta       180
tggactctaa tgacaatctc cgagttcatt cttgccttca tttgggttct catccaacct       240
ttccggtggc gaccggtgtc ccgttccgtc ataccagaga atatgccgaa ggacatcagt       300
ttgccggcgg tggacgtgtt tgtatgcaca gctgaccctc aaaaagaacc cacagtggag       360
gtgatgaaca caattttatc agccatggct ttagactacc cggcggagaa gctcgccgtg       420
tatctttccg atgatggggg ttctgctgtc accttatatg ctataaaaga agcttgttgt       480
tttgctaaga tgtggcttcc gttttgtaac aagtatggga tcaaatcaag gtgtcccgag       540
gcttattttt caaagcttgc cgctgacgag tggcttcacc ggagtgtgga attcgtggca       600
gaagaaaagg aggtcaaggc taattatgaa gagttcaaga gaaatgtgca gaaatttggt       660
gagcaacaag aaaacagtcg tgttgtgcat gatcgtcacc ctcatgttga gattatacac       720
aataattgga ataacgaaga ccaagctcat gagatgccac tccttgttta tgtctctcgt       780
gaaagaagac catctcacca tcctcgattc aaagctggag ctcttaacac ccttcttcga       840
gtttctggca tcatcagcaa cagccctac atactggttc tagactgtga catgtactgc       900
aatgacccaa cctcagctag acaagcaatg tgcttccatc ttgatcccca actgtctaaa       960
aatcttgctt ttgtacaatt ccctcaaata ttctataacg ctagtaagaa tgacgtctat      1020
gatgcccaag tcagggcggc ataccagaca aagtggcagg gtatggatgg acttcaagga      1080
ccaattttt ctggcactgg ctttactta aagaggaagg caatgtatgg aaaccctgat      1140
caagatgata attgtctact caagccatat aagaaatttg gcatgtctgg agaatttgta      1200
gaatcactta aggtccttaa cgaacaagat ggtacccaga gaaaattatt ggatggattt      1260
ttacaagagg ccaaactatt ggcctcgtgt gcctatgaaa caaagacaag ttggggtaaa      1320
gagattggat tctcatatga ctgtttaata gagagcactt tcactggtta tcttttgcac      1380
tgcagagggt ggatatctgt ttatctttat cccaagagac catgtttttt aggatgctgt      1440
cctactgata tgaaggatgc catggttcaa tataccaagt ggatgtctga gctattttca      1500
attgctatct caagattcaa tcctctgctc tatggggtgg caagaatgtc cattcttcaa      1560
agcctgtgtt atggatcctt tacactggcg cctattttgt catttccttt gttcttatat      1620
ggaacggttc ctcaattatg cctcttgaaa ggcatatctt tgtttccaaa ggtttcggac      1680
ccatggtttg ctgtgtttgc agctatcttt gtatcctccc tgtgtcaaca ctggttcgag      1740
gtcctctctt gtgatggtac atttacgact tggtgtaatg aacagcggag ttggcttata      1800
aagtcggttt ccggtagttt gtttggagtt gtgggcgcaa tcttgcagcg gctaggcttg      1860
aagacaaagt ttagtttatc aaacaaagcc atggacaaag aaaagctgga gaaatatgaa      1920
aagggtaaat ttaatttcca aggggctgcc atgttcatgg ttcctgtgtc tattttagtc      1980
atactgaaca catttttgctt cctcggtggg ttttggaaag tgatcataat gaagaatatc      2040
ctggacatgt ttggacaact ttctctctct gcctacgttt tggttctcag ttgtccagtt      2100
cttgaaggga tgttaactag aatcagcaag aaaatggtct ga                         2142
```

<210> SEQ ID NO 2
<211> LENGTH: 713
<212> TYPE: PRT

<213> ORGANISM: Quillaja saponaria

<400> SEQUENCE: 2

```
Met Lys Ser Pro Ser Asn Pro Asn Gln Lys Pro Ile Leu His Thr Cys
1               5                   10                  15

Thr Ile Gln Gln Pro Arg Ala Thr Leu Asn Lys Ile His Ser Leu Ile
            20                  25                  30

His Phe Ser Ala Ile Leu Val Leu Phe Tyr Tyr Arg Ile Thr Arg Leu
        35                  40                  45

Phe Phe Thr Asp Asp Phe Lys Val Pro Lys Leu Leu Trp Thr Leu Met
    50                  55                  60

Thr Ile Ser Glu Phe Ile Leu Ala Phe Ile Trp Val Leu Ile Gln Pro
65                  70                  75                  80

Phe Arg Trp Arg Pro Val Ser Arg Ser Val Ile Pro Glu Asn Met Pro
                85                  90                  95

Lys Asp Ile Ser Leu Pro Ala Val Asp Val Phe Val Cys Thr Ala Asp
            100                 105                 110

Pro Gln Lys Glu Pro Thr Val Glu Val Met Asn Thr Ile Leu Ser Ala
        115                 120                 125

Met Ala Leu Asp Tyr Pro Ala Glu Lys Leu Ala Val Tyr Leu Ser Asp
    130                 135                 140

Asp Gly Gly Ser Ala Val Thr Leu Tyr Ala Ile Lys Glu Ala Cys Cys
145                 150                 155                 160

Phe Ala Lys Met Trp Leu Pro Phe Cys Asn Lys Tyr Gly Ile Lys Ser
                165                 170                 175

Arg Cys Pro Glu Ala Tyr Phe Ser Lys Leu Ala Ala Asp Glu Trp Leu
            180                 185                 190

His Arg Ser Val Glu Phe Val Ala Glu Glu Lys Glu Val Lys Ala Asn
        195                 200                 205

Tyr Glu Glu Phe Lys Arg Asn Val Gln Lys Phe Gly Glu Gln Gln Glu
    210                 215                 220

Asn Ser Arg Val Val His Asp Arg His Pro His Val Glu Ile Ile His
225                 230                 235                 240

Asn Asn Trp Asn Asn Glu Asp Gln Ala His Glu Met Pro Leu Leu Val
                245                 250                 255

Tyr Val Ser Arg Glu Arg Arg Pro Ser His His Pro Arg Phe Lys Ala
            260                 265                 270

Gly Ala Leu Asn Thr Leu Leu Arg Val Ser Gly Ile Ile Ser Asn Ser
        275                 280                 285

Pro Tyr Ile Leu Val Leu Asp Cys Asp Met Tyr Cys Asn Asp Pro Thr
    290                 295                 300

Ser Ala Arg Gln Ala Met Cys Phe His Leu Asp Pro Gln Leu Ser Lys
305                 310                 315                 320

Asn Leu Ala Phe Val Gln Phe Pro Gln Ile Phe Tyr Asn Ala Ser Lys
                325                 330                 335

Asn Asp Val Tyr Asp Ala Gln Val Arg Ala Ala Tyr Gln Thr Lys Trp
            340                 345                 350

Gln Gly Met Asp Gly Leu Gln Gly Pro Ile Phe Ser Gly Thr Gly Phe
        355                 360                 365

Tyr Leu Lys Arg Lys Ala Met Tyr Gly Asn Pro Asp Gln Asp Asn
    370                 375                 380

Cys Leu Leu Lys Pro Tyr Lys Lys Phe Gly Met Ser Gly Glu Phe Val
385                 390                 395                 400
```

Glu Ser Leu Lys Val Leu Asn Glu Gln Asp Gly Thr Gln Lys Lys Leu
                405                 410                 415

Leu Asp Gly Phe Leu Gln Glu Ala Lys Leu Leu Ala Ser Cys Ala Tyr
            420                 425                 430

Glu Thr Lys Thr Ser Trp Gly Lys Glu Ile Gly Phe Ser Tyr Asp Cys
            435                 440                 445

Leu Ile Glu Ser Thr Phe Thr Gly Tyr Leu Leu His Cys Arg Gly Trp
450                 455                 460

Ile Ser Val Tyr Leu Tyr Pro Lys Arg Pro Cys Phe Leu Gly Cys Cys
465                 470                 475                 480

Pro Thr Asp Met Lys Asp Ala Met Val Gln Tyr Thr Lys Trp Met Ser
            485                 490                 495

Glu Leu Phe Ser Ile Ala Ile Ser Arg Phe Asn Pro Leu Leu Tyr Gly
            500                 505                 510

Val Ala Arg Met Ser Ile Leu Gln Ser Leu Cys Tyr Gly Ser Phe Thr
            515                 520                 525

Leu Ala Pro Ile Leu Ser Phe Pro Leu Phe Leu Tyr Gly Thr Val Pro
            530                 535                 540

Gln Leu Cys Leu Leu Lys Gly Ile Ser Leu Phe Pro Lys Val Ser Asp
545                 550                 555                 560

Pro Trp Phe Ala Val Phe Ala Ala Ile Phe Val Ser Ser Leu Cys Gln
                565                 570                 575

His Trp Phe Glu Val Leu Ser Cys Asp Gly Thr Phe Thr Thr Trp Cys
            580                 585                 590

Asn Glu Gln Arg Ser Trp Leu Ile Lys Ser Val Ser Gly Ser Leu Phe
            595                 600                 605

Gly Val Val Gly Ala Ile Leu Gln Arg Leu Gly Leu Lys Thr Lys Phe
            610                 615                 620

Ser Leu Ser Asn Lys Ala Met Asp Lys Glu Lys Leu Glu Lys Tyr Glu
625                 630                 635                 640

Lys Gly Lys Phe Asn Phe Gln Gly Ala Ala Met Phe Met Val Pro Val
                645                 650                 655

Ser Ile Leu Val Ile Leu Asn Thr Phe Cys Phe Leu Gly Gly Phe Trp
                660                 665                 670

Lys Val Ile Ile Met Lys Asn Ile Leu Asp Met Phe Gly Gln Leu Ser
            675                 680                 685

Leu Ser Ala Tyr Val Leu Val Leu Ser Cys Pro Val Leu Glu Gly Met
            690                 695                 700

Leu Thr Arg Ile Ser Lys Lys Met Val
705                 710

<210> SEQ ID NO 3
<211> LENGTH: 1479
<212> TYPE: DNA
<213> ORGANISM: Quillaja saponaria

<400> SEQUENCE: 3
atggtggagt ctccagcaga tcatgatgtg ctcaaaatca ttgtccttcc atgggtaacc      60
tcaggtcaca tgattcccat ggtagatgca gccagactat tgctatgca tggtgcagat     120 gttaccatca tcaccacccc agctaatgcc cttacattcc agaaatccgt cgaccgtgat     180
ttcaattccg tcgtttaat cagaactcac acccttaaat tccctgcagc agaagttggt     240
gtacctgaag gagttgaaaa cttcaacaat acttcccctg aaatgacctc caaagtctac     300
cttggagtct caatgctccg agaaccaacc caacaattga ttgaggatct gcgtccagat     360

```
tgtcttatca ctgatatgtt ctatccttgg gctgtggatg ttgctgacaa attaggcatt    420
ccaaggctaa tttttcaagg tcctggaagt tttggtttgt cagctatgca ttctatcaaa    480
cagtatgagc cctttaagtc agtaacttca gatactgaga cattcccact acctggattg    540
ccgcataagg tagagatgac aaggttgcag ataccaaaat gggttcgtga gccaaatggg    600
tacactcaat tgatgggcag ggtaaaagat tcggagagaa gaagctatgg gtcattggtg    660
aatagctttt atgacttcga aggcccttat gaagagcact ataggaaggc aacaggacag    720
agggtttgga gcattggacc agtttcagtt tgggtgaacc aagatgctgc agataaggtt    780
ggaagaggac aggatcttgt tgctgaagac aaaacagct ggttgaattg gctcaattcc    840
aaagagaaaa actctgttct gtatgtaagt tttgggagca tggccaagtt cccatctgct    900
cagcttcttg aaatagctca tgggcttgaa gcttcaggtc atagtttcat ctgggttgtc    960
agaaaagttg acggggatga tgatgtagac gtgtggcttc agattttga aagaaaatg    1020 aaagagaaca caagggtttt catcataagg aattgggcac acaattgct catattggac   1080 catccagcaa ttggaggttt gctgaatcac agtggatgga attcagtact ggaaggtgct   1140
acagcaggct tgccaatgat cacttggcct ctgtatgccg agcattttta caatgaaagg   1200
ttggttctag atgtgttgaa aattggagta ccagttgggg tgaaggagtg gaagaacttg   1260
catgaggtgg gtgagttggt gagaagggat gcaattgcca aggcaattaa attgttaatg   1320
ggtagtggag aagaagctga ggtaatgagg aaaaaagcca aagagcttgg tgttggagca   1380
aagaaaggta ttcaggttgg aggttcttct cataccaatt tgatagcagt gattgatgag   1440
ttaaagtcac taaagaaatc aagaattcag ggtgtctga                           1479

<210> SEQ ID NO 4
<211> LENGTH: 492
<212> TYPE: PRT
<213> ORGANISM: Quillaja saponaria

<400> SEQUENCE: 4

Met Val Glu Ser Pro Ala Asp His Asp Val Leu Lys Ile Ile Val Leu
1               5                   10                  15

Pro Trp Val Thr Ser Gly His Met Ile Pro Met Val Asp Ala Ala Arg
                20                  25                  30

Leu Phe Ala Met His Gly Ala Asp Val Thr Ile Ile Thr Thr Pro Ala
            35                  40                  45

Asn Ala Leu Thr Phe Gln Lys Ser Val Asp Arg Asp Phe Asn Ser Gly
        50                  55                  60

Arg Leu Ile Arg Thr His Thr Leu Lys Phe Pro Ala Ala Glu Val Gly
65                  70                  75                  80

Val Pro Glu Gly Val Glu Asn Phe Asn Asn Thr Ser Pro Glu Met Thr
                85                  90                  95

Ser Lys Val Tyr Leu Gly Val Ser Met Leu Arg Glu Pro Thr Gln Gln
            100                 105                 110

Leu Ile Glu Asp Leu Arg Pro Asp Cys Leu Ile Thr Asp Met Phe Tyr
        115                 120                 125

Pro Trp Ala Val Asp Val Ala Asp Lys Leu Gly Ile Pro Arg Leu Ile
    130                 135                 140

Phe Gln Gly Pro Gly Ser Phe Gly Leu Ser Ala Met His Ser Ile Lys
145                 150                 155                 160

Gln Tyr Glu Pro Phe Lys Ser Val Thr Ser Asp Thr Glu Thr Phe Pro
                165                 170                 175
```

Leu Pro Gly Leu Pro His Lys Val Glu Met Thr Arg Leu Gln Ile Pro
            180                 185                 190

Lys Trp Val Arg Glu Pro Asn Gly Tyr Thr Gln Leu Met Gly Arg Val
            195                 200                 205

Lys Asp Ser Glu Arg Arg Ser Tyr Gly Ser Leu Val Asn Ser Phe Tyr
210                 215                 220

Asp Phe Glu Gly Pro Tyr Glu His Tyr Arg Lys Ala Thr Gly Gln
225                 230                 235                 240

Arg Val Trp Ser Ile Gly Pro Val Ser Val Trp Val Asn Gln Asp Ala
                245                 250                 255

Ala Asp Lys Val Gly Arg Gly Gln Asp Leu Val Ala Glu Asp Gln Asn
            260                 265                 270

Ser Trp Leu Asn Trp Leu Asn Ser Lys Glu Lys Asn Ser Val Leu Tyr
            275                 280                 285

Val Ser Phe Gly Ser Met Ala Lys Phe Pro Ser Ala Gln Leu Leu Glu
            290                 295                 300

Ile Ala His Gly Leu Glu Ala Ser Gly His Ser Phe Ile Trp Val Val
305                 310                 315                 320

Arg Lys Val Asp Gly Asp Asp Val Asp Val Trp Leu Pro Asp Phe
                325                 330                 335

Glu Lys Lys Met Lys Glu Asn Asn Lys Gly Phe Ile Ile Arg Asn Trp
            340                 345                 350

Ala Pro Gln Leu Leu Ile Leu Asp His Pro Ala Ile Gly Gly Leu Leu
            355                 360                 365

Asn His Ser Gly Trp Asn Ser Val Leu Glu Gly Ala Thr Ala Gly Leu
            370                 375                 380

Pro Met Ile Thr Trp Pro Leu Tyr Ala Glu His Phe Tyr Asn Glu Arg
385                 390                 395                 400

Leu Val Leu Asp Val Leu Lys Ile Gly Val Pro Val Gly Val Lys Glu
                405                 410                 415

Trp Lys Asn Leu His Glu Val Gly Glu Leu Val Arg Arg Asp Ala Ile
            420                 425                 430

Ala Lys Ala Ile Lys Leu Leu Met Gly Ser Gly Glu Glu Ala Glu Val
            435                 440                 445

Met Arg Lys Lys Ala Lys Glu Leu Gly Val Gly Ala Lys Lys Gly Ile
450                 455                 460

Gln Val Gly Gly Ser Ser His Thr Asn Leu Ile Ala Val Ile Asp Glu
465                 470                 475                 480

Leu Lys Ser Leu Lys Lys Ser Arg Ile Gln Gly Val
            485                 490

<210> SEQ ID NO 5
<211> LENGTH: 1515
<212> TYPE: DNA
<213> ORGANISM: Quillaja saponaria

<400> SEQUENCE: 5
atggtctccg gcgacgacga tgtttctcgt cggccactga agtttactt cattgcacac      60 ccctcacctg gccatattgc ccctctgacc aaaatagccc atctcttcgc tgccctcggt    120
gagcacgtga ctattctcac tactcccgcc aatgtccact ccatgagaa atccatcgac     180 aaaggaaagg cttccggcta tcatgttaac atccacaccg ttaaatttcc ttctaaagag    240
gtcggtctcc ctgacggcat cgaaaacttc tcttacgcct ccgatgttga aacagcagct    300

-continued

```
aaaatttggg ctggattcgc catgctacaa actgaaatgg agcaatatat ggagcttaac    360
ccacccgatt gcatcgttgc cgacatgttc acctcctgga cctccgactt tgctatcaaa    420
ttgggaatca caagaatcgt tttcaacgtc tattgtattt tcacacgctg tttggaagaa    480
gccatccgat caccggactc gccacacttg aacaaagaaa tctctgataa tgaaccgttt    540
gttatcccgg gtctaccaga ccccataaca attacccgag ctcaactgcc cgacggtacc    600
ttttctccca tgaaagaact agctagaaca gctgagttga agagctttgg aatggtgatc    660
aacgggtttt ccgaactcga aaccgattac atcgagcatt acaagaaaat catgggtcac    720
aaacggattt ggcatgtcgg acccccttcag ctaatccacc gtaacgatga agacaaaatt    780
cagaggagcc acaagacagc ggtgctgagt gataacgata acgagttagt gagttggctt    840
aactcgaaga aacccgactc agttatttac atttgcttcg gtagtgcaac tcgtttctct    900
aatcaccagc tctatgaaat cgcctgtgga ttagaagctt ccgggcaccc atttttgtgg    960
ggcctacttt gggtgccaga agatgaagat aacgatgacg tgggcaacaa atggttgcca   1020
gctttcgaag aaagaattaa aaaggaaaat aagggaatga ttttaagggg gtgggctcca   1080
cagatgttaa tcttaaacca cccggcgatc ggtggtttca tgacgcattg tggttggaat   1140
gcggtggtgg aagcactttc attcggtgtt ccgactatta cgcttccagt tttctcggag   1200
cagttttata ctgagagact gatatcacaa gtgctcaaga ctggtgtgga ggttggtgca   1260
gagaagtgga cctatgcatt tgatgcgggg aaatatccgg tgagtaggga aaagatagcg   1320
acggcggtga agaagatatt agacgatgga gaagaggcag aaggaatgag aaagcgggcc   1380
agggagatga aagaaaaagc ccaaaaaagt gttgaagaag gtggatcctc ttataataat   1440
ttaacggcta tgattgaaga tcttaaagaa tttagggcta acaatggcaa ggctgcacaa   1500
gatcatgaat cgtga                                                    1515
```

```
<210> SEQ ID NO 6
<211> LENGTH: 504
<212> TYPE: PRT
<213> ORGANISM: Quillaja saponaria

<400> SEQUENCE: 6

Met Val Ser Gly Asp Asp Asp Val Ser Arg Arg Pro Leu Lys Val Tyr
1               5                   10                  15

Phe Ile Ala His Pro Ser Pro Gly His Ile Ala Pro Leu Thr Lys Ile
            20                  25                  30

Ala His Leu Phe Ala Ala Leu Gly Glu His Val Thr Ile Leu Thr Thr
        35                  40                  45

Pro Ala Asn Val His Phe His Glu Lys Ser Ile Asp Lys Gly Lys Ala
    50                  55                  60

Ser Gly Tyr His Val Asn Ile His Thr Val Lys Phe Pro Ser Lys Glu
65                  70                  75                  80

Val Gly Leu Pro Asp Gly Ile Glu Asn Phe Ser Tyr Ala Ser Asp Val
                85                  90                  95

Glu Thr Ala Ala Lys Ile Trp Ala Gly Phe Ala Met Leu Gln Thr Glu
            100                 105                 110

Met Glu Gln Tyr Met Glu Leu Asn Pro Pro Asp Cys Ile Val Ala Asp
        115                 120                 125

Met Phe Thr Ser Trp Thr Ser Asp Phe Ala Ile Lys Leu Gly Ile Thr
    130                 135                 140

Arg Ile Val Phe Asn Val Tyr Cys Ile Phe Thr Arg Cys Leu Glu Glu
145                 150                 155                 160
```

Ala Ile Arg Ser Pro Asp Ser Pro His Leu Asn Lys Glu Ile Ser Asp
                165                 170                 175

Asn Glu Pro Phe Val Ile Pro Gly Leu Pro Asp Pro Ile Thr Ile Thr
            180                 185                 190

Arg Ala Gln Leu Pro Asp Gly Thr Phe Ser Pro Met Lys Glu Leu Ala
        195                 200                 205

Arg Thr Ala Glu Leu Lys Ser Phe Gly Met Val Ile Asn Gly Phe Ser
    210                 215                 220

Glu Leu Glu Thr Asp Tyr Ile Glu His Tyr Lys Lys Ile Met Gly His
225                 230                 235                 240

Lys Arg Ile Trp His Val Gly Pro Leu Gln Leu Ile His Arg Asn Asp
                245                 250                 255

Glu Asp Lys Ile Gln Arg Ser His Lys Thr Ala Val Leu Ser Asp Asn
            260                 265                 270

Asp Asn Glu Leu Val Ser Trp Leu Asn Ser Lys Lys Pro Asp Ser Val
        275                 280                 285

Ile Tyr Ile Cys Phe Gly Ser Ala Thr Arg Phe Ser Asn His Gln Leu
    290                 295                 300

Tyr Glu Ile Ala Cys Gly Leu Glu Ala Ser Gly His Pro Phe Leu Trp
305                 310                 315                 320

Gly Leu Leu Trp Val Pro Glu Asp Glu Asp Asn Asp Val Gly Asn
                325                 330                 335

Lys Trp Leu Pro Ala Phe Glu Glu Arg Ile Lys Lys Glu Asn Lys Gly
            340                 345                 350

Met Ile Leu Arg Gly Trp Ala Pro Gln Met Leu Ile Leu Asn His Pro
        355                 360                 365

Ala Ile Gly Gly Phe Met Thr His Cys Gly Trp Asn Ala Val Val Glu
    370                 375                 380

Ala Leu Ser Phe Gly Val Pro Thr Ile Thr Leu Pro Val Phe Ser Glu
385                 390                 395                 400

Gln Phe Tyr Thr Glu Arg Leu Ile Ser Gln Val Leu Lys Thr Gly Val
                405                 410                 415

Glu Val Gly Ala Glu Lys Trp Thr Tyr Ala Phe Asp Ala Gly Lys Tyr
            420                 425                 430

Pro Val Ser Arg Glu Lys Ile Ala Thr Ala Val Lys Lys Ile Leu Asp
        435                 440                 445

Asp Gly Glu Glu Ala Glu Gly Met Arg Lys Arg Ala Arg Glu Met Lys
    450                 455                 460

Glu Lys Ala Gln Lys Ser Val Glu Glu Gly Gly Ser Ser Tyr Asn Asn
465                 470                 475                 480

Leu Thr Ala Met Ile Glu Asp Leu Lys Glu Phe Arg Ala Asn Asn Gly
                485                 490                 495

Lys Ala Ala Gln Asp His Glu Ser
            500

<210> SEQ ID NO 7
<211> LENGTH: 1689
<212> TYPE: DNA
<213> ORGANISM: Avena strigosa

<400> SEQUENCE: 7
atggctgtgg aggttcaccg ccgggctccc gcgccccatg gccggggcac cggggagaag    60
ggccgcgtgc aggccgggga cgcgctgccg ctgccgatcc gccacaccaa cctcatcttc   120

```
tcggcgctct tcgccgcctc cctcgcatac ctcatgcgcc gctggaggga gaagatccgc    180
aactccacgc cgctccacgt cgtggggctc accgagatct tcgccatctg cggcctcgtc    240
gcctccctca tctacctcct cagcttcttc ggcatcgcct tcgtgcagtc cgtcgtatcc    300
aacagcgacg acgaggacga ggacttcctc atcgcggctg cagcatccca ggcccccccg    360
ccgccctcct ccaagcccgc gccgcagcag tgcgccctgc tgcagagcgc cggagtcgcg    420
cccgagaaaa tgcccgagga ggacgaggaa atcgtcgccg gggtcgtcgc agggaagatc    480
ccctcctacg tgctcgagac caggctaggc gactgccgca gggcagccgg gatccgccgc    540
gaggcgctgc gccggatcac cggcaggag atcgacggcc ttcccctcga cggcttcgac    600
tacgactcga ttctcggaca gtgctgcgag atgcccgtcg ggtacgtgca gctgccggtc    660
ggcgtcgcgg gccgctcgt cctcgacggc cgccgcatat acgtcccgat ggccaccacg    720
gagggctgcc taatcgccag caccaaccgc ggatgcaagg ccattgccga gtccggaggc    780
gcatccagcg tcgtgtaccg cgacgggatg accgcgccc cgtagcccg cttcccctcc    840 gcacgacgcg ccgcagagct caaggcttc ctggagaatc cggccaacta cgacaccctg    900
tccgtggtct ttaacagatc aagcagattt gcaaggctgc aggggtcaa gtgcgccatg    960 gctggggagga acttgtacat gaggttcacc tgcagcaccg gggatgccat ggggatgaac   1020
atggtctcca agggcgtcca aaatgtgctc gactatctgc aggaggactt ccctgacatg   1080
gacgttgtca gcatctcagg caacttttgt tccgacaaga aatcagctgc tgtaaactgg   1140
attgaaggcc gtggaaagtc cgtggtttgt gaggcagtaa tcagagagga agttgtccac   1200
aaggttctca agaccaacgt tcagtcactc gtggagttga atgtgatcaa gaaccttgct   1260
ggctcagcag ttgctggtgc tcttgggggt ttcaacgccc acgcaagcaa catcgtaacg   1320
gctatcttca ttgccactgg tcaggatcct gcacagaatg tggagagctc acagtgtatc   1380
actatgttgg aagctgtaaa tgatggcaga gaccttcaca tctccgttac aatgccatct   1440
atcgaggtgg gcacagttgg tggaggcacg cagctggcct cacagtcggc ctgcttggac   1500
ctactgggcg tcaaaggcgc caacagggaa tctccggggt cgaacgctag gctgctggcc   1560
acggtggtgg ctggtgccgt cctagctggg gagctgtccc tcatctccgc ccaagctgcc   1620
ggccatctgg tccagagcca catgaaatac aacagatcca gcaaggacat gtccaagatc   1680
gcctgctga                                                          1689
```

<210> SEQ ID NO 8
<211> LENGTH: 562
<212> TYPE: PRT
<213> ORGANISM: Avena strigosa

<400> SEQUENCE: 8

```
Met Ala Val Glu Val His Arg Arg Ala Pro Ala Pro His Gly Arg Gly
1               5                   10                  15

Thr Gly Glu Lys Gly Arg Val Gln Ala Gly Asp Ala Leu Pro Leu Pro
            20                  25                  30

Ile Arg His Thr Asn Leu Ile Phe Ser Ala Leu Phe Ala Ala Ser Leu
        35                  40                  45

Ala Tyr Leu Met Arg Arg Trp Arg Glu Lys Ile Arg Asn Ser Thr Pro
    50                  55                  60

Leu His Val Val Gly Leu Thr Glu Ile Phe Ala Ile Cys Gly Leu Val
65                  70                  75                  80

Ala Ser Leu Ile Tyr Leu Leu Ser Phe Phe Gly Ile Ala Phe Val Gln
                85                  90                  95
```

```
Ser Val Val Ser Asn Ser Asp Glu Asp Glu Asp Phe Leu Ile Ala
            100                 105                 110
Ala Ala Ala Ser Gln Ala Pro Pro Pro Ser Ser Lys Pro Ala Pro
        115                 120                 125
Gln Gln Cys Ala Leu Leu Gln Ser Ala Gly Val Ala Pro Glu Lys Met
    130                 135                 140
Pro Glu Glu Asp Glu Glu Ile Val Ala Gly Val Ala Gly Lys Ile
145                 150                 155                 160
Pro Ser Tyr Val Leu Glu Thr Arg Leu Gly Asp Cys Arg Arg Ala Ala
                165                 170                 175
Gly Ile Arg Arg Glu Ala Leu Arg Arg Ile Thr Gly Arg Glu Ile Asp
            180                 185                 190
Gly Leu Pro Leu Asp Gly Phe Asp Tyr Asp Ser Ile Leu Gly Gln Cys
        195                 200                 205
Cys Glu Met Pro Val Gly Tyr Val Gln Leu Pro Val Gly Val Ala Gly
    210                 215                 220
Pro Leu Val Leu Asp Gly Arg Arg Ile Tyr Val Pro Met Ala Thr Thr
225                 230                 235                 240
Glu Gly Cys Leu Ile Ala Ser Thr Asn Arg Gly Cys Lys Ala Ile Ala
                245                 250                 255
Glu Ser Gly Gly Ala Ser Ser Val Val Tyr Arg Asp Gly Met Thr Arg
            260                 265                 270
Ala Pro Val Ala Arg Phe Pro Ser Ala Arg Arg Ala Ala Glu Leu Lys
        275                 280                 285
Gly Phe Leu Glu Asn Pro Ala Asn Tyr Asp Thr Leu Ser Val Val Phe
    290                 295                 300
Asn Arg Ser Ser Arg Phe Ala Arg Leu Gln Gly Val Lys Cys Ala Met
305                 310                 315                 320
Ala Gly Arg Asn Leu Tyr Met Arg Phe Thr Cys Ser Thr Gly Asp Ala
                325                 330                 335
Met Gly Met Asn Met Val Ser Lys Gly Val Gln Asn Val Leu Asp Tyr
            340                 345                 350
Leu Gln Glu Asp Phe Pro Asp Met Asp Val Val Ser Ile Ser Gly Asn
        355                 360                 365
Phe Cys Ser Asp Lys Lys Ser Ala Ala Val Asn Trp Ile Glu Gly Arg
    370                 375                 380
Gly Lys Ser Val Val Cys Glu Ala Val Ile Arg Glu Glu Val Val His
385                 390                 395                 400
Lys Val Leu Lys Thr Asn Val Gln Ser Leu Val Glu Leu Asn Val Ile
                405                 410                 415
Lys Asn Leu Ala Gly Ser Ala Val Ala Gly Ala Leu Gly Gly Phe Asn
            420                 425                 430
Ala His Ala Ser Asn Ile Val Thr Ala Ile Phe Ile Ala Thr Gly Gln
        435                 440                 445
Asp Pro Ala Gln Asn Val Glu Ser Ser Gln Cys Ile Thr Met Leu Glu
    450                 455                 460
Ala Val Asn Asp Gly Arg Asp Leu His Ile Ser Val Thr Met Pro Ser
465                 470                 475                 480
Ile Glu Val Gly Thr Val Gly Gly Gly Thr Gln Leu Ala Ser Gln Ser
                485                 490                 495
Ala Cys Leu Asp Leu Leu Gly Val Lys Gly Ala Asn Arg Glu Ser Pro
            500                 505                 510
```

```
Gly Ser Asn Ala Arg Leu Leu Ala Thr Val Val Ala Gly Ala Val Leu
            515                 520                 525

Ala Gly Glu Leu Ser Leu Ile Ser Ala Gln Ala Ala Gly His Leu Val
        530                 535                 540

Gln Ser His Met Lys Tyr Asn Arg Ser Ser Lys Asp Met Ser Lys Ile
545                 550                 555                 560

Ala Cys

<210> SEQ ID NO 9
<211> LENGTH: 1275
<212> TYPE: DNA
<213> ORGANISM: Avena strigosa

<400> SEQUENCE: 9
atggcgcccg agaaaatgcc cgaggaggac gaggaaatcg tcgccggggt cgtcgcaggg      60
aagatcccct cctacgtgct cgagaccagg ctaggcgact gccgcagggc agccgggatc     120
cgccgcgagg cgctgcgccg gatcaccggc agggagatcg acggccttcc cctcgacggc     180
ttcgactacg actcgattct cggacagtgc tgcgagatgc ccgtcgggta cgtgcagctg     240
ccggtcggcg tcgcggggcc gctcgtcctc gacggccgcc gcatatacgt cccgatggcc     300
accacggagg gctgcctaat cgccagcacc aaccgcggat gcaaggccat tgccgagtcc     360
ggaggcgcat ccagcgtcgt gtaccgcgac gggatgaccc cgcccccgt agcccgcttc      420 ccctccgcac gacgcgccgc agagctcaag ggcttcctgg agaatccggc caactacgac     480
accctgtccg tggtctttaa cagatcaagc agatttgcaa ggctgcaggg ggtcaagtgc     540
gccatggctg ggaggaactt gtacatgagg ttcacctgca gcaccgggga tgccatgggg     600
atgaacatgg tctccaaggg cgtccaaaat gtgctcgact atctgcagga ggacttccct     660
gacatggacg ttgtcagcat ctcaggcaac ttttgttccg acaagaaatc agctgctgta     720
aactggattg aaggccgtgg aaagtccgtg gtttgtgagg cagtaatcag agaggaagtt     780
gtccacaagg ttctcaagac caacgttcag tcactcgtgg agttgaatgt gatcaagaac     840
cttgctggct cagcagttgc tggtgctctt gggggtttca acgccacgc aagcaacatc      900 gtaacggcta tcttcattgc cactggtcag atcctgcac agaatgtgga gagctcacag      960
tgtatcacta tgttggaagc tgtaaatgat ggcagagacc ttcacatctc cgttacaatg    1020
ccatctatcg aggtgggcac agttggtgga ggcacgcagc tggcctcaca gtcggcctgc    1080
ttggacctac tgggcgtcaa aggcgccaac agggaatctc cggggtcgaa cgctaggctg    1140
ctggccacgg tggtggctgg tgccgtccta gctggggagc tgtccctcat ctccgcccaa    1200
gctgccggcc atctggtcca gagccacatg aaatacaaca gatccagcaa ggacatgtcc    1260
aagatcgcct gctga                                                      1275

<210> SEQ ID NO 10
<211> LENGTH: 424
<212> TYPE: PRT
<213> ORGANISM: Avena strigosa

<400> SEQUENCE: 10

Met Ala Pro Glu Lys Met Pro Glu Glu Asp Glu Glu Ile Val Ala Gly
1               5                  10                  15

Val Val Ala Gly Lys Ile Pro Ser Tyr Val Leu Glu Thr Arg Leu Gly
            20                  25                  30

Asp Cys Arg Arg Ala Ala Gly Ile Arg Arg Glu Ala Leu Arg Arg Ile
        35                  40                  45
```

Thr Gly Arg Glu Ile Asp Gly Leu Pro Leu Asp Gly Phe Asp Tyr Asp
    50                  55                  60

Ser Ile Leu Gly Gln Cys Cys Glu Met Pro Val Gly Tyr Val Gln Leu
 65                  70                  75                  80

Pro Val Gly Val Ala Gly Pro Leu Val Leu Asp Gly Arg Arg Ile Tyr
                 85                  90                  95

Val Pro Met Ala Thr Thr Glu Gly Cys Leu Ile Ala Ser Thr Asn Arg
                100                 105                 110

Gly Cys Lys Ala Ile Ala Glu Ser Gly Ala Ser Ser Val Val Tyr
             115                 120                 125

Arg Asp Gly Met Thr Arg Ala Pro Val Ala Arg Phe Pro Ser Ala Arg
             130                 135                 140

Arg Ala Ala Glu Leu Lys Gly Phe Leu Glu Asn Pro Ala Asn Tyr Asp
145                 150                 155                 160

Thr Leu Ser Val Val Phe Asn Arg Ser Arg Phe Ala Arg Leu Gln
                165                 170                 175

Gly Val Lys Cys Ala Met Ala Gly Arg Asn Leu Tyr Met Arg Phe Thr
             180                 185                 190

Cys Ser Thr Gly Asp Ala Met Gly Met Asn Met Val Ser Lys Gly Val
             195                 200                 205

Gln Asn Val Leu Asp Tyr Leu Gln Glu Asp Phe Pro Asp Met Asp Val
    210                 215                 220

Val Ser Ile Ser Gly Asn Phe Cys Ser Asp Lys Lys Ser Ala Ala Val
225                 230                 235                 240

Asn Trp Ile Glu Gly Arg Gly Lys Ser Val Val Cys Glu Ala Val Ile
                245                 250                 255

Arg Glu Glu Val Val His Lys Val Leu Lys Thr Asn Val Gln Ser Leu
            260                 265                 270

Val Glu Leu Asn Val Ile Lys Asn Leu Ala Gly Ser Ala Val Ala Gly
                275                 280                 285

Ala Leu Gly Gly Phe Asn Ala His Ala Ser Asn Ile Val Thr Ala Ile
            290                 295                 300

Phe Ile Ala Thr Gly Gln Asp Pro Ala Gln Asn Val Glu Ser Ser Gln
305                 310                 315                 320

Cys Ile Thr Met Leu Glu Ala Val Asn Asp Gly Arg Asp Leu His Ile
                325                 330                 335

Ser Val Thr Met Pro Ser Ile Glu Val Gly Thr Val Gly Gly Gly Thr
            340                 345                 350

Gln Leu Ala Ser Gln Ser Ala Cys Leu Asp Leu Leu Gly Val Lys Gly
            355                 360                 365

Ala Asn Arg Glu Ser Pro Gly Ser Asn Ala Arg Leu Leu Ala Thr Val
            370                 375                 380

Val Ala Gly Ala Val Leu Ala Gly Glu Leu Ser Leu Ile Ser Ala Gln
385                 390                 395                 400

Ala Ala Gly His Leu Val Gln Ser His Met Lys Tyr Asn Arg Ser Ser
                405                 410                 415

Lys Asp Met Ser Lys Ile Ala Cys
            420

<210> SEQ ID NO 11
<211> LENGTH: 2277
<212> TYPE: DNA
<213> ORGANISM: Quillaja saponaria

<400> SEQUENCE: 11

```
atgtggaggc tgaagatagc agaaggtggt tccgatccat atctgttcag cacaaacaac    60
ttcgtgggtc gccagacatg ggagttcgaa ccggaggccg gcacacctga ggagcgagca   120
gaggtcgaag ctgcccgcca aaacttttac aacaaccgtt accaggtcaa gccctgtgac   180
gacctccttt ggagatatca gttcctgaga gagaagaatt caaacaaac aataccgcct    240
gtcaaggttg aagatggcca agaaattact tatgagatgg ccacaacctc aatgcagagg   300
gcggcccgtc acctatcagc cttgcaggcc agcgatggcc attggccagc tcaaattgct   360
ggccccttgt tcttcatgcc acccttggtc ttttgtgtgt acattactgg gcatcttaat   420
acagtattcc catctgaaca tcgcaaagaa atccttcgtt acatgtacta tcaccagaac   480
gaagatggtg ggtggggact gcacatagag ggtcacagca ccatgttttg cacagcactc   540
aactacattt gtatgcgtat ccttggggaa ggaccagagg ggggtcaaga caatgcttgt   600
gccagagcac gaatgtggat tcttgatcat ggtggtgtaa cacatattcc atcttgggga   660
aagacctggc tttcgatact tggtctattt gagtggtctg gaagcaatcc aatgcctcca   720
gagttttgga tccttccttc atttcttcct atgcatccag caaaaatgtg gtgctattgc   780
cggatggttt acatgcccat gtcttattta tatgggaaaa ggtttgttgg cccaatcacg   840
cctctcattg ttcagttaag agaggaaata cacactcaaa attaccatga atcaactgg    900
aagtcagtcc gccatctatg tgcaaaggag gatatctact atccccatcc actcatccaa   960
gatttgattt gggacagttt gtacatacta acggagcctc ttctcactcg ctggcccttg  1020
aacaagttgg tgcgggagag ggctctccaa gtaacaatga agcatatcca ctatgaagat  1080
gaaaatagtc gatacataac cattggatgt gtggaaaagg tgttatgtat gcttgcttgt  1140
tgggttgatg atccaaatgg agatgctttc aagaagcacc ttgctcgagt cccagattac  1200
gtatgggtct ctgaagatgg aattactatg cagagttttg gtagtcaaga atgggatgct  1260
ggctttgccg tccaggctct gcttgcttct aatcttaccg aggaacttgg ccctgctctt  1320
gccaaaggac atgacttcat aaagcaatct caggttaagg acaatccttc aggtgacttc  1380
aaaagcatgt atcgtcacat ttctagagga tcatggacct tctctgacca agatcatgga  1440
tggcaagttt ctgattgcac tgcagaaggt ctgaagtgtt gcctgctttt gtcgatgttg  1500
ccaccagaaa ttgttggtga aaaaatgaa ccacaaaggc tatttgattc tgtcaatgtg   1560
ctgctctctc tacagagcaa aaaaggtggt ttagctgcct gggagccagc aggggcgcaa  1620
gattggttgg aattactcaa tcccacagaa ttttttgcgg acattgtcgt tgagcatgaa  1680
tatgttgaat gtactggatc agcaattcag gcattagttt tgttcaagaa gctgtatccg  1740
gggcacagga aaaagagat tgacagttc attacaaatg ctgtccggtt ccttgagaat    1800
acacaaacgg cagatggctc ttggtatgga aactggggag tttgcttcac ctatggttgt  1860
tggttcgcac tgggagggct agcagcagct ggcaagactt acaacaactg tcctgcaata  1920
cgcaaagctg ttaatttcct acttacaaca caaagagaag acgtggttg gggagaaagc   1980
tatctttcaa gcccaaaaaa gatatatgta cccctggaag gaagccgatc aaatgtggta  2040
catactgcat gggctatgat gggtctaatt catgctgggc aggctgaaag agactcaact  2100
cctcttcatc gtgcagcaaa gttgatcatc aattatcaac tagaaaatgg cgattggccg  2160
caacaggaaa tcactggagt attcatgaaa aactgcatgt acattaccc tatgtacaga   2220
aacatctacc caatgtgggc tcttgcagaa taccggaggc gggttccatt gccttaa     2277
```

```
<210> SEQ ID NO 12
<211> LENGTH: 758
<212> TYPE: PRT
<213> ORGANISM: Quillaja saponaria

<400> SEQUENCE: 12
```

| | | | | | | | | | | | | | | |
|---|---|---|---|---|---|---|---|---|---|---|---|---|---|---|
| Met | Trp | Arg | Leu | Lys | Ile | Ala | Glu | Gly | Gly | Ser | Asp | Pro | Tyr | Leu | Phe |
| 1 | | | | 5 | | | | | 10 | | | | | 15 | |
| Ser | Thr | Asn | Asn | Phe | Val | Gly | Arg | Gln | Thr | Trp | Glu | Phe | Glu | Pro | Glu |
| | | | 20 | | | | | 25 | | | | | 30 | | |
| Ala | Gly | Thr | Pro | Glu | Glu | Arg | Ala | Glu | Val | Glu | Ala | Ala | Arg | Gln | Asn |
| | | 35 | | | | | 40 | | | | | 45 | | | |
| Phe | Tyr | Asn | Asn | Arg | Tyr | Gln | Val | Lys | Pro | Cys | Asp | Asp | Leu | Leu | Trp |
| | 50 | | | | | 55 | | | | | 60 | | | | |
| Arg | Tyr | Gln | Phe | Leu | Arg | Glu | Lys | Asn | Phe | Lys | Gln | Thr | Ile | Pro | Pro |
| 65 | | | | | 70 | | | | | 75 | | | | | 80 |
| Val | Lys | Val | Glu | Asp | Gly | Gln | Glu | Ile | Thr | Tyr | Glu | Met | Ala | Thr | Thr |
| | | | | 85 | | | | | 90 | | | | | 95 | |
| Ser | Met | Gln | Arg | Ala | Ala | Arg | His | Leu | Ser | Ala | Leu | Gln | Ala | Ser | Asp |
| | | | 100 | | | | | 105 | | | | | 110 | | |
| Gly | His | Trp | Pro | Ala | Gln | Ile | Ala | Gly | Pro | Leu | Phe | Phe | Met | Pro | Pro |
| | | 115 | | | | | 120 | | | | | 125 | | | |
| Leu | Val | Phe | Cys | Val | Tyr | Ile | Thr | Gly | His | Leu | Asn | Thr | Val | Phe | Pro |
| | 130 | | | | | 135 | | | | | 140 | | | | |
| Ser | Glu | His | Arg | Lys | Glu | Ile | Leu | Arg | Tyr | Met | Tyr | His | Gln | Asn |
| 145 | | | | | 150 | | | | | 155 | | | | | 160 |
| Glu | Asp | Gly | Gly | Trp | Gly | Leu | His | Ile | Glu | Gly | His | Ser | Thr | Met | Phe |
| | | | | 165 | | | | | 170 | | | | | 175 | |
| Cys | Thr | Ala | Leu | Asn | Tyr | Ile | Cys | Met | Arg | Ile | Leu | Gly | Glu | Gly | Pro |
| | | | 180 | | | | | 185 | | | | | 190 | | |
| Glu | Gly | Gly | Gln | Asp | Asn | Ala | Cys | Ala | Arg | Ala | Arg | Met | Trp | Ile | Leu |
| | | 195 | | | | | 200 | | | | | 205 | | | |
| Asp | His | Gly | Gly | Val | Thr | His | Ile | Pro | Ser | Trp | Gly | Lys | Thr | Trp | Leu |
| | 210 | | | | | 215 | | | | | 220 | | | | |
| Ser | Ile | Leu | Gly | Leu | Phe | Glu | Trp | Ser | Gly | Ser | Asn | Pro | Met | Pro | Pro |
| 225 | | | | | 230 | | | | | 235 | | | | | 240 |
| Glu | Phe | Trp | Ile | Leu | Pro | Ser | Phe | Leu | Pro | Met | His | Pro | Ala | Lys | Met |
| | | | | 245 | | | | | 250 | | | | | 255 | |
| Trp | Cys | Tyr | Cys | Arg | Met | Val | Tyr | Met | Pro | Met | Ser | Tyr | Leu | Tyr | Gly |
| | | | 260 | | | | | 265 | | | | | 270 | | |
| Lys | Arg | Phe | Val | Gly | Pro | Ile | Thr | Pro | Leu | Ile | Val | Gln | Leu | Arg | Glu |
| | | 275 | | | | | 280 | | | | | 285 | | | |
| Glu | Ile | His | Thr | Gln | Asn | Tyr | His | Glu | Ile | Asn | Trp | Lys | Ser | Val | Arg |
| | 290 | | | | | 295 | | | | | 300 | | | | |
| His | Leu | Cys | Ala | Lys | Glu | Asp | Ile | Tyr | Tyr | Pro | His | Pro | Leu | Ile | Gln |
| 305 | | | | | 310 | | | | | 315 | | | | | 320 |
| Asp | Leu | Ile | Trp | Asp | Ser | Leu | Tyr | Ile | Leu | Thr | Glu | Pro | Leu | Leu | Thr |
| | | | | 325 | | | | | 330 | | | | | 335 | |
| Arg | Trp | Pro | Leu | Asn | Lys | Leu | Val | Arg | Glu | Arg | Ala | Leu | Gln | Val | Thr |
| | | | 340 | | | | | 345 | | | | | 350 | | |
| Met | Lys | His | Ile | His | Tyr | Glu | Asp | Glu | Asn | Ser | Arg | Tyr | Ile | Thr | Ile |
| | | 355 | | | | | 360 | | | | | 365 | | | |
| Gly | Cys | Val | Glu | Lys | Val | Leu | Cys | Met | Leu | Ala | Cys | Trp | Val | Asp | Asp |
| | 370 | | | | | 375 | | | | | 380 | | | | |

```
Pro Asn Gly Asp Ala Phe Lys Lys His Leu Ala Arg Val Pro Asp Tyr
385                 390                 395                 400

Val Trp Val Ser Glu Asp Gly Ile Thr Met Gln Ser Phe Gly Ser Gln
                405                 410                 415

Glu Trp Asp Ala Gly Phe Ala Val Gln Ala Leu Leu Ala Ser Asn Leu
            420                 425                 430

Thr Glu Glu Leu Gly Pro Ala Leu Ala Lys Gly His Asp Phe Ile Lys
        435                 440                 445

Gln Ser Gln Val Lys Asp Asn Pro Ser Gly Asp Phe Lys Ser Met Tyr
    450                 455                 460

Arg His Ile Ser Arg Gly Ser Trp Thr Phe Ser Asp Gln Asp His Gly
465                 470                 475                 480

Trp Gln Val Ser Asp Cys Thr Ala Glu Gly Leu Lys Cys Cys Leu Leu
                485                 490                 495

Leu Ser Met Leu Pro Pro Glu Ile Val Gly Glu Lys Met Glu Pro Gln
            500                 505                 510

Arg Leu Phe Asp Ser Val Asn Val Leu Leu Ser Leu Gln Ser Lys Lys
        515                 520                 525

Gly Gly Leu Ala Ala Trp Glu Pro Ala Gly Ala Gln Asp Trp Leu Glu
    530                 535                 540

Leu Leu Asn Pro Thr Glu Phe Phe Ala Asp Ile Val Val Glu His Glu
545                 550                 555                 560

Tyr Val Glu Cys Thr Gly Ser Ala Ile Gln Ala Leu Val Leu Phe Lys
                565                 570                 575

Lys Leu Tyr Pro Gly His Arg Lys Lys Glu Ile Asp Ser Phe Ile Thr
            580                 585                 590

Asn Ala Val Arg Phe Leu Glu Asn Thr Gln Thr Ala Asp Gly Ser Trp
        595                 600                 605

Tyr Gly Asn Trp Gly Val Cys Phe Thr Tyr Gly Cys Trp Phe Ala Leu
    610                 615                 620

Gly Gly Leu Ala Ala Ala Gly Lys Thr Tyr Asn Asn Cys Pro Ala Ile
625                 630                 635                 640

Arg Lys Ala Val Asn Phe Leu Leu Thr Thr Gln Arg Glu Asp Gly Gly
                645                 650                 655

Trp Gly Glu Ser Tyr Leu Ser Ser Pro Lys Lys Ile Tyr Val Pro Leu
            660                 665                 670

Glu Gly Ser Arg Ser Asn Val Val His Thr Ala Trp Ala Met Met Gly
        675                 680                 685

Leu Ile His Ala Gly Gln Ala Glu Arg Asp Ser Thr Pro Leu His Arg
    690                 695                 700

Ala Ala Lys Leu Ile Ile Asn Tyr Gln Leu Glu Asn Gly Asp Trp Pro
705                 710                 715                 720

Gln Gln Glu Ile Thr Gly Val Phe Met Lys Asn Cys Met Leu His Tyr
                725                 730                 735

Pro Met Tyr Arg Asn Ile Tyr Pro Met Trp Ala Leu Ala Glu Tyr Arg
            740                 745                 750

Arg Arg Val Pro Leu Pro
        755

<210> SEQ ID NO 13
<211> LENGTH: 1443
<212> TYPE: DNA
<213> ORGANISM: Quillaja saponaria

<400> SEQUENCE: 13
```

```
atggagcact tgtatctctc ccttgtgctc ctgtttgttt cctcaatctc cctctccctc    60
ttcttcctgt tctacaaaca caaatctatg ttcaccgggg ccaacctacc acctggtaaa   120
atcggttacc cattgatcgg agagagcttg gagttcttgt ccacgggatg aagggccac    180
ccggagaaat tcatcttcga tcgcatgagc aagtactcat cccaaatctt caagacctcg   240
attttagggg aaccaacggc ggtgttcccg ggagccgtat gcaacaagtt cctcttctcc   300
aacgagaaca agctggtgaa tgcatggtgg cctgcctccg tggacaagat ctttccttcc   360
tcactccaga catcctccaa agaagaggcc aagaagatga ggaagttgct tcctcagttt   420
ctcaagcccg aagctctgca ccgctacatt ggtattatgg attctattgc cagagacac    480
tttgccgata gctgggaaaa caaaaaccaa gtcattgtct ttcctctagc aaagaggtat   540
actttctggc tggcttgccg tttgttcatt agcgtcgagg atccgaccca cgtatccaga   600
tttgctgacc cgttccaact tttggccgcc ggaatcatat caatcccaat cgacttgcca   660
gggacaccgt tccgcaaggc aatcaatgcg tcccagttca tcaggaagga attgttggcc   720
atcatcaggc agagaaagat cgatttgggt gaagggaagg catctccgac gcaggacata   780
ctgtctcaca tgttgctcac atgcgacgag aacggacaat acatgaatga attggacatt   840
gccgacaaga ttcttggctt gttggtcggc ggacatgaca ctgccagtgc cgcttgcact   900
ttcattgtca agttcctcgc tgagcttccc cacatttatg aacaagtcta caaggagcaa   960
atggagattg caaaatcaaa agtgccagga gagttgttga attgggagga catccaaaag  1020
atgaaatatt cgtggaacgt agcttgtgaa gtgatgagac ttgcccctcc actccaagga  1080
gctttcaggg aagccattac tgacttcgtc ttcaacggtt tctccattcc aaaaggctgg  1140
aagttgtact ggagcgcaaa ttccacccac aaaagtccgg attatttccc tgagcccgac  1200
aagttcgacc caactagatt cgaaggaaat ggacctgcgc cttacacctt tgttccattt  1260
gggggaggac ccaggatgtg cccgggcaaa gagtatgccc gattggaaat acttgtgttc  1320
atgcataact tggtgaagag gttcaagtgg gagaaattgg ttcctgatga aaagattgtg  1380
gttgatccaa tgcccattcc agcaagggt cttcctgttc gcctttatcc tcacaaagct  1440
tga                                                                1443
```

<210> SEQ ID NO 14
<211> LENGTH: 480
<212> TYPE: PRT
<213> ORGANISM: Quillaja saponaria

<400> SEQUENCE: 14

```
Met Glu His Leu Tyr Leu Ser Leu Val Leu Leu Phe Val Ser Ser Ile
1               5                   10                  15

Ser Leu Ser Leu Phe Phe Leu Phe Tyr Lys His Lys Ser Met Phe Thr
            20                  25                  30

Gly Ala Asn Leu Pro Pro Gly Lys Ile Gly Tyr Pro Leu Ile Gly Glu
        35                  40                  45

Ser Leu Glu Phe Leu Ser Thr Gly Trp Lys Gly His Pro Glu Lys Phe
    50                  55                  60

Ile Phe Asp Arg Met Ser Lys Tyr Ser Ser Gln Ile Phe Lys Thr Ser
65                  70                  75                  80

Ile Leu Gly Glu Pro Thr Ala Val Phe Pro Gly Ala Val Cys Asn Lys
                85                  90                  95

Phe Leu Phe Ser Asn Glu Asn Lys Leu Val Asn Ala Trp Trp Pro Ala
            100                 105                 110
```

Ser Val Asp Lys Ile Phe Pro Ser Ser Leu Gln Thr Ser Ser Lys Glu
            115                 120                 125

Glu Ala Lys Lys Met Arg Lys Leu Leu Pro Gln Phe Leu Lys Pro Glu
        130                 135                 140

Ala Leu His Arg Tyr Ile Gly Ile Met Asp Ser Ile Ala Gln Arg His
145                 150                 155                 160

Phe Ala Asp Ser Trp Glu Asn Lys Asn Gln Val Ile Val Phe Pro Leu
                165                 170                 175

Ala Lys Arg Tyr Thr Phe Trp Leu Ala Cys Arg Leu Phe Ile Ser Val
            180                 185                 190

Glu Asp Pro Thr His Val Ser Arg Phe Ala Asp Pro Phe Gln Leu Leu
        195                 200                 205

Ala Ala Gly Ile Ile Ser Ile Pro Ile Asp Leu Pro Gly Thr Pro Phe
210                 215                 220

Arg Lys Ala Ile Asn Ala Ser Gln Phe Ile Arg Lys Glu Leu Leu Ala
225                 230                 235                 240

Ile Ile Arg Gln Arg Lys Ile Asp Leu Gly Glu Gly Lys Ala Ser Pro
                245                 250                 255

Thr Gln Asp Ile Leu Ser His Met Leu Leu Thr Cys Asp Glu Asn Gly
            260                 265                 270

Gln Tyr Met Asn Glu Leu Asp Ile Ala Asp Lys Ile Leu Gly Leu Leu
        275                 280                 285

Val Gly Gly His Asp Thr Ala Ser Ala Ala Cys Thr Phe Ile Val Lys
290                 295                 300

Phe Leu Ala Glu Leu Pro His Ile Tyr Glu Gln Val Tyr Lys Glu Gln
305                 310                 315                 320

Met Glu Ile Ala Lys Ser Lys Val Pro Gly Glu Leu Leu Asn Trp Glu
                325                 330                 335

Asp Ile Gln Lys Met Lys Tyr Ser Trp Asn Val Ala Cys Glu Val Met
            340                 345                 350

Arg Leu Ala Pro Pro Leu Gln Gly Ala Phe Arg Glu Ala Ile Thr Asp
        355                 360                 365

Phe Val Phe Asn Gly Phe Ser Ile Pro Lys Gly Trp Lys Leu Tyr Trp
370                 375                 380

Ser Ala Asn Ser Thr His Lys Ser Pro Asp Tyr Phe Pro Glu Pro Asp
385                 390                 395                 400

Lys Phe Asp Pro Thr Arg Phe Glu Gly Asn Gly Pro Ala Pro Tyr Thr
                405                 410                 415

Phe Val Pro Phe Gly Gly Gly Pro Arg Met Cys Pro Gly Lys Glu Tyr
            420                 425                 430

Ala Arg Leu Glu Ile Leu Val Phe Met His Asn Leu Val Lys Arg Phe
        435                 440                 445

Lys Trp Glu Lys Leu Val Pro Asp Glu Lys Ile Val Val Asp Pro Met
450                 455                 460

Pro Ile Pro Ala Lys Gly Leu Pro Val Arg Leu Tyr Pro His Lys Ala
465                 470                 475                 480

<210> SEQ ID NO 15
<211> LENGTH: 1506
<212> TYPE: DNA
<213> ORGANISM: Quillaja saponaria

<400> SEQUENCE: 15
atgatatata ataatgatag taatgataat gaattagtaa tcagctcagt tcagcaacca     60

```
tccatggatc ctttcttcat ttttggctta cttctcttgg ctctctttct ctctgtttct    120
tttcttctct acctttcccg tagagcctat gcttctctcc caacccctcc gccgggggaag   180 ctcggcttcc ccgtcgtcgg cgagagtctc gaatttctct ccacccgacg caaaggtgtt   240
cctgagaaat tcgtcttcga cagaatggcc aaatactgtc gggatgtctt aagacatca    300 atattgggag caaccaccgc cgtcatgtgc ggcaccgccg gtaacaaatt cttgttctcc   360
aacgagaaaa aacacgtcac tggttggtgg ccgaaatctg tagagctgat tttcccaacc   420
tcacttgaga aatcatccaa cgaagaatcc atcatgatga acaattcct tcccaacttc    480 ttgaaaccag aacctttgca gaagtacata cccgttatgg acataattac caaagacac    540 ttcaatacaa gctgggaagg acgcaacgtg gtcaaagtgt ttcctacggc tgccgaattc   600
accacgttgc tggcttgtcg ggtattcctc agtgttgagg atcccattga agtagccaag   660
atttcagagc catttgaaat cttagctgct gggtttcttt caatacccat aaatcttccg   720
ggtaccaaat taaataaagc ggttaaggca gcggatcaga ttagacgc aattgtacag     780 attttgaaac ggagaagggt tgaaattgcg gagaataaag caaatggaat gcaagatata   840
gcgtccatgt tgttgacgac accaactaat gctgggtttt atatgaccga ggctcacatt   900
tctgagaaaa ttttgggtat gattgttggt ggccgtgata ctgctagtac tgttatcacc   960
ttcatcatca gtatttggc agagaatcct gaaatttata ataaggtcta tgaggagcaa   1020
atggaagtgg taaagtcaaa gaaccaggt gagttgctga actgggaaga tgtgcagaaa   1080
atgaagtact cttggtgcgt agcatgtgaa gctatgcgac ttgctcctcc tgttcaaggt   1140
ggtttcaagg tggccattaa tgactttgtg tattctgggt tcaacattcg caagggttgg   1200
aagttatatt ggagtgccat tgcaacacac atgaatccag aatatttccc agaacctgag   1260
aaattcaacc cctcaaggtt tgaagggaag ggaccagtac cttacagctt cgtacccttc   1320
ggaggcggac ctcggatgtg tcccgggaaa gagtattccc ggctggaaac acttgttttc   1380
atgcatcatt tggtgacgag gtacaattgg gagaaagtgt atcccacaga aagataaca   1440 gtggatccaa tgccattccc tgtcaacggc ctccccattc gccttattcc tcacaagcac   1500
caatga                                                              1506
```

<210> SEQ ID NO 16
<211> LENGTH: 501
<212> TYPE: PRT
<213> ORGANISM: Quillaja saponaria

<400> SEQUENCE: 16

```
Met Ile Tyr Asn Asn Asp Ser Asn Asp Asn Glu Leu Val Ile Ser Ser
1               5                   10                  15

Val Gln Gln Pro Ser Met Asp Pro Phe Ile Phe Gly Leu Leu Leu
            20                  25                  30

Leu Ala Leu Phe Leu Ser Val Ser Phe Leu Leu Tyr Leu Ser Arg Arg
        35                  40                  45

Ala Tyr Ala Ser Leu Pro Asn Pro Pro Gly Lys Leu Gly Phe Pro
    50                  55                  60

Val Val Gly Glu Ser Leu Glu Phe Leu Ser Thr Arg Arg Lys Gly Val
65                  70                  75                  80

Pro Glu Lys Phe Val Phe Asp Arg Met Ala Lys Tyr Cys Arg Asp Val
                85                  90                  95

Phe Lys Thr Ser Ile Leu Gly Ala Thr Thr Ala Val Met Cys Gly Thr
            100                 105                 110
```

```
Ala Gly Asn Lys Phe Leu Phe Ser Asn Glu Lys Lys His Val Thr Gly
            115                 120                 125

Trp Trp Pro Lys Ser Val Glu Leu Ile Phe Pro Thr Ser Leu Glu Lys
130                 135                 140

Ser Ser Asn Glu Glu Ser Ile Met Met Lys Gln Phe Leu Pro Asn Phe
145                 150                 155                 160

Leu Lys Pro Glu Pro Leu Gln Lys Tyr Ile Pro Val Met Asp Ile Ile
                165                 170                 175

Thr Gln Arg His Phe Asn Thr Ser Trp Glu Gly Arg Asn Val Val Lys
            180                 185                 190

Val Phe Pro Thr Ala Ala Glu Phe Thr Thr Leu Leu Ala Cys Arg Val
            195                 200                 205

Phe Leu Ser Val Glu Asp Pro Ile Glu Val Ala Lys Ile Ser Glu Pro
            210                 215                 220

Phe Glu Ile Leu Ala Ala Gly Phe Leu Ser Ile Pro Ile Asn Leu Pro
225                 230                 235                 240

Gly Thr Lys Leu Asn Lys Ala Val Lys Ala Ala Asp Gln Ile Arg Asp
                245                 250                 255

Ala Ile Val Gln Ile Leu Lys Arg Arg Arg Val Glu Ile Ala Glu Asn
            260                 265                 270

Lys Ala Asn Gly Met Gln Asp Ile Ala Ser Met Leu Leu Thr Thr Pro
            275                 280                 285

Thr Asn Ala Gly Phe Tyr Met Thr Glu Ala His Ile Ser Glu Lys Ile
            290                 295                 300

Leu Gly Met Ile Val Gly Gly Arg Asp Thr Ala Ser Thr Val Ile Thr
305                 310                 315                 320

Phe Ile Ile Lys Tyr Leu Ala Glu Asn Pro Glu Ile Tyr Asn Lys Val
                325                 330                 335

Tyr Glu Glu Gln Met Glu Val Val Lys Ser Lys Lys Pro Gly Glu Leu
            340                 345                 350

Leu Asn Trp Glu Asp Val Gln Lys Met Lys Tyr Ser Trp Cys Val Ala
            355                 360                 365

Cys Glu Ala Met Arg Leu Ala Pro Pro Val Gln Gly Gly Phe Lys Val
            370                 375                 380

Ala Ile Asn Asp Phe Val Tyr Ser Gly Phe Asn Ile Arg Lys Gly Trp
385                 390                 395                 400

Lys Leu Tyr Trp Ser Ala Ile Ala Thr His Met Asn Pro Glu Tyr Phe
                405                 410                 415

Pro Glu Pro Glu Lys Phe Asn Pro Ser Arg Phe Glu Gly Lys Gly Pro
            420                 425                 430

Val Pro Tyr Ser Phe Val Pro Phe Gly Gly Pro Arg Met Cys Pro
            435                 440                 445

Gly Lys Glu Tyr Ser Arg Leu Glu Thr Leu Val Phe Met His His Leu
            450                 455                 460

Val Thr Arg Tyr Asn Trp Glu Lys Val Tyr Pro Thr Glu Lys Ile Thr
465                 470                 475                 480

Val Asp Pro Met Pro Phe Pro Val Asn Gly Leu Pro Ile Arg Leu Ile
                485                 490                 495

Pro His Lys His Gln
            500

<210> SEQ ID NO 17
<211> LENGTH: 1524
```

-continued

<212> TYPE: DNA
<213> ORGANISM: Quillaja saponaria

<400> SEQUENCE: 17

```
atgtggttca cagtaggatt ggtcttggtt ttcgccctat tcatacgtct ctacagcagt    60
ctgtggttga agcctcgtgc aactcggatt aagcttagca atcaaggaat taaaggtcca   120
aaaccagcat ttcttctggg taatgttgca gagatgagaa gatttcaatc taagcttcca   180
aaatctgaac tcaaacaagg ccaagtttct catgattggg cttctaaatc tctgtttcca   240
tttttcagtc tttggtccca gaaatacgga atacgttcg tgttctcatt ggggaacata    300
caggtgctct atgtttctga tcatgagttg gtgaaagaaa ttaatcagaa tacctcttta   360
gatttgggca aacccaagta cctgcagaag gagcgtggcc ctttgctggg acaaggtatt   420
ttgacctcca atggacagct tgggcgtac cagagaaaaa tcatgactcc tgaactctac    480
aaggagaaaa tcaagggcat gtgcgagttg atggtggaat ctgtagcttg gttggttgag   540
gaatggggaa cgaagatcca agctgagggt ggggcagcag acattagaat agacgaggat   600
cttagaagct tctctggtga tgtaatttca aaagcttgtt ttgggagctg ctatgccgga   660
gggagggaaa tctttcttag gctcagagct cttcaacacc aaattgcttc caaagcctta   720
ctcatgggct tccctggatt aaagtacctg cccattaaga gcaacagaga gatatggaga   780
ttggagaagg agatcttcca gctgattatg aagctggctg aagatagaaa aaaagaacaa   840
catgagagag acctattaca gattataatt gagggagcta aaagtagtga tctgagttcg   900
gaagcaatgg caaaattcat tgtggacaac tgcaagaatg tctacttggc tggccatgaa   960
actactgcaa tgtctgctgg ttggactttg cttctcttgg ctaatcatcc tgagtggcaa  1020
gcccgtgtcc gtgatgagat tttacaagtc accgagggcc gcaatcctga ttttgacatg  1080
ctgcacaaga tgaaactgtt aacaatggta attcaggagg cactgcgact ctacccaaca  1140
gtcatattca tgtcaagaga agcattggaa gatattaatg ttggaaacat ccaagttcca  1200
aaaggtgtta acatatggat acctgtggta aatcttcaaa gggacacaac ggtatggggt  1260
gcagacgcaa acgagtttaa tcctgaaagg tttgccaatg gagttaacaa ttcatgcaag  1320
gttccacaac tttacctacc atttggagct ggacctcgca tttgtcctgg aattaatctg  1380
gccatgactg agatcaagat acttctgtgt atcctgctca ccaagttttc gttttcagtt  1440
tcacccaact atcgccactc accggtgttt aaattggtgc ttgagcctga aaatggaatc  1500
aatgtcatca tgaagaagct ctaa                                          1524
```

<210> SEQ ID NO 18
<211> LENGTH: 507
<212> TYPE: PRT
<213> ORGANISM: Quillaja saponaria

<400> SEQUENCE: 18

```
Met Trp Phe Thr Val Gly Leu Val Leu Val Phe Ala Leu Phe Ile Arg
1               5                   10                  15

Leu Tyr Ser Ser Leu Trp Leu Lys Pro Arg Ala Thr Arg Ile Lys Leu
            20                  25                  30

Ser Asn Gln Gly Ile Lys Gly Pro Lys Pro Ala Phe Leu Leu Gly Asn
        35                  40                  45

Val Ala Glu Met Arg Arg Phe Gln Ser Lys Leu Pro Lys Ser Glu Leu
    50                  55                  60

Lys Gln Gly Gln Val Ser His Asp Trp Ala Ser Lys Ser Leu Phe Pro
65                  70                  75                  80
```

-continued

Phe Phe Ser Leu Trp Ser Gln Lys Tyr Gly Asn Thr Phe Val Phe Ser
                85                  90                  95

Leu Gly Asn Ile Gln Val Leu Tyr Val Ser Asp His Glu Leu Val Lys
            100                 105                 110

Glu Ile Asn Gln Asn Thr Ser Leu Asp Leu Gly Lys Pro Lys Tyr Leu
            115                 120                 125

Gln Lys Glu Arg Gly Pro Leu Leu Gly Gln Gly Ile Leu Thr Ser Asn
130                 135                 140

Gly Gln Leu Trp Ala Tyr Gln Arg Lys Ile Met Thr Pro Glu Leu Tyr
145                 150                 155                 160

Lys Glu Lys Ile Lys Gly Met Cys Glu Leu Met Val Glu Ser Val Ala
                165                 170                 175

Trp Leu Val Glu Glu Trp Gly Thr Lys Ile Gln Ala Glu Gly Gly Ala
            180                 185                 190

Ala Asp Ile Arg Ile Asp Glu Asp Leu Arg Ser Phe Ser Gly Asp Val
            195                 200                 205

Ile Ser Lys Ala Cys Phe Gly Ser Cys Tyr Ala Gly Gly Arg Glu Ile
210                 215                 220

Phe Leu Arg Leu Arg Ala Leu Gln His Gln Ile Ala Ser Lys Ala Leu
225                 230                 235                 240

Leu Met Gly Phe Pro Gly Leu Lys Tyr Leu Pro Ile Lys Ser Asn Arg
                245                 250                 255

Glu Ile Trp Arg Leu Glu Lys Glu Ile Phe Gln Leu Ile Met Lys Leu
            260                 265                 270

Ala Glu Asp Arg Lys Lys Glu Gln His Glu Arg Asp Leu Leu Gln Ile
            275                 280                 285

Ile Ile Glu Gly Ala Lys Ser Ser Asp Leu Ser Ser Glu Ala Met Ala
290                 295                 300

Lys Phe Ile Val Asp Asn Cys Lys Asn Val Tyr Leu Ala Gly His Glu
305                 310                 315                 320

Thr Thr Ala Met Ser Ala Gly Trp Thr Leu Leu Leu Ala Asn His
                325                 330                 335

Pro Glu Trp Gln Ala Arg Val Arg Asp Glu Ile Leu Gln Val Thr Glu
            340                 345                 350

Gly Arg Asn Pro Asp Phe Asp Met Leu His Lys Met Lys Leu Leu Thr
            355                 360                 365

Met Val Ile Gln Glu Ala Leu Arg Leu Tyr Pro Thr Val Ile Phe Met
370                 375                 380

Ser Arg Glu Ala Leu Glu Asp Ile Asn Val Gly Asn Ile Gln Val Pro
385                 390                 395                 400

Lys Gly Val Asn Ile Trp Ile Pro Val Val Asn Leu Gln Arg Asp Thr
                405                 410                 415

Thr Val Trp Gly Ala Asp Ala Asn Glu Phe Asn Pro Glu Arg Phe Ala
            420                 425                 430

Asn Gly Val Asn Asn Ser Cys Lys Val Pro Gln Leu Tyr Leu Pro Phe
            435                 440                 445

Gly Ala Gly Pro Arg Ile Cys Pro Gly Ile Asn Leu Ala Met Thr Glu
450                 455                 460

Ile Lys Ile Leu Leu Cys Ile Leu Leu Thr Lys Phe Ser Phe Ser Val
465                 470                 475                 480

Ser Pro Asn Tyr Arg His Ser Pro Val Phe Lys Leu Val Leu Glu Pro
                485                 490                 495

Glu Asn Gly Ile Asn Val Ile Met Lys Lys Leu
        500                 505

<210> SEQ ID NO 19
<211> LENGTH: 1524
<212> TYPE: DNA
<213> ORGANISM: Artificial Sequence
<220> FEATURE:
<223> OTHER INFORMATION: Synthetic sequence

<400> SEQUENCE: 19

| | | | | | |
|---|---|---|---|---|---|
| atgtggttca | cagtaggatt | ggtcttggtt | ttcgccctat | tcatacgtct | ctacagcagt | 60 |
| ctgtggttga | agcctcgtgc | aactcggatt | aagcttagca | atcaaggaat | taaaggtcca | 120 |
| aaaccagcat | ttcttctggg | taatgttgca | gagatgagaa | gatttcaatc | taagcttcca | 180 |
| aaatctgaac | tcaaacaagg | ccaagtttct | catgattggg | cttctaaatc | tctgtttcca | 240 |
| tttttcagtc | tttggtccca | gaaatacgga | aatacgttcg | tgttctcatt | ggggaacata | 300 |
| caggtgctct | atgtttctga | tcatgagttg | gtgaaagaaa | ttaatcagaa | tacctcttta | 360 |
| gatttgggca | aacccaagta | cctgcagaag | gagcgtggcc | ctttgctggg | acaaggtatt | 420 |
| ttgacctcca | atggacagct | ttgggcgtac | cagagaaaaa | tcatgactcc | tgaactctac | 480 |
| aaggagaaaa | tcaagggcat | gtgcgagttg | atggtggaat | ctgtagcttg | gttggttgag | 540 |
| gaatggggaa | cgaagatcca | agctgagggt | ggggcagcag | acattagaat | agacgaggat | 600 |
| cttagaagct | tctctggtga | tgtaatttca | aaagcttgtt | ttgggagctg | ctatgccgga | 660 |
| gggagggaaa | tctttcttag | gctcagagct | cttcaacacc | aaattgcttc | caaagcctta | 720 |
| ctcatgggct | tccctggatt | aaagtacctg | cccattaaga | gcaacagaga | gatatggaga | 780 |
| ttggagaagg | agatcttcca | gctgattatg | aagctggctg | aagatagaaa | aaaagaacaa | 840 |
| catgagagag | acctattaca | gattataatt | gagggagcta | aaagtagtga | tctgagttcg | 900 |
| gaagcaatgg | caaaattcat | tgtggacaac | tgcaagaatg | tctacttggc | tggccatgaa | 960 |
| actactgcaa | tgtctgctgg | ttggactttg | cttctcttgg | ctaatcatcc | tgagtggcaa | 1020 |
| gcccgtgtcc | gtgatgagat | tttacaagtc | accgagggcc | gcaatcctga | ttttgacatg | 1080 |
| ctgcacaaga | tgaaactgtt | aacaatggta | attcaggagg | cactgcgact | ctacccaaca | 1140 |
| gtcatattca | tgtcaagaga | agcattggaa | gatattaatg | ttggaaacat | ccaagttcca | 1200 |
| aaaggtgtta | acatatggat | acctgtggta | atcttcaaa | gggacacaac | ggtatggggt | 1260 |
| gcagacgcaa | acgagtttaa | tcctgaaagg | tttgccaatg | gagttaacaa | ttcatgcaag | 1320 |
| gttccacaac | tttacctacc | atttggagct | ggacctcgca | tttgtcctgg | aattaatctg | 1380 |
| gccatgactg | agatcaagat | acttctgtgt | atcctgctca | ccaagttttc | gttttcagtt | 1440 |
| tcacccaact | atcgccactc | accggtgttt | aaattggtgc | ttgagcctga | aaatggaatc | 1500 |
| aatgtcatca | tgaagaagct | ctaa | | | | 1524 |

<210> SEQ ID NO 20
<211> LENGTH: 495
<212> TYPE: PRT
<213> ORGANISM: Artificial Sequence
<220> FEATURE:
<223> OTHER INFORMATION: Synthetic sequence

<400> SEQUENCE: 20

Met Glu Lys Lys Lys Gly Glu Leu Lys Ser Ile Phe Leu Pro Phe Leu
1               5                   10                  15

Ser Thr Ser His Ile Ile Pro Leu Val Asp Met Ala Arg Leu Phe Ala

-continued

```
               20                  25                  30
Leu His Asp Val Asp Val Thr Ile Ile Thr Thr Ala His Asn Ala Thr
             35                  40                  45
Val Phe Gln Lys Ser Ile Asp Leu Asp Ala Ser Arg Gly Arg Pro Ile
 50                  55                  60
Arg Thr His Val Val Asn Phe Pro Ala Ala Gln Val Gly Leu Pro Val
 65                  70                  75                  80
Gly Ile Glu Ala Phe Asn Val Asp Thr Pro Arg Glu Met Thr Pro Arg
                 85                  90                  95
Ile Tyr Met Gly Leu Ser Leu Leu Gln Gln Val Phe Glu Lys Leu Phe
                100                 105                 110
His Asp Leu Gln Pro Asp Phe Ile Val Thr Asp Met Phe His Pro Trp
            115                 120                 125
Ser Val Asp Ala Ala Lys Leu Gly Ile Pro Arg Ile Met Phe His
            130                 135                 140
Gly Ala Ser Tyr Leu Ala Arg Ser Ala Ala His Ser Val Glu Gln Tyr
145                 150                 155                 160
Ala Pro His Leu Glu Ala Lys Phe Asp Thr Asp Lys Phe Val Leu Pro
                165                 170                 175
Gly Leu Pro Asp Asn Leu Glu Met Thr Arg Leu Gln Leu Pro Asp Trp
                180                 185                 190
Leu Arg Ser Pro Asn Gln Tyr Thr Glu Leu Met Arg Thr Ile Lys Gln
            195                 200                 205
Ser Glu Lys Lys Ser Tyr Gly Ser Leu Phe Asn Ser Phe Tyr Asp Leu
            210                 215                 220
Glu Ser Ala Tyr Tyr Glu His Tyr Lys Ser Ile Met Gly Thr Lys Ser
225                 230                 235                 240
Trp Gly Ile Gly Pro Val Ser Leu Trp Ala Asn Gln Asp Ala Gln Asp
                245                 250                 255
Lys Ala Ala Arg Gly Tyr Ala Lys Glu Glu Glu Lys Glu Gly Trp
                260                 265                 270
Leu Lys Trp Leu Asn Ser Lys Ala Glu Ser Ser Val Leu Tyr Val Ser
            275                 280                 285
Phe Gly Ser Ile Asn Lys Phe Pro Tyr Ser Gln Leu Val Glu Ile Ala
            290                 295                 300
Arg Ala Leu Glu Asp Ser Gly His Asp Phe Ile Trp Val Val Arg Lys
305                 310                 315                 320
Asn Asp Gly Gly Glu Gly Asp Asn Phe Leu Glu Glu Phe Glu Lys Arg
                325                 330                 335
Met Lys Glu Ser Asn Lys Gly Tyr Leu Ile Trp Gly Trp Ala Pro Gln
                340                 345                 350
Leu Leu Ile Leu Glu Asn Pro Ala Ile Gly Gly Leu Val Thr His Cys
            355                 360                 365
Gly Trp Asn Thr Val Val Glu Ser Val Asn Ala Gly Leu Pro Met Ala
370                 375                 380
Thr Trp Pro Leu Phe Ala Glu His Phe Phe Asn Glu Lys Leu Val Val
385                 390                 395                 400
Asp Val Leu Lys Ile Gly Val Pro Val Gly Ala Lys Glu Trp Arg Asn
                405                 410                 415
Trp Asn Glu Phe Gly Ser Glu Val Val Lys Arg Glu Glu Ile Gly Asn
                420                 425                 430
Ala Ile Ala Ser Leu Met Ser Glu Glu Glu Asp Gly Gly Met Arg
            435                 440                 445
```

Lys Arg Ala Lys Glu Leu Ser Val Ala Ala Lys Ser Ala Ile Lys Val
            450                 455                 460

Gly Gly Ser Ser His Asn Asn Met Lys Glu Leu Ile Arg Glu Leu Lys
465                 470                 475                 480

Glu Ile Lys Leu Ser Lys Glu Ala Gln Glu Thr Ala Pro Asn Pro
                485                 490                 495

<210> SEQ ID NO 21
<211> LENGTH: 1212
<212> TYPE: DNA
<213> ORGANISM: Avena strigosa

<400> SEQUENCE: 21

| | | | | | |
|---|---|---|---|---|---|
| atgggggcgc | tgtcgcggcc | ggaggaggtg | gtggcgctgg | tcaagctgag | ggtggcggcg | 60 |
| gggcagatca | agcgccagat | cccggccgag | gaacactggg | ccttcgccta | cgacatgctc | 120 |
| cagaaggtct | cccgcagctt | cgcgctcgtc | atccagcagc | tcggacccga | actccgcaat | 180 |
| gccgtgtgca | tcttctacct | cgtgctccgg | gccctggaca | ccgtcgagga | cgacaccagc | 240 |
| atccccaacg | acgtgaagct | gcccatcctt | cgggatttct | accgccatgt | ctacaacccc | 300 |
| gactggcgtt | attcatgtgg | aacaaaccac | tacaaggtgc | tgatggataa | gttcagactc | 360 |
| gtctccacgg | ctttcctgga | gctaggcgaa | ggatatcaaa | aggcaattga | agaaatcact | 420 |
| aggcgaatgg | gagcaggaat | ggcaaaattt | atatgccagg | aggttgaaac | gattgatgac | 480 |
| tataatgagt | actgccacta | tgtagcaggg | ctagtaggct | atggactttc | caggctcttt | 540 |
| catgctgctg | ggacagaaga | tctggcttca | gatcaacttt | cgaattcaat | gggtttgttt | 600 |
| cttcagaaaa | ccaatataat | aagggattat | ttggaggata | taaatgagat | accaaagtgc | 660 |
| cgtatgtttt | ggcctcgaga | aaatatggagt | aaatatgcag | ataaacttga | ggacctcaag | 720 |
| tatgaggaaa | attcagaaaa | agcagtgcaa | tgcttgaatg | atatggtgac | taatgctttg | 780 |
| gtccacgccg | aagactgtct | tcaatacatg | tctgcgttga | aggataatac | taattttcgg | 840 |
| ttttgtgcaa | tacctcagat | aatggcaatt | gggacatgtg | ctatttgcta | caataatgtg | 900 |
| aaagtcttta | gaggagttgt | taagatgagg | cgtgggctca | ctgcacgaat | aattgatgag | 960 |
| acaaaatcaa | tgtcagatgt | ctattctgct | ttctatgagt | tctcttcatt | gctagagtca | 1020 |
| aagattgacg | ataacgaccc | aagttctgca | ctaacacgga | agcgtgtaga | ggcaataaag | 1080 |
| aggacttgca | agtcatccgg | tttactaaag | agaagcggat | acgacctgga | aaagtcaaag | 1140 |
| tataggcata | tgttgatcat | gcttgcactt | ctgttggtgg | ctattatctt | cggtgtactg | 1200 |
| tacgccaagt | ga | | | | | 1212 |

<210> SEQ ID NO 22
<211> LENGTH: 403
<212> TYPE: PRT
<213> ORGANISM: Avena strigosa

<400> SEQUENCE: 22

Met Gly Ala Leu Ser Arg Pro Glu Glu Val Val Ala Leu Val Lys Leu
1               5                   10                  15

Arg Val Ala Ala Gly Gln Ile Lys Arg Gln Ile Pro Ala Glu Glu His
                20                  25                  30

Trp Ala Phe Ala Tyr Asp Met Leu Gln Lys Val Ser Arg Ser Phe Ala
            35                  40                  45

Leu Val Ile Gln Gln Leu Gly Pro Glu Leu Arg Asn Ala Val Cys Ile
        50                  55                  60

```
Phe Tyr Leu Val Leu Arg Ala Leu Asp Thr Val Glu Asp Thr Ser
 65                  70                  75                  80

Ile Pro Asn Asp Val Lys Leu Pro Ile Leu Arg Asp Phe Tyr Arg His
                 85                  90                  95

Val Tyr Asn Pro Asp Trp Arg Tyr Ser Cys Gly Thr Asn His Tyr Lys
            100                 105                 110

Val Leu Met Asp Lys Phe Arg Leu Val Ser Thr Ala Phe Leu Glu Leu
        115                 120                 125

Gly Glu Gly Tyr Gln Lys Ala Ile Glu Ile Thr Arg Arg Met Gly
    130                 135                 140

Ala Gly Met Ala Lys Phe Ile Cys Gln Glu Val Glu Thr Ile Asp Asp
145                 150                 155                 160

Tyr Asn Glu Tyr Cys His Tyr Val Ala Gly Leu Val Gly Tyr Gly Leu
                165                 170                 175

Ser Arg Leu Phe His Ala Ala Gly Thr Glu Asp Leu Ala Ser Asp Gln
            180                 185                 190

Leu Ser Asn Ser Met Gly Leu Phe Leu Gln Lys Thr Asn Ile Ile Arg
        195                 200                 205

Asp Tyr Leu Glu Asp Ile Asn Glu Ile Pro Lys Cys Arg Met Phe Trp
210                 215                 220

Pro Arg Glu Ile Trp Ser Lys Tyr Ala Asp Lys Leu Glu Asp Leu Lys
225                 230                 235                 240

Tyr Glu Glu Asn Ser Glu Lys Ala Val Gln Cys Leu Asn Asp Met Val
                245                 250                 255

Thr Asn Ala Leu Val His Ala Glu Asp Cys Leu Gln Tyr Met Ser Ala
            260                 265                 270

Leu Lys Asp Asn Thr Asn Phe Arg Phe Cys Ala Ile Pro Gln Ile Met
        275                 280                 285

Ala Ile Gly Thr Cys Ala Ile Cys Tyr Asn Asn Val Lys Val Phe Arg
    290                 295                 300

Gly Val Val Lys Met Arg Arg Gly Leu Thr Ala Arg Ile Ile Asp Glu
305                 310                 315                 320

Thr Lys Ser Met Ser Asp Val Tyr Ser Ala Phe Tyr Glu Phe Ser Ser
                325                 330                 335

Leu Leu Glu Ser Lys Ile Asp Asp Asn Asp Pro Ser Ser Ala Leu Thr
            340                 345                 350

Arg Lys Arg Val Glu Ala Ile Lys Arg Thr Cys Lys Ser Ser Gly Leu
        355                 360                 365

Leu Lys Arg Arg Gly Tyr Asp Leu Glu Lys Ser Lys Tyr Arg His Met
    370                 375                 380

Leu Ile Met Leu Ala Leu Leu Val Ala Ile Ile Phe Gly Val Leu
385                 390                 395                 400

Tyr Ala Lys
```

<210> SEQ ID NO 23
<211> LENGTH: 2325
<212> TYPE: DNA
<213> ORGANISM: Arabidopsis thaliana

<400> SEQUENCE: 23

| | | |
|---|---|---|
| atgaaaaaca tgatgaatta taaattaaaa ctctgttctg tctcaaaaaa ctcaaaagga | 60 |
| gtctctctct cacctacacc acacctaacc aaacccccta cgattcacac agagagagat | 120 |
| cttcttcttc cttcttcttc cttcttcttt cttcttcttt cttcttctag ctacaacatc | 180 |

| | |
|---|---|
| tacaacgcca tgtcctcttc ttcttcttcg tcaacctcca tgatcgatct catggcagca | 240 |
| atcatcaaag gagagcctgt aattgtctcc gacccagcta atgcctccgc ttacgagtcc | 300 |
| gtagctgctg aattatcctc tatgcttata gagaatcgtc aattcgccat gattgttacc | 360 |
| acttccattg ctgttcttat tggttgcatc gttatgctcg tttggaggag atccggttct | 420 |
| gggaattcaa aacgtgtcga gcctcttaag cctttggtta ttaagcctcg tgaggaagag | 480 |
| attgatgatg ggcgtaagaa agttaccatc tttttcggta cacaaactgg tactgctgaa | 540 |
| ggttttgcaa aggctttagg agaagaagct aaagcaagat atgaaaagac cagattcaaa | 600 |
| atcgttgatt tggatgatta cgcggctgat gatgatgagt atgaggagaa attgaagaaa | 660 |
| gaggatgtgg ctttcttctt cttagccaca tatggagatg gtgagcctac cgacaatgca | 720 |
| gcgagattct acaaatggtt caccgagggg aatgacagag agaatggct taagaacttg | 780 |
| aagtatggag tgtttggatt aggaaacaga caatatgagc attttaataa ggttgccaaa | 840 |
| gttgtagatg acattcttgt cgaacaaggt gcacagcgtc ttgtacaagt tggtcttgga | 900 |
| gatgatgacc agtgtattga agatgacttt accgcttggc gagaagcatt gtggcccgag | 960 |
| cttgatacaa tactgaggga agaagggat acagctgttg ccacaccata cactgcagct | 1020 |
| gtgttagaat acagagtttc tattcacgac tctgaagatg ccaaattcaa tgatataaac | 1080 |
| atggcaaatg gaatggtta cactgtgttt gatgctcaac atccttacaa agcaaatgtc | 1140 |
| gctgttaaaa gggagcttca tactcccgag tctgatcgtt cttgtatcca tttggaattt | 1200 |
| gacattgctg gaagtggact tacgtatgaa actggagatc atgttggtgt actttgtgat | 1260 |
| aacttaagtg aaactgtaga tgaagctctt agattgctgg atatgtcacc tgatacttat | 1320 |
| ttctcacttc acgctgaaaa agaagacggc acaccaatca gcagctcact gcctcctccc | 1380 |
| ttcccacctt gcaacttgag aacagcgctt acacgatatg catgtctttt gagttctcca | 1440 |
| aagaagtctg ctttagttgc gttggctgct catgcatctg atcctaccga agcagaacga | 1500 |
| ttaaaacacc ttgcttcacc tgctggaaag gatgaatatt caaagtgggt agtagagagt | 1560 |
| caaagaagtc tacttgaggt gatggccgag tttccttcag ccaagccacc acttggtgtc | 1620 |
| ttcttcgctg gagttgctcc aaggttgcag cctaggttct attcgatatc atcatcgccc | 1680 |
| aagattgctg aaactagaat tcacgtcaca tgtgcactgg tttatgagaa aatgccaact | 1740 |
| ggcaggattc ataagggagt gtgttccact tggatgaaga atgctgtgcc ttacgagaag | 1800 |
| agtgaaaact gttcctcggc gccgatattt gttaggcaat ccaacttcaa gcttccttct | 1860 |
| gattctaagg taccgatcat catgatcggt ccagggactg gattagctcc attcagagga | 1920 |
| ttccttcagg aaagactagc gttggtagaa tctggtgttg aacttgggcc atcagttttg | 1980 |
| ttctttggat gcagaaaccg tagaatggat ttcatctacg aggaagagct ccagcgattt | 2040 |
| gttgagagtg gtgctctcgc agagctaagt gtcgccttct ctcgtgaagg acccaccaaa | 2100 |
| gaatacgtac agcacaagat gatggacaag gcttctgata tctggaatat gatctctcaa | 2160 |
| ggagcttatt tatatgtttg tggtgacgcc aaaggcatgg caagagatgt tcacagatct | 2220 |
| ctccacacaa tagctcaaga acaggggtca atggattcaa ctaaagcaga gggcttcgtg | 2280 |
| aagaatctgc aaacgagtgg aagatatctt agagatgtat ggtaa | 2325 |

<210> SEQ ID NO 24
<211> LENGTH: 774
<212> TYPE: PRT
<213> ORGANISM: Arabidopsis thaliana -continued

```
<400> SEQUENCE: 24

Met Lys Asn Met Met Asn Tyr Lys Leu Lys Leu Cys Ser Val Ser Lys
1               5                   10                  15

Asn Ser Lys Gly Val Ser Leu Ser Pro Thr Pro His Leu Thr Lys Pro
            20                  25                  30

Pro Thr Ile His Thr Glu Arg Asp Leu Leu Pro Ser Ser Ser Phe
        35                  40                  45

Phe Phe Leu Leu Leu Ser Ser Ser Ser Tyr Asn Ile Tyr Asn Ala Met
    50                  55                  60

Ser Ser Ser Ser Ser Ser Thr Ser Met Ile Asp Leu Met Ala Ala
65                  70                  75                  80

Ile Ile Lys Gly Glu Pro Val Ile Val Ser Asp Pro Ala Asn Ala Ser
                85                  90                  95

Ala Tyr Glu Ser Val Ala Ala Glu Leu Ser Ser Met Leu Ile Glu Asn
            100                 105                 110

Arg Gln Phe Ala Met Ile Val Thr Thr Ser Ile Ala Val Leu Ile Gly
            115                 120                 125

Cys Ile Val Met Leu Val Trp Arg Arg Ser Gly Ser Gly Asn Ser Lys
130                 135                 140

Arg Val Glu Pro Leu Lys Pro Leu Val Ile Lys Pro Arg Glu Glu Glu
145                 150                 155                 160

Ile Asp Asp Gly Arg Lys Lys Val Thr Ile Phe Phe Gly Thr Gln Thr
                165                 170                 175

Gly Thr Ala Glu Gly Phe Ala Lys Ala Leu Gly Glu Glu Ala Lys Ala
            180                 185                 190

Arg Tyr Glu Lys Thr Arg Phe Lys Ile Val Asp Leu Asp Asp Tyr Ala
            195                 200                 205

Ala Asp Asp Asp Glu Tyr Glu Glu Lys Leu Lys Lys Glu Asp Val Ala
210                 215                 220

Phe Phe Phe Leu Ala Thr Tyr Gly Asp Gly Glu Pro Thr Asp Asn Ala
225                 230                 235                 240

Ala Arg Phe Tyr Lys Trp Phe Thr Glu Gly Asn Asp Arg Gly Glu Trp
                245                 250                 255

Leu Lys Asn Leu Lys Tyr Gly Val Phe Gly Leu Gly Asn Arg Gln Tyr
            260                 265                 270

Glu His Phe Asn Lys Val Ala Lys Val Val Asp Ile Leu Val Glu
            275                 280                 285

Gln Gly Ala Gln Arg Leu Val Gln Val Gly Leu Gly Asp Asp Asp Gln
290                 295                 300

Cys Ile Glu Asp Asp Phe Thr Ala Trp Arg Glu Ala Leu Trp Pro Glu
305                 310                 315                 320

Leu Asp Thr Ile Leu Arg Glu Glu Gly Asp Thr Ala Val Ala Thr Pro
                325                 330                 335

Tyr Thr Ala Ala Val Leu Glu Tyr Arg Val Ser Ile His Asp Ser Glu
            340                 345                 350

Asp Ala Lys Phe Asn Asp Ile Asn Met Ala Asn Gly Asn Gly Tyr Thr
            355                 360                 365

Val Phe Asp Ala Gln His Pro Tyr Lys Ala Asn Val Ala Val Lys Arg
370                 375                 380

Glu Leu His Thr Pro Glu Ser Asp Arg Ser Cys Ile His Leu Glu Phe
385                 390                 395                 400

Asp Ile Ala Gly Ser Gly Leu Thr Tyr Glu Thr Gly Asp His Val Gly
                405                 410                 415
```

```
Val Leu Cys Asp Asn Leu Ser Glu Thr Val Asp Glu Ala Leu Arg Leu
                420                 425                 430

Leu Asp Met Ser Pro Asp Thr Tyr Phe Ser Leu His Ala Glu Lys Glu
            435                 440                 445

Asp Gly Thr Pro Ile Ser Ser Leu Pro Pro Phe Pro Pro Cys
        450                 455                 460

Asn Leu Arg Thr Ala Leu Thr Arg Tyr Ala Cys Leu Leu Ser Ser Pro
465                 470                 475                 480

Lys Lys Ser Ala Leu Val Ala Leu Ala Ala His Ala Ser Asp Pro Thr
                485                 490                 495

Glu Ala Glu Arg Leu Lys His Leu Ala Ser Pro Ala Gly Lys Asp Glu
            500                 505                 510

Tyr Ser Lys Trp Val Val Glu Ser Gln Arg Ser Leu Leu Glu Val Met
        515                 520                 525

Ala Glu Phe Pro Ser Ala Lys Pro Pro Leu Gly Val Phe Ala Gly
    530                 535                 540

Val Ala Pro Arg Leu Gln Pro Arg Phe Tyr Ser Ile Ser Ser Ser Pro
545                 550                 555                 560

Lys Ile Ala Glu Thr Arg Ile His Val Thr Cys Ala Leu Val Tyr Glu
                565                 570                 575

Lys Met Pro Thr Gly Arg Ile His Lys Gly Val Cys Ser Thr Trp Met
            580                 585                 590

Lys Asn Ala Val Pro Tyr Glu Lys Ser Glu Asn Cys Ser Ser Ala Pro
        595                 600                 605

Ile Phe Val Arg Gln Ser Asn Phe Lys Leu Pro Ser Asp Ser Lys Val
    610                 615                 620

Pro Ile Ile Met Ile Gly Pro Gly Thr Gly Leu Ala Pro Phe Arg Gly
625                 630                 635                 640

Phe Leu Gln Glu Arg Leu Ala Leu Val Glu Ser Gly Val Glu Leu Gly
                645                 650                 655

Pro Ser Val Leu Phe Phe Gly Cys Arg Asn Arg Arg Met Asp Phe Ile
            660                 665                 670

Tyr Glu Glu Glu Leu Gln Arg Phe Val Glu Ser Gly Ala Leu Ala Glu
        675                 680                 685

Leu Ser Val Ala Phe Ser Arg Glu Gly Pro Thr Lys Glu Tyr Val Gln
    690                 695                 700

His Lys Met Met Asp Lys Ala Ser Asp Ile Trp Asn Met Ile Ser Gln
705                 710                 715                 720

Gly Ala Tyr Leu Tyr Val Cys Gly Asp Ala Lys Gly Met Ala Arg Asp
                725                 730                 735

Val His Arg Ser Leu His Thr Ile Ala Gln Glu Gln Gly Ser Met Asp
            740                 745                 750

Ser Thr Lys Ala Glu Gly Phe Val Lys Asn Leu Gln Thr Ser Gly Arg
        755                 760                 765

Tyr Leu Arg Asp Val Trp
    770
```

<210> SEQ ID NO 25
<211> LENGTH: 2124
<212> TYPE: DNA
<213> ORGANISM: Quillaja saponaria

<400> SEQUENCE: 25
atggcgaccg tctcctccct ccacacttgc actgtacagc aacccgtgc agccattaat    60

```
cgaattcaca ttttcttaca ctttattgcc atactttcc tcttttacta ccgggtcacc      120
ggtcttttct atgacaatgc agtacccact ttagcttggt ctctaatgac cttagctgag     180
ttgattttcg ccttcgtttg ggtgctcagc caagccttcc ggtggcgccc ggtgttgcgt      240
tcagttattc ctgagaggat tcccaaagat gtacgattgc ccgcggtgga tatcttaatt      300
tgtacggctg acccattaaa ggaaccgacg gtggaggtga tgaacactgt cttgtccgcc      360
atggcattgg actatcctgc ggagaatctg gctgtatatc tttctgatga cggggggttct    420 ccggtcacct tatttgctat gaagcaagtg ggtccgtttg ctaagctgtg cttccgtttt     480
tgcaacaagt acgaatcaa aacaaggcat cctgagtctt ttttctcggc atttgcggat      540
gacgaaaggc ttcaccggag tgatgaattc agggcagagg aggaggcgat caaggacaaa    600
tatgaagaat ttaagagaac tatagagaaa tatggtggag aaggaaaaaa tagtcatgtt     660
gtacaagacc ggcctcctca tgtggagatt atacatgaca ctaggaagat tagagagaac    720
agtgaagacc aagctgtgcc tcttcttgtc tacgtctctc gtgagaaaag accatcctac    780
aattctcggt tcaaagcagg agctctgaac acccttcttc gagtttctgg ggtaatcagc    840
aatagcccat atgtattggt gttagactgt gacatgtact gcaatgatcc aacatcagct    900
agacaagcaa tgtgcttcca tcttgatcca caaatgtctc gcactctctc ttttgtacaa    960
ttcccccagg ttttctacaa tgttagtaaa aatgatatct atgatggcca agctagggca   1020
gcctttaaga caaagtggca aggtatggat ggactacgtg ggccactgct ttctggtact   1080
ggcttttatt tgaagaggaa gtccttgtat ggaagtccaa accaagaaga tgattgttta   1140
cttgagcccc ataagaattt tggaaagtgt gacaagctca tagaatcagt aaaggtcatt   1200
tatgaacgtg atgtttcaat aaaggcagat tcatcagatg ccattttgca agatgccaaa   1260
caattagcat cttgtcccta tgaaacaaac acaagctggg gcaaagaggt tgggttctcg   1320
tatgactgct tattagagag tacattcaca ggttatctgt tgcactgcag agggtggaca   1380
tcagtttatc tttatccaaa gaagccatgt ttcttagggt gtactccagt tgatatgaag   1440
gaagccatgg ttcagtatac gaagtggatt tctgaattat ttttacttgc tatctcaaga   1500
ttcaaccctc tgacatttgg gatatccaga atgtccattc tccagagcat gtgttacgga   1560
taccttacaa tcatgcccat tttatctgtt gctatgatct tctatgccac agttcctcaa   1620
ttgtgcctct tgagaggcgt acctctgttt cccaaggttt cagacccatg gtttgcagtg   1680
ttcctagcaa tatttgtgtc ctccctctgt cagcacttaa ttgaagtcct cacgagtgat   1740
ggcacgctca agacttggtg gaatgaacaa agaaattggg tgataaagtc tggttccggt   1800
agcgtatttg gagctctgag tggaatattg aagtggtttg gcatgaagat taaatttggt   1860
ttatcaaaca aagccgtgga caagaaaag cttgagaaat atgaaaaggg taagtttgat   1920
ttccaagggg ctgccatgtt tatggttccc ttaactatat cagtcatctt gaacacatta   1980
tgccttatcg gtggtttatg gagagtaatc acacttaaaa acttcgaaga gatgtcaggg   2040
cagttcatca tctccttgta ctttctagct ctcagctatc caattcttga agggttacta   2100
agaaaaggca agggaaaggc ctaa                                           2124
```

<210> SEQ ID NO 26
<211> LENGTH: 707
<212> TYPE: PRT
<213> ORGANISM: Quillaja saponaria

<400> SEQUENCE: 26

```
Met Ala Thr Val Ser Ser Leu His Thr Cys Thr Val Gln Gln Pro Arg
1               5                   10                  15

Ala Ala Ile Asn Arg Ile His Ile Phe Leu His Phe Ile Ala Ile Leu
            20                  25                  30

Phe Leu Phe Tyr Tyr Arg Val Thr Gly Leu Phe Tyr Asp Asn Ala Val
        35                  40                  45

Pro Thr Leu Ala Trp Ser Leu Met Thr Leu Ala Glu Leu Ile Phe Ala
    50                  55                  60

Phe Val Trp Val Leu Ser Gln Ala Phe Arg Trp Arg Pro Val Leu Arg
65                  70                  75                  80

Ser Val Ile Pro Glu Arg Ile Pro Lys Asp Val Arg Leu Pro Ala Val
                85                  90                  95

Asp Ile Leu Ile Cys Thr Ala Asp Pro Leu Lys Glu Pro Thr Val Glu
                100                 105                 110

Val Met Asn Thr Val Leu Ser Ala Met Ala Leu Asp Tyr Pro Ala Glu
            115                 120                 125

Asn Leu Ala Val Tyr Leu Ser Asp Asp Gly Gly Ser Pro Val Thr Leu
130                 135                 140

Phe Ala Met Lys Gln Val Gly Pro Phe Ala Lys Leu Trp Leu Pro Phe
145                 150                 155                 160

Cys Asn Lys Tyr Gly Ile Lys Thr Arg His Pro Glu Ser Phe Phe Ser
                165                 170                 175

Ala Phe Ala Asp Asp Glu Arg Leu His Arg Ser Asp Glu Phe Arg Ala
            180                 185                 190

Glu Glu Glu Ala Ile Lys Asp Lys Tyr Glu Glu Phe Lys Arg Thr Ile
        195                 200                 205

Glu Lys Tyr Gly Gly Glu Gly Lys Asn Ser His Val Val Gln Asp Arg
210                 215                 220

Pro Pro His Val Glu Ile Ile His Asp Thr Arg Lys Ile Arg Glu Asn
225                 230                 235                 240

Ser Glu Asp Gln Ala Val Pro Leu Leu Val Tyr Val Ser Arg Glu Lys
            245                 250                 255

Arg Pro Ser Tyr Asn Ser Arg Phe Lys Ala Gly Ala Leu Asn Thr Leu
            260                 265                 270

Leu Arg Val Ser Gly Val Ile Ser Asn Ser Pro Tyr Val Leu Val Leu
        275                 280                 285

Asp Cys Asp Met Tyr Cys Asn Asp Pro Thr Ser Ala Arg Gln Ala Met
        290                 295                 300

Cys Phe His Leu Asp Pro Gln Met Ser Arg Thr Leu Ser Phe Val Gln
305                 310                 315                 320

Phe Pro Gln Val Phe Tyr Asn Val Ser Lys Asn Asp Ile Tyr Asp Gly
                325                 330                 335

Gln Ala Arg Ala Ala Phe Lys Thr Lys Trp Gln Gly Met Asp Gly Leu
            340                 345                 350

Arg Gly Pro Leu Leu Ser Gly Thr Gly Phe Tyr Leu Lys Arg Lys Ser
        355                 360                 365

Leu Tyr Gly Ser Pro Asn Gln Glu Asp Asp Cys Leu Leu Glu Pro His
    370                 375                 380

Lys Asn Phe Gly Lys Cys Asp Lys Leu Ile Glu Ser Val Lys Val Ile
385                 390                 395                 400

Tyr Glu Arg Asp Val Ser Ile Lys Ala Asp Ser Ser Asp Ala Ile Leu
                405                 410                 415

Gln Asp Ala Lys Gln Leu Ala Ser Cys Pro Tyr Glu Thr Asn Thr Ser
```

```
Trp Gly Lys Glu Val Gly Phe Ser Tyr Asp Cys Leu Leu Glu Ser Thr
            420                 425                 430
Phe Thr Gly Tyr Leu Leu His Cys Arg Gly Trp Thr Ser Val Tyr Leu
        435                 440                 445
Tyr Pro Lys Lys Pro Cys Phe Leu Gly Cys Thr Pro Val Asp Met Lys
    450                 455                 460
465                 470                 475                 480
Glu Ala Met Val Gln Tyr Thr Lys Trp Ile Ser Glu Leu Phe Leu Leu
                485                 490                 495
Ala Ile Ser Arg Phe Asn Pro Leu Thr Phe Gly Ile Ser Arg Met Ser
            500                 505                 510
Ile Leu Gln Ser Met Cys Tyr Gly Tyr Leu Thr Ile Met Pro Ile Leu
        515                 520                 525
Ser Val Ala Met Ile Phe Tyr Ala Thr Val Pro Gln Leu Cys Leu Leu
    530                 535                 540
Arg Gly Val Pro Leu Phe Pro Lys Val Ser Asp Pro Trp Phe Ala Val
545                 550                 555                 560
Phe Leu Ala Ile Phe Val Ser Ser Leu Cys Gln His Leu Ile Glu Val
                565                 570                 575
Leu Thr Ser Asp Gly Thr Leu Lys Thr Trp Trp Asn Glu Gln Arg Asn
            580                 585                 590
Trp Val Ile Lys Ser Gly Ser Gly Ser Val Phe Gly Ala Leu Ser Gly
        595                 600                 605
Ile Leu Lys Trp Phe Gly Met Lys Ile Lys Phe Gly Leu Ser Asn Lys
    610                 615                 620
Ala Val Asp Lys Glu Lys Leu Glu Lys Tyr Glu Lys Gly Lys Phe Asp
625                 630                 635                 640
Phe Gln Gly Ala Ala Met Phe Met Val Pro Leu Thr Ile Ser Val Ile
                645                 650                 655
Leu Asn Thr Leu Cys Leu Ile Gly Gly Leu Trp Arg Val Ile Thr Leu
            660                 665                 670
Lys Asn Phe Glu Glu Met Ser Gly Gln Phe Ile Ile Ser Leu Tyr Phe
        675                 680                 685
Leu Ala Leu Ser Tyr Pro Ile Leu Glu Gly Leu Leu Arg Lys Gly Lys
    690                 695                 700
Gly Lys Ala
705

<210> SEQ ID NO 27
<211> LENGTH: 1485
<212> TYPE: DNA
<213> ORGANISM: Quillaja saponaria

<400> SEQUENCE: 27
atggtctccg gcgacgacga cgtttctcgt cggccactga agtttactt tattgcacac      60 ccctcacctg gccatattgc ccctctaacc aaaatagccc aactctttgc tgcacgtggt    120
gagcacgtga ctattcttac tactcccgcc aatgtccact tcatgagaa atccatcgac     180 aaaggaaaga cttccggcta tcatgttaac atccacgccg ttaaatttcc ttctaaagag    240
gtcggtctcc ccgacggcat cgaaaacttc tctcacgcct ccgataatga acagcagcc    300 aaaatttggg ccggattctc catgcttcaa actgaaatgg agcaatatat ggaacaaaac    360
ccacccgatt gcattgttgc cgacatgttc aaccgctgga cttccgactt cgctatcaaa    420
ttgggaatcc cgagaatagt tttcaacgtc tactgtattt tcacacgctg tttggaagaa    480
```

```
gcaatcagat cacctgactc gccacacttg aaactaaact ccgataatga acagtttatt    540
attccgggtc tacccgaccc cataacaatt acccgagctc aactgcccga cggtgccttt    600
tctgtcgtca agaacaagt tagtgaagct gagttgaaaa gcttcggaat ggtgatcaac     660
gggttttccg aactcgaaac cgaatacatc gagtattaca agaatatcat gggtcgaaaa    720
cggatttggc atgtcggacc ccttcagctc atttaccaaa acgatgaccc caaagttcag    780
aggagccaga agacagcggt cgtgagtgac aacgagttag tgagttggct tgactcgaag    840
aaacccgact cagtgattta catttccttc ggtagtgcaa ttcgtttctc taataagcag    900
ctctatgaaa tagcatgtgg attagaagct tccggctacc cattttttgtg ggccttactt    960 tgggtgccag aagatgacga cgacgtgggc aacaaatggt tgcctgattt cgaagaaaga   1020
ataaaaagag aaaataaggg aataattttc aggggtgggg ccccacagat gttaatctta   1080
aaccacccgg cgatcggtgg tttcatgacg cattgtggtt ggaatgcggt ggtggaagcg   1140
ctttctttcg gtgttccgac tattacgctt ccggttttct cggagcagtt ttatactgag   1200
agactgatat cacaagtgct caagactggt gtcgaggtcg gtgcagagaa gtggacctat   1260
gcatttgatg cggggaaata tccggtgagt cgggaaaaga tagcgacggc ggtgaagaag   1320
atattagact gtggagaaga ggcagaagga atgagaaagc gggccaggga gatgaaagaa   1380
aaagcccaaa aaagtgttga agaaggtggg tcctcttata ataatttaac ggctatgatt   1440
gaagatctta agaatttag ggctaacaat ggcaaggttg catga                    1485
```

<210> SEQ ID NO 28
<211> LENGTH: 494
<212> TYPE: PRT
<213> ORGANISM: Quillaja saponaria

<400> SEQUENCE: 28

```
Met Val Ser Gly Asp Asp Val Ser Arg Arg Pro Leu Lys Val Tyr
1               5                   10                  15

Phe Ile Ala His Pro Ser Pro Gly His Ile Ala Pro Leu Thr Lys Ile
            20                  25                  30

Ala Gln Leu Phe Ala Ala Arg Gly Glu His Val Thr Ile Leu Thr Thr
        35                  40                  45

Pro Ala Asn Val His Phe His Glu Lys Ser Ile Asp Lys Gly Lys Thr
    50                  55                  60

Ser Gly Tyr His Val Asn Ile His Ala Val Lys Phe Pro Ser Lys Glu
65                  70                  75                  80

Val Gly Leu Pro Asp Gly Ile Glu Asn Phe Ser His Ala Ser Asp Asn
                85                  90                  95

Glu Thr Ala Ala Lys Ile Trp Ala Gly Phe Ser Met Leu Gln Thr Glu
            100                 105                 110

Met Glu Gln Tyr Met Glu Gln Asn Pro Pro Asp Cys Ile Val Ala Asp
        115                 120                 125

Met Phe Asn Arg Trp Thr Ser Asp Phe Ala Ile Lys Leu Gly Ile Pro
    130                 135                 140

Arg Ile Val Phe Asn Val Tyr Cys Ile Phe Thr Arg Cys Leu Glu Glu
145                 150                 155                 160

Ala Ile Arg Ser Pro Asp Ser Pro His Leu Lys Leu Asn Ser Asp Asn
                165                 170                 175

Glu Gln Phe Ile Ile Pro Gly Leu Pro Asp Pro Ile Thr Ile Thr Arg
            180                 185                 190
```

```
Ala Gln Leu Pro Asp Gly Ala Phe Ser Val Val Lys Glu Gln Val Ser
            195                 200                 205

Glu Ala Glu Leu Lys Ser Phe Gly Met Val Ile Asn Gly Phe Ser Glu
        210                 215                 220

Leu Glu Thr Glu Tyr Ile Glu Tyr Tyr Lys Asn Ile Met Gly Arg Lys
225                 230                 235                 240

Arg Ile Trp His Val Gly Pro Leu Gln Leu Ile Tyr Gln Asn Asp Asp
                245                 250                 255

Pro Lys Val Gln Arg Ser Gln Lys Thr Ala Val Val Ser Asp Asn Glu
            260                 265                 270

Leu Val Ser Trp Leu Asp Ser Lys Lys Pro Asp Ser Val Ile Tyr Ile
        275                 280                 285

Ser Phe Gly Ser Ala Ile Arg Phe Ser Asn Lys Gln Leu Tyr Glu Ile
    290                 295                 300

Ala Cys Gly Leu Glu Ala Ser Gly Tyr Pro Phe Leu Trp Ala Leu Leu
305                 310                 315                 320

Trp Val Pro Glu Asp Asp Asp Val Gly Asn Lys Trp Leu Pro Asp
                325                 330                 335

Phe Glu Glu Arg Ile Lys Arg Glu Asn Lys Gly Ile Ile Phe Arg Gly
            340                 345                 350

Trp Ala Pro Gln Met Leu Ile Leu Asn His Pro Ala Ile Gly Gly Phe
        355                 360                 365

Met Thr His Cys Gly Trp Asn Ala Val Val Glu Ala Leu Ser Phe Gly
    370                 375                 380

Val Pro Thr Ile Thr Leu Pro Val Phe Ser Glu Gln Phe Tyr Thr Glu
385                 390                 395                 400

Arg Leu Ile Ser Gln Val Leu Lys Thr Gly Val Glu Val Gly Ala Glu
                405                 410                 415

Lys Trp Thr Tyr Ala Phe Asp Ala Gly Lys Tyr Pro Val Ser Arg Glu
            420                 425                 430

Lys Ile Ala Thr Ala Val Lys Lys Ile Leu Asp Cys Gly Glu Glu Ala
        435                 440                 445

Glu Gly Met Arg Lys Arg Ala Arg Glu Met Lys Glu Lys Ala Gln Lys
    450                 455                 460

Ser Val Glu Glu Gly Gly Ser Ser Tyr Asn Asn Leu Thr Ala Met Ile
465                 470                 475                 480

Glu Asp Leu Lys Glu Phe Arg Ala Asn Asn Gly Lys Val Ala
                485                 490

<210> SEQ ID NO 29
<211> LENGTH: 1491
<212> TYPE: DNA
<213> ORGANISM: Quillaja saponaria

<400> SEQUENCE: 29
atggtctccg cgacgatac cgtttcacgg ccactgatag tttactttat tgcacacccc      60
tcacctggcc atattgcccc tctaaccaaa atagcccaac tcttcgctgc acgtggtgag     120
cacgtcacta ttcttactac tcccgccaat gtccacttcc atgagaaatc catcgacaaa     180
agaaagaatt ccggctatca tgttaacatc cacaccgtta aatttccttc taaagaggtc     240
ggtctccctg acggcatcga aaacttctct cacgcctccg ataatgaaac agcagccaaa     300
atttgggccg gattctccat gcttcaaact gaaatggagc aatatatgga acaaaaccca     360
cccgattgca tcgttgccga catgttcaac cgctggactt ccgacttcgc tatcaaattg     420
```

-continued

```
ggaatcccga gaatagtttt caacgtctac tgtattttca cacgctgttt ggaagaagca    480
atcagatcac ctgactcgcc acacttgaaa ctaaactccg ataatgaaca gtttattatt    540
cccggtctac ccgaccccat aacaattacc cgagctcaac tccccgacgg tgccttttct    600
gtcgtcaaag aacaagttag tgaagctgag ttgaaaagct tcggaatggt gatcaacggg    660
ttttccgaac tcgaaactga atacatcgag tattacaaga atatcatggg tcgcaaacgg    720
atttggcatg tcggacccct tcagctaatt taccaaaacg acgacccaa agttcagagg    780 agccagaaga cagcggtctt gagtgacaac gagttagtga gttggcttga ctcgaagaaa    840
cccgactcag tgatttacat ttccttcggt agtgcaattc gtttctctaa taagcagctc    900
tatgaaatcg catgtggatt agaagcttcc ggctacccat ttttgtgggc cttactttgg    960
gtgccagaag atgatgacga cgtgggcaac aaatggttgc cgggtttcga agaaagaata   1020
aaaagagaaa ataagggaat aattttcagg gggtgggccc cacagatgtt aatcttaaac   1080
cacccggcga tcgtggtttt catgacgcat tgtggttgga atgcggtggt ggaagcactt   1140
tcattcggtg ttccgactat tacgcttcca gtttctcgg agcagtttta tactgagaga   1200
ctgatatcac aagtgctcaa gactggtgtg gaggttggtg cagagaagtg gacctatgca   1260
tttgatgcgg ggaaatatcc ggtgagtagg gaaaagatag cgacggcggt gaagaagata   1320
ttagacgatg gagaagaggc agaaggaatg agaaagcggg ccagggagat gaaagaaaaa   1380
gcccaaaaaa gtgttgaaga aggtggatcc tcttataata atttaacggc tatgattgaa   1440
gatcttaaag aatttagggc taacaatggc aaggctgcaa tgaaatcatg a             1491
```

<210> SEQ ID NO 30
<211> LENGTH: 496
<212> TYPE: PRT
<213> ORGANISM: Quillaja saponaria

<400> SEQUENCE: 30

```
Met Val Ser Gly Asp Asp Thr Val Ser Arg Pro Leu Ile Val Tyr Phe
1               5                   10                  15

Ile Ala His Pro Ser Pro Gly His Ile Ala Pro Leu Thr Lys Ile Ala
            20                  25                  30

Gln Leu Phe Ala Ala Arg Gly Glu His Val Thr Ile Leu Thr Thr Pro
        35                  40                  45

Ala Asn Val His Phe His Glu Lys Ser Ile Asp Lys Arg Lys Asn Ser
    50                  55                  60

Gly Tyr His Val Asn Ile His Thr Val Lys Phe Pro Ser Lys Glu Val
65                  70                  75                  80

Gly Leu Pro Asp Gly Ile Glu Asn Phe Ser His Ala Ser Asp Asn Glu
                85                  90                  95

Thr Ala Ala Lys Ile Trp Ala Gly Phe Ser Met Leu Gln Thr Glu Met
            100                 105                 110

Glu Gln Tyr Met Glu Gln Asn Pro Pro Asp Cys Ile Val Ala Asp Met
        115                 120                 125

Phe Asn Arg Trp Thr Ser Asp Phe Ala Ile Lys Leu Gly Ile Pro Arg
    130                 135                 140

Ile Val Phe Asn Val Tyr Cys Ile Phe Thr Arg Cys Leu Glu Glu Ala
145                 150                 155                 160

Ile Arg Ser Pro Asp Ser Pro His Leu Lys Leu Asn Ser Asp Asn Glu
                165                 170                 175

Gln Phe Ile Ile Pro Gly Leu Pro Asp Pro Ile Thr Ile Thr Arg Ala
            180                 185                 190
```

Gln Leu Pro Asp Gly Ala Phe Ser Val Val Lys Glu Gln Val Ser Glu
        195                 200                 205

Ala Glu Leu Lys Ser Phe Gly Met Val Ile Asn Gly Phe Ser Glu Leu
    210                 215                 220

Glu Thr Glu Tyr Ile Glu Tyr Tyr Lys Asn Ile Met Gly Arg Lys Arg
225                 230                 235                 240

Ile Trp His Val Gly Pro Leu Gln Leu Ile Tyr Gln Asn Asp Asp Pro
                245                 250                 255

Lys Val Gln Arg Ser Gln Lys Thr Ala Val Leu Ser Asp Asn Glu Leu
                260                 265                 270

Val Ser Trp Leu Asp Ser Lys Lys Pro Asp Ser Val Ile Tyr Ile Ser
            275                 280                 285

Phe Gly Ser Ala Ile Arg Phe Ser Asn Lys Gln Leu Tyr Glu Ile Ala
        290                 295                 300

Cys Gly Leu Glu Ala Ser Gly Tyr Pro Phe Leu Trp Ala Leu Leu Trp
305                 310                 315                 320

Val Pro Glu Asp Asp Asp Val Gly Asn Lys Trp Leu Pro Gly Phe
                325                 330                 335

Glu Glu Arg Ile Lys Arg Glu Asn Lys Gly Ile Ile Phe Arg Gly Trp
                340                 345                 350

Ala Pro Gln Met Leu Ile Leu Asn His Pro Ala Ile Gly Gly Phe Met
            355                 360                 365

Thr His Cys Gly Trp Asn Ala Val Val Glu Ala Leu Ser Phe Gly Val
        370                 375                 380

Pro Thr Ile Thr Leu Pro Val Phe Ser Glu Gln Phe Tyr Thr Glu Arg
385                 390                 395                 400

Leu Ile Ser Gln Val Leu Lys Thr Gly Val Glu Val Gly Ala Glu Lys
                405                 410                 415

Trp Thr Tyr Ala Phe Asp Ala Gly Lys Tyr Pro Val Ser Arg Glu Lys
                420                 425                 430

Ile Ala Thr Ala Val Lys Lys Ile Leu Asp Asp Gly Glu Glu Ala Glu
            435                 440                 445

Gly Met Arg Lys Arg Ala Arg Glu Met Lys Glu Lys Ala Gln Lys Ser
        450                 455                 460

Val Glu Glu Gly Gly Ser Ser Tyr Asn Asn Leu Thr Ala Met Ile Glu
465                 470                 475                 480

Asp Leu Lys Glu Phe Arg Ala Asn Asn Gly Lys Ala Ala Met Lys Ser
                485                 490                 495

<210> SEQ ID NO 31
<211> LENGTH: 1515
<212> TYPE: DNA
<213> ORGANISM: Quillaja saponaria

<400> SEQUENCE: 31
atggtctccg gcgacgacga tgtttctcgt cggccactga agtttactt cattgcacac      60 ccctcacctg gccatattgc ccctctgacc aaaatagccc atctcttcgc tgccctcggt     120
gagcacgtga ctattctcac tactcccgcc aatgtccact ccatgagaa atccatcgac      180 aaaggaaagg cttccggcta tcatgttaac atccacaccg ttaaatttcc ttctaaagag    240
gtcggtctcc ctgacggcat cgaaaacttc tcttacgcct ccgatgttga aacagcagct    300
aaaatttggg ctggattcgc catgctacaa actgaaatgg agcaatatat ggagcttaac    360
ccacccgatt gcatcgttgc cgacatgttc acctcctgga cctccgactt tgctatcaaa    420

```
ttgggaatca caagaatcgt tttcaacgtc tattgtattt tcacacgctg tttggaagaa      480
gccatccgat caccggactc gccacacttg aacaaagaaa tctctgataa tgaaccgttt      540
gttatcccgg gtctaccaga ccccataaca attacccgag ctcaactgcc cgacggtacc      600
ttttctccca tgaaagaact agctagaaca gctgagttga agagctttgg aatggtgatc      660
aacgggtttt ccgaactcga aaccgattac atcgagcatt acaagaaaat catgggtcac      720
aaacggattt ggcatgtcgg accccttcag ctaatccacc gtaacgatga agacaaaatt      780
cagaggagcc acaagacagc ggtgctgagt gataacgata acgagttagt gagttggctt      840
aactcgaaga aacccgactc agttatttac atttgcttcg gtagtgcaac tcgtttctct      900
aatcaccagc tctatgaaat cgcctgtgga ttagaagctt ccgggcaccc attttttgtgg     960
ggcctacttt gggtgccaga agatgaagat aacgatgacg tgggcaacaa atggttgcca      1020
gctttcgaag aaagaattaa aaaggaaaat aagggaatga ttttaagggg gtgggctcca      1080
cagatgttaa tcttgaatca cccggcgatc ggtggtttca tgacgcattg tggttggaat      1140
gcggcggtgg aggcgctttc ttccggtgtt ccgattatta catttccggt tttctcggat      1200
cagtttttata tgaaaggct gatatcacaa gtgcataagt gtgggtgtgg ggttggtacg      1260
gaggcgtgga gctatgcatt cgatgccggg aagaatccgg tgggtcggga aaagataatg      1320
acggcggtga agaagatatt agacggtgga gaagaggcgg aaggaatgag aaagagggcc      1380
cgggagctga agaaatagc taaagaagt gtggaagaag gtgggtcctc ttataataat        1440
ttaacggcta tgattcaaga tctgaaagaa tttagagcta acaatggcaa ggctgcacaa      1500
gatcatgaat cgtga                                                       1515
```

<210> SEQ ID NO 32
<211> LENGTH: 504
<212> TYPE: PRT
<213> ORGANISM: Quillaja saponaria

<400> SEQUENCE: 32

```
Met Val Ser Gly Asp Asp Val Ser Arg Arg Pro Leu Lys Val Tyr
1               5                   10                  15

Phe Ile Ala His Pro Ser Pro Gly His Ile Ala Pro Leu Thr Lys Ile
                20                  25                  30

Ala His Leu Phe Ala Ala Leu Gly Glu His Val Thr Ile Leu Thr Thr
            35                  40                  45

Pro Ala Asn Val His Phe His Glu Lys Ser Ile Asp Lys Gly Lys Ala
        50                  55                  60

Ser Gly Tyr His Val Asn Ile His Thr Val Lys Phe Pro Ser Lys Glu
65                  70                  75                  80

Val Gly Leu Pro Asp Gly Ile Glu Asn Phe Ser Tyr Ala Ser Asp Val
                85                  90                  95

Glu Thr Ala Ala Lys Ile Trp Ala Gly Phe Ala Met Leu Gln Thr Glu
            100                 105                 110

Met Glu Gln Tyr Met Glu Leu Asn Pro Pro Asp Cys Ile Val Ala Asp
        115                 120                 125

Met Phe Thr Ser Trp Thr Ser Asp Phe Ala Ile Lys Leu Gly Ile Thr
    130                 135                 140

Arg Ile Val Phe Asn Val Tyr Cys Ile Phe Thr Arg Cys Leu Glu Glu
145                 150                 155                 160

Ala Ile Arg Ser Pro Asp Ser Pro His Leu Asn Lys Glu Ile Ser Asp
                165                 170                 175
```

-continued

```
Asn Glu Pro Phe Val Ile Pro Gly Leu Pro Asp Pro Ile Thr Ile Thr
            180                 185                 190

Arg Ala Gln Leu Pro Asp Gly Thr Phe Ser Pro Met Lys Glu Leu Ala
        195                 200                 205

Arg Thr Ala Glu Leu Lys Ser Phe Gly Met Val Ile Asn Gly Phe Ser
    210                 215                 220

Glu Leu Glu Thr Asp Tyr Ile Glu His Tyr Lys Lys Ile Met Gly His
225                 230                 235                 240

Lys Arg Ile Trp His Val Gly Pro Leu Gln Leu Ile His Arg Asn Asp
                245                 250                 255

Glu Asp Lys Ile Gln Arg Ser His Lys Thr Ala Val Leu Ser Asp Asn
            260                 265                 270

Asp Asn Glu Leu Val Ser Trp Leu Asn Ser Lys Lys Pro Asp Ser Val
        275                 280                 285

Ile Tyr Ile Cys Phe Gly Ser Ala Thr Arg Phe Ser Asn His Gln Leu
    290                 295                 300

Tyr Glu Ile Ala Cys Gly Leu Glu Ala Ser Gly His Pro Phe Leu Trp
305                 310                 315                 320

Gly Leu Leu Trp Val Pro Glu Asp Glu Asn Asp Asp Val Gly Asn
                325                 330                 335

Lys Trp Leu Pro Ala Phe Glu Gly Arg Ile Lys Lys Glu Asn Lys Gly
            340                 345                 350

Met Ile Leu Arg Gly Trp Ala Pro Gln Met Leu Ile Leu Asn His Pro
        355                 360                 365

Ala Ile Gly Gly Phe Met Thr His Cys Gly Trp Asn Ala Ala Val Glu
    370                 375                 380

Ala Leu Ser Ser Gly Val Pro Ile Ile Thr Phe Pro Val Phe Ser Asp
385                 390                 395                 400

Gln Phe Tyr Asn Glu Arg Leu Ile Ser Gln Val His Lys Cys Gly Val
                405                 410                 415

Gly Val Gly Thr Glu Ala Trp Ser Tyr Ala Phe Asp Ala Gly Lys Asn
            420                 425                 430

Pro Val Gly Arg Glu Lys Ile Met Thr Ala Val Lys Lys Ile Leu Asp
        435                 440                 445

Gly Gly Glu Glu Ala Glu Gly Met Arg Lys Arg Ala Arg Glu Leu Lys
    450                 455                 460

Glu Ile Ala Lys Arg Ser Val Glu Glu Gly Gly Ser Ser Tyr Asn Asn
465                 470                 475                 480

Leu Thr Ala Met Ile Gln Asp Leu Lys Glu Phe Arg Ala Asn Asn Gly
                485                 490                 495

Lys Ala Ala Gln Asp His Glu Ser
            500
```

<210> SEQ ID NO 33
<211> LENGTH: 56
<212> TYPE: DNA
<213> ORGANISM: Quillaja saponaria

<400> SEQUENCE: 33
ggggacaagt ttgtacaaaa aagcaggctt aatgaaatcc ccctctaacc caaatc      56

<210> SEQ ID NO 34
<211> LENGTH: 56
<212> TYPE: DNA
<213> ORGANISM: Quillaja saponaria

```
<400> SEQUENCE: 34
ggggaccact tgtacaaga aagctgggta tcagaccatt ttcttgctga ttctag          56

<210> SEQ ID NO 35
<211> LENGTH: 53
<212> TYPE: DNA
<213> ORGANISM: Quillaja saponaria

<400> SEQUENCE: 35
ggggacaagt ttgtacaaaa aagcaggctt aatggtggag tctccagcag atc           53

<210> SEQ ID NO 36
<211> LENGTH: 55
<212> TYPE: DNA
<213> ORGANISM: Quillaja saponaria

<400> SEQUENCE: 36
ggggaccact tgtacaaga aagctgggta tcagacaccc tgaattcttg atttc          55

<210> SEQ ID NO 37
<211> LENGTH: 53
<212> TYPE: DNA
<213> ORGANISM: Quillaja saponaria

<400> SEQUENCE: 37
ggggacaagt ttgtacaaaa aagcaggctt aatggtctcc ggcgacgacg atg           53

<210> SEQ ID NO 38
<211> LENGTH: 55
<212> TYPE: DNA
<213> ORGANISM: Quillaja saponaria

<400> SEQUENCE: 38
ggggaccact tgtacaaga aagctgggta tcacgattca tgatcttgtg cagcc          55

<210> SEQ ID NO 39
<211> LENGTH: 44
<212> TYPE: PRT
<213> ORGANISM: Artificial Sequence
<220> FEATURE:
<223> OTHER INFORMATION: Synthetic sequence

<400> SEQUENCE: 39

Trp Ala Pro Gln Ala Leu Ile Leu Ser His Arg Ala Ala Gly Ala Phe
1               5                   10                  15

Val Thr His Cys Gly Trp Asn Ser Thr Leu Glu Ala Val Ala Ala Gly
                20                  25                  30

Leu Pro Val Val Thr Trp Pro His Phe Thr Asp Gln
            35                  40

<210> SEQ ID NO 40
<211> LENGTH: 44
<212> TYPE: PRT
<213> ORGANISM: Artificial Sequence
<220> FEATURE:
<223> OTHER INFORMATION: Synthetic sequence

<400> SEQUENCE: 40

Trp Val Pro Gln Ala Leu Ile Leu Asp His Pro Ser Ile Gly Gly Phe
1               5                   10                  15

Leu Thr His Cys Gly Trp Asn Ala Thr Val Glu Ala Ile Ser Ser Gly
                20                  25                  30
```

```
Val Pro Met Val Thr Met Pro Gly Phe Gly Asp Gln
        35                  40

<210> SEQ ID NO 41
<211> LENGTH: 44
<212> TYPE: PRT
<213> ORGANISM: Artificial Sequence
<220> FEATURE:
<223> OTHER INFORMATION: Synthetic sequence

<400> SEQUENCE: 41

Trp Ala Pro Gln Val Glu Leu Leu Lys His Glu Ala Thr Gly Val Phe
1               5                   10                  15

Val Thr His Cys Gly Trp Asn Ser Val Leu Glu Ser Val Ser Gly Gly
            20                  25                  30

Val Pro Met Ile Cys Arg Pro Phe Phe Gly Asp Gln
        35                  40

<210> SEQ ID NO 42
<211> LENGTH: 44
<212> TYPE: PRT
<213> ORGANISM: Artificial Sequence
<220> FEATURE:
<223> OTHER INFORMATION: Synthetic sequence

<400> SEQUENCE: 42

Trp Ala Pro Gln Leu Leu Ile Leu Asp His Pro Ala Ile Gly Gly Leu
1               5                   10                  15

Leu Asn His Ser Gly Trp Asn Ser Val Leu Glu Gly Ala Thr Ala Gly
            20                  25                  30

Leu Pro Met Ile Thr Trp Pro Leu Tyr Ala Glu His
        35                  40

<210> SEQ ID NO 43
<211> LENGTH: 44
<212> TYPE: PRT
<213> ORGANISM: Artificial Sequence
<220> FEATURE:
<223> OTHER INFORMATION: Synthetic sequence

<400> SEQUENCE: 43

Trp Val Pro Gln Gly Leu Ile Leu Lys His Asp Ala Ile Gly Gly Phe
1               5                   10                  15

Leu Thr His Cys Gly Ala Asn Ser Val Val Glu Ala Ile Cys Glu Gly
            20                  25                  30

Val Pro Leu Ile Thr Met Pro Arg Phe Gly Asp His
        35                  40

<210> SEQ ID NO 44
<211> LENGTH: 44
<212> TYPE: PRT
<213> ORGANISM: Artificial Sequence
<220> FEATURE:
<223> OTHER INFORMATION: Synthetic sequence

<400> SEQUENCE: 44

Trp Ala Pro Gln Val Glu Leu Leu Asn His Glu Ala Met Gly Val Phe
1               5                   10                  15

Val Ser His Gly Gly Trp Asn Ser Val Leu Glu Ser Val Ser Ala Gly
            20                  25                  30

Val Pro Met Ile Cys Arg Pro Ile Phe Gly Asp His
        35                  40
```

<210> SEQ ID NO 45
<211> LENGTH: 44
<212> TYPE: PRT
<213> ORGANISM: Artificial Sequence
<220> FEATURE:
<223> OTHER INFORMATION: Synthetic sequence

<400> SEQUENCE: 45

Trp Ala Pro Gln Ile Gln Val Leu Ser His Asp Ala Val Gly Val Val
1               5                   10                  15

Ile Thr His Gly Gly Trp Asn Ser Val Val Glu Ser Ile Ala Ala Gly
            20                  25                  30

Val Pro Val Ile Cys Arg Pro Phe Phe Gly Asp His
        35                  40

<210> SEQ ID NO 46
<211> LENGTH: 44
<212> TYPE: PRT
<213> ORGANISM: Artificial Sequence
<220> FEATURE:
<223> OTHER INFORMATION: Synthetic sequence

<400> SEQUENCE: 46

Trp Ala Pro Gln Leu Leu Ile Leu Glu Asn Pro Ala Ile Gly Gly Leu
1               5                   10                  15

Val Thr His Cys Gly Trp Asn Thr Val Val Glu Ser Val Asn Ala Gly
            20                  25                  30

Leu Pro Met Ala Thr Trp Pro Leu Phe Ala Glu His
        35                  40

<210> SEQ ID NO 47
<211> LENGTH: 51
<212> TYPE: DNA
<213> ORGANISM: Artificial Sequence
<220> FEATURE:
<223> OTHER INFORMATION: Synthetic sequence

<400> SEQUENCE: 47
ggggacaagt ttgtacaaaa aagcaggctt aatggcgacc gtctcctccc t         51

<210> SEQ ID NO 48
<211> LENGTH: 51
<212> TYPE: DNA
<213> ORGANISM: Artificial Sequence
<220> FEATURE:
<223> OTHER INFORMATION: Synthetic sequence

<400> SEQUENCE: 48
ggggaccact ttgtacaaga aagctgggta ttaggccttt cccttgcctt t         51

<210> SEQ ID NO 49
<211> LENGTH: 53
<212> TYPE: DNA
<213> ORGANISM: Artificial Sequence
<220> FEATURE:
<223> OTHER INFORMATION: Synthetic sequence

<400> SEQUENCE: 49
ggggacaagt ttgtacaaaa aagcaggctt aatggtctcc ggcgacgacg atg       53

<210> SEQ ID NO 50
<211> LENGTH: 55
<212> TYPE: DNA

```
<213> ORGANISM: Artificial Sequence
<220> FEATURE:
<223> OTHER INFORMATION: Synthetic sequence

<400> SEQUENCE: 50
ggggaccact tgtacaaga aagctgggta tcacgattca tgatcttgtg cagcc          55

<210> SEQ ID NO 51
<211> LENGTH: 53
<212> TYPE: DNA
<213> ORGANISM: Artificial Sequence
<220> FEATURE:
<223> OTHER INFORMATION: Synthetic sequence

<400> SEQUENCE: 51
ggggacaagt tgtacaaaa aagcaggctt aatggtctcc ggcgacgacg acg            53

<210> SEQ ID NO 52
<211> LENGTH: 57
<212> TYPE: DNA
<213> ORGANISM: Artificial Sequence
<220> FEATURE:
<223> OTHER INFORMATION: Synthetic sequence

<400> SEQUENCE: 52
ggggaccact tgtacaaga aagctgggta tcatgcaacc ttgccattgt tagccct        57

<210> SEQ ID NO 53
<211> LENGTH: 52
<212> TYPE: DNA
<213> ORGANISM: Artificial Sequence
<220> FEATURE:
<223> OTHER INFORMATION: Synthetic sequence

<400> SEQUENCE: 53
ggggacaagt tgtacaaaa aagcaggctt aatggtctcc ggcgacgacg ac             52

<210> SEQ ID NO 54
<211> LENGTH: 55
<212> TYPE: DNA
<213> ORGANISM: Artificial Sequence
<220> FEATURE:
<223> OTHER INFORMATION: Synthetic sequence

<400> SEQUENCE: 54
ggggaccact tgtacaaga aagctgggta tcatgatttc attgcagcct tgcca          55
```